(12) United States Patent
Farrell et al.

(10) Patent No.: US 11,988,673 B2
(45) Date of Patent: May 21, 2024

(54) MULTIPLEXED IMMUNOHISTOCHEMISTRY USING RECOMBINANT ANTIBODIES WITH EPITOPE TAGS

(71) Applicant: Ventana Medical Systems, Inc., Tucson, AZ (US)

(72) Inventors: Michael Farrell, Tucson, AZ (US); Antony Hubbard, Tucson, AZ (US); Eric May, Oro Valley, AZ (US); Lei Tang, Oro Valley, AZ (US); Tsu-Shuen Tsao, Tucson, AZ (US); Wenjun Zhang, Tucson, AZ (US)

(73) Assignee: Ventana Medical Systems, Inc., Tucson, AZ (US)

(*) Notice: Subject to any disclaimer, the term of this patent is extended or adjusted under 35 U.S.C. 154(b) by 55 days.

(21) Appl. No.: 17/389,757

(22) Filed: Jul. 30, 2021

(65) Prior Publication Data
US 2022/0057408 A1 Feb. 24, 2022

Related U.S. Application Data

(60) Division of application No. 16/123,750, filed on Sep. 6, 2018, now Pat. No. 11,112,413, which is a continuation of application No. PCT/US2017/021157, filed on Mar. 7, 2017.

(60) Provisional application No. 62/461,651, filed on Feb. 21, 2017, provisional application No. 62/418,667, filed on Nov. 7, 2016, provisional application No. 62/305,440, filed on Mar. 8, 2016.

(51) Int. Cl.
| | | |
|---|---|---|
| *G01N 33/68* | (2006.01) | |
| *C07K 16/18* | (2006.01) | |
| *C07K 16/28* | (2006.01) | |
| *C07K 16/32* | (2006.01) | |

(52) U.S. Cl.
CPC ......... *G01N 33/6878* (2013.01); *C07K 16/18* (2013.01); *C07K 16/2809* (2013.01); *C07K 16/2815* (2013.01); *C07K 16/2827* (2013.01); *C07K 16/2887* (2013.01); *C07K 16/2896* (2013.01); *C07K 16/32* (2013.01); *C07K 2319/40* (2013.01); *C07K 2319/42* (2013.01); *G01N 2570/00* (2013.01)

(58) Field of Classification Search
CPC ............... C07K 16/18; C07K 16/2809; C07K 16/2815; C07K 16/2827; C07K 16/2887; C07K 16/2896; C07K 16/32; C07K 2319/40; C07K 2319/42
See application file for complete search history.

(56) References Cited

U.S. PATENT DOCUMENTS

| | | | |
|---|---|---|---|
| 2008/0299555 A1 | 12/2008 | Nitta et al. | |
| 2012/0034223 A1* | 2/2012 | Hall ................... | C07K 16/1235 424/134.1 |
| 2014/0363427 A1 | 12/2014 | Williamson et al. | |

FOREIGN PATENT DOCUMENTS

| | | |
|---|---|---|
| WO | 2009/111729 A1 | 9/2009 |
| WO | 2010/051635 A1 | 5/2010 |

OTHER PUBLICATIONS

Wang et al., "Enhancement of scFv fragment reactivity with target antigens in binding assays following mixing with anti-tag monoclonal antibodies," J. Immunol. Methods, 2004, vol. 294, No. 1-2, pp. 23-35.*
Duncan et al., "Cleavage site for sterol-regulated protease localized to a leu-ser bond in the lumenal loop of sterol regulatory element-binding protein-2," J. Biol. Chem., 1997, vol. 272, pp. 12778-12785.*
García-Martínez et al., "Tumor-infiltrating immune cell profiles and their change after neoadjuvant chemotherapy predict response and prognosis of breast cancer," Breast Cancer Res., 2014, Nov. 29;16(6):488, pp. 1-17.*
Stack et al., "Multiplexed immunohistochemistry, imaging, and quantitation: A review, with an assessment of Tyramide signal amplification, multispectral imaging and multiplex analysis," Methods, 2014, vol. 70, issue 1, pp. 46-58.*
Vira et al., "Fluorescent labeled antibodies—balancing functionality and degree of labeling," Anal. Biochem., 2010, vol. 402, No. 2, pp. 146-150.*
Jarvik and Telmer, "Epitope Tagging," Annu. Rev. Genet. 32:601-618 (1998).
Zhang, "Multiple Tandem Epitope Tagging for Enhanced Detection of Protein Expressed in Mammalian Cells," Molecular Biotechnology 19:313-321 (2001).
International Searching Authority, International Preliminary Report on Patentability for International Patent Application No. PCT/US2017/021157 (dated Sep. 11, 2018).
International Searching Authority, International Search Report for International Patent Application No. PCT/US2017/021157 (dated Sep. 14, 2017).
International Searching Authority, Written Opinion of the International Searching Authority for International Patent Application No. PCT/US2017/021157 (dated Sep. 14, 2017).
Goodrow, Marvin H. et al., Strategies for Immunoassay Hapten Design, ACS Symposium Series, 1995, pp. 119-139, Chapter 9.
Lloyd, C. et al., Modelling the human immune response: performance of a 1011 human antibody repertoire against a broad panel of therapeutically relevant antigens, Protein Engineering, Design & Selection, 2009, pp. 159-168, vol. 22 No. 3.

(Continued)

*Primary Examiner* — Galina M. Yakovleva
(74) *Attorney, Agent, or Firm* — Charney IP Law LLC; Thomas M. Finetti

(57) ABSTRACT

The present disclosure is directed to epitope-tagged antibodies, as well as methods of employing the epitope-tagged antibodies for detecting one or more targets in a biological sample, e.g. a tissue sample.

16 Claims, 117 Drawing Sheets
(35 of 117 Drawing Sheet(s) Filed in Color)
Specification includes a Sequence Listing.

(56) References Cited

OTHER PUBLICATIONS

Szurdoki, Ferenc et al., Important Factors in Hapten Design and Enzyme-Linked Immunosorbent Assay Development, Immunoanalysis of Agrochemicals, 1995, pp. 39-63, ACS Symposium Series, vol. 586, Chapter 4.
ThermoFisher Scientific, Pierce Anti-HA Agarose, 3 pages, printed Nov. 4, 2020, retrieved at: https://www.thermofisher.com/order/catalog/product/26181?us&en#/26181?us&en.

* cited by examiner

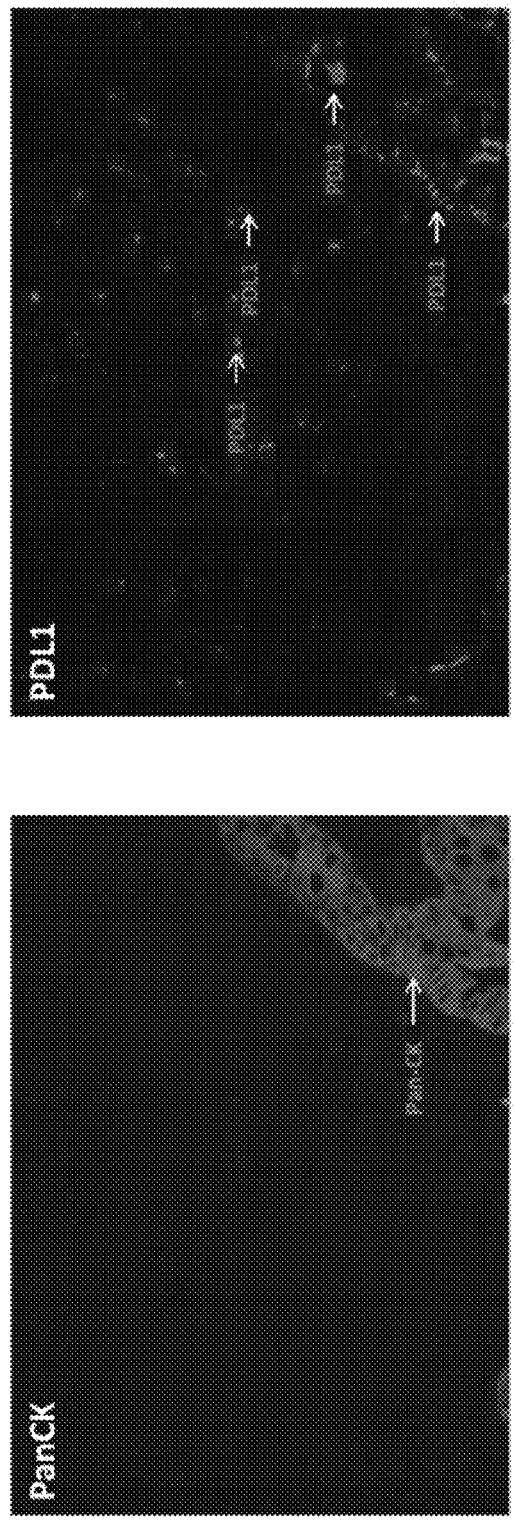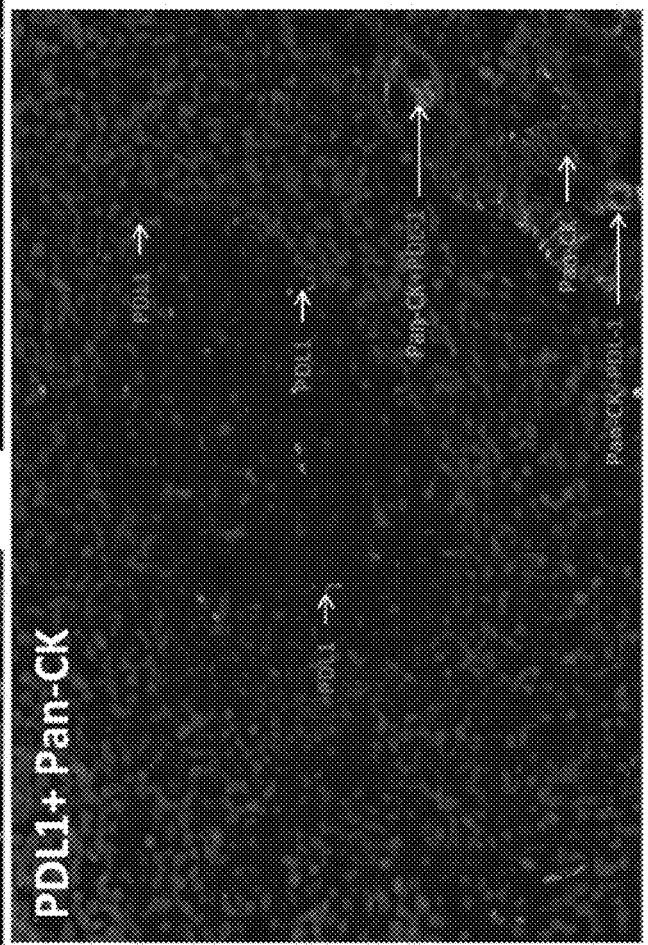
FIG. 10C

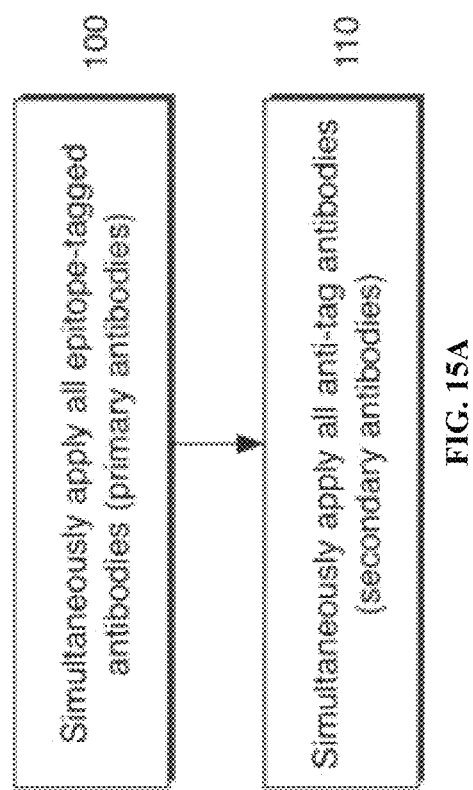

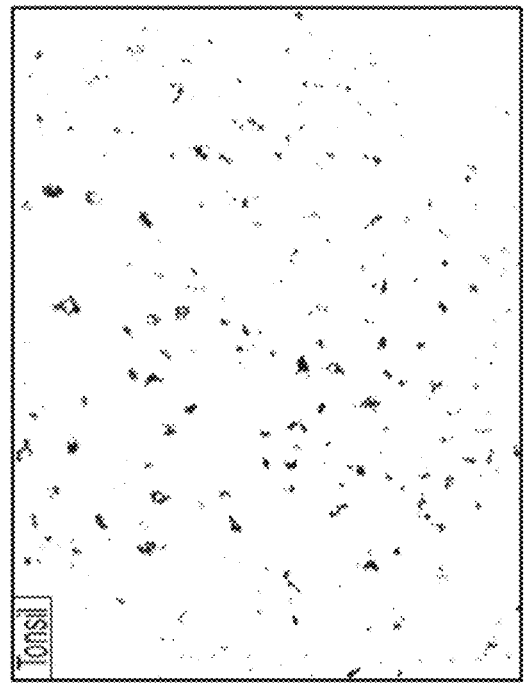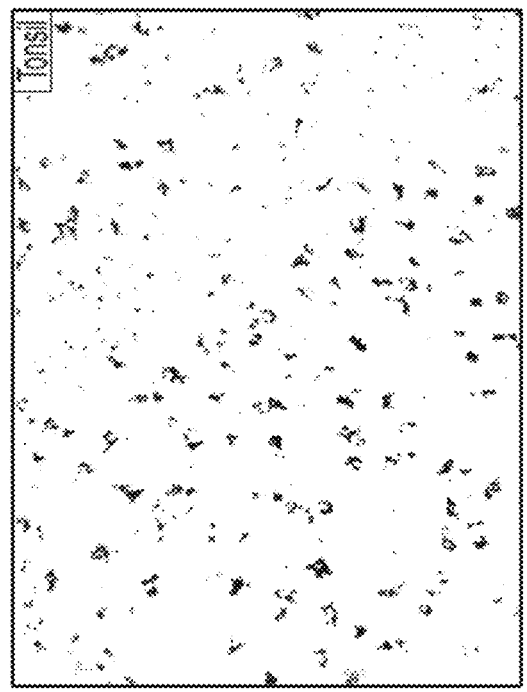
FIG. 17A

CD8 Tagged with AU5 H4K0 is Detected by Anti-AU5 Antibody on Tonsil Tissue
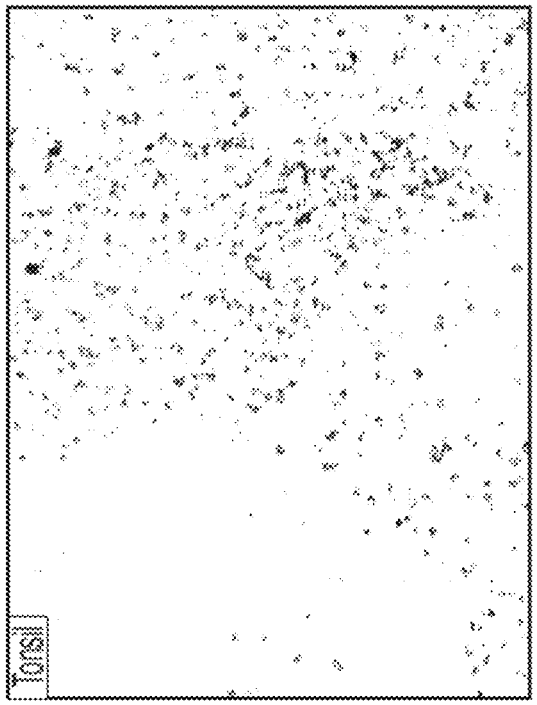
CD8 (SP239) Tagged with AU5 H4K0
1.0μg/ml in Diluent 90103
Detected with 1:30 Dilution of 1mg/ml Anti-AU5 Mouse
Monoclonal Ab (Abcam Cat# ab24576) in Diluent 90840,
Followed with OmniMap Goat Anti-mouse-HRP (Ventana
Cat# 760-4310)
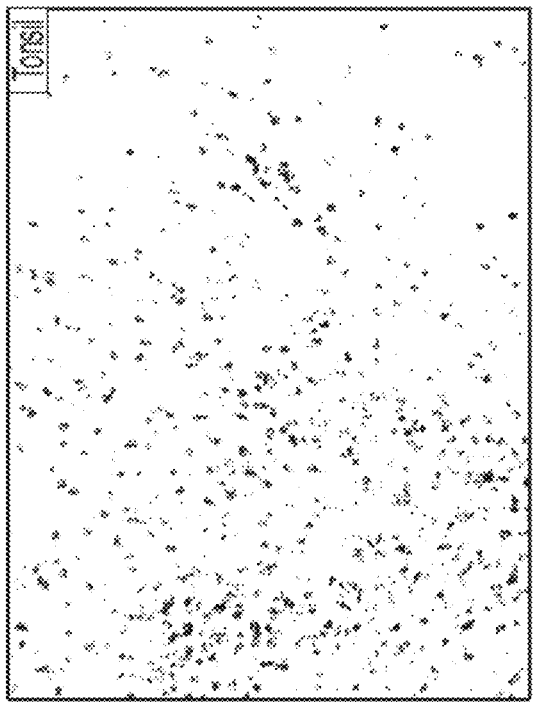
CD8 (SP239) Native
1μg/ml in Diluent 90103
Detected with UltraView DAB Universal Detection Kit
(Ventana Cat# 760-500)
FIG. 17B CD8 Tagged with E2 H4K0 is Detected by Anti-E2 Antibody on Tonsil Tissue
CD8 (SP239) Tagged with E2 H4K0
1.0µg/ml in Diluent 90103
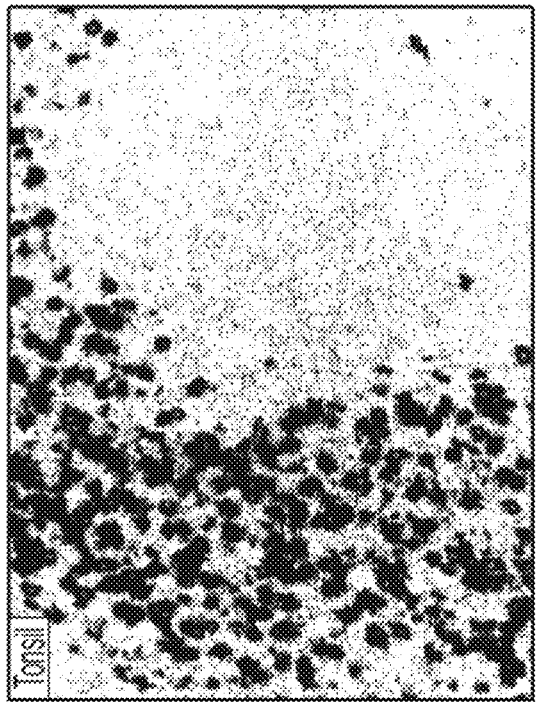
Detected with 1/250 Dilution of 1mg/ml Anti-E2 Mouse Monoclonal

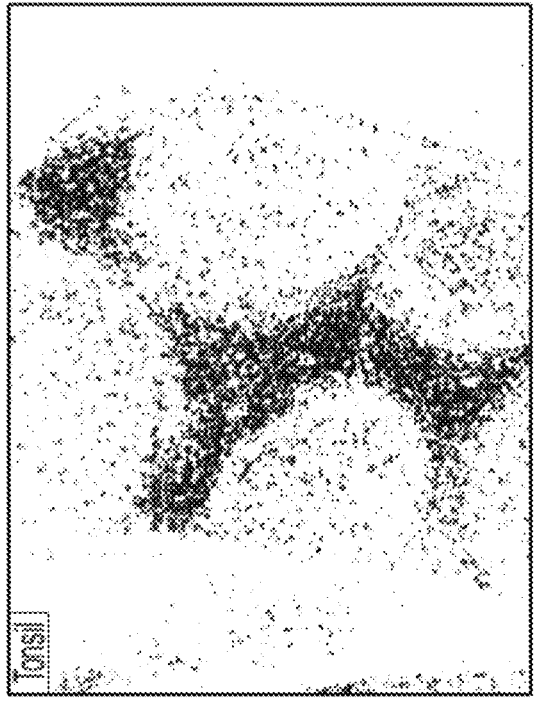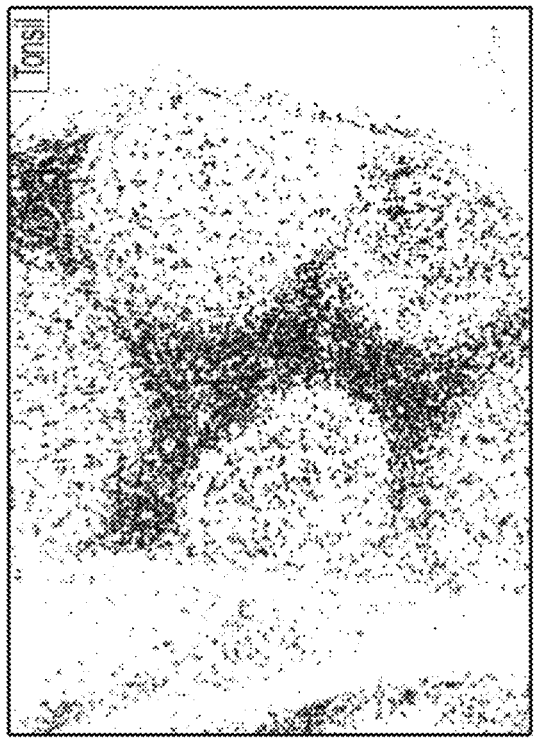
FIG. 17D

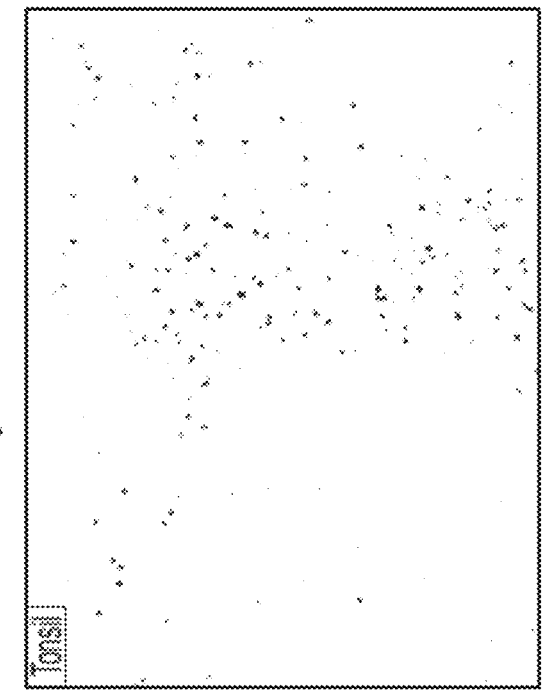
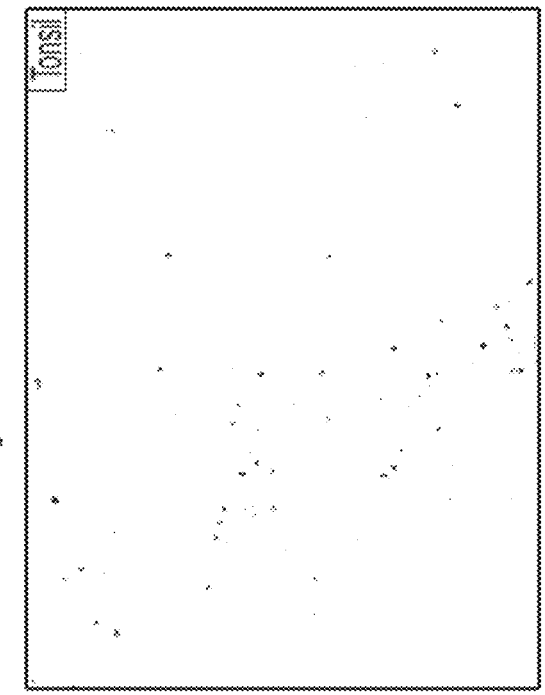
FIG. 17E

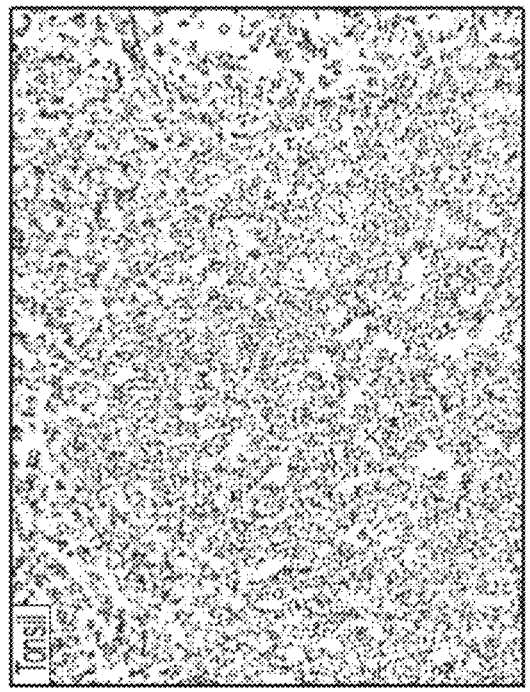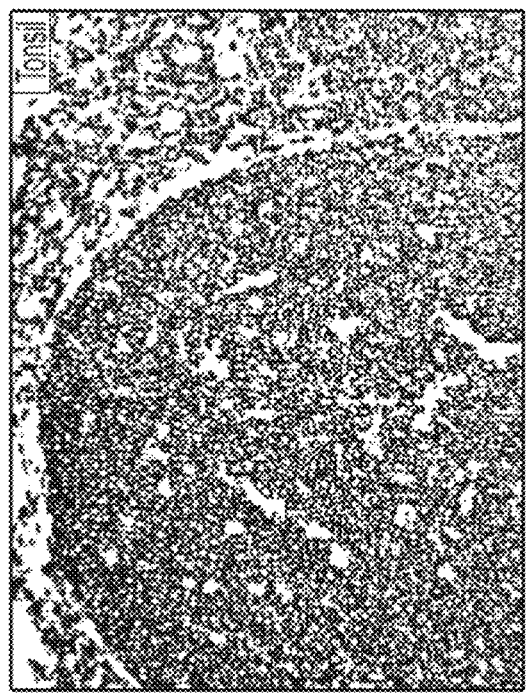
FIG. 17F

FIG. 19

Protocol Summary

Procedure: AH Anti-Tag Multiplex v3 (v1.02.0042)
Benchmark ULTRA IHC/ISH Staining Module
Ventana Medical Systems, Inc., 1910 Innovation Park Drive Tucson, Arizona USA

| Protocol No | Protocol Name | Creation Date |
|---|---|---|
| 756 | SB_FL_v3_32min | 12/15/2014 |

1. Paraffin (Selected)
2. Deparaffinization (Selected)
3. Warmup Slide to (72 Deg C) from Medium Temperatures (Deparaffinization)
4. Cell Conditioning (Selected)
5. Ultra CC1 (Selected)
6. Warmup Slide to (100 Deg C), and Incubate for 4 Minutes (Cell Conditioner #1)
7. CC1 8 Min (Selected)
8. CC1 16 Min (Selected)
9. CC1 24 Min (Selected)
10. CC1 32 Min (Selected)
11. CC1 40 Min (Selected)
12. CC1 48 Min (Selected)
13. CC1 56 Min (Selected)
14. CC1 64 Min (Selected)
15. 1st Antibody Manual Application (Selected)
16. Hand Apply (Primary Antibody), and Incubate for (0 Hr 32 Min)
17. Blocker (Selected)
18. Apply One Drop of (OPTION 2) (2nd Option), and Incubate for (32 Minutes)
19. 3rd Wash after Primary Ab (Selected)
20. 2nd Antibody Manual Application (Selected)
21. Hand Apply (Secondary Antibody), and Incubate for (0 Hr 32 Min)

FIG. 21

Protocol Summary
Procedure: AH Anti-Tag Multiplex v6 (v1.02.0857)
Benchmark ULTRA IHC/ISH Staining Module
Ventana Medical Systems, Inc., 1910 Innovation Park Drive Tucson, Arizona USA

| Protocol No | Protocol Name | Creation Date |
|---|---|---|
| 793 | Ms Rb Tag_plex | 02/24/2015 |

1. Paraffin (Selected)
2. Deparaffinization (Selected)
3. Warmup Slide to (72 Deg C) from Medium Temperatures (Deparaffinization)
4. Cell Conditioning (Selected)
5. Ultra CC1 (Selected)
6. Warmup Slide to (100 Deg C), and Incubate for 4 Minutes (Cell Conditioner #1)
7. CC1 8 Min (Selected)
8. CC1 16 Min (Selected)
9. CC1 24 Min (Selected)
10. CC1 32 Min (Selected)
11. CC1 40 Min (Selected)
12. CC1 48 Min (Selected)
13. CC1 56 Min (Selected)
14. CC1 64 Min (Selected)
15. Research Fork #1 (Selected)
16. Hand Apply (Antibody), and Incubate for (0 Hr 16 Min)
17. Blocker (Selected)
18. Apply One Drop of (OPTION 2) (Option 1), and Incubate for (32 Minutes)
19. 3rd Wash after Primary Ab (Selected)
20. Research Fork #2 (Selected)
21. Hand Apply (Secondary Antibody), and Incubate for (0 Hr 32 Min)
22. Research Fork #9 (Selected)
23. Apply Three Drops of (NEG CTL Rbt Ig) (Antibody), and Incubate for (32 Minutes)
24. Research Fork #3 (Selected)
25. Apply One Drop of (OPTION 2) (Option 2), and Incubate for (32 Minutes)
26. Research Fork #4 (Selected)
27. Hand Apply (Primary Antibody), and Incubate for (0 Hr 32 Min)
28. Research Fork #5 (Selected)
29. Research Fork #6 (Selected)
30. Apply One Drop of (OPTION 2) (Option 3), and Incubate for (32 Minutes)
31. Research Fork #7 (Selected)
32. Research Fork #8 (Selected)
33. Counterstain Options (Selected)
34. Apply One Drop of (HEMATOXYLIN II) (Counterstain), Apply Coverslip, and Incubate for (4 Minutes)

FIG. 22

Protocol Summary
Procedure: #759 : Test_PanCK+Multiplex (12/15/2014)
Procedure: AH Anti Tag Multiplex v4 (v1.02.0047)
BenchMark ULtra IHC/ISH Staining Module
Ventana Medical Systems, INC., 1910 Innovation Park Tucson, Arizona USA

| Step No | Procedure Step |
|---|---|
| 1 | Enable Mixers |
| 2 | Disable Mixers |
| 3 | [72°C is the Standard temperature] |
| 4 | Warmup Slide to [72 Deg C] from Medium Temperature (Deparaffinization) |
| 5 | Incubate for 4 Minutes |
| 6 | Apply EZPrep Volume Adjust |
| 7 | Rinse Slide With EZ Prep |
| 8 | Apply EZPrep Volume Adjust |
| 9 | Apply Coverslip |
| 10 | Rinse Slide With EZ Prep |
| 11 | Apply EZPrep Volume Adjust |
| 12 | Apply Coverslip |
| 13 | Enable Mixers |
| 14 | Disable Slide Heater |
| 15 | Pause Point (Landing Zone) |
| 16 | Rinse Slide with EZPrep |
| 17 | Apply Long Cell Conditioner #1 |
| 18 | Apply CC Coverslip Long |
| 19 | [100°C is the Standard Temperature] |
| 20 | Warmup Slide to [100 Deg C], and Incubate for 4 Minutes (Cell Conditioner #1) |
| 21 | Incubate for 4 Minutes |
| 22 | Incubate for 8 Minutes |
| 23 | Apply Cell Conditioner #1 |
| 24 | Apply CC Medium Coverslip No BB |
| 25 | Incubate for 8 Minutes |
| 26 | Incubate for 8 Minutes |
| 27 | Apply Cell Conditioner #1 |
| 28 | Apply CC Medium Coverslip No BB |
| 29 | Incubate for 8 Minutes |
| 30 | Incubate for 8 Minutes |
| 31 | Apply Cell Conditioner #1 |
| 32 | Apply CC Medium Coverslip No BB |
| 33 | Incubate for 8 Minutes |
| 34 | Apply Cell Conditioner #1 |
| 35 | Apply CC Medium Coverslip No BB |

FIG. 23

Protocol Summary
Procedure #768: Test PanCK+Multiplex (12/15/2014)
Procedure: AH Anti-Tag Multiplex v4 (v1.02.0047)
BenchMark ULtra IHC/ISH Staining Module
Ventana Medical Systems, INC., 1910 Innovation Park Tucson, Arizona USA

| Step No | Procedure Step |
|---|---|
| 36 | Apply Cell Conditioner #1 |
| 37 | Apply CC Medium Coverslip No BB |
| 38 | Apply Cell Conditioner #1 |
| 39 | Apply CC Medium Coverslip No BB |
| 40 | Disable Slide Heater |
| 41 | Apply Cell Conditioner #1 |
| 42 | Apply CC Medium Coverslip No BB |
| 43 | Rinse Slide With Reaction Buffer |
| 44 | Adjust Slide Volume With Reaction Buffer |
| 45 | Apply Coverslip |

* One Drop is One Reagent Dispense
Ventana Medical Systems, Inc., Innovation Park Drive Tucson, Arizona USA
VSS v12.3 Build 035

| Step No | Procedure Step |
|---|---|
| 46 | Rinse Slide With Reaction Buffer |
| 47 | Adjust Slide Volume With Reaction Buffer |
| 48 | Apply Coverslip |
| 49 | Pause Point (Landing Zone) |
| 50 | Warmup Slide to 36 Deg C |
| 51 | Rinse Slide With Reaction Buffer |
| 52 | Adjust Slide Volume With Reaction Buffer |
| 53 | Apply One Drop of [ANTI-PAN KERATIN] (Antibody), Apply Coverslip, and Incubate for [0 Hr 16 Min] |
| 54 | Rinse Slide With Reaction Buffer |
| 55 | Adjust Slide Volume With Reaction Buffer |
| 56 | Apply Coverslip |
| 57 | Rinse Slide With Reaction Buffer |
| 58 | Adjust Slide Volume With Reaction Buffer |
| 59 | Apply Coverslip |
| 60 | Apply One Drop of [PRETREATMENT 1] (Pretreatment #1), and Incubate for [32 Minutes] |
| 61 | Rinse Slide With Reaction Buffer |
| 62 | Adjust Slide Volume With Reaction Buffer |
| 63 | [Blocking Buffer] |
| 64 | Apply Coverslip |
| 65 | Rinse Slide With Reaction Buffer |
| 66 | Adjust Slide Volume With Reaction Buffer |
| 67 | Apply Coverslip |

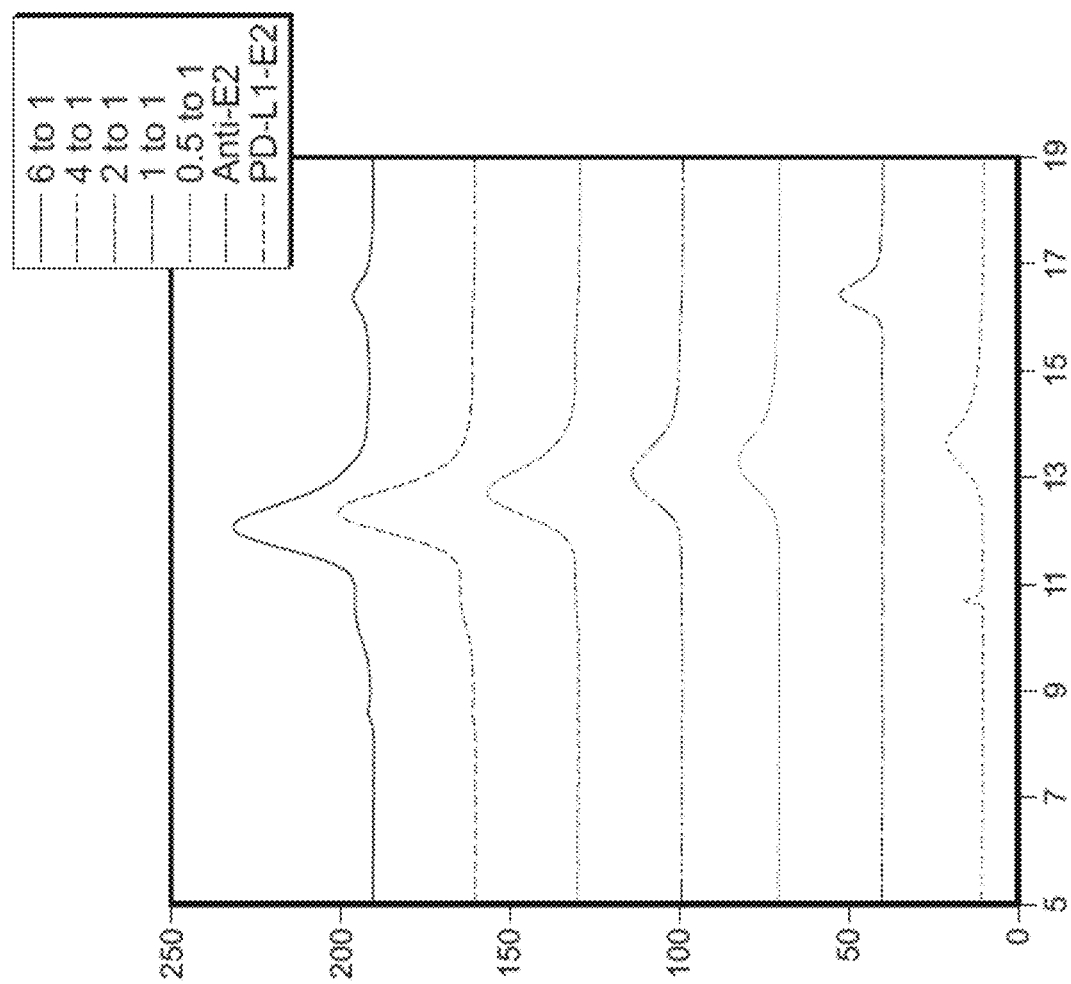

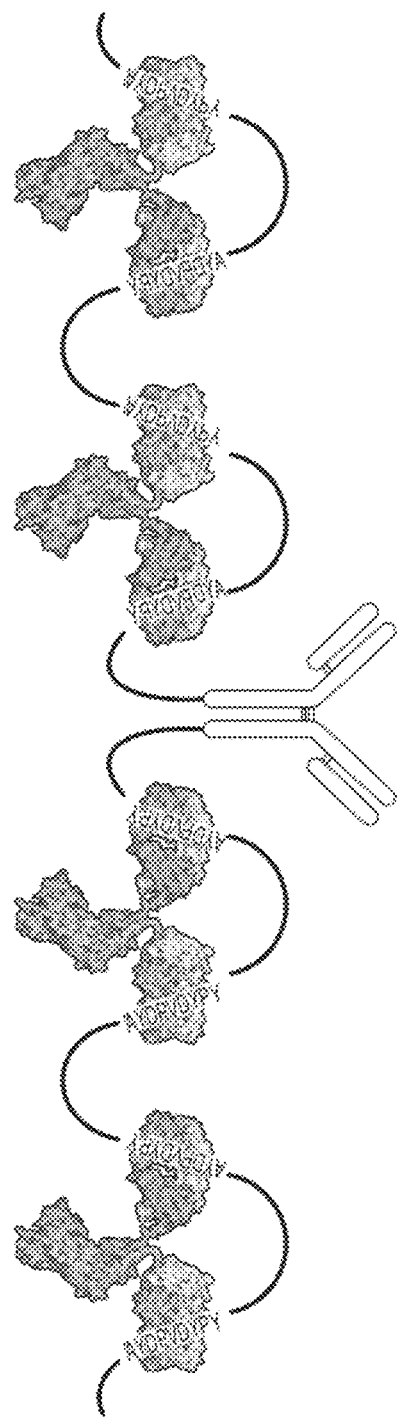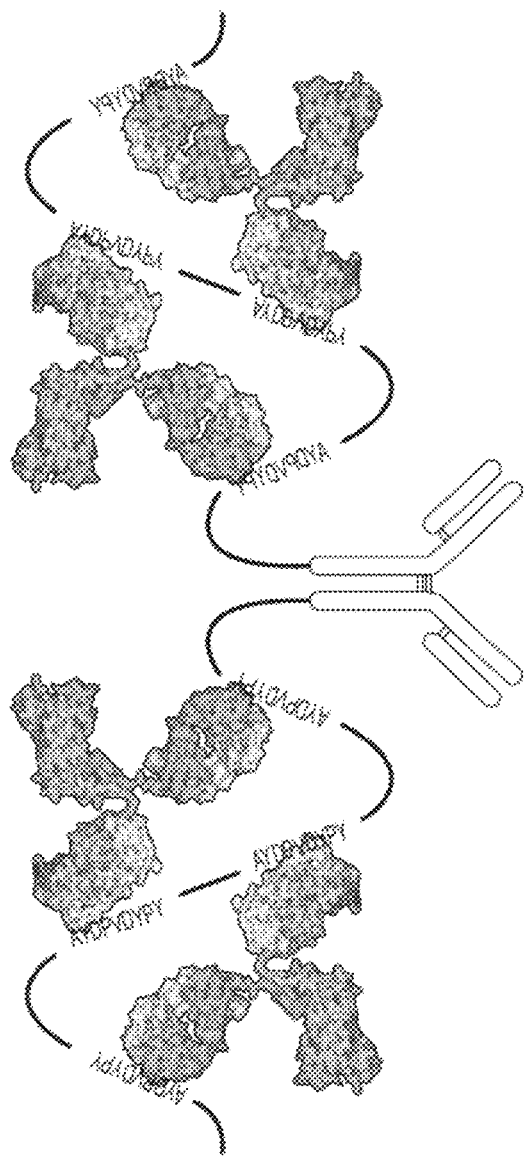

MULTIPLEXED IMMUNOHISTOCHEMISTRY USING RECOMBINANT ANTIBODIES WITH EPITOPE TAGS

CROSS REFERENCE TO RELATED APPLICATIONS

This is a divisional patent application of U.S. Patent Application No. U.S. Ser. No. 16/123,750, filed Sep. 6, 2018, which is a continuation of PCT application, International Patent Application No. PCT/US2017021157, filed Mar. 7, 2017, which claims the benefit of U.S. Provisional Patent Application No. U.S. 62/461,651, filed Feb. 21, 2017, and the benefit of U.S. Provisional Patent Application No. U.S. 62/418,667, filed Nov. 7, 2016, and the benefit of U.S. Provisional Patent Application No. U.S. 62/305,440, filed Mar. 8 2016, the disclosures of which are hereby incorporated by reference herein in their entireties.

REFERENCE TO SEQUENCE LISTING SUBMITTED AS A COMPLIANT ASCII TEXT FILE (.TXT)

Pursuant to EFS-Web legal framework and 37 CFR §§ 1.821-825 (see MPEP § 2442.03(a)), a Sequence Listing is the form of an ASCII-compliant text file (entitled "Ventana-049_ST25_40143344," and 29.4 kilobytes (KB) in size) is submitted concurrently with the instant application, and the entire contents of the Sequence Listing are incorporated herein by reference.

BACKGROUND OF THE DISCLOSURE

A. Field of the Subject Disclosure

The present disclosure provides for antibodies comprising epitope tags.

B. Description of Related Art

Cell staining methods, including immunohistochemistry (IHC) and in situ hybridization analysis (ISH), are useful tools in histological diagnosis and the study of tissue morphology. IHC employs specific binding agents or moieties, such as antibodies, to detect an antigen of interest that may be present in a tissue sample. IHC is widely used in clinical and diagnostic applications, such as to diagnose particular disease states or conditions. For example, particular cancer types can be diagnosed based on the presence of a particular marker molecule in a sample obtained from a subject. IHC is also widely used in basic research to understand biomarker distribution and localization in different tissues. Biological samples also can be examined using in situ hybridization techniques, such as silver in situ hybridization (SISH), chromogenic in situ hybridization (CISH) and fluorescence in situ hybridization (FISH), collectively referred to as ISH. ISH is distinct from IHC in that ISH detects nucleic acids in tissue whereas IHC detects proteins in tissue.

Characterization and quantitation of the multitude of proteins expressed by an organism's genome are the focus of proteomics. Multiplex immunohistochemistry (MIHC) represents a major unmet technological need to detect and analyze multivariate protein targets in paraffin-embedded formalin-fixed tissues with broad applications in research and diagnostics. Multiplex immunohistochemistry (MIHC) techniques are attempting to address the need for detecting and analyzing multivariate protein targets in formalin-fixed, paraffin-embedded tissues. Effective MIHC techniques have broad applications in research and diagnostics. However, there are few, if any, efficient and reproducible methods that allow simultaneous and quantitative detection of multiple protein targets in tissues.

Epitope tagging is a recombinant DNA method for making a gene product immunoreactive to an already existing antibody (Jarvik and Telmer, Annu. Rev. Genet. 32:601-618, 1998). Typically, the process involves inserting a nucleotide sequence encoding a peptide tag into a gene of interest and expressing the gene in an appropriate host. The protein can then be detected and/or purified by virtue of its interaction with the antibody specific to the epitope tag. This approach can elucidate the size of the tagged protein as well as its abundance, cellular location, posttranslational modifications and interactions with other proteins. In particular, antibodies recognizing the peptide tag facilitate purification and/or isolation of tagged proteins.

BRIEF SUMMARY OF THE DISCLOSURE

In one aspect of the present disclosure is a recombinant antibody that expresses an epitope tag (referred to herein as an "epitope-tagged antibody"). In another aspect of the present disclosure is an antibody comprising at least one epitope tag construct. In some embodiments, the epitope tag construct comprises tandem epitope tag repeats separated by spacers. In some embodiments, the epitope tag construct has the general structure -[Spacer]-[Epitope Tag]-, which may be repeated one or more times (e.g. from 1 to 12 times). In some embodiments, the at least one epitope tag construct is expressed at a C-terminal end of a heavy chain constant region or at a C-terminal end of a light chain constant region of an antibody. In other embodiments, the at least one epitope tag construct is expressed at both the C-terminal end of the heavy chain constant region and at the C-terminal end of the light chain constant region.

In some embodiments, the epitope tag is selected from the group consisting of V5, HA, VSV, AU1, AU5, OLLAS, E, E2, KT3, AU1, and OLLAS. In some embodiments, the epitope tag comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9.

In some embodiments, the epitope tag construct comprises between 2 and 8 epitope tags. In some embodiments, the epitope tag construct comprises 4 epitope tags. In some embodiments, the epitope tag construct comprises 5 epitope tags. In some embodiments, the epitope-tagged antibody comprises between 4 and 10 epitope tags. In some embodiments, a ratio of a number of epitope tags incorporated at the C-terminal end of a heavy chain constant region to a number of epitope tags incorporated at the C-terminal end of a light chain constant region ranges from about 2:1 to about 1:2. In some embodiments, a number of epitope tags incorporated at the C-terminal end of a heavy chain constant region ranges from between 2 to 6 epitope tags, and a number of epitope tags incorporated at the C-terminal end of a light chain constant region ranges from between 0 to 4 epitope tags.

In some embodiments, at least a portion of an amino acid sequence constituting at least one spacer of the epitope tag construct is selected from the group consisting of SEQ ID NO: 10, SEQ ID NO: 11, SEQ ID NO: 12, SEQ ID NO: 13, and SEQ ID NO: 14. In some embodiments, at least a portion of an amino acid sequence constituting a first spacer of the epitope tag construct is selected from one of SEQ ID NO: 10, SEQ ID NO: 11, SEQ ID NO: 12, SEQ ID NO: 13, and SEQ ID NO: 14; and wherein at least a portion of an amino acid sequence constituting a second spacer of the epitope tag construct is selected from another one of SEQ ID NO: 10, SEQ ID NO: 11, SEQ ID NO: 12, SEQ ID NO: 13, and SEQ ID NO: 14.

In some embodiments, a molecular weight of an epitope tag construct ranges from between about 5 g/mol to about 35 g/mol. In some embodiments, a combined molecular weight of all epitope tag constructs of any epitope-tagged antibody ranges from between about 5 g/mol to about 50 g/mol. In some embodiments, a combined molecular weight of all epitope tag constructs of any epitope-tagged antibody is less than 30% of the molecular weight of the corresponding native antibody.

In some embodiments, the epitope-tagged antibody is specific to a target selected from the group consisting of CD3, CD8, CD20, CD68, PDL1, FoxP3, HER2, and EGFR2. In some embodiments, the epitope tag construct comprises an amino acid sequence selected from the group consisting of SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, and SEQ ID NO: 32. In some embodiments, the antibody comprises two epitope tag constructs conjugated to terminal ends of a heavy chain constant region and a light chain constant region, wherein each of the two epitope tag constructs comprise the same sequence, wherein the sequence is selected from the group consisting of SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, and SEQ ID NO: 32.

In another aspect of the present disclosure is a kit comprising an epitope-tagged antibody, such as those described herein, and detection reagents for detecting the epitope-tagged antibody. In some embodiments, the detection reagents are anti-tag antibodies specific for an expressed epitope tag of the epitope-tagged antibody, and where the anti-tag antibody comprises a detectable moiety. In some embodiments, the detectable moiety is a fluorophore. In some embodiments, the detectable moiety is an enzyme, and additional chromogenic substrates for the enzyme are included within the detection kit. In some embodiments, the kit further comprises at least one unmodified antibody or antibody conjugate; and further detection reagents to detect the at least one unmodified antibody or antibody conjugate. In some embodiments, the kit further comprises at least one nucleic acid probe and yet further detection reagents to detect the at least one nucleic acid probe.

In another aspect of the present disclosure is a method for detecting a target in a sample (e.g. a tissue sample), comprising contact the sample with an epitope-tagged antibody (such as those disclosed herein) and detecting the target using the expressed epitope tags of the antibody. In some embodiments, the sample is contacted with two or more different epitope-tagged antibodies, where each epitope-tagged antibody is specific for a different target and wherein each antibody expresses different epitope tags. In some embodiments, the sample is contacted simultaneously with the two or more different epitope-tagged antibodies. In some embodiments, the method further comprises contacting the sample with detection reagents for detecting the different epitope-tagged antibodies. In some embodiments, the detection reagents are anti-tag antibodies specific for the different expressed epitope tags of the epitope-tagged antibodies. In some embodiments, the anti-tag antibodies specific for the different expressed epitope tags of the epitope-tagged antibodies are introduced simultaneously. In some embodiments, each of the anti-tag antibodies are conjugated to fluorophores. In some embodiments, the method further comprises contacting the sample with one or more unmodified antibodies or antibody conjugates. In some embodiments, the one or more unmodified antibodies or antibody conjugates are introduced to the sample prior to the introduction of the epitope-tagged antibody.

In another aspect of the present disclosure is a method of multiplex detection comprising (i) simultaneously contacting a tissue sample with two or more epitope-tagged antibodies, wherein each epitope-tagged antibody comprises different epitope tags; and (ii) simultaneously contacting the tissue sample with two or more anti-tag antibodies, wherein each anti-tag antibody is specific to one of the epitope-tagged antibodies, and where each anti-tag antibody comprises a different detectable moiety. In some embodiments, the two or more epitope-tagged antibodies are applied as a mixture; and where the two or more anti-tag antibodies are applied as a mixture. In some embodiments, the epitope-tagged antibodies comprise an epitope tag selected from the group consisting of V5, HA, VSV, AU1, AU5, OLLAS, E, E2, KT3, AU1, and OLLAS. In some embodiments, the epitope-tagged antibodies comprise an epitope tag having an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9. In some embodiments, the epitope-tagged antibodies comprise between 4 and 10 epitope tags.

In some embodiments, the anti-tag antibodies are conjugated to a fluorescent moiety. In some embodiments, the fluorescent moiety is selected from the group consisting of fluorescent moiety selected from xanthene derivatives, cyanine derivatives, squaraine derivatives, naphthalene derivatives, coumarin derivatives, oxadiazole derivatives, anthracene derivatives, pyrene derivatives, oxazine derivatives, acridine derivatives, arylmethine derivatives, and tetrapyrrole derivatives.

In some embodiments, the method further comprises contacting the tissue sample with at least one unmodified antibody. In some embodiments, the step of contacting the tissue sample with at least one unmodified antibody occurs before the tissue sample is contacted with the two or more epitope-tagged antibodies.

In another aspect of the present disclosure is a method of detecting multiple targets in a single tissue sample comprising (i) contacting the tissue sample with a first specific binding entity to detect a first target, the first specific binding entity selected from the group consisting of an unmodified antibody, an antibody conjugate, or an epitope-tagged antibody; (ii) contacting the tissue sample with first detection reagents to detect the first specific binding entity; (iii) contacting the sample with a second specific binding entity to detect a second target, the second specific binding entity comprising an epitope-tagged antibody; and (iv) contacting the tissue sample with second detection reagents to detect the second specific binding entity, the second detection reagents comprising an anti-tag antibody conjugated to a detectable moiety.

In some embodiments, method further comprises contacting the sample with a third specific binding entity to detect a third target, the third specific binding entity selected from the group consisting of an unmodified antibody, an antibody conjugate, or an epitope-tagged antibody; and contacting the tissue sample with third detection reagents to detect the third specific binding entity. In some embodiments, the third specific binding entity is an epitope-tagged antibody, and wherein the second and third specific binding entities are introduced simultaneously.

In some embodiments, the first and third specific binding entities are unmodified antibodies or antibody conjugates, wherein the first and third specific binding entities are introduced simultaneously. In some embodiments, the introduction of the first and third detection reagents occurs before introduction of the second specific binding entity. In some embodiments, the first and third specific binding entities are unmodified antibodies or antibody conjugates, and wherein the first and third specific binding entities are introduced sequentially.

In some embodiments, the epitope-tagged antibodies comprise an epitope tag selected from the group consisting of V5, HA, VSV, AU1, AU5, OLLAS, E, E2, KT3, AU1, and OLLAS.. In some embodiments, the epitope-tagged antibodies comprise an epitope tag having an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9. In some embodiments, the epitope-tagged antibodies comprise between 4 and 10 epitope tags. In some embodiments, the anti-tag antibodies are conjugated to a fluorescent moiety. In some embodiments, the fluorescent moiety is selected from the group consisting of fluorescent moiety selected from xanthene derivatives, cyanine derivatives, squaraine derivatives, naphthalene derivatives, coumarin derivatives, oxadiazole derivatives, anthracene derivatives, pyrene derivatives, oxazine derivatives, acridine derivatives, arylmethine derivatives, and tetrapyrrole derivatives. In some embodiments, at least one of the first, second, or third specific binding entities is specific for a target selected from the group consisting of CD3, CD8, CD20, CD68, PDL1, FoxP3, HER2, and EGFR2.

In another aspect of the present disclosure is an epitope tag construct comprising tandem repeat epitope tags separated by spacers, the epitope tag construct comprising from 2 to 6 epitope tags. In some embodiments, the epitope tag constructs comprise an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9. In some embodiments, the epitope tag constructs comprise an amino acid sequence having at least 90% identity of a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9. In some embodiments, at least one of the spacers separating the epitope tags of the epitope tag construct comprises an amino acid sequence selected from the group consisting of SEQ ID NO: 10, SEQ ID NO: 11, SEQ ID NO: 12, SEQ ID NO: 13, and SEQ ID NO: 14. In some embodiments, at least one of the spacers separating the epitope tags of the epitope tag construct comprises an amino acid sequence having at least 90% identity to a sequence selected from the group consisting of SEQ ID NO: 10, SEQ ID NO: 11, SEQ ID NO: 12, SEQ ID NO: 13, and SEQ ID NO: 14. In some embodiments, a molecular weight of the epitope tag construct ranges from between about 5 g/mol to about 35 g/mol. In some embodiments, a molecular weight of the epitope tag construct ranges from between about 5 g/mol to about 25 g/mol. In some embodiments, the epitope-tag construct comprises the amino acid sequence of SEQ ID NO: 16. In some embodiments, epitope tag construct comprises the amino acid sequence of SEQ ID NO: 18. In some embodiments, epitope tag construct comprises the amino acid sequence of SEQ ID NO: 20. In some embodiments, epitope tag construct comprises the amino acid sequence of SEQ ID NO: 22. In some embodiments, epitope tag construct comprises the amino acid sequence of SEQ ID NO: 24. In some embodiments, epitope tag construct comprises the amino acid sequence of SEQ ID NO: 26. In some embodiments, epitope tag construct comprises the amino acid sequence of SEQ ID NO: 28. In some embodiments, epitope tag construct comprises the amino acid sequence of SEQ ID NO: 30. In some embodiments, epitope tag construct comprises the amino acid sequence of SEQ ID NO: 32. In some embodiments, the epitope-tag construct comprises an amino acid sequence having at least 90% identity to that of SEQ ID NO: 16. In some embodiments, epitope tag construct comprises an amino acid sequence having at least 90% identity to that of SEQ ID NO: 18. In some embodiments, epitope tag construct comprises an amino acid sequence having at least 90% identity to that of SEQ ID NO: 20. In some embodiments, epitope tag construct comprises an amino acid sequence having at least 90% identity to that of SEQ ID NO: 22. In some embodiments, epitope tag construct comprises an amino acid sequence having at least 90% identity to that of SEQ ID NO: 24. In some embodiments, epitope tag construct comprises an amino acid sequence having at least 90% identity to that of SEQ ID NO: 26. In some embodiments, epitope tag construct comprises an amino acid sequence having at least 90% identity to that of SEQ ID NO: 28. In some embodiments, epitope tag construct comprises an amino acid sequence having at least 90% identity to that of SEQ ID NO: 30. In some embodiments, epitope tag construct comprises an amino acid sequence having at least 90% identity to that of SEQ ID NO: 32.

In another aspect of the present disclosure is an epitope tag gene comprising a nucleic acid sequence selected from the group consisting of (i) a nucleic acid sequence of SEQ ID NO: 15, (ii) a nucleic acid sequence having at least 90% identity to that of SEQ ID NO: 15, (iii) a nucleic acid sequence having at least 95% identity to that of SEQ ID NO: 15, and (iv) a nucleic acid sequence having at least 97% identity to that of SEQ ID NO: 15.

In another aspect of the present disclosure is an epitope tag gene comprising a nucleic acid sequence selected from the group consisting of (i) a nucleic acid sequence of SEQ ID NO: 17, (ii) a nucleic acid sequence having at least 90% identity to that of SEQ ID NO: 17, (iii) a nucleic acid sequence having at least 95% identity to that of SEQ ID NO: 17, and (iv) a nucleic acid sequence having at least 97% identity to that of SEQ ID NO: 17.

In another aspect of the present disclosure is an epitope tag gene comprising a nucleic acid sequence selected from the group consisting of (i) a nucleic acid sequence of SEQ ID NO: 19, (ii) a nucleic acid sequence having at least 90% identity to that of SEQ ID NO: 19, (iii) a nucleic acid sequence having at least 95% identity to that of SEQ ID NO: 19, and (iv) a nucleic acid sequence having at least 97% identity to that of SEQ ID NO: 19.

In another aspect of the present disclosure is an epitope tag gene comprising a nucleic acid sequence selected from the group consisting of (i) a nucleic acid sequence of SEQ ID NO: 21, (ii) a nucleic acid sequence having at least 90% identity to that of SEQ ID NO: 21, (iii) a nucleic acid sequence having at least 95% identity to that of SEQ ID NO: 21, and (iv) a nucleic acid sequence having at least 97% identity to that of SEQ ID NO: 21.

In another aspect of the present disclosure is an epitope tag gene comprising a nucleic acid sequence selected from the group consisting of (i) a nucleic acid sequence of SEQ ID NO: 23, (ii) a nucleic acid sequence having at least 90% identity to that of SEQ ID NO: 23, (iii) a nucleic acid sequence having at least 95% identity to that of SEQ ID NO: 239, and (iv) a nucleic acid sequence having at least 97% identity to that of SEQ ID NO: 23.

In another aspect of the present disclosure is an epitope tag gene comprising a nucleic acid sequence selected from the group consisting of (i) a nucleic acid sequence of SEQ ID NO: 25, (ii) a nucleic acid sequence having at least 90% identity to that of SEQ ID NO: 25, (iii) a nucleic acid sequence having at least 95% identity to that of SEQ ID NO: 25, and (iv) a nucleic acid sequence having at least 97% identity to that of SEQ ID NO: 25.

In another aspect of the present disclosure is an epitope tag gene comprising a nucleic acid sequence selected from the group consisting of (i) a nucleic acid sequence of SEQ ID NO: 27, (ii) a nucleic acid sequence having at least 90% identity to that of SEQ ID NO: 27, (iii) a nucleic acid sequence having at least 95% identity to that of SEQ ID NO: 7, and (iv) a nucleic acid sequence having at least 97% identity to that of SEQ ID NO: 27.

In another aspect of the present disclosure is an epitope tag gene comprising a nucleic acid sequence selected from the group consisting of (i) a nucleic acid sequence of SEQ ID NO: 29, (ii) a nucleic acid sequence having at least 90% identity to that of SEQ ID NO: 29, (iii) a nucleic acid sequence having at least 95% identity to that of SEQ ID NO: 29, and (iv) a nucleic acid sequence having at least 97% identity to that of SEQ ID NO: 29.

In another aspect of the present disclosure is an epitope tag gene comprising a nucleic acid sequence selected from the group consisting of (i) a nucleic acid sequence of SEQ ID NO: 31, (ii) a nucleic acid sequence having at least 90% identity to that of SEQ ID NO: 31, (iii) a nucleic acid sequence having at least 95% identity to that of SEQ ID NO: 31, and (iv) a nucleic acid sequence having at least 97% identity to that of SEQ ID NO: 31.

In another aspect of the present disclosure is a panel comprising two or more antibodies, where at least one of the antibodies is an epitope-tagged antibody. In some embodiments, the panel comprises an epitope-tagged antibody selected from the group consisting of an epitope-tagged antibody specific for FoxP3, an epitope-tagged antibody specific for CD20, an epitope-tagged antibody specific for CD68, an epitope-tagged antibody specific for FoxP3, an epitope-tagged antibody specific for pan-CK, an epitope-tagged antibody specific for PDL1, or any combination thereof. In another aspect of the present disclosure is a panel comprising an epitope-tagged antibody specific for FoxP3, an epitope-tagged antibody specific for CD20, and an epitope-tagged antibody specific for CD68. In some embodiments, the panel further comprises an additional specific binding entity. In another aspect of the present disclosure is a panel comprising an epitope-tagged antibody specific for FoxP3, an epitope-tagged antibody specific for CD8, and an epitope-tagged antibody specific for CD68. In some embodiments, the panel further comprises an additional specific binding entity. In another aspect of the present disclosure is a panel comprising an epitope-tagged antibody specific for FoxP3, an epitope-tagged antibody specific for CD8, an epitope-tagged antibody specific for CD68, and an unmodified antibody specific to pan-CK. In some embodiments, the panel further comprises an additional specific binding entity. In another aspect of the present disclosure is a panel comprising an epitope-tagged antibody specific for FoxP3, an epitope-tagged antibody specific for CD20, an epitope-tagged antibody specific for CD68, and an unmodified antibody specific to pan-CK. In some embodiments, the panel further comprises an additional specific binding entity. In another aspect of the present disclosure is a panel comprising an epitope-tagged antibody specific to CD20, an epitope-tagged antibody specific for CD68, an unmodified antibody specific for pan-CK, and an unmodified antibody specific for PDL1. In another aspect of the present disclosure is a panel comprising an epitope-tagged antibody specific to CD20, an epitope-tagged antibody specific for CD68, an unmodified antibody specific for pan-CK, and an unmodified antibody specific for CD3. In some embodiments, the panel further comprises an additional specific binding entity. In another aspect of the present disclosure is a panel comprising an epitope-tagged antibody specific for FoxP3, an epitope-tagged antibody specific for CD8, an epitope-tagged antibody specific for CD68, an epitope-tagged antibody specific for CD3, and an epitope-tagged antibody specific for CD20. In some embodiments, the panel further comprises an additional specific binding entity.

In another aspect of the present disclosure are kits comprising any of the aforementioned panels (assays), where the kits may further comprise detection reagents for detecting the epitope-tagged antibodies of the panel (assay).

In another aspect of the present disclosure is an epitope-tagged antibody comprising an antibody and at least one epitope tag construct, the epitope tag construct comprising alternating spacers and epitope tags and having the general structure -[Spacer]a-[Epitope Tag]b-, where a and b are each an integer ranging from 1 to 10, and wherein a distance between successive -[Epitope Tags]- of the at least one epitope tag construct is from 8 to 18 nm. In an embodiment, each epitope tag has an even number of epitopes. By way of example only, the distance may be measured by a contour length, i.e. the linear length of the peptide backbone. By way of another example only, the distance can be a linear length between the epitope tags, e.g. the epitope tags in the tertiary structure. In some embodiments, the distance is less than 12 nm. In some embodiments, the distance is less than 10 nm. In some embodiments, the distance is less than 9 nm. In some embodiments, the distance is optimized such that it facilitates bivalent binding of anti-tag antibodies between Epitope Tags. In some embodiments, the distance facilitates bivalent binding between adjacent epitope tags. In other embodiments, the distance facilitates bivalent binding between non-adjacent epitope tags. In some embodiments, a portion of a first heavy chain of the anti-tag antibody binds to a first Epitope Tag of the epitope tag construct and wherein a portion of a second heavy chain of the same anti-tag antibody binds to a second, adjacent Epitope Tag of the epitope tag construct. In some embodiments, a portion of a first heavy chain of the anti-tag antibody binds to a first Epitope Tag of the epitope tag construct and wherein a portion of a second heavy chain of the same anti-tag antibody binds to a second, non-adjacent Epitope Tag of the epitope tag construct. In some embodiments, a distance between contiguous epitopes is such that the epitopes are accessible by both arms of an anti-tag antibody with elbow angles between about 120 degrees and about 220 degrees, or about 120 degrees to about 200 degrees, or about 140 degrees to about 200 degrees. In some embodiments, a distance between non-contiguous epitopes is such that the epitopes are accessible by both arms of an anti-tag antibody with elbow angles between about 120 degrees and about 220 degrees, or about 120 degrees to about 200 degrees, or about 140 degrees to about 200 degrees.

In another aspect of the present disclosure is an epitope-tagged antibody comprising an antibody and at least one epitope tag construct, the epitope tag construct comprising alternating spacers and epitope tags and having the general structure -[Spacer]a-[Epitope Tag]b-, where a and b are each an integer ranging from 1 to 10, and wherein the -[Spacer]- has a size (e.g. the sum of all atom lengths and bond lengths) which is from 8 to 18 nm in length. In some embodiments, the size is less than 12 nm. In some embodiments, the -[Spacer]- is sized to facilitate bivalent binding of anti-tag antibodies between Epitope Tags. In some embodiments, any two adjacent Epitope Tags are spaced a distance apart from one another which approximates the distance between antigen binding sites of an anti-tag antibody. In some embodiments, any two non-adjacent Epitope Tags are spaced a distance apart from one another which approximates the distance between antigen binding sites of an anti-tag antibody. In some embodiments, a first antigen binding site binds to a first Epitope Tag of the at least one epitope tag construct and wherein a second antigen binding site binds to a second, adjacent Epitope Tag of the at least one epitope tag construct. In some embodiments, a first antigen binding site binds to a first Epitope Tag of the at least one epitope tag construct and wherein a second antigen binding site binds to a second, non-adjacent Epitope Tag of the at least one epitope tag construct. In some embodiments, a spacer length between contiguous epitopes is such that the contiguous epitopes are accessible by both arms of an anti-tag antibody with elbow angles between about 120 degrees and about 220 degrees, or about 120 degrees to about 200 degrees, or about 140 degrees to about 200 degrees. In some embodiments, a spacer length is chosen that places non-contiguous epitopes in a configuration that the epitopes are accessible by both arms of an anti-tag antibody with elbow angles between about 120 degrees and about 220 degrees, or about 120 degrees to about 200 degrees, or about 140 degrees to about 200 degrees.

In another aspect of the present disclosure is a system comprising an epitope-tagged antibody as described herein; and a set of detection reagents for depositing a dye in proximity to each epitope-tagged antibody when the epitope-tagged antibody is bound to a tissue sample, the set of detection reagents comprising an anti-tag specific detection agent specific for the epitope tag of epitope-tagged antibody. In some embodiments, the anti-tag specific detection agent is conjugated to a dye. In some embodiments, the set of detection reagents further comprises a first enzyme and a substrate reactive with the first enzyme to deposit the dye on the tissue sample in proximity to the first enzyme. In some embodiments, the anti-tag specific binding agent is conjugated to the enzyme.

In some embodiments, (i) the anti-tag specific binding agent is conjugated to a hapten, and (ii) the first enzyme is conjugated to an antibody reactive with the hapten. In some embodiments, the anti-tag specific binding agent is an anti-tag antibody and the first enzyme is conjugated to an anti-species antibody specific for the Ig species of the anti-tag antibody. In some embodiments, the anti-tag specific binding agent is conjugated to a first member of a first specific binding pair, and wherein the first enzyme is conjugated to a second member of the first specific binding pair. In some embodiments, the first member of the first specific binding pair is biotin and the second member of the first specific binding pair is a biotin-binding protein. In some embodiments, the biotin-binding protein is selected from the group consisting of avidin, an avidin derivative (such as NEUTRAVIDIN), and streptavidin. In some embodiments, wherein the first member of the first specific binding pair is a hapten and the second member of the first specific binding pair is an anti-hapten antibody. In some embodiments, the first anti-tag specific binding agent is conjugated to a horseradish peroxidase enzyme; the first enzyme is conjugated to a first member of a first specific binding pair; and the set of detection reagents further comprises a signaling conjugate, the signaling conjugate comprising a tyramide reactive with the second enzyme, wherein the tyramide is conjugated to a second member of the first specific binding pair. In some embodiments, the first member of the first specific binding pair is a biotin-binding protein; and the second member of the first specific binding pair is biotin. In some embodiments, the biotin-binding protein is selected from the group consisting of avidin, an avidin derivative (such as NEUTRAVIDIN), and streptavidin. In some embodiments, the first member of the first specific binding pair is a hapten and the second member of the first specific binding pair is an anti-hapten antibody. In some embodiments, the first anti-tag specific binding agent is conjugated to a second enzyme; the first enzyme is conjugated to a first member of a first specific binding pair; and the set of detection reagents further comprises a signaling conjugate, the signaling conjugate comprising a quinone methide reactive with the second enzyme, wherein the quinone methide is conjugated to a second member of the first specific binding pair. In some embodiments, the first member of the first specific binding pair is a biotin-binding protein; and the second member of the first specific binding pair is biotin. In some embodiments, biotin-binding protein is selected from the group consisting of avidin, an avidin derivative (such as NEUTRAVIDIN), and streptavidin. In some embodiments, the first member of the first specific binding pair is a hapten and the second member of the first specific binding pair is an anti-hapten antibody.

In some embodiments, the above-described system comprises a plurality of the epitope-tagged antibodies (described above and herein), each of the plurality of the epitope-tagged antibodies is specific for a different biomarker, and wherein the set of detection reagents includes means for depositing a first dye in proximity to at least one of the plurality epitope-tagged antibodies, and at least a second dye in proximity to at least another of the plurality epitope-tagged antibodies. In some embodiments, the system further comprises an automated slide stainer. In some embodiments, the system further comprises a slide scanner. In some embodiments, the system further comprises an image analysis system. In some embodiments, the system further comprises a laboratory information system (LIS). In some embodiments, the LIS comprises a database storing processing steps performed on one or more tissue sections of a sample, and/or processing steps to be performed on one or more tissue sections of the sample. In some embodiments, the LIS further comprises a set of instructions directing the automated slide stainer to deposit the epitope-tagged antibody or the plurality of epitope-tagged antibodies, and the detection reagents on the one or more sections of a tissue sample.

Applicants have discovered that the epitope-tagged antibodies according to the present disclosure avoid cross-reactivity often observed when same-species primary antibodies are used in multiplex assays. As a result, multiple epitope-tagged primary antibodies may be pooled together as a single reagent in a multiplex assay. Moreover, Applicants have found that the epitope-tagged antibodies of the present disclosure are more stable than chemically modified antibodies, such as those antibodies chemically conjugated to a hapten, and are able to be manufactured consistently. In addition, Applicants have found that the epitope-tagged antibodies provide a linear signal detection cascade that allows for direct quantitative correlation of protein expression levels, in comparison to detection using signal amplification methods, e.g. tyramide signal amplification. As such, Applicants submit that a MIHC assay employing a plurality of epitope-tagged antibodies, alone or in conjunction with unmodified antibodies, antibody conjugates or other specific binding entities, effectively allows for the detection of multiple targets in a tissue sample, where the MIHC assay may be completed in less than five hours, and where the MIHC allows for signal co-localization.

BRIEF DESCRIPTION OF THE FIGURES

The patent file or application file contains at least one drawing executed in color. Copies of this patent or patent application publication with color drawings will be provided by the Office upon request and payment of the necessary fee.

FIG. 10A, FIG. 10B, FIG. 10C, FIG. 10D, FIG. 10E, FIG. 10F, and FIG. 10G are images of tissue samples stained according to a multiplex IHC assay utilizing two unmodified antibodies and two different epitope-tagged antibodies.

FIG. 15A, FIG. 15B, and FIG. 15C provide flowcharts illustrating various methods of conducting multiplex IHC assays utilizing one or more epitope-tagged antibodies and/or one or more unmodified antibodies or antibody conjugates.

FIG. 17A, FIG. 17B, FIG. 17C, FIG. 17D, FIG. 17E, and FIG. 17F provide images showing the comparative staining performances of epitope-tagged antibodies as compared with corresponding native antibodies (unmodified antibodies).

FIG. 19 illustrates the stability of epitope-tagged antibodies, the stability determined by accelerated stability testing studies; The Arrhenius model was followed to predict real-time stability of tested antibodies (1 ug/ml concentration in diluent 90103) at intended storage conditions (i.e. 4° C.) based on data collected at elevated temperatures (i.e. 37° C. and 45° C.) for shorter periods (e.g. 5 to 10 days).

FIG. 21 sets forth a step-wise assay procedure.

FIG. 22 sets forth a step-wise assay procedure.

Figure 23:
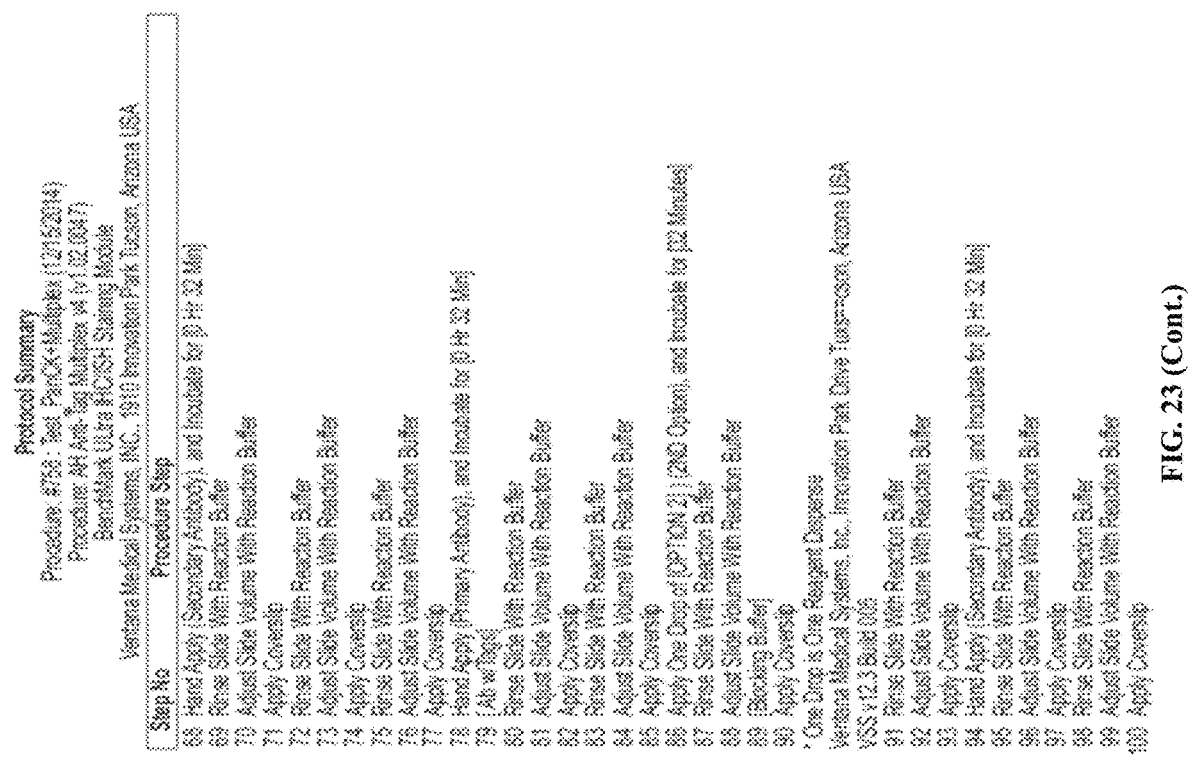

FIG. 23 sets forth a step-wise assay procedure.

FIG. 34A sets forth size exclusion chromatography elution profiles of 0.5 µM anti-PD-L1-E2 (H4K0), 0.5 µM anti-E2, and anti-E2 mixed with 0.5 µM anti-PD-L1-E2 at varying molar ratios from 0.5:1 to 6:1.

FIG. 35A illustrates the bivalent binding of an anti-tag antibody to the expressed epitope tags of an epitope-tagged antibody, wherein binding occurs between adjacent epitope tags.

FIG. 35B illustrates the bivalent binding of an anti-tag antibody to the expressed epitope tags of an epitope-tagged antibody, wherein bind occurs between non-adjacent epitope tags.

DETAILED DESCRIPTION

Figure 1:
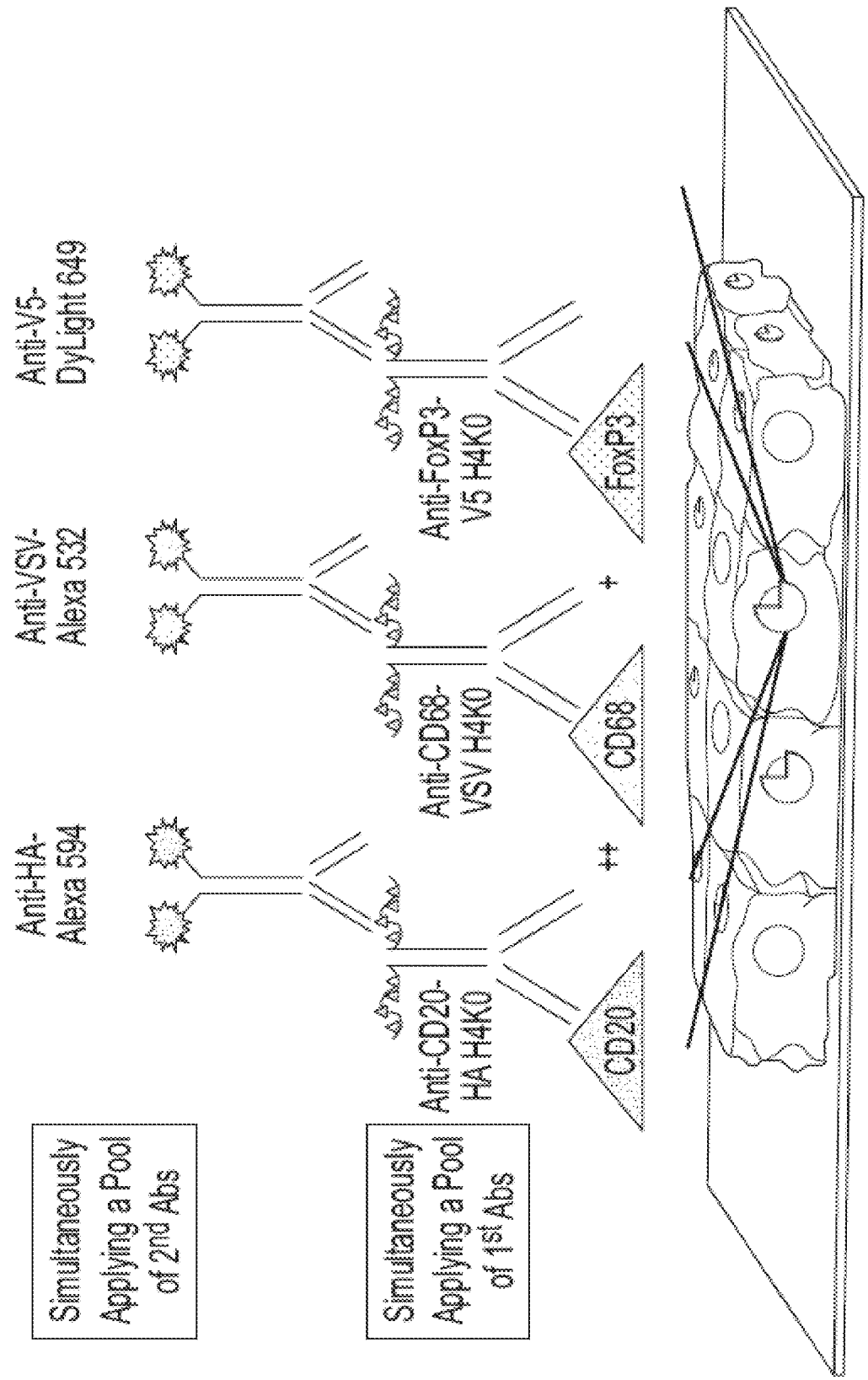
FIG. 1 illustrates a multiplex IHC assay utilizing three different epitope-tagged antibodies.

In general, the present disclosure is directed to epitope-tagged antibodies, as well as methods of employing the epitope-tagged antibodies for detecting one or more targets in a biological sample, e.g. a tissue sample.

As used herein, the singular terms "a," "an," and "the" include plural referents unless the context clearly indicates otherwise. Similarly, the word "or" is intended to include "and" unless the context clearly indicates otherwise.

As used herein, the terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein, the term "affinity" refers to the non-random interaction of two molecules. The term "affinity" refers to the strength of interactions and can be expressed quantitatively as a dissociation constant (KD). One or both of the two molecules may be a peptide (e.g. antibody). Binding affinity (i.e., KD) can be determined using standard techniques. For example, the affinity can be a measure of the strength of the binding of an individual epitope with an antibody molecule.

As used herein, the term "antibody," refers to immunoglobulins or immunoglobulin-like molecules, including by way of example and without limitation, IgA, IgD, IgE, IgG and IgM, combinations thereof, and similar molecules produced during an immune response in any vertebrate, (e.g., in mammals such as humans, goats, rabbits and mice) and antibody fragments (such as F(ab')2 fragments, Fab' fragments, Fab'-SH fragments and Fab fragments as are known in the art, recombinant antibody fragments (such as sFv fragments, dsFv fragments, bispecific sFv fragments, bispecific dsFv fragments, F(ab)'2 fragments, single chain Fv proteins ("scFv"), disulfide stabilized Fv proteins ("dsFv"), diabodies, and triabodies (as are known in the art), and camelid antibodies) that specifically bind to a molecule of interest (or a group of highly similar molecules of interest) to the substantial exclusion of binding to other molecules. Antibody further refers to a polypeptide ligand comprising at least a light chain or heavy chain immunoglobulin variable region which specifically recognizes and binds an epitope of an antigen. Antibodies may be composed of a heavy and a light chain, each of which has a variable region, termed the variable heavy (VH) region and the variable light (VL) region. Together, the VH region and the VL region are responsible for binding the antigen recognized by the antibody. The term antibody also includes intact immunoglobulins and the variants and portions of them well known in the art.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins.

As used herein, the term "avidity" refers to the cooperative and synergistic bonding of two or more molecules. "Avidity" refers to the overall stability of the complex between two or more populations of molecules, that is, the functional combining strength of an interaction.

As used herein, "biological sample" or "tissue sample" can be any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. The samples may be tumor samples, including those from melanoma, renal cell carcinoma, and non-small-cell lung cancers. In some embodiments, the samples are analyzed for the of cancer by detecting targets, including biomarkers (e.g. proteins or nucleic acid sequences), within the tissue sample. The described embodiments of the disclosed method can also be applied to samples that do not have abnormalities, diseases, disorders, etc., referred to as "normal" samples or "control" samples. For example, it may be useful to test a subject for cancer by taking tissue samples from multiple locations, and these samples may be used as controls and compared to later samples to determine whether a particular cancer has spread beyond its primary origin.

As used herein, "conjugate" refers to two or more molecules (and/or materials such as nanoparticles) that are covalently linked into a larger construct. In some embodiments, a conjugate includes one or more biomolecules (such as peptides, proteins, enzymes, sugars, polysaccharides, lipids, glycoproteins, and lipoproteins) covalently linked to one or more other molecules, such as one or more other biomolecules. In other embodiments, a conjugate includes one or more specific-binding molecules (such as antibodies) covalently linked to one or more detectable labels (such as a fluorophore, a luminophore, fluorescent nanoparticles, haptens, enzymes and combinations thereof).

As used herein, "detection probes" include nucleic acid probes or primary antibodies which bind to specific targets (e.g. nucleic acid sequences, proteins, etc.). The detection probes may include a label for direct detection, such as radioactive isotopes, enzyme substrates, co-factors, ligands, chemiluminescent or fluorescent agents, haptens (including, but not limited to, DNP), and enzymes. Alternatively, the detection probes may contain no label or tag and may be detected indirectly (e.g. with a secondary antibody that is specific for the detection probe).

As used herein, "haptens" are small molecules that can combine specifically with an antibody, but typically are substantially incapable of being immunogenic except in combination with a carrier molecule. In some embodiments, haptens include, but are not limited to, pyrazoles (e.g. nitropyrazoles); nitrophenyl compounds; benzofurazans; triterpenes; ureas (e.g. phenyl ureas); thioureas (e.g. phenyl thioureas); rotenone and rotenone derivatives; oxazole (e.g. oxazole sulfonamides); thiazoles (e.g. thiazole sulfonamides); coumarin and coumarin derivatives; and cyclolignans. Additional non-limiting examples of haptens include thiazoles; nitroaryls; benzofurans; triterpenes; and cyclolignans. Specific examples of haptens include di-nitrophenyl, biotin, digoxigenin, and fluorescein, and any derivatives or analogs thereof. Other haptens are described in U.S. Pat. Nos. 8,846,320; 8,618,265; 7,695,929; 8,481,270; and 9,017,954, the disclosures of which are incorporated herein by reference in their entirety. The haptens themselves may be suitable for direct detection, i.e. they may give off a suitable signal for detection.

As used herein, the term "hydrodynamic radius," as used herein, denotes the radius of a sphere having equivalent hydrodynamic properties as a given structure. The hydrodynamic radius is derived from the diffusion coefficient by the Stokes Einstein equation.

As used herein, "immunohistochemistry" refers to a method of determining the presence or distribution of an antigen in a sample by detecting interaction of the antigen with a specific binding agent, such as an antibody. A sample is contacted with an antibody under conditions permitting antibody-antigen binding. Antibody-antigen binding can be detected by means of a detectable label conjugated to the antibody (direct detection) or by means of a detectable label conjugated to a secondary antibody, which binds specifically to the primary antibody (indirect detection).

As used herein, "multiplex," "multiplexed," or "multiplexing" refer to detecting multiple targets in a sample concurrently, substantially simultaneously, or sequentially. Multiplexing can include identifying and/or quantifying multiple distinct nucleic acids (e.g., DNA, RNA, mRNA, miRNA) and polypeptides (e.g., proteins) both individually and in any and all combinations.

As used herein, the term "primary antibody" refers to an antibody which binds specifically to a target protein antigen in a tissue sample. A primary antibody is generally the first antibody used in an immunohistochemical procedure. Epitope-tagged antibodies, unmodified antibodies, or antibody conjugates, each described herein, are examples of primary antibodies. Primary antibodies may thus serve as "detection probes" for detecting a target within a tissue sample.

As used herein, the term "secondary antibody" herein refers to an antibody which binds specifically to a detection probe or portion thereof (e.g. a hapten or a primary antibody), thereby forming a bridge between the detection probe and a subsequent reagent (e.g. a label, an enzyme, etc.), if any. A secondary antibody may be used to indirectly detect detection probes, e.g. primary antibodies. Examples of secondary antibodies include anti-tag antibodies, anti-species antibodies, and anti-label antibodies, each described herein.

As used herein, the term "specific binding entity" refers to a member of a specific-binding pair. Specific binding pairs are pairs of molecules that are characterized in that they bind each other to the substantial exclusion of binding to other molecules (for example, specific binding pairs can have a binding constant that is at least 103 M-1 greater, 104 M-1 greater or 105 M-1 greater than a binding constant for either of the two members of the binding pair with other molecules in a biological sample). Particular examples of specific binding moieties include specific binding proteins (for example, antibodies, lectins, avidins such as streptavidins, and protein A). Specific binding moieties can also include the molecules (or portions thereof) that are specifically bound by such specific binding proteins. Specific binding entities include primary antibodies, described above, or nucleic acid probes.

As used herein, "target" means any molecule for which the presence, location and/or concentration is or can be determined. Examples of targets include nucleic acid sequences and proteins, such as those disclosed herein.

Epitope Tagged Antibodies

In one aspect of the present disclosure are recombinant antibodies that express one or more molecularly engineered epitope tags ("epitope-tagged antibodies"). In general, expression of the epitope tags (short amino acid sequences, namely antigenic peptide sequences) allows the epitope-tagged antibody to be recognized and/or detected (such as with an anti-tag antibody, described further herein). Thus, the epitope tagged antibodies disclosed herein are suitable for use in immunohistochemical assays, including in multiplex immunohistochemical assays, and thereby may be used as primary antibodies or detection probes such that targets within a tissue sample may be detected.

An epitope-tagged antibody may be derived from any native antibody. Thus, like native or unmodified antibodies, the epitope-tagged antibodies show specificity for a particular target. For example, an epitope-tagged antibody may be derived from antibodies specific for cluster of differentiation markers (e.g. CD3, CD8, CD20, CD68), HER2, FoxP3, PDL1, and EGFR2. Other non-limiting targets, e.g. protein targets, for which the epitope-tagged antibodies may be developed for detection purposes are disclosed further herein.

Figure 20A:
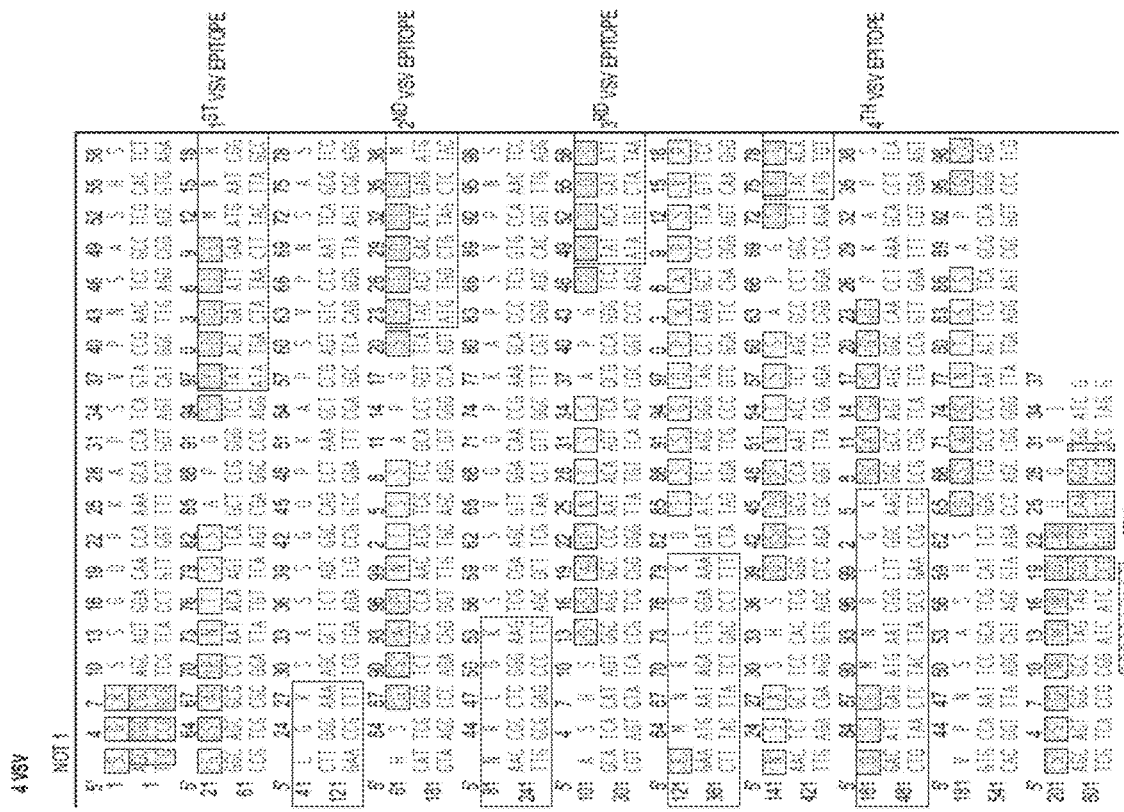
FIG. 20A, FIG. 20B, FIG. 20C, FIG. 20D, FIG. 20E, and FIG. 20F illustrate the structure of an epitope tag construct and the spatial and structural relationships between the epitope tags and spacers comprising the epitope tag construct.
Figure 20B:
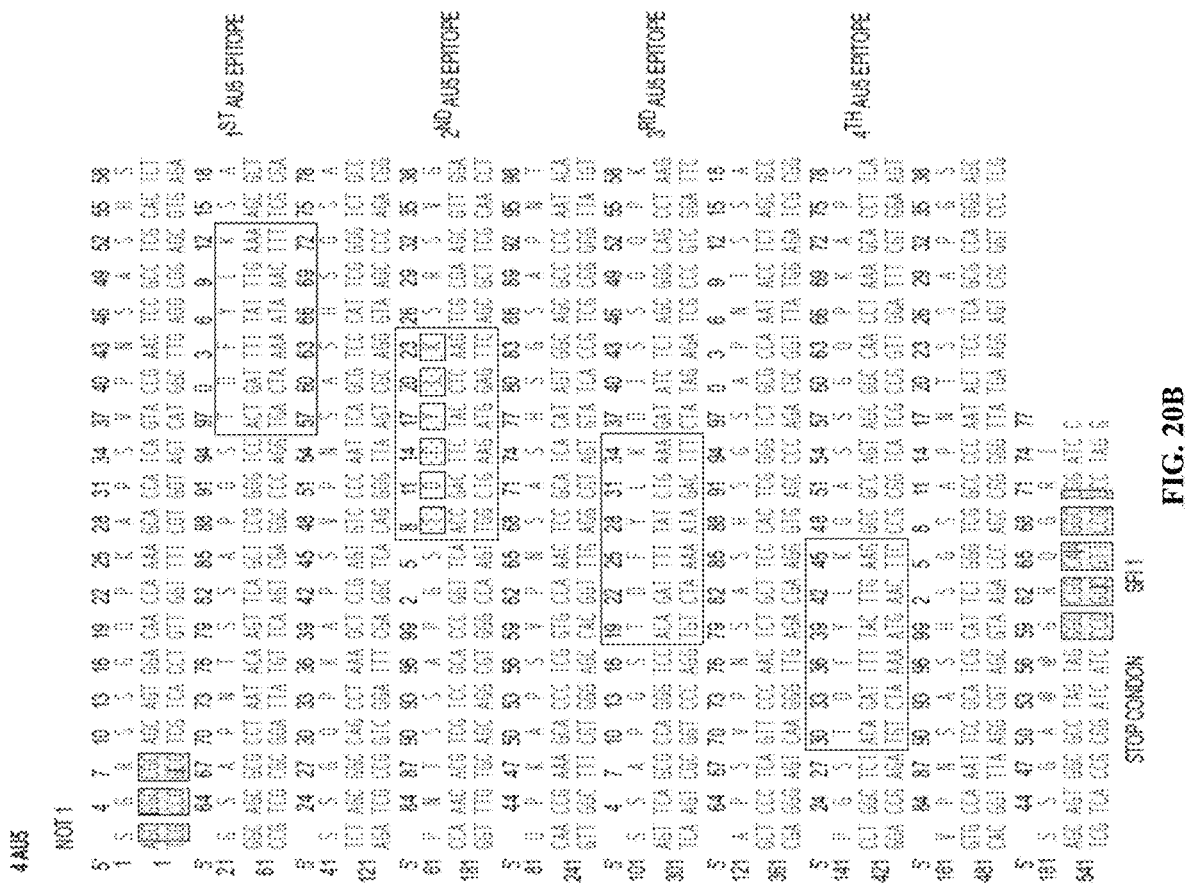
Figure 20C:
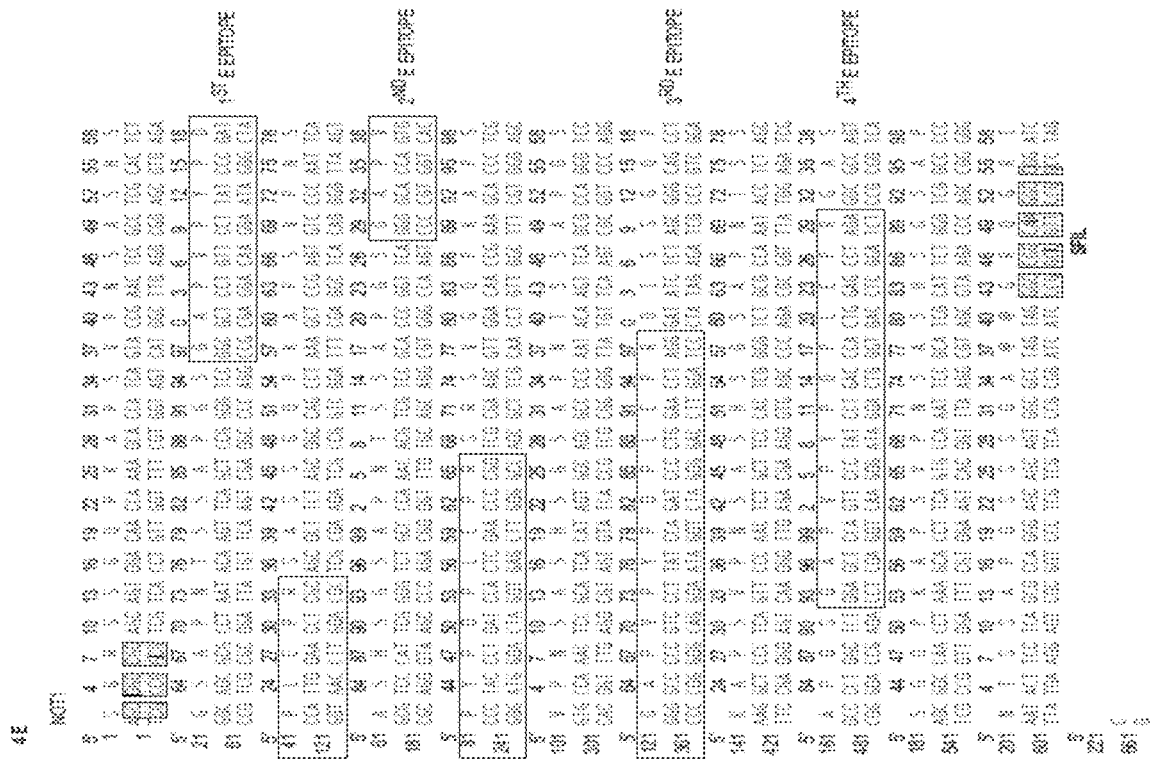
Figure 20D:
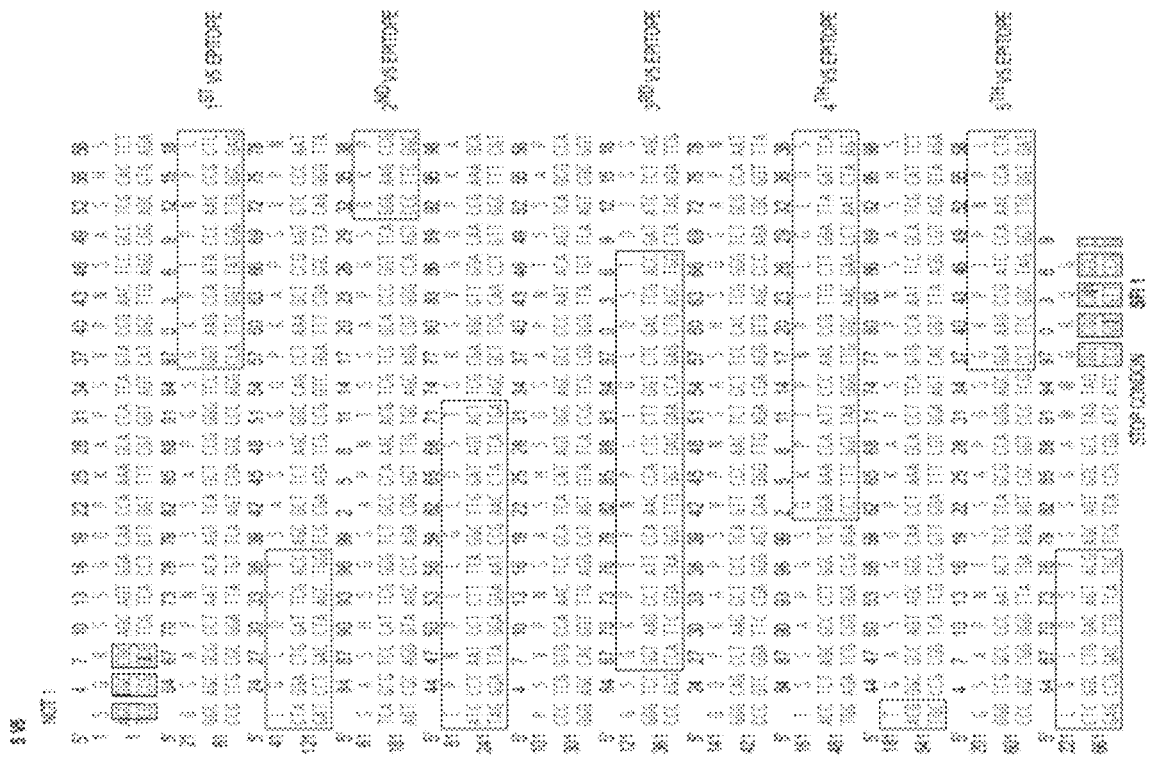
Figure 20E:
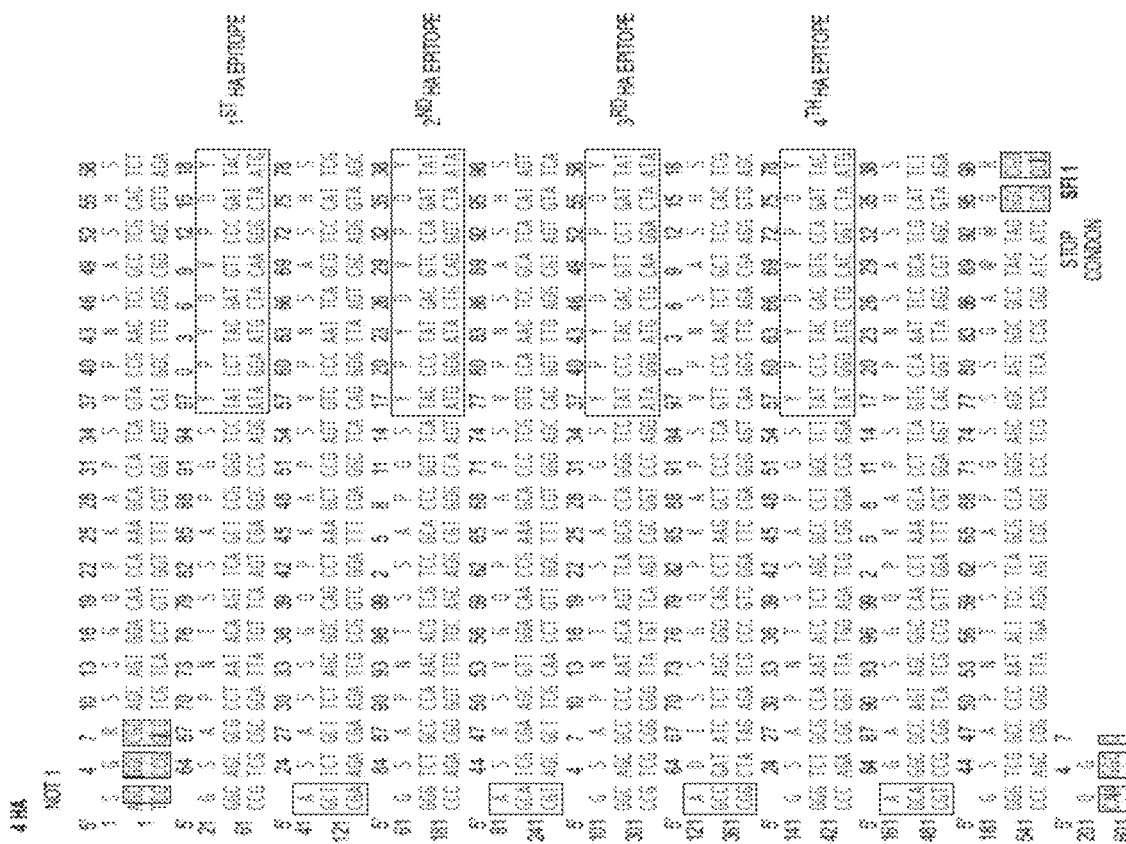
Figure 20F:
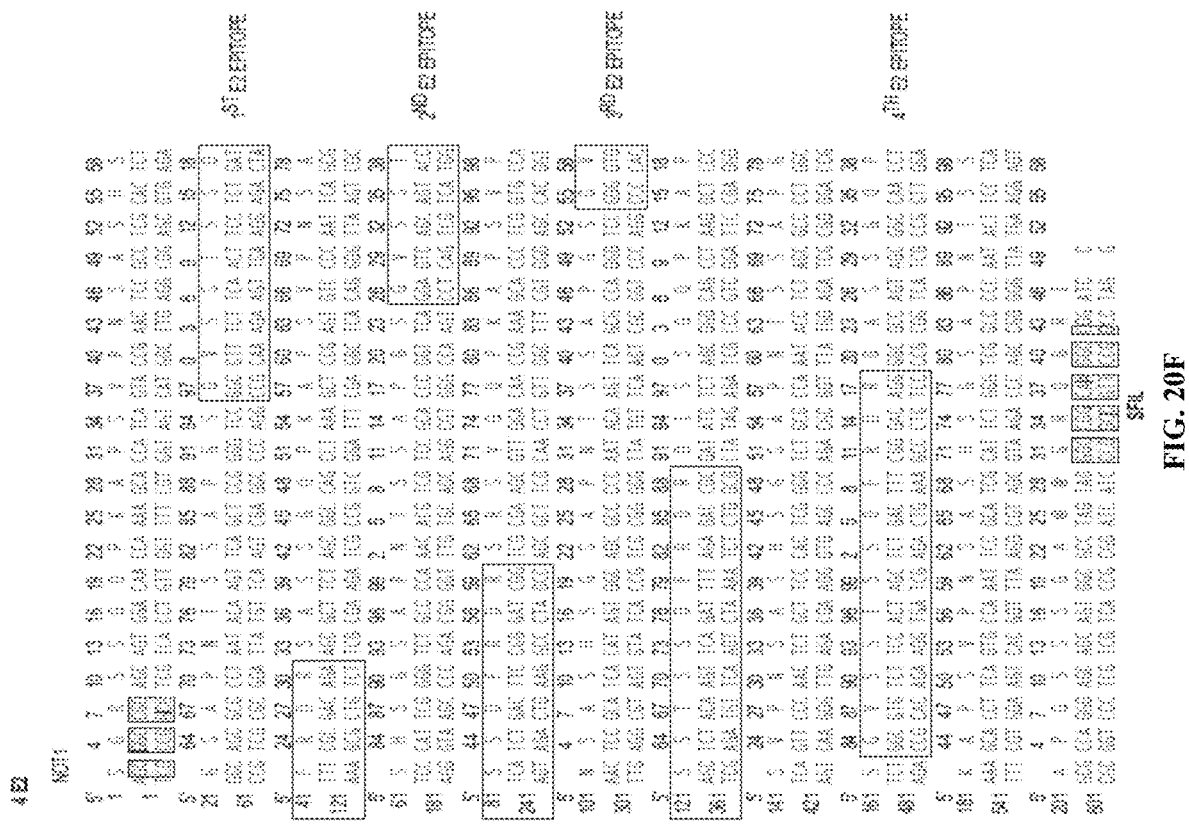

In general, the epitope-tagged antibodies comprise at least one epitope tag construct, the epitope tag constructing comprising alternating spacers and epitope tags. As used here, the term "epitope tag construct" refers to alternating epitope tags and spacers, e.g. an amino acid sequence comprising tandem repeat epitope tags separated by spacers (see, for instance, FIG. 20A).

For illustration purposes only, the epitope tagged antibodies of the present disclosure may have the structure:

Ab-([Spacer]-[Epitope Tag])$_n$-[Spacer], where n is an integer ranging from 1 to 20, "Ab" is an antibody, and "Epitope Tag" and "Spacer" are as defined herein, and where each of the "Spacers" may be the same or different, and where ([Spacer]-[Epitope Tag]) represents an example of an epitope tag construct.

The epitope-tagged antibodies are engineered such that the epitope tags and spacers are incorporated at the terminal end of a heavy chain constant region, at the terminal end of a light chain constant region, or at both the terminal ends of a heavy chain constant region and a light chain constant region. In some embodiments, an epitope tag construct is comprised at the C-terminal end of a heavy chain constant region of an antibody, a C-terminal end of light chain constant region of an antibody, or at both the C-terminal ends of heavy and light chain constant regions of an antibody.

In other embodiments, an epitope tag construct is comprised solely at the C-terminal end of the heavy chain constant region of the antibody. In other embodiments, an epitope tag construct is comprised solely at the C-terminal end of the light chain constant region of the antibody. In some embodiments, the heavy chain constant regions are identified herein by the notation "H;" while the light chain constant regions are identified herein by the notation "K." For example, the notation H4K4 may refer to an epitope-tagged antibody comprising four epitope tags at a terminal end of a heavy chain constant region and an additional four epitope tags at a terminal end of a light chain constant region. Likewise, the notation H4K0 may refer to an epitope-tagged antibody comprising four epitope tags at a terminal end of a heavy chain constant region, and no epitope tags at a terminal end of a light chain constant region.

Any type of epitope tag may be incorporated into an antibody, provided that the epitope tag does not impair the function of the antibody (i.e. impede the ability of the antibody to bind to targets or prevent the antibody from being detected). In some embodiments, an epitope tag and its configuration on IgG (the number of tags, tag's position on IgG) is considered during selection such that it minimizes any tertiary structure disruptions of the antibody to which it is incorporated. In some embodiments, an epitope tag is selected such that it has no cross-reactivity with human proteins. In some embodiments, the epitope tag has a nucleotide sequence comprising between about 6 and about 20 bases. In other embodiments, the epitope tag has a nucleotide sequence comprising between about 6 and about 16 bases. The sequence for the epitope tag may be derived from a naturally occurring source or may be synthetic.

In some embodiments, the epitope tag is selected from a VSV epitope tag (SEQ ID NO: 1), an AU5 epitope tag (SEQ ID NO: 2), an E epitope tag (SEQ ID NO: 3), a V5 epitope tag (SEQ ID NO: 4), an HA epitope tag (SEQ ID NO: 5), or an E2 epitope tag (SEQ ID NO: 6). Other suitable epitope tags that may be incorporated within epitope-tagged antibodies include FLAG, AU1 (SEQ ID NO: 8), OLLAS (SEQ ID NO: 9), and KT3 (SEQ ID NO: 7). Of course, these exemplified epitope tags may be modified according to procedures known to those of ordinary skill in the art.

The epitope-tagged antibodies (or any epitope tag construct incorporated into an epitope-tagged antibody) may comprise or express one epitope tag or a plurality of epitope tags. In general, the epitope tagged antibodies of the present disclosure may comprise any number of epitope tags provided that the epitope tags do not interfere with or reduce the function of the antibody. In some embodiments, the epitope tagged antibodies comprise at least 2 epitope tags. In other embodiments, the epitope tagged antibodies comprise at least 3 epitope tags. In yet other embodiments, the epitope tagged antibodies comprise at least 4 epitope tags. In further embodiments, the epitope tagged antibodies comprise between 2 and 20 epitope tags. In yet further embodiments, the epitope tagged antibodies comprise between 2 and 12 epitope tags. In even further embodiments, the epitope tagged antibodies comprise between 3 and 9 epitope tags. In one particular embodiment, the epitope tagged antibodies comprise 4 epitope tags. In another particular embodiment, the epitope tagged antibodies comprise 5 epitope tags.

In some embodiments, any epitope tag construct comprises between 2 and 10 epitope tags. In some embodiments, any epitope tag construct comprises between 2 and 8 epitope tags. In other embodiments, any epitope tag construct comprises between 2 and 5 epitope tags. In yet other embodiments, any epitope tag construct comprises 4 or 5 epitope tags.

In some embodiments, the number of epitope tags incorporated (or "expressed") at the C-terminal end of a heavy chain constant region is greater than the number of epitope tags incorporated at the C-terminal end of a light chain constant region (i.e. the number of epitope tags constituting an epitope tag construct incorporated at the C-terminal end of a heavy chain constant region is greater than the number of epitope tags constituting an epitope tag construct incorporated at the C-terminal end of a light chain constant region). In other embodiments, the number of epitope tags incorporated at the C-terminal end of a heavy chain constant region is less than the number of epitope tags incorporated at the C-terminal end of a light chain constant region (i.e. the number of epitope tags constituting an epitope tag construct at the C-terminal end of a heavy chain constant region is less than the number of epitope tags constituting an epitope tag construct at the C-terminal end of a light chain constant region).

In some embodiments, a ratio of the number of epitope tags incorporated at the C-terminal end of a heavy chain constant region to the number of epitope tags incorporated at the C-terminal end of a light chain constant region ranges from 4:1 to about 1:4. In other embodiments, a ratio of the number of epitope tags incorporated at the C-terminal end of a heavy chain constant region to the number of epitope tags incorporated at the C-terminal end of a light chain constant region is ranges from 2:1 to about 1:2. In yet other embodiments, a ratio of the number of epitope tags incorporated at the C-terminal end of a heavy chain constant region to the number of epitope tags incorporated at the C-terminal end of a light chain constant region is ranges from 1.5:1 to about 1:1.5. In further embodiments, a ratio of the number of epitope tags incorporated at the C-terminal end of a heavy chain constant region to the number of epitope tags incorporated at the C-terminal end of a light chain constant region is about 1:1.

In some embodiments, between 2 and 8 epitope tags are incorporated at the C-terminal end of a heavy chain constant region and between 2 and 8 epitope tags are incorporated at the C-terminal end of a light chain constant region. In some embodiments, between 2 and 8 epitope tags are incorporated at the C-terminal end of a heavy chain constant region and between 0 and 5 epitope tags are incorporated at the C-terminal end of a light chain constant region. In other embodiments, between 2 and 6 epitope tags are incorporated at the C-terminal end of a heavy chain constant region and between 0 and 4 epitope tags are incorporated at the C-terminal end of a light chain constant region. In other embodiments, 4 or 5 epitope tags are incorporated at the C-terminal end of a heavy chain constant region and between 2 and 5 epitope tags are incorporated at the C-terminal end of a light chain constant region. In yet other embodiments, 4 or 5 epitope tags are incorporated at the C-terminal end of a heavy chain constant region and 0, 1, or 2 epitope tags are incorporated at the C-terminal end of a light chain constant region. In further embodiments, 4 or 5 epitope tags are incorporated at the C-terminal end of a heavy chain constant region and no epitope tags are incorporated at the C-terminal end of a light chain constant region. In other embodiments, at least 2 epitope tags are incorporated at the C-terminal end of a light chain constant region and at least 1 epitope tag is incorporated at the C-terminal end of a heavy chain constant region. In other embodiments, at least 3 epitope tags are incorporated at the C-terminal end of a light chain constant region and at least 1 epitope tag is incorporated at the C-terminal end of a heavy chain constant region.

In one particular embodiment, the epitope-tagged antibody has the configuration H1K0. In another particular embodiment, the epitope-tagged antibody has the configuration H2K0. In another particular embodiment, the epitope-tagged antibody has the configuration H3K0. In another particular embodiment, the epitope-tagged antibody has the configuration H4K0. In another particular embodiment, the epitope-tagged antibody has the configuration H5K0. In another particular embodiment, the epitope-tagged antibody has the configuration H0K1. In another particular embodiment, the epitope-tagged antibody has the configuration H0K2. In another particular embodiment, the epitope-tagged antibody has the configuration H0K3. In another particular embodiment, the epitope-tagged antibody has the configuration H0K4. In another particular embodiment, the epitope-tagged antibody has the configuration H2K2. In another particular embodiment, the epitope-tagged antibody has the configuration H3K3. In another particular embodiment, the epitope-tagged antibody has the configuration H4K4.

As noted herein, the epitope tags are separated from each other by a spacer. In some embodiments, a spacer is provided at the terminal end of the heavy and/or light chain constant region such that any epitope tag construct is "coupled" to the spacer rather than directly to the terminal end of the respective constant region. In some embodiments, an additional sequence (e.g. a linking or coupling sequence) is provided between the terminal end of the heavy and/or light chain constant region, bridging the terminal end to the spacer (or to the epitope-tag construct). Likewise, in some embodiments, at least one additional spacer is provided after a terminal epitope tag of an epitope tag construct, but prior to any stop codon sequence. FIGS. 20A through 20F further illustrate the structure of an epitope tag construct and the spatial and structural relationships between epitope tags (outlined within rectangular boxes) and spacers (sequences between the epitope tags). FIGS. 20A through 20F also illustrate restriction sites within the "epitope tag gene" (defined herein) and the position of a stop codon.

The spacer itself is selected such that the amino acid sequence the spacer (or its resulting tertiary structure) of does not interfere with any folding protein domains of the antibody. In some embodiments, the spacer comprises a nucleic acid sequence having between about 20 bases and about 60 bases. In some embodiments, the size of any spacer is selected such that the spacer sufficiently separates epitope tags to facilitate the binding of multiple anti-tag antibodies to the epitope-tagged antibody.

In some embodiments, the spacers comprise an amino acid sequence selected from SEQ ID NO: 10, SEQ ID NO: 11, SEQ ID NO: 12, SEQ ID NO: 13, SEQ ID NO: 14, or SEQ ID NO: 15. In some embodiments, the spacers comprise an amino acid sequence having at least 75% identity to a sequence selected from SEQ ID NO: 10, SEQ ID NO: 11, SEQ ID NO: 12, SEQ ID NO: 13, or SEQ ID NO: 14. In some embodiments, the spacers comprise an amino acid sequence having at least 80% identity to a sequence selected from SEQ ID NO: 10, SEQ ID NO: 11, SEQ ID NO: 12, SEQ ID NO: 13, or SEQ ID NO: 14. In some embodiments, the spacers comprise an amino acid sequence having at least 85% identity to a sequence selected from SEQ ID NO: 10, SEQ ID NO: 11, SEQ ID NO: 12, SEQ ID NO: 13, or SEQ ID NO: 14. In some embodiments, the spacers comprise an amino acid sequence having at least 90% identity to a sequence selected from SEQ ID NO: 10, SEQ ID NO: 11, SEQ ID NO: 12, SEQ ID NO: 13, or SEQ ID NO: 14. In some embodiments, the spacers comprise an amino acid sequence having at least 95% identity to a sequence selected from SEQ ID NO: 10, SEQ ID NO: 11, SEQ ID NO: 12, SEQ ID NO: 13, or SEQ ID NO: 14.

In some embodiments, at least a portion of the amino acid sequence constituting the spacer comprises an amino acid sequence including a sequence of SEQ ID NO: 10, SEQ ID NO: 11, SEQ ID NO: 12, SEQ ID NO: 13, or SEQ ID NO: 14. In some embodiments, at least a portion of the amino acid sequence constituting the spacer comprises an amino acid sequence having at least 75% to a sequence of SEQ ID NO: 10, SEQ ID NO: 11, SEQ ID NO: 12, SEQ ID NO: 13, or SEQ ID NO: 14. In some embodiments, at least a portion of the amino acid sequence constituting the spacer comprises an amino acid sequence including a sequence of SEQ ID NO: 10, SEQ ID NO: 11, SEQ ID NO: 12, SEQ ID NO: 13, or SEQ ID NO: 14. In some embodiments, at least a portion of the amino acid sequence constituting the spacer comprises an amino acid sequence having at least 80% to a sequence of SEQ ID NO: 10, SEQ ID NO: 11, SEQ ID NO: 12, SEQ ID NO: 13, or SEQ ID NO: 14. In some embodiments, at least a portion of the amino acid sequence constituting the spacer comprises an amino acid sequence including a sequence of SEQ ID NO: 10, SEQ ID NO: 11, SEQ ID NO: 12, SEQ ID NO: 13, or SEQ ID NO: 14. In some embodiments, at least a portion of the amino acid sequence constituting the spacer comprises an amino acid sequence having at least 85% to a sequence of SEQ ID NO: 10, SEQ ID NO: 11, SEQ ID NO: 12, SEQ ID NO: 13, or SEQ ID NO: 14. In some embodiments, at least a portion of the amino acid sequence constituting the spacer comprises an amino acid sequence including a sequence of SEQ ID NO: 10, SEQ ID NO: 11, SEQ ID NO: 12, SEQ ID NO: 13, or SEQ ID NO: 14. In some embodiments, at least a portion of the amino acid sequence constituting the spacer comprises an amino acid sequence having at least 90% to a sequence of SEQ ID NO: 10, SEQ ID NO: 11, SEQ ID NO: 12, SEQ ID NO: 13, or SEQ ID NO: 14. In some embodiments, at least a portion of the amino acid sequence constituting the spacer comprises an amino acid sequence including a sequence of SEQ ID NO: 10, SEQ ID NO: 11, SEQ ID NO: 12, SEQ ID NO: 13, or SEQ ID NO: 14. In some embodiments, at least a portion of the amino acid sequence constituting the spacer comprises an amino acid sequence having at least 95% to a sequence of SEQ ID NO: 10, SEQ ID NO: 11, SEQ ID NO: 12, SEQ ID NO: 13, or SEQ ID NO: 14.

The spacers separating the epitope tags may be the same or different. For example, if an epitope tag construct comprises five epitope tags, the spacers between the five epitope tags of the construct may be same or different. In some embodiments, the spacers separating the epitope tags of any epitope tag construct are all the same. In other embodiments, the spacers separating the epitope tags of any epitope tag construct are all different from one another. In yet other embodiments, at least some of the spacers separating the epitope tags of any epitope tag construct are the same. In some embodiments, a portion of any spacer may be the same or different than a portion of another spacer. In some embodiments, a portion of any sequence of any spacer may be the same as a portion of a sequence of another spacer. In some embodiments, at least a portion of some of the spacers is the same.

In some embodiments, any epitope tag construct comprises at least one spacer comprising the sequence of SEQ ID NO: 10, SEQ ID NO: 11, SEQ ID NO: 12, or SEQ ID NO: 13, SEQ ID NO: 14 (or at least a portion of the amino acid sequence constituting the spacer comprises an amino acid sequence including a sequence of SEQ ID NO: 10, SEQ ID NO: 11, SEQ ID NO: 12, SEQ ID NO: 13, or SEQ ID NO: 14). In other embodiments, any epitope tag construct comprises at least one spacer comprising the sequence of one of SEQ ID NO: 10, SEQ ID NO: 11, SEQ ID NO: 12, SEQ ID NO: 13, or SEQ ID NO: 14 (or at least a portion of the amino acid sequence constituting the spacer comprises an amino acid sequence including a sequence of SEQ ID NO: 10, SEQ ID NO: 11, SEQ ID NO: 12, SEQ ID NO: 13, or SEQ ID NO: 14); and at least a second spacer comprising the sequence of another one of SEQ ID NO: 10, SEQ ID NO: 11, SEQ ID NO: 12, SEQ ID NO: 13, or SEQ ID NO: 14 (or at least a portion of the amino acid sequence constituting the spacer comprises an amino acid sequence including a sequence of SEQ ID NO: 10, SEQ ID NO: 11, SEQ ID NO: 12, SEQ ID NO: 13, or SEQ ID NO: 14).

In some embodiments, the molecular weight of an epitope tag construct ranges from between about 5 g/mol to about 35 g/mol. In other embodiments, the molecular weight of an epitope tag construct ranges from between about 5 g/mol to about 30 g/mol. In other embodiments, the molecular weight of an epitope tag construct ranges from between about 10 g/mol to about 30 g/mol. In other embodiments, the molecular weight of an epitope tag construct ranges from between about 5 g/mol to about 25 g/mol. In other embodiments, the molecular weight of an epitope tag construct ranges from between about 5 g/mol to about 20 g/mol. In other embodiments, the molecular weight of an epitope tag construct ranges from between about 7.5 g/mol to about 15 g/mol. In other embodiments, the molecular weight of an epitope tag construct ranges does not exceed 20 g/mol. In other embodiments, the molecular weight of an epitope tag construct ranges does not exceed 15 g/mol.

In some embodiments, a distance between successive -[Epitope Tags]-of the at least one epitope tag construct ranges from between about 8 nm to about 18 nm. In some embodiments, a distance between successive -[Epitope Tags]- of the at least one epitope tag construct is less than 18 nm. In some embodiments, a distance between successive -[Epitope Tags]- of the at least one epitope tag construct is less than 16 nm. In some embodiments, a distance between successive -[Epitope Tags]- of the at least one epitope tag construct is less than 14 nm. In some embodiments, a distance between successive -[Epitope Tags]- of the at least one epitope tag construct is less than 12 nm. In some embodiments, a distance between successive -[Epitope Tags]- of the at least one epitope tag construct is less than 11 nm. In some embodiments, a distance between successive -[Epitope Tags]- of the at least one epitope tag construct is less than 10 nm. In some embodiments, the -[Spacer]- is sized to facilitate bivalent binding of anti-tag antibodies between adjacent Epitope Tags (see FIG. 35A). As such, in some embodiments, any two adjacent Epitope Tags are spaced a distance apart from one another which approximates the distance between antigen binding sites of an anti-tag antibody. In some embodiments, a first antigen binding site binds to a first Epitope Tag of the at least one epitope tag construct and wherein a second antigen binding site binds to a second, adjacent Epitope Tag of the at least one epitope tag construct.

While the spacing may facilitate the bivalent binding of antibodies, the skilled artisan will appreciate that it is also possible for antibodies, e.g. anti-tag antibodies, to "skip" an epitope tag and bind a non-adjacent epitope tag (see FIG. 35B). For example, the epitope tag antibody may comprise first, second, and third epitope tags, where the first and second epitope tags are adjacent to one another (but, of course, separated by a spacer). In this example, a first antigen binding site of an anti-tag antibody may bind to the first epitope tag and a second antigen binding site of the anti-tag antibody may bind to the third epitope tag. The skilled artisan will also appreciate that the combined flexibility and the length of the spacers may form a spatial arrangement of contiguous or non-contiguous epitopes that could be accessed by both arms of an anti-tag antibody with elbow angles between about 120 degrees and about 220 degrees. In some embodiments, the elbow angles range from about 120 degrees to about 200 degrees. In some embodiments, the elbow angles range from about 140 degrees to about 200 degrees.

In some embodiments, the combined molecular weight of all epitope tag constructs of any epitope-tagged antibody is between about 5 g/mol to about 80 g/mol. In other embodiments, the combined molecular weight of all epitope tag constructs of any epitope-tagged antibody is between about 5 g/mol to about 50 g/mol. In yet other embodiments, the combined molecular weight of all epitope tag constructs of any epitope-tagged antibody is between about 10 g/mol to about 40 g/mol. In further embodiments, the combined molecular weight of all epitope tag constructs of any epitope-tagged antibody is between about 15 g/mol to about 30 g/mol.

In yet further embodiments, the combined molecular weight of all epitope tag constructs of any epitope-tagged antibody is less than 40% of the molecular weight of the native antibody (i.e. the molecular weight of a corresponding unmodified antibody having the same specificity and/or functional characteristics). In yet further embodiments, the combined molecular weight of all epitope tag constructs of any epitope-tagged antibody is less than 30% of the molecular weight of the native antibody. In yet further embodiments, the combined molecular weight of all epitope tag constructs of any epitope-tagged antibody is less than 25% of the molecular weight of the native antibody.

Engineering of Epitope Taig Constructs and Epitope-Tagged Antibodies

The epitope-tagged antibodies of the present disclosure may be generated according to methods known to those of ordinary skill in the art. In general, an "epitope gene" comprising tandem repeat epitope tags separated with spacers is synthesized and the sequence verified. In some embodiments, the epitope gene comprises a nucleic acid sequence of any of SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31. In other embodiments, the epitope gene comprises a nucleic acid sequence having at least 80% identify to any of SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31. In yet other embodiments, the epitope gene comprises a nucleic acid sequence having at least 90% identify to any of SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31. In further embodiments, the epitope gene comprises a nucleic acid sequence having at least 95% identify to any of SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31. In yet further embodiments, the epitope gene comprises a nucleic acid sequence having about 97% identify to any of SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, or SEQ ID NO: 31.

Following epitope gene synthesis, the epitope gene is cloned into an appropriate vector (e.g. pUC57-Kan) using midi-scale DNA preparation (e.g. to preserve the sequence and to propagate the gene by means of the vector). The epitope gene is then cloned at the C-terminal end of a heavy chain constant region or the C-terminal end of a light chain constant region of the antibody of interest by means of a restriction site at the C-terminal end (e.g. 5'Not1 and 3'Sfil) and inserted into the multiple cloning site (MCS) of an antibody expression vector. To make the final heavy constant chain region—epitope tag construct or final light constant chain region—epitope tag construct, maxi-scale DNA preparation is used. The DNA constructs (heavy constant chain region—epitope tag construct or final light constant chain region—epitope tag construct) are then transiently transfected into HEK293 cells via route antibody expression and production processes, as known to those of ordinary skill in the art.

Alternatively, an antibody expression vector is selected from one that is currently used in antibody expression and production, i.e. an antibody expression vector used to produce a native, unmodified antibody. After the epitope gene is synthesized and inserted into a vector, e.g. pUC57, the epitope gene is cloned into the antibody expression vector downstream of the antibody gene (e.g. via Not1 and Sfil site) with the correct reading frame. In this manner, a library of epitope vectors may be built using an existing antibody expression vector. Next, the IgG H and K chain gene sequence of the antibody of interest are extracted from the antibody expression vector via the restriction sites (e.g. Nhe1 and Not1) and inserted into the epitope vector via the same restriction site (e.g. Nhe1 and Not1). The IgG H or K chain sequence is located upstream of the tag sequence with the correct reading frame. In the culture system, the epitope vector expresses the IgG H or K chain and the tag at the C-terminal end of IgG.

Examples of Specific Epitope Tag Constructs and Epitope-Tagged Antibodies

Provided herein are specific examples of epitope tag constructs which may be engineered to be incorporated at a terminal end of a heavy and/or light chain constant region of an antibody. The skilled artisan will appreciate that epitope constructs having more or less epitope tags may be produced by altering the epitope tag gene according to the procedures described above and according to other methods known to those of skill in the art. As such, the examples which follow are non-limiting examples.

Epitope-Tagged Antibody Comprising an Epitope Construct Having Four VSV Epitope Tags In some embodiments is an epitope-tagged antibody that expresses the VSV epitope tag. In some embodiments, an epitope-tagged antibody comprises at least one epitope tag construct, the at least one epitope tag construct including four VSV epitope tags. In some embodiments, the epitope tag construct includes four epitope tags having the amino acid sequence of SEQ ID NO: 1. In some embodiments, the epitope tag construct has at least one spacer which includes at least one of the amino acid sequences of SEQ ID NO: 10, SEQ ID NO: 11, SEQ ID NO: 12, SEQ ID NO: 13, or SEQ ID NO: 14. In some embodiments, the epitope-tagged antibody comprises an amino acid sequence of SEQ ID NO: 16. In some embodiments, the epitope-tagged antibody comprises an amino acid sequence of SEQ ID NO: 16 at a C-terminal end of a heavy chain constant region. In othe6 at a C-terminal end of a light chain constant region. In yet other embodiments, the epitope-tagged antibody comprises an amino acid sequence of SEQ ID NO: 16 at both a C-terminal end of a heavy chain constant region and a C-terminal end of a light chain constant region. In some embodiments, the epitope-tagged antibody is specific to at least one of CD3, CD8, CD20, CD68, HER2, FoxP3, PDL1, and EGFR2. In some embodiments, this particular epitope gene may be modified to have, for example, five epitope tags.

Epitope-Tagged Antibody Comprising an Epitope Construct Having Four AU5 Epitope Tags In some embodiments is an epitope-tagged antibody that expresses the AU5 epitope tag. In some embodiments, an epitope-tagged antibody comprises at least one epitope tag construct, the at least one epitope tag construct including four AU5 epitope tags. In some embodiments, the epitope tag construct includes four epitope tags having the amino acid sequence of SEQ ID NO: 2. In some embodiments, the epitope tag construct has at least one spacer which includes at least one of the amino acid sequences of SEQ ID NO: 10, SEQ ID NO: 11, SEQ ID NO: 12, SEQ ID NO: 13, or SEQ ID NO: 14. In some embodiments, the epitope-tagged antibody comprises an amino acid sequence of SEQ ID NO: 18.

In some embodiments, the epitope-tagged antibody comprises an amino acid sequence of SEQ ID NO: 18 at a C-terminal end of a heavy chain constant region. In other embodiments, the epitope-tagged antibody comprises an amino acid sequence of SEQ ID NO: 18 at a C-terminal end of a light chain constant region. In yet other embodiments, the epitope-tagged antibody comprises an amino acid sequence of SEQ ID NO: 18 at both a C-terminal end of a heavy chain constant region and a C-terminal end of a light chain constant region. In some embodiments, the epitope-tagged antibody is specific to at least one of CD3, CD8, CD20, CD68, HER2, FoxP3, PDL1, and EGFR2. In some embodiments, this particular epitope gene may be modified to have, for example, five epitope tags.

Epitope-Tagged Antibody Comprising an Epitope Construct Having Four E Epitope Tags In some embodiments is an epitope-tagged antibody that expresses the E epitope tag. In some embodiments, an epitope-tagged antibody comprises at least one epitope tag construct, the at least one epitope tag construct including four E epitope tags. In some embodiments, the epitope tag construct includes four epitope tags having the amino acid sequence of SEQ ID NO: 3. In some embodiments, the epitope tag construct has at least one spacer which includes at least one of the amino acid sequences of SEQ ID NO: 10, SEQ ID NO: 11, SEQ ID NO: 12, SEQ ID NO: 13, or SEQ ID NO: 14. In some embodiments, the epitope-tagged antibody comprises an amino acid sequence of SEQ ID NO: 20. In some embodiments, the epitope-tagged antibody comprises an amino acid sequence of SEQ ID NO: 20 at a C-terminal end of a heavy chain constant region. In other embodiments, the epitope-tagged antibody comprises an amino acid sequence of SEQ ID NO: 20 at a C-terminal end of a light chain constant region. In yet other embodiments, the epitope-tagged antibody comprises an amino acid sequence of SEQ ID NO: 20 at both a C-terminal end of a heavy chain constant region and a C-terminal end of a light chain constant region. In some embodiments, the epitope-tagged antibody is specific to at least one of CD3, CD8, CD20, CD68, HER2, FoxP3, PDL1, and EGFR2. In some embodiments, this particular epitope gene may be modified to have, for example, five epitope tags.

Epitope-Tagged Antibody Comprising an Epitope Construct Having Five V5 Epitope Tags In some embodiments is an epitope-tagged antibody that expresses the V5 epitope tag. In some embodiments, an epitope-tagged antibody comprises at least one epitope tag construct, the at least one epitope tag construct including five V5 epitope tags. In some embodiments, the epitope tag construct includes five epitope tags having the amino acid sequence of SEQ ID NO: 4. In some embodiments, the epitope tag construct has at least one spacer which includes at least one of the amino acid sequences of SEQ ID NO: 10, SEQ ID NO: 11, SEQ ID NO: 12, SEQ ID NO: 13, or SEQ ID NO: 14. In some embodiments, the epitope-tagged antibody comprises an amino acid sequence of SEQ ID NO: 22. In some embodiments, the epitope-tagged antibody comprises an amino acid sequence of SEQ ID NO: 22 at a C-terminal end of a heavy chain constant region. In other embodiments, the epitope-tagged antibody comprises an amino acid sequence of SEQ ID NO: 22 at a C-terminal end of a light chain constant region. In yet other embodiments, the epitope-tagged antibody comprises an amino acid sequence of SEQ ID NO: 22 at both a C-terminal end of a heavy chain constant region and a C-terminal end of a light chain constant region. In some embodiments, the epitope-tagged antibody is specific to at least one of CD3, CD8, CD20, CD68, HER2, FoxP3, PDL1, and EGFR2. In some embodiments, this particular epitope gene may be modified to have, for example, four epitope tags.

Epitope-Tagged Antibody Comprising an Epitope Construct Having Four HA Epitope Tags In some embodiments is an epitope-tagged antibody that expresses HA epitope tags. In some embodiments, an epitope-tagged antibody comprises at least one epitope tag construct, the at least one epitope tag construct including four HA epitope tags. In some embodiments, the epitope tag construct includes four epitope tags having the amino acid sequence of SEQ ID NO: 5. In some embodiments, the epitope tag construct has at least one spacer which includes at least one of the amino acid sequences of SEQ ID NO: 10, SEQ ID NO: 11, SEQ ID NO: 12, SEQ ID NO: 13, or SEQ ID NO: 14. In some embodiments, the epitope-tagged antibody comprises an amino acid sequence of SEQ ID NO: 24. In some embodiments, the epitope-tagged antibody comprises an amino acid sequence of SEQ ID NO: 24 at a C-terminal end of a heavy chain constant region. In other embodiments, the epitope-tagged antibody comprises an amino acid sequence of SEQ ID NO: 24 at a C-terminal end of a light chain constant region. In yet other embodiments, the epitope-tagged antibody comprises an amino acid sequence of SEQ ID NO: 24 at both a C-terminal end of a heavy chain constant region and a C-terminal end of a light chain constant region. In some embodiments, the epitope-tagged antibody is specific to at least one of CD3, CD8, CD20, CD68, HER2, FoxP3, PDL1, and EGFR2. In some embodiments, this particular epitope gene may be modified to have, for example, five epitope tags.

Epitope-Tagged Antibody Comprising an Epitope Construct Having Four E2 Epitope Tags In some embodiment is an epitope-tagged antibody that expresses the E2 epitope tag. In some embodiments, an epitope-tagged antibody comprises at least one epitope tag construct, the at least one epitope tag construct including four E2 epitope tags. In some embodiments, the epitope tag construct includes four epitope tags having the amino acid sequence of SEQ ID NO: 6. In some embodiments, the epitope tag construct has at least one spacer which includes at least one of the amino acid sequences of SEQ ID NO: 10, SEQ ID NO: 11, SEQ ID NO: 12, SEQ ID NO: 13, or SEQ ID NO: 14. In some embodiments, the epitope-tagged antibody comprises an amino acid sequence of SEQ ID NO: 26. In some embodiments, the epitope-tagged antibody comprises an amino acid sequence of SEQ ID NO: 26 at a C-terminal end of a heavy chain constant region. In other embodiments, the epitope-tagged antibody comprises an amino acid sequence of SEQ ID NO: 26 at a C-terminal end of a light chain constant region. In yet other embodiments, the epitope-tagged antibody comprises an amino acid sequence of SEQ ID NO: 26 at both a C-terminal end of a heavy chain constant region and a C-terminal end of a light chain constant region. In some embodiments, the epitope-tagged antibody is specific to at least one of CD3, CD8, CD20, CD68, HER2, FoxP3, PDL1, and EGFR2. In some embodiments, this particular epitope gene may be modified to have, for example, five epitope tags.

Epitope-Tagged Antibody Comprising an Epitope Construct Having Four KT3 Epitope Tags In some embodiment is an epitope-tagged antibody that expresses the KT3 epitope tag. In some embodiments, an epitope-tagged antibody comprises at least one epitope tag construct, the at least one epitope tag construct including four KT3 epitope tags. In some embodiments, the epitope tag construct includes four epitope tags having the amino acid sequence of SEQ ID NO: 7. In some embodiments, the epitope tag construct has at least one spacer which includes at least one of the amino acid sequences of SEQ ID NO: 10, SEQ ID NO: 11, SEQ ID NO: 12, SEQ ID NO: 13, or SEQ ID NO: 14. In some embodiments, the epitope-tagged antibody comprises an amino acid sequence of SEQ ID NO: 28. In some embodiments, the epitope-tagged antibody comprises an amino acid sequence of SEQ ID NO: 28 at a C-terminal end of a heavy chain constant region. In other embodiments, the epitope-tagged antibody comprises an amino acid sequence of SEQ ID NO: 28 at a C-terminal end of a light chain constant region. In yet other embodiments, the epitope-tagged antibody comprises an amino acid sequence of SEQ ID NO: 28 at both a C-terminal end of a heavy chain constant region and a C-terminal end of a light chain constant region. In some embodiments, the epitope-tagged antibody is specific to at least one of CD3, CD8, CD20, CD68, HER2, FoxP3, PDL1, and EGFR2. In some embodiments, this particular epitope gene may be modified to have, for example, five epitope tags.

Epitope-Tagged Antibody Comprising an Epitope Construct Having Four AU1 Epitope Tags In some embodiment is an epitope-tagged antibody that expresses the AU1 epitope tag. In some embodiments, an epitope-tagged antibody comprises at least one epitope tag construct, the at least one epitope tag construct including four AU1 epitope tags. In some embodiments, the epitope tag construct includes four epitope tags having the amino acid sequence of SEQ ID NO: 8. In some embodiments, the epitope tag construct has at least one spacer which includes at least one of the amino acid sequences of SEQ ID NO: 10, SEQ ID NO: 11, SEQ ID NO: 12, SEQ ID NO: 13, or SEQ ID NO: 14. In some embodiments, the epitope-tagged antibody comprises an amino acid sequence of SEQ ID NO: 32. In some embodiments, the epitope-tagged antibody comprises an amino acid sequence of SEQ ID NO: 32 at a C-terminal end of a heavy chain constant region. In other embodiments, the epitope-tagged antibody comprises an amino acid sequence of SEQ ID NO: 32 at a C-terminal end of a light chain constant region. In yet other embodiments, the epitope-tagged antibody comprises an amino acid sequence of SEQ ID NO: 32 at both a C-terminal end of a heavy chain constant region and a C-terminal end of a light chain constant region. In some embodiments, the epitope-tagged antibody is specific to at least one of CD3, CD8, CD20, CD68, HER2, FoxP3, PDL1, and EGFR2. In some embodiments, this particular epitope gene may be modified to have, for example, five epitope tags.

Epitope-Tagged Antibody Comprising an Epitope Construct Having Four OLLAS Epitope Tags In some embodiment is an epitope-tagged antibody that expresses the OLLAS epitope tag. In some embodiments, an epitope-tagged antibody comprises at least one epitope tag construct, the at least one epitope tag construct including four OLLAS epitope tags. In some embodiments, the epitope tag construct includes four epitope tags having the amino acid sequence of SEQ ID NO: 9. In some embodiments, the epitope tag construct has at least one spacer which includes at least one of the amino acid sequences of SEQ ID NO: 10, SEQ ID NO: 11, SEQ ID NO: 12, SEQ ID NO: 13, or SEQ ID NO: 14. In some embodiments, the epitope-tagged antibody comprises an amino acid sequence of SEQ ID NO: 30. In some embodiments, the epitope-tagged antibody comprises an amino acid sequence of SEQ ID NO: 30 at a C-terminal end of a heavy chain constant region. In other embodiments, the epitope-tagged antibody comprises an amino acid sequence of SEQ ID NO: 30 at a C-terminal end of a light chain constant region. In yet other embodiments, the epitope-tagged antibody comprises an amino acid sequence of SEQ ID NO: 30 at both a C-terminal end of a heavy chain constant region and a C-terminal end of a light chain constant region. In some embodiments, the epitope-tagged antibody is specific to at least one of CD3, CD8, CD20, CD68, HER2, FoxP3, PDL1, and EGFR2. In some embodiments, this particular epitope gene may be modified to have, for example, five epitope tags.

Characterization

The epitope-tagged antibodies disclosed herein, as well as their native, unmodified counterparts, can be detected with anti-species secondary antibodies in ELISA and IHC. In an ELISA study, an epitope peptide was coated on the plate, the epitope-tagged primary antibody was applied, followed with goat anti-rabbit secondary antibodies conjugated to horseradish peroxidase, and 3,3'-Diaminobenzidine (DAB) was used as a chromogenic substrate for the enzyme. In IHC, the epitope-tagged primary antibody was applied to human tonsil tissue, followed with goat anti-rabbit secondary antibodies conjugated to horseradish peroxidase, and 3,3'-Diaminobenzidine (DAB) was used as a chromogenic substrate for the enzyme. The primary antibodies (i.e. epitope-tagged antibodies and the corresponding native, unmodified antibodies) both were tested at 1 μg/mL concentrations (see FIGS. 16A through 16F and FIGS. 17A through 17F). Only the anti-CD3 epitope-tagged antibody (see FIG. 17D) performed less than ideally and, without wishing to be bound by any particular theory, it is speculated that the presence of four epitope tags at the C-terminal end of the heavy chain constant region and an additional four epitope tags at the C-terminal end of the light chain constant region may have introduced a steric hindrance which prevented the antibody from functioning ideally, although it still did function in staining assays.

Figure 18:
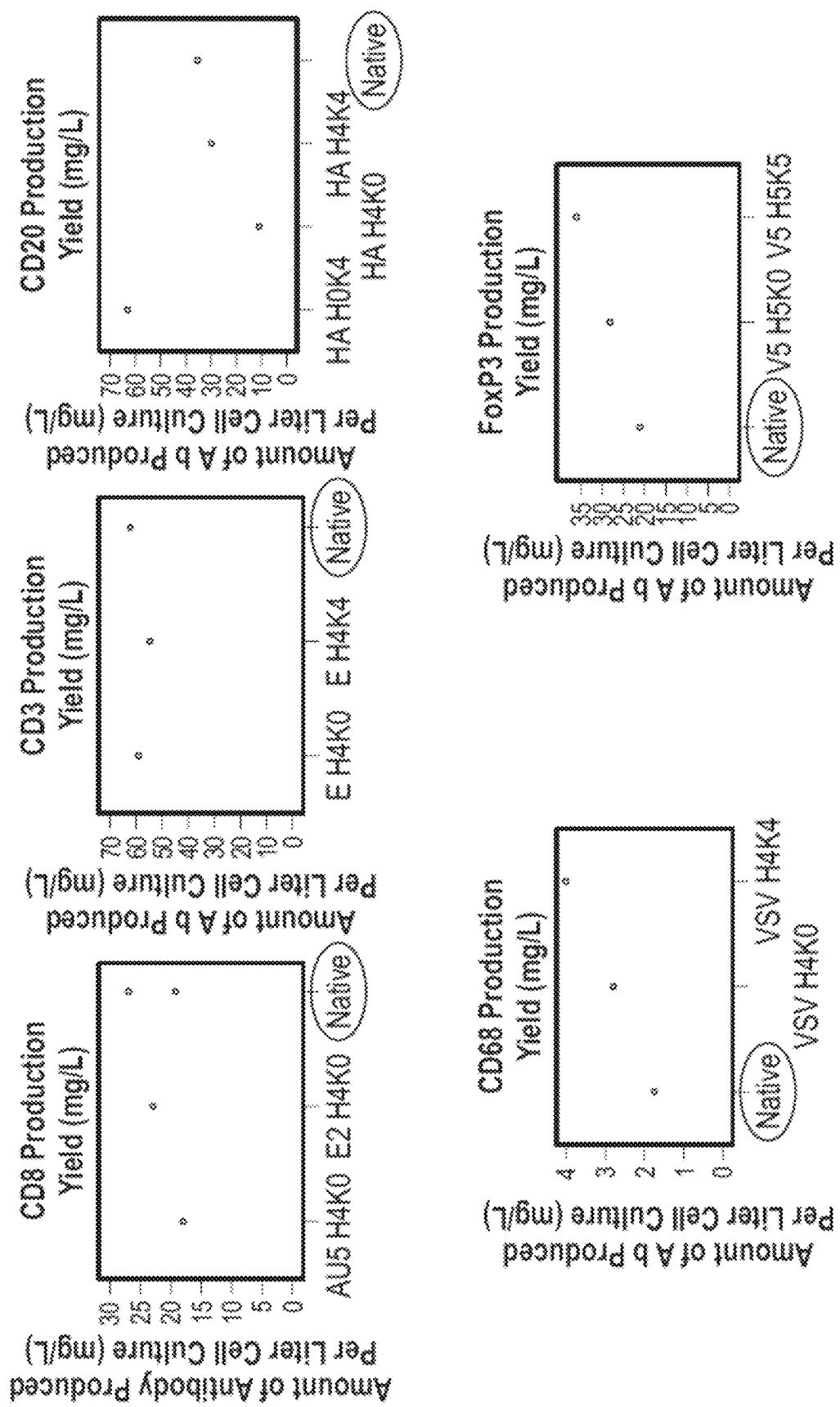
FIG. 18 illustrates the production yield of epitope-tagged antibodies as compared with corresponding native antibodies.
Figure 19:
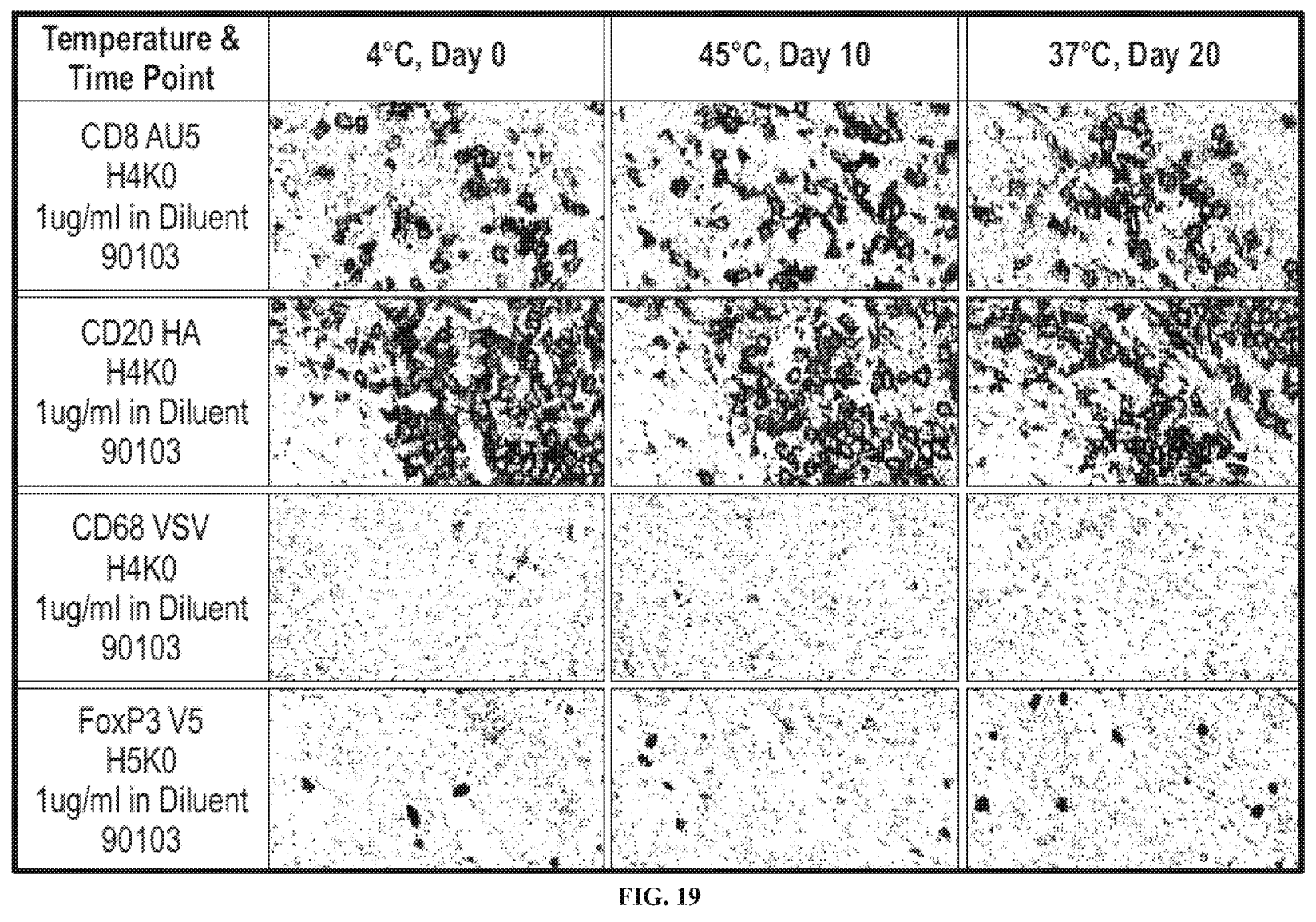

Moreover, as shown in FIG. 18, Applicants have demonstrated that epitope tagging of antibodies has no negative impact on the yield of antibody production as compared with the yield of antibody production of counterpart native antibodies. Additionally, the epitope-tagged antibodies were shown, in an accelerated stability study, to be stable for 24-months (equivalent to 4° C. storage in the accelerated stability study shown in FIG. 19). The Arrhenius model was followed to predict real-time stability of tested antibodies (1 ug/ml concentration in diluent 90103) at intended storage conditions (i.e. 4° C.) based on data collected at elevated temperatures (i.e. 37° C. and 45° C.) for shorter periods (e.g. 5 to 10 days).

Applicants have also conducted tests utilizing surface plasmon resonance to determine binding kinetics between anti-tag antibodies and the tandem tags present on the disclosed epitope-tagged antibodies. As noted in Example 12, Applicants have discovered that the kinetics are avidity catalyzed between the anti-tag antibodies and the tandem tags on the epitope-tagged antibodies (see FIGS. 31A through 31E). As noted herein, "avidity" refers to the overall stability of a complex between two or more populations of molecules (e.g. an anti-tag antibody and the respective tag), i.e., the functional combining strength of an interaction between the two populations of molecules. "Avidity catalyzed" here refers to the cooperative and synergistic bonding of anti-tag antibodies to tandem tags, possibly, two or more than two tags, in the epitope-tagged antibodies. For example, binding of an anti-V5 antibody to the tandem V5 tags on a recombinant antibody of the present disclosure, e.g. a CD68 epitope-tagged antibody, has been found to be at least 240-fold avidity catalyzed to a single V5 tag (see FIG. 31A). Likewise, binding of an anti-HA antibody to the tandem HA tags on a recombinant antibody of the present disclosure, e.g. a CD20 epitope-tagged antibody, has been found to be at least 2000-fold avidity catalyzed to a single HA tag (see FIG. 31D). Without wishing to be bound by any particular theory, it is believed that such kinetics significantly improve secondary antibody performance. In addition, Applicants believe that the association rates between the anti-tag antibodies and the tags of the epitope-tagged antibodies are rapid and that the dissociation rates are either out of the instrument's specification or were drifting positively for all tag configurations studied (see FIGS. 32A through 32D).

Applicants have also conducted (a) dynamic light scattering (DLS) experiments to determine (i) hydrodynamic radii of the epitope-tagged antibodies in solution, and (ii) temperature induced aggregation; (b) differential scanning calorimetry (DSC) experiments to determine the influence of the epitope tags on melting temperatures of IgG domains; and (c) SEC experiments to determine the homogeneity of the samples. By virtue of the DSC experiments, Applicants have discovered that the recombinant epitope-tagged antibodies of the present disclosure occur as monomeric immunoglobulins G (IgG) in solution, consistent with the expected DSC pattern for such a monomeric antibody (see FIGS. 28A through 28E). From this, Applicants concluded that the tags of the epitope-tagged antibodies did not disturb the proper folding of the antibody as a whole. As such, the epitope-tagged antibodies maintained proper folding consisting with the primary antibodies from which they were derived, while also adding flexibility to the tandem tags and further allowing accessibility to the epitope tags.

Figure 26:
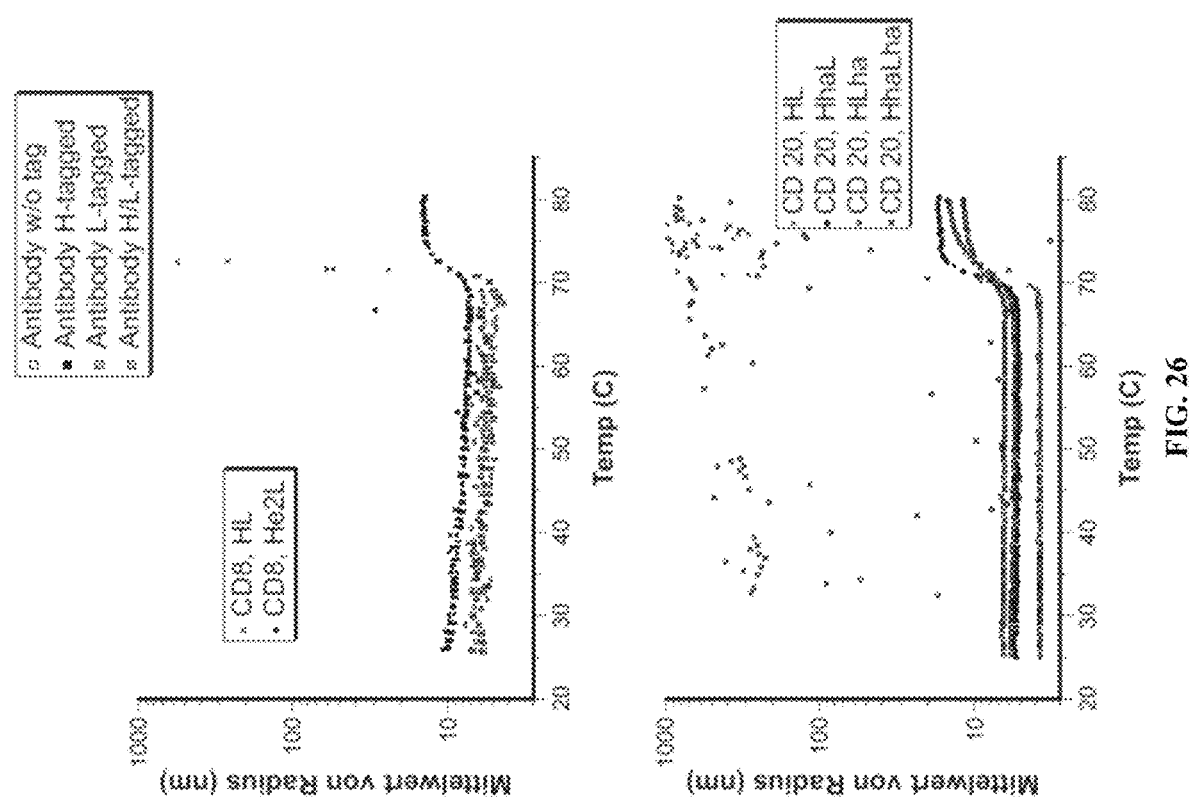
FIG. 26 sets forth dynamic light scattering data for several different epitope-tagged antibodies and their respective untagged antibody.
Figure 26:
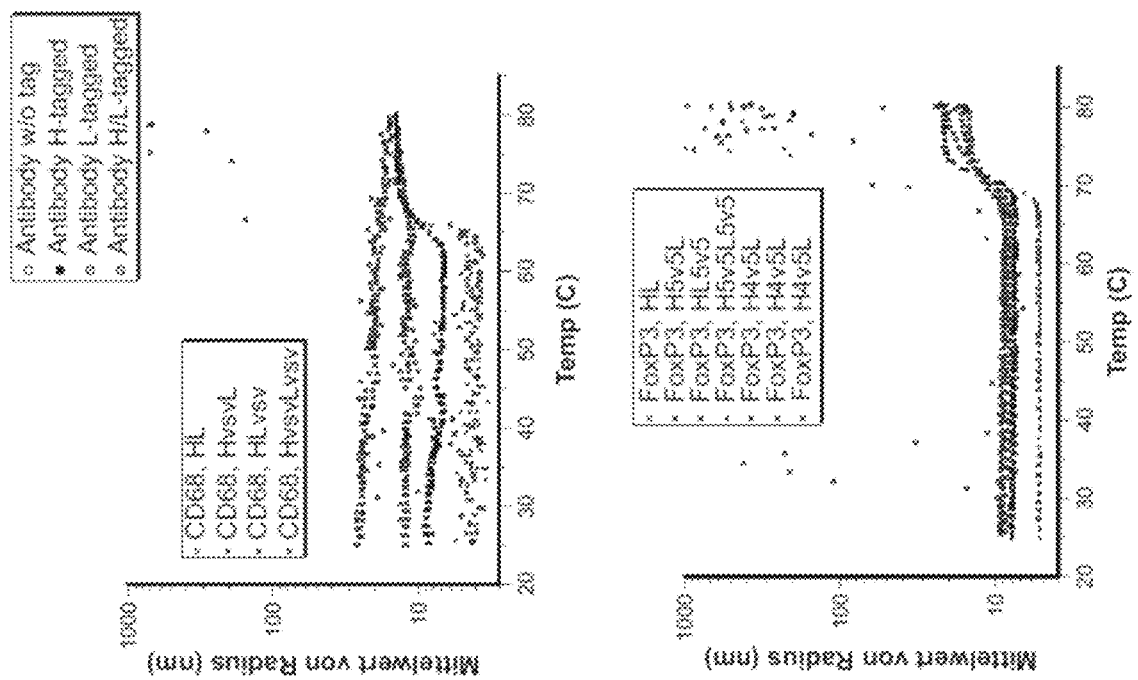
Figure 26:
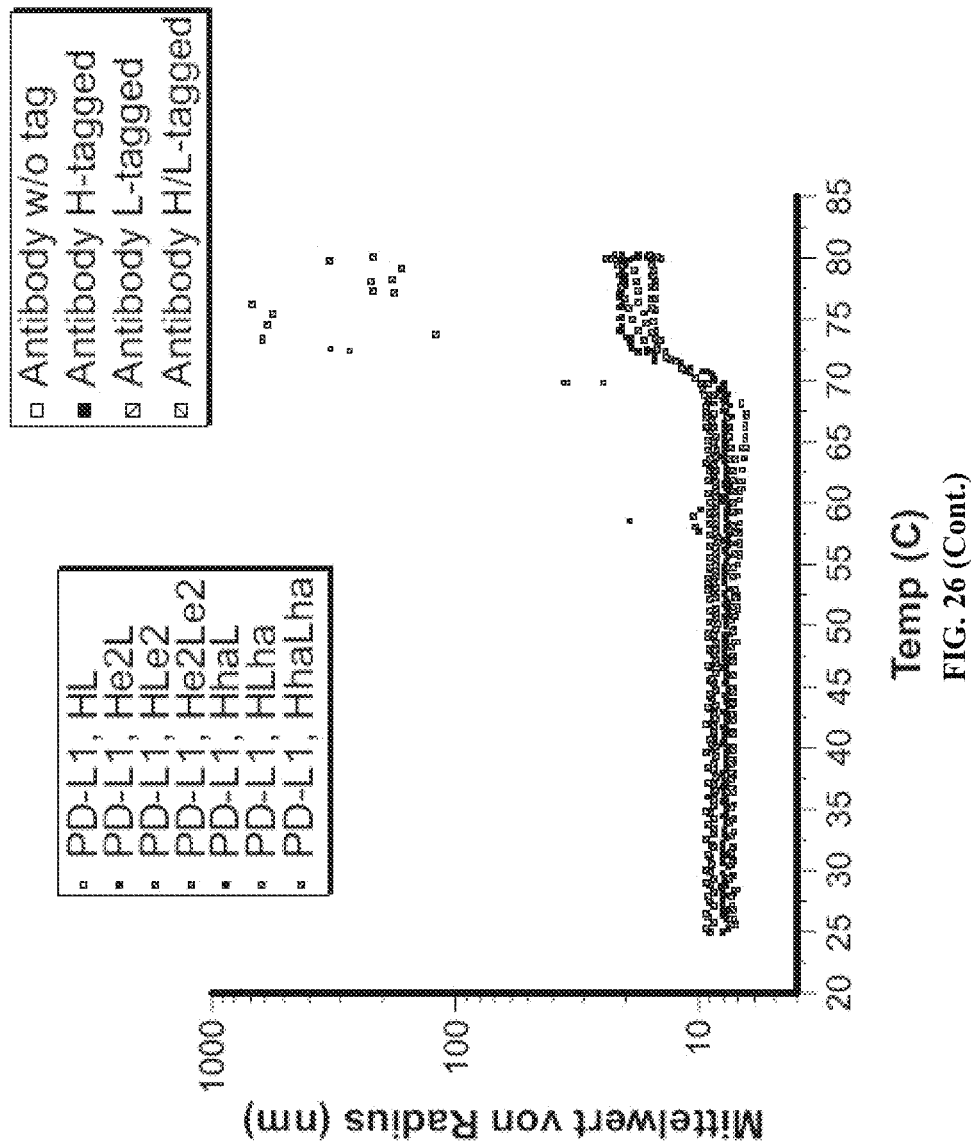

DLS is a technique that may be used to determine the size distribution profile of small particles in suspension, or polymers, e.g. biomolecules, in solution. The DLS experiments conducted by Applicants have shown that the hydrodynamic radius of the epitope-tagged antibodies suggests the relatively unstructured and very flexible nature of the tags, which allow adequate accessibility to the anti-tag antibodies. Applicants have shown that at temperatures greater than 70° C., the untagged antibodies formed substantially large aggregates (i.e. greater than 1000 nm) and precipitated. In contrast, the presently disclosed epitope tagged-antibodies formed particles with hydrodynamic radii of between about 7 nm and about 25 nm. These particles were smaller in the case of epitope-tagged antibodies having tags on both the heavy and light chains, as compared with those epitope-tagged antibodies having tags on only the heavy chain or only the light chain. Notably, Applicants observed no significant differences between the various types of epitope tags incorporated into the epitope-tagged antibodies, including each of the types of tags disclosed herein (see FIG. 26, and also FIGS. 29A through 29E).

The DLS and DSC data also indicated that incorporation of the epitope tags within the light chain of the antibody at least partially destabilized the Fab/CH2 domain and resulted in a decrease in the $T_{agg}$ value up to 4K. In some instances, the DLS data showed a slight increase in $T_{agg}$ of about 1 K and DSC measurements, suggesting an increase of the transition temperature (0.1 K or less) of Peak 1 (see FIGS. 28A through 28E).

Figure 27A:
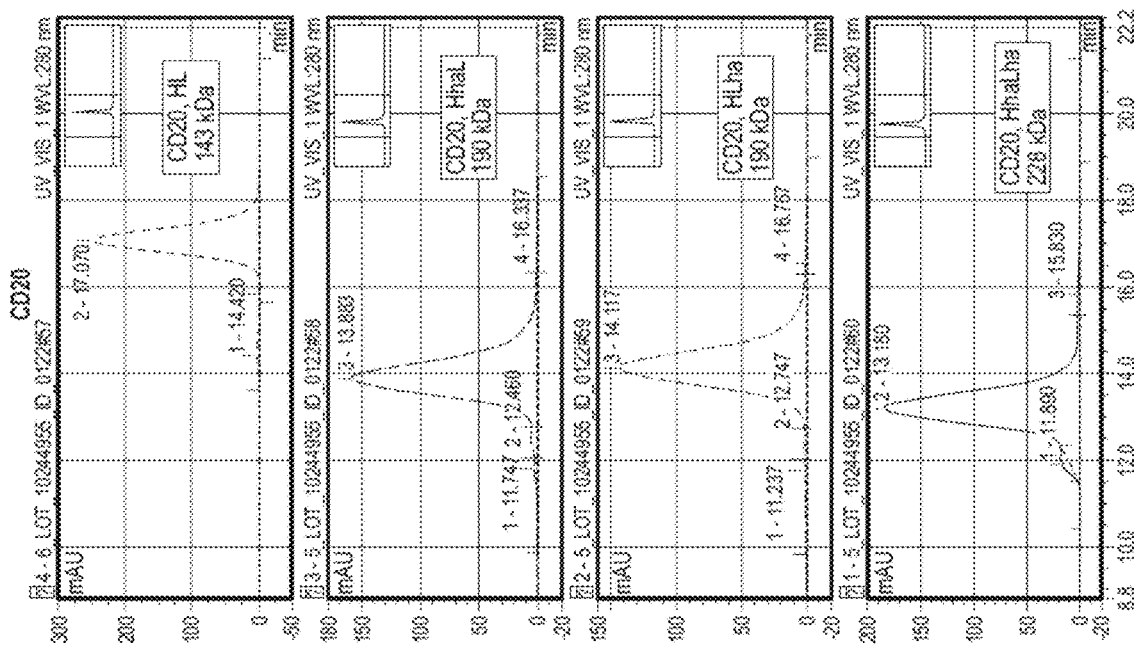
FIG. 27A, FIG. 27B, and FIG. 27C set forth SEC data for various epitope-tagged antibodies and their respective untagged antibody.
Figure 27B:
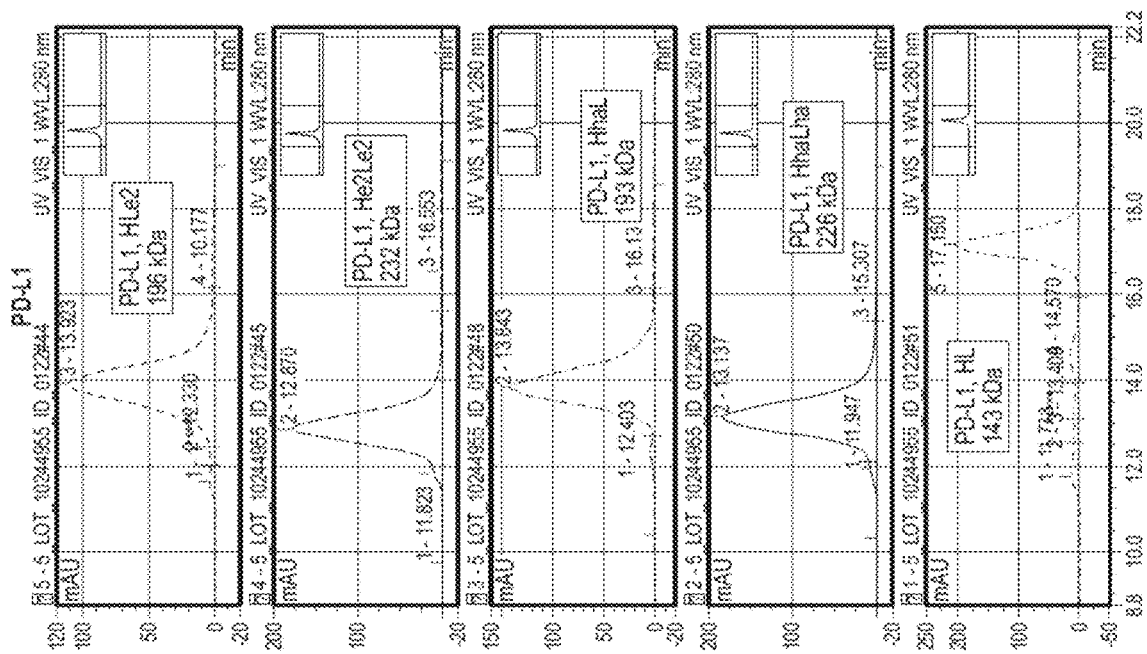
Figure 27C:
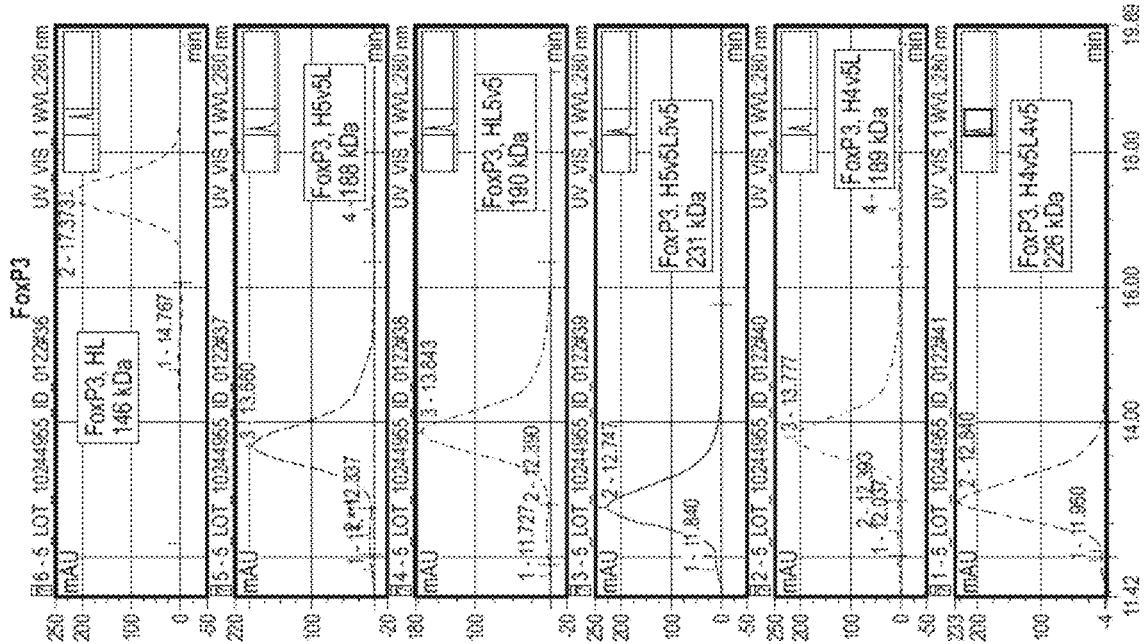
Figure 28A:
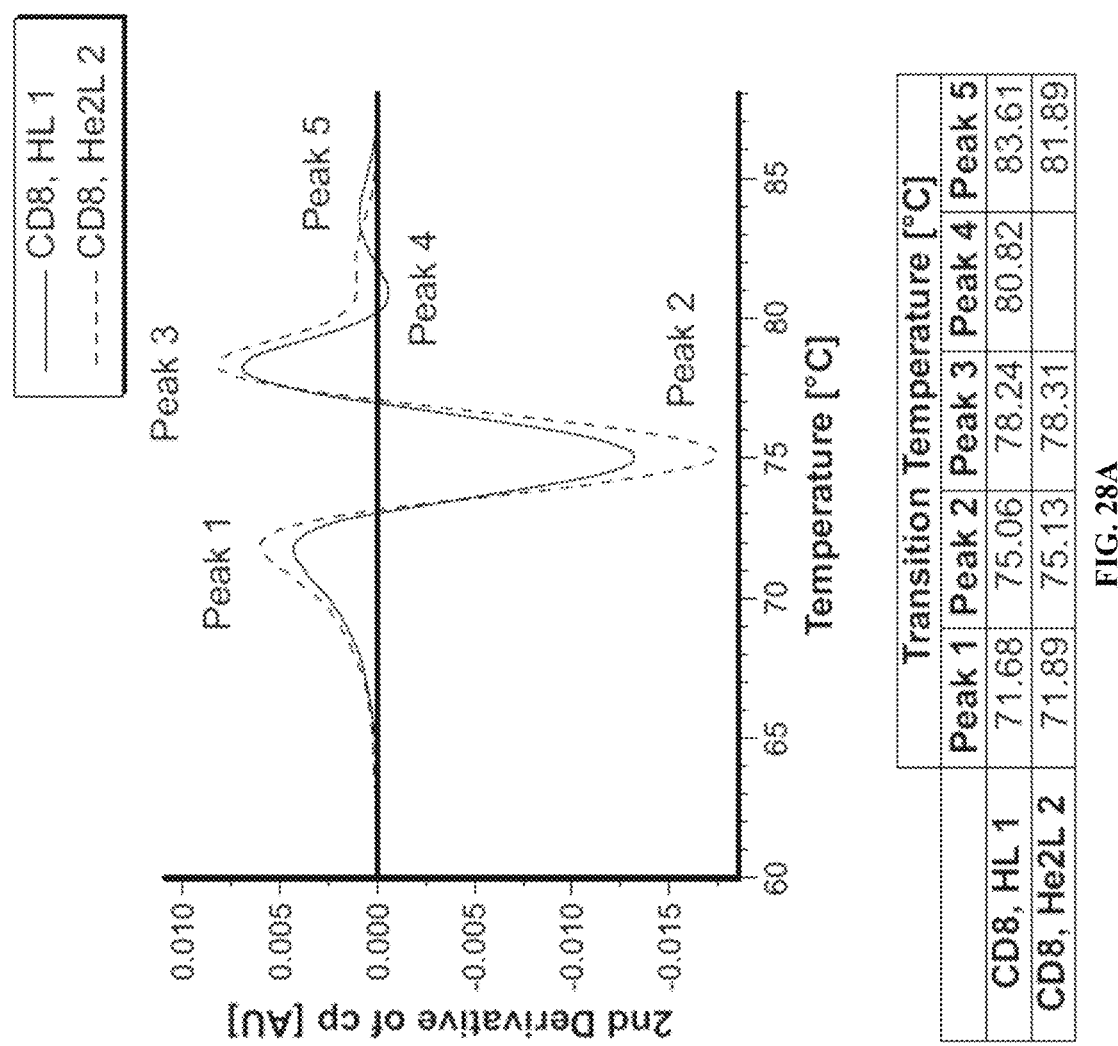
FIG. 28A, FIG. 28B, FIG. 28C, FIG. 28D, and FIG. 28E set forth DSC data for various epitope-tagged antibodies and their respective untagged antibody.
Figure 28B:
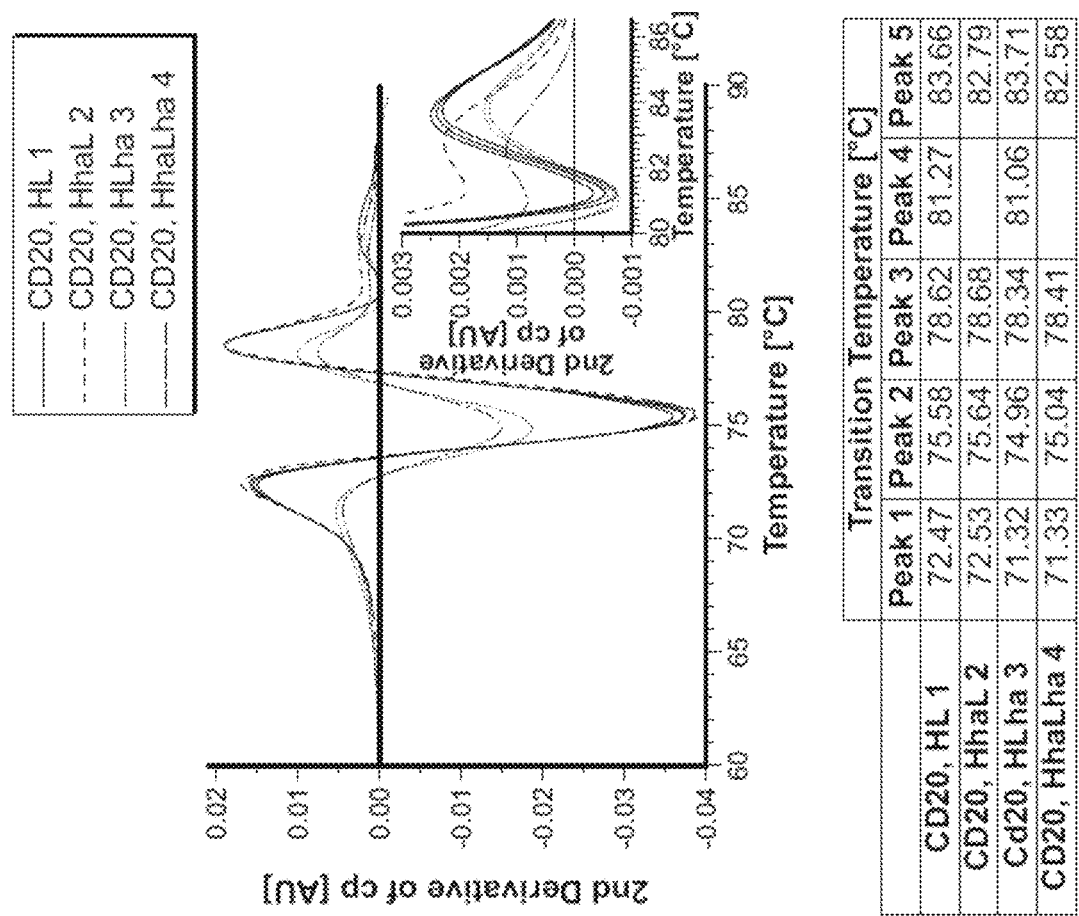
Figure 28C:
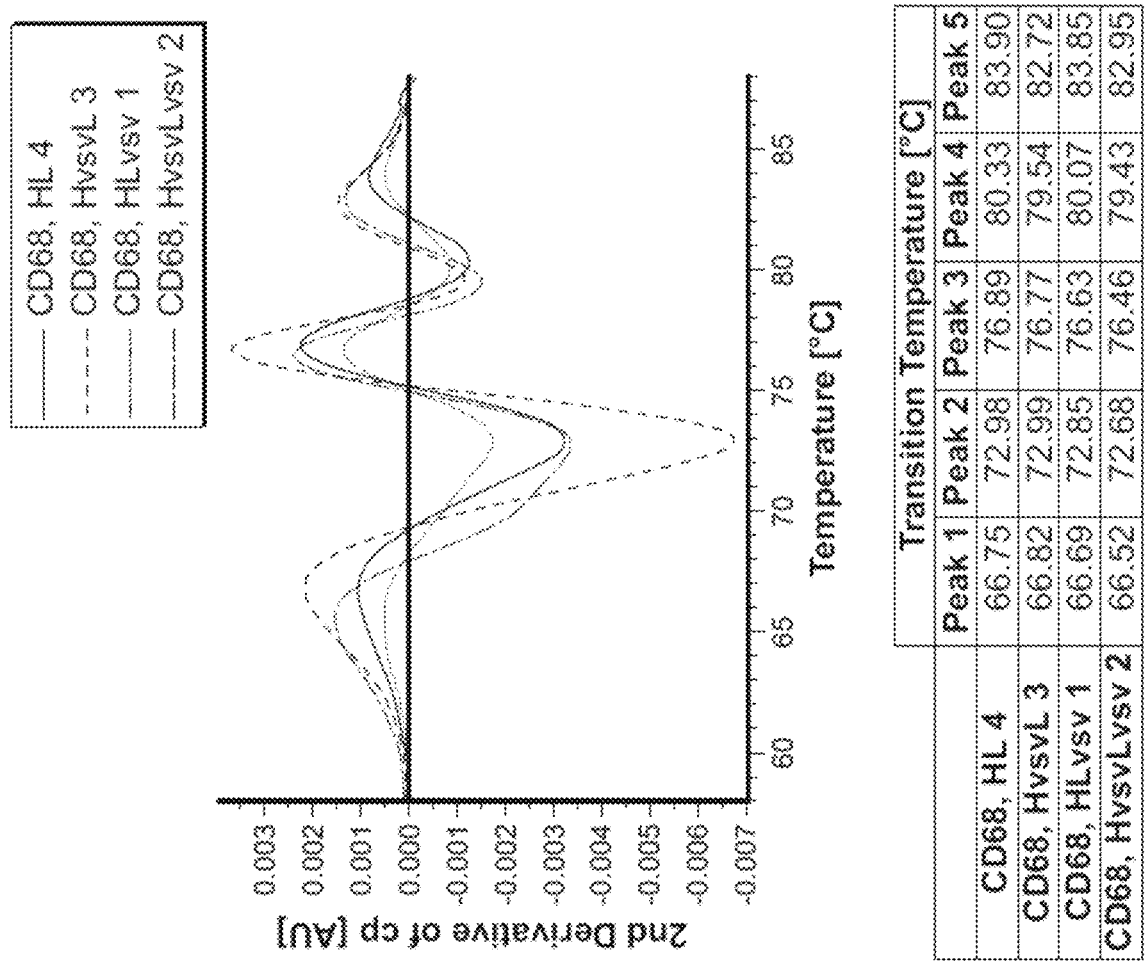
Figure 28D:
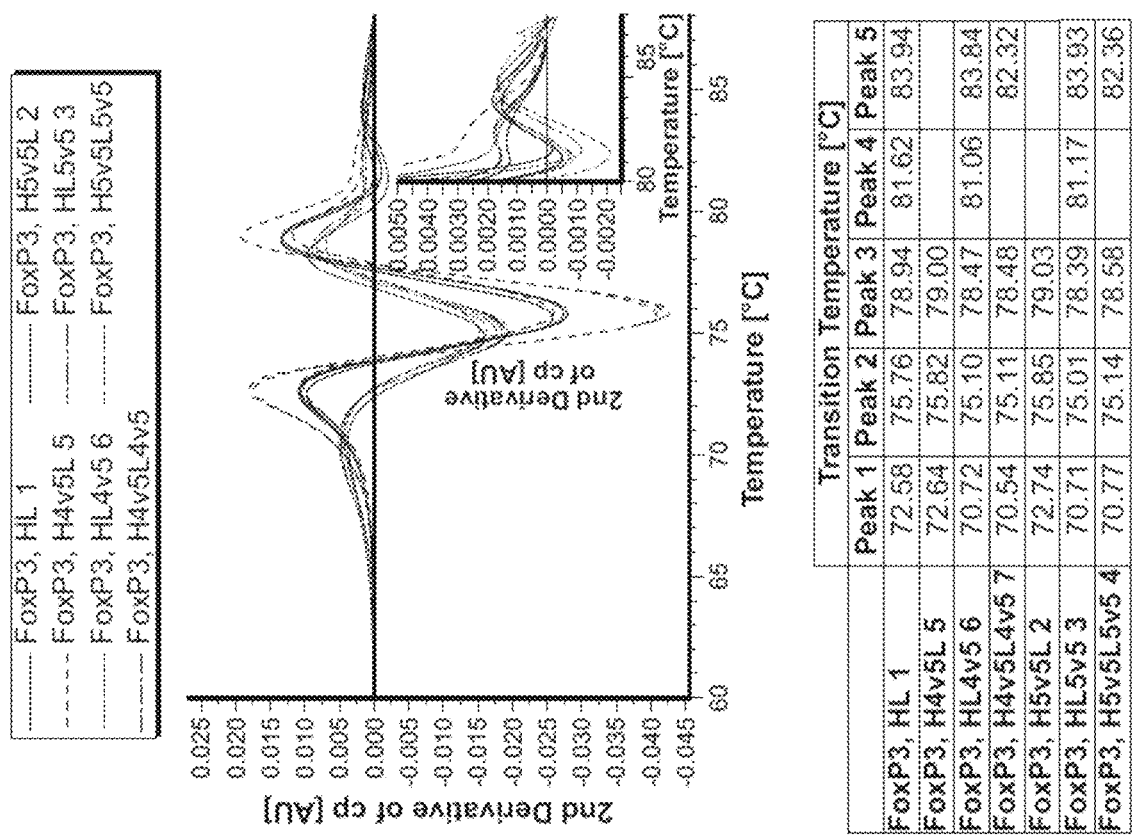
Figure 28E:
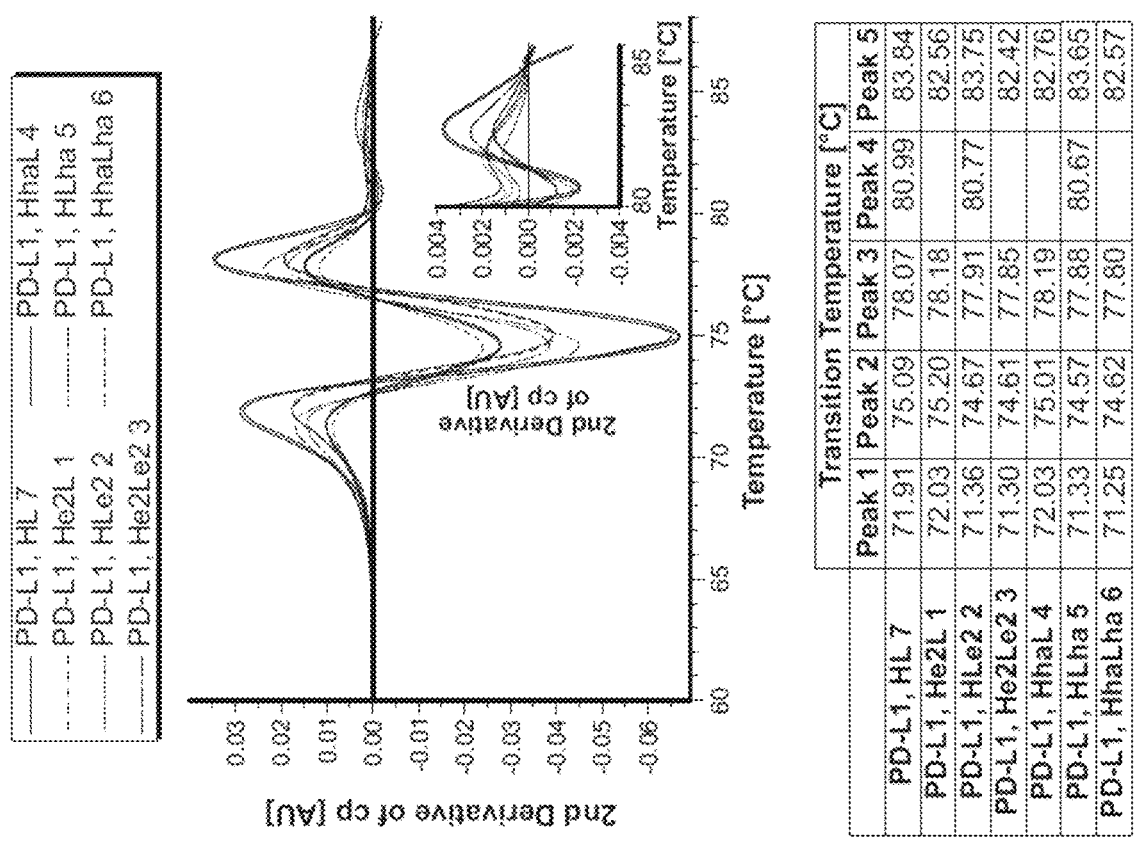
Figure 29A:
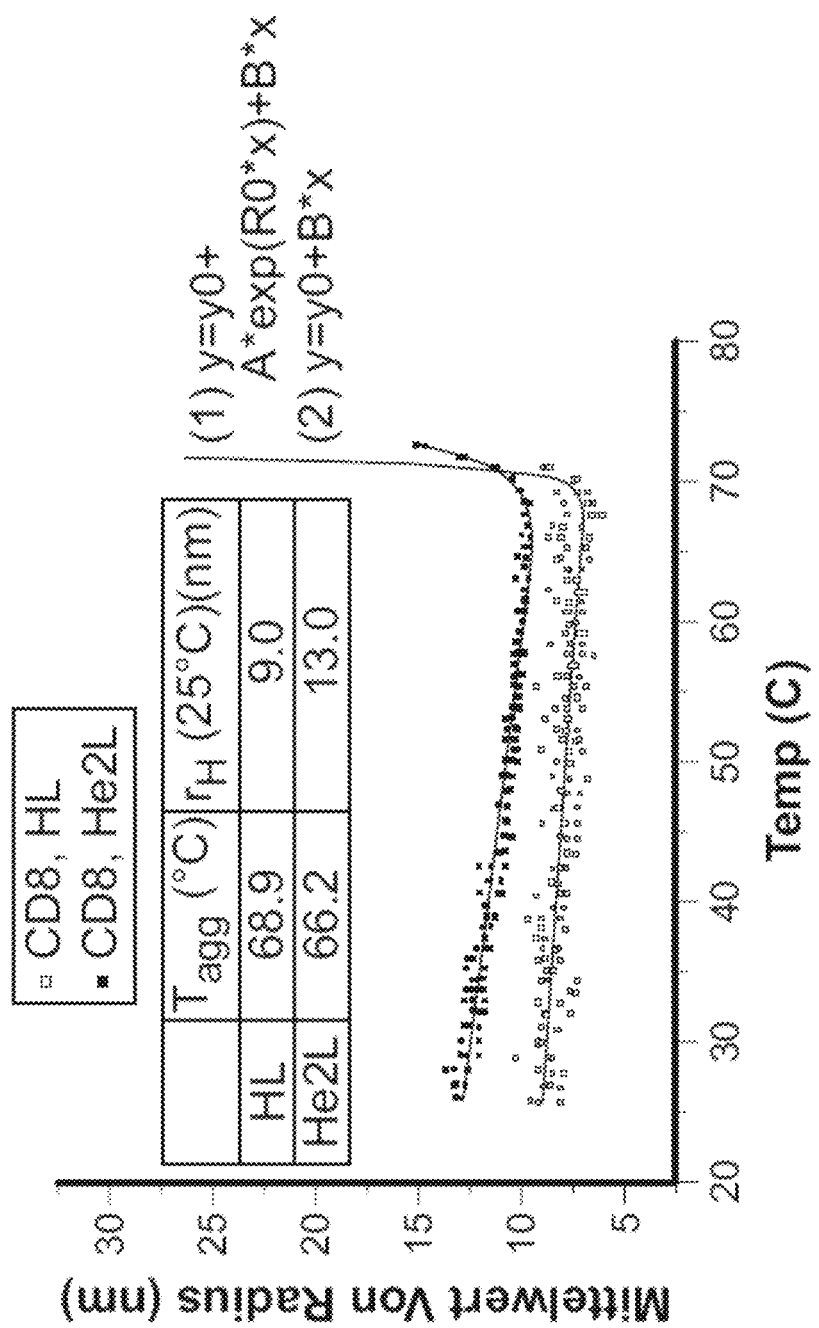
FIG. 29A, FIG. 29B, FIG. 29C, FIG. 29D, and FIG. 29E set forth DLS data for various epitope-tagged antibodies and their respective untagged antibody.
Figure 29B:
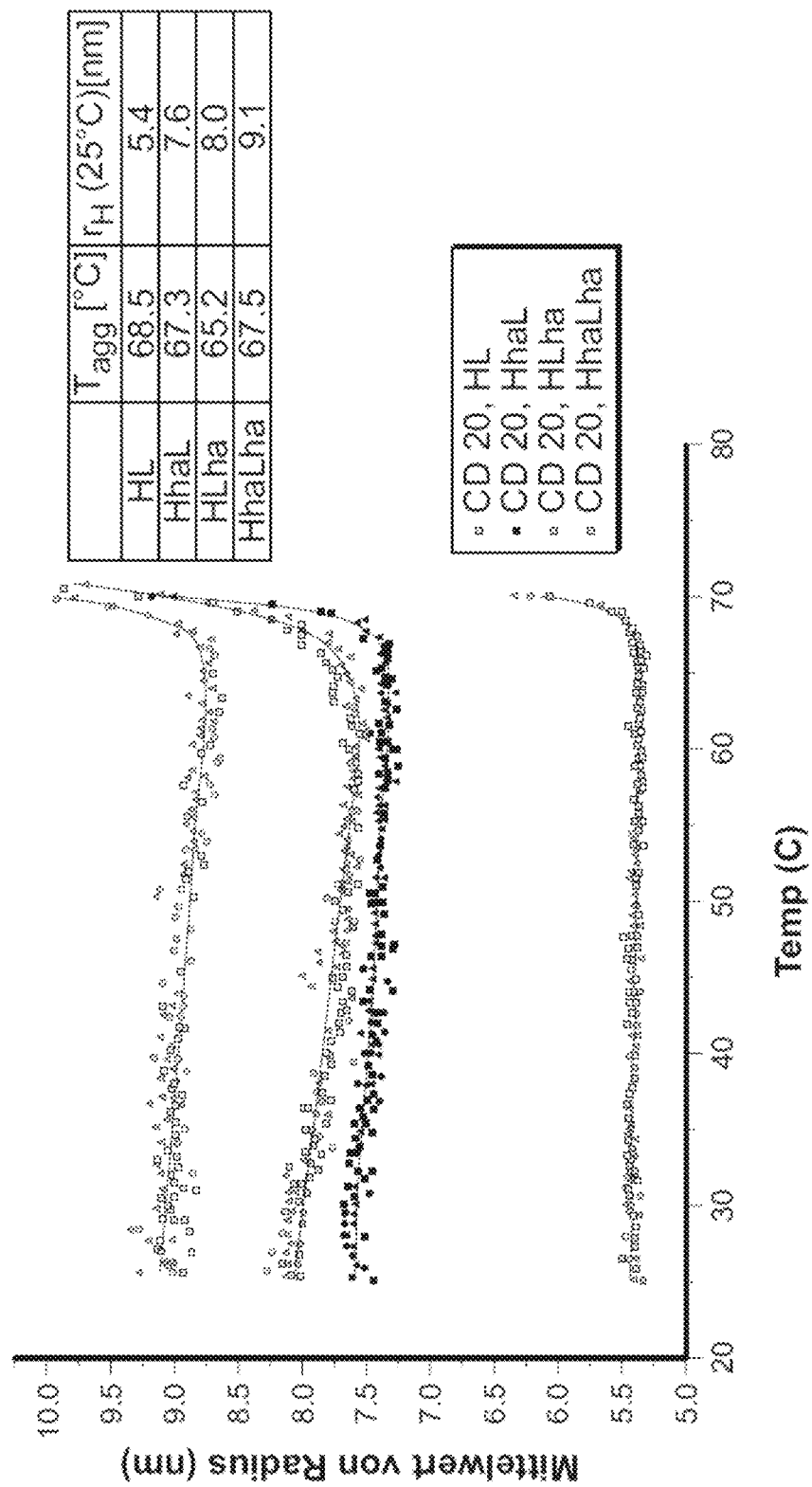
Figure 29C:
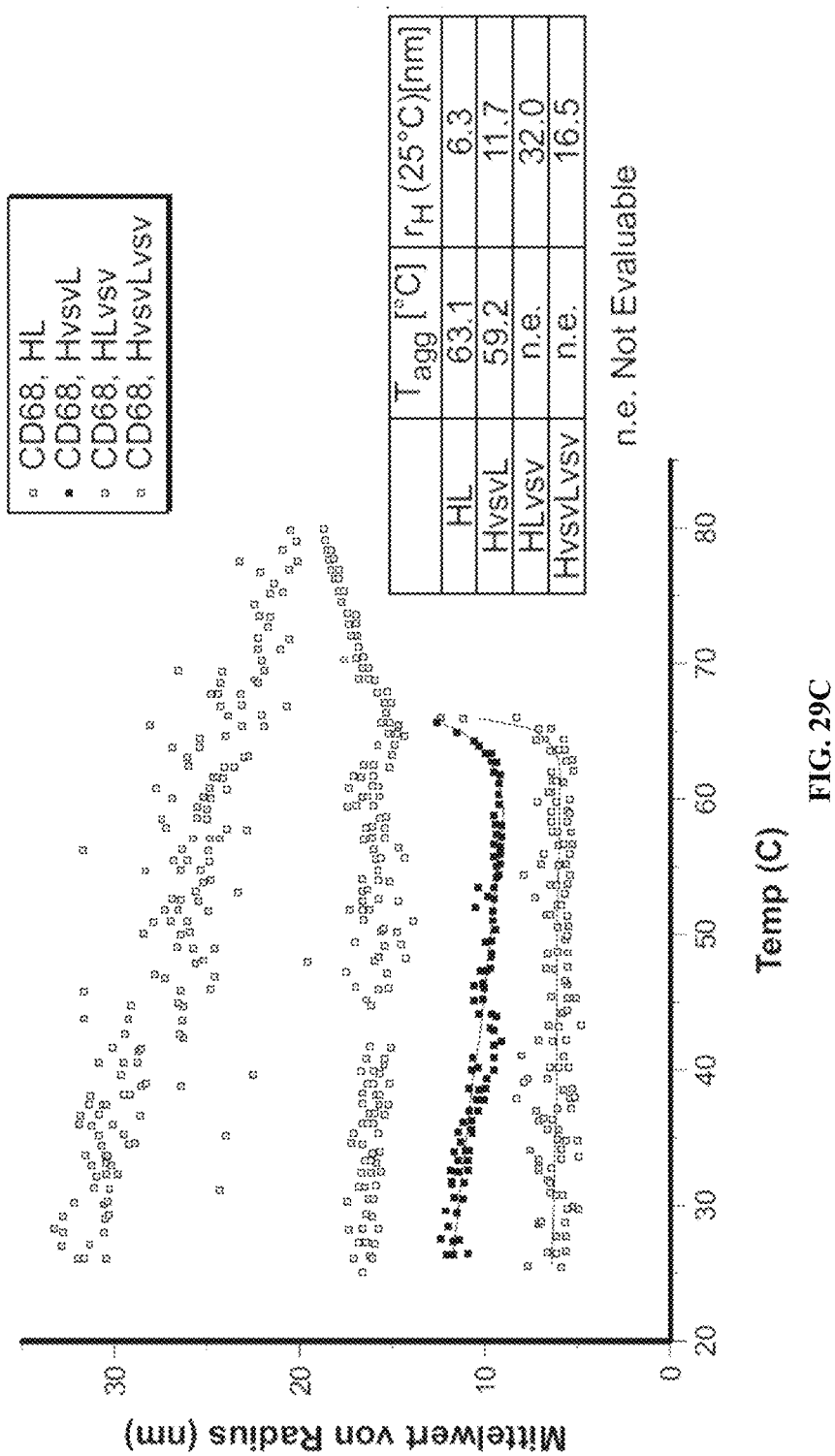
Figure 29D:
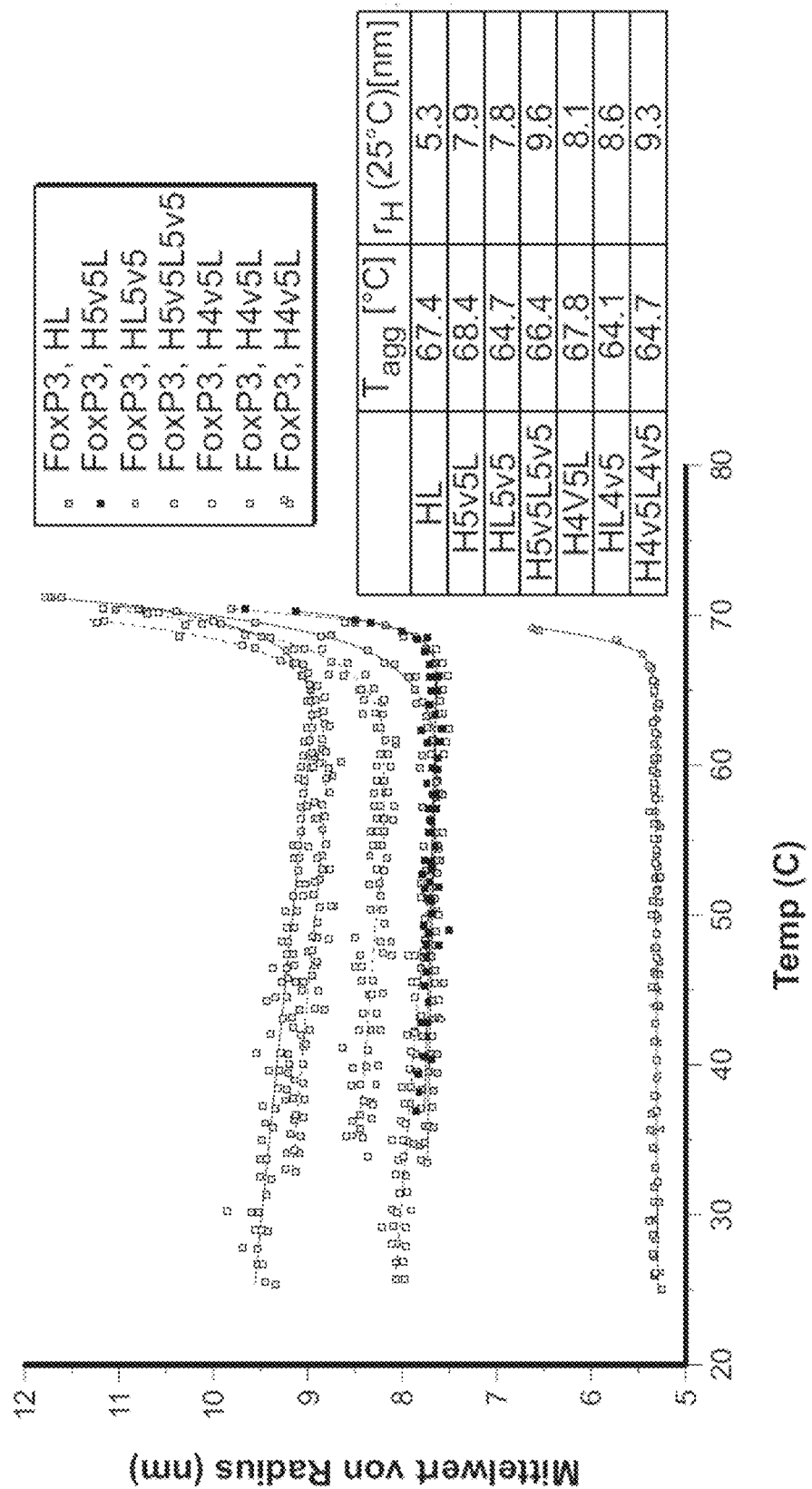
Figure 29E:
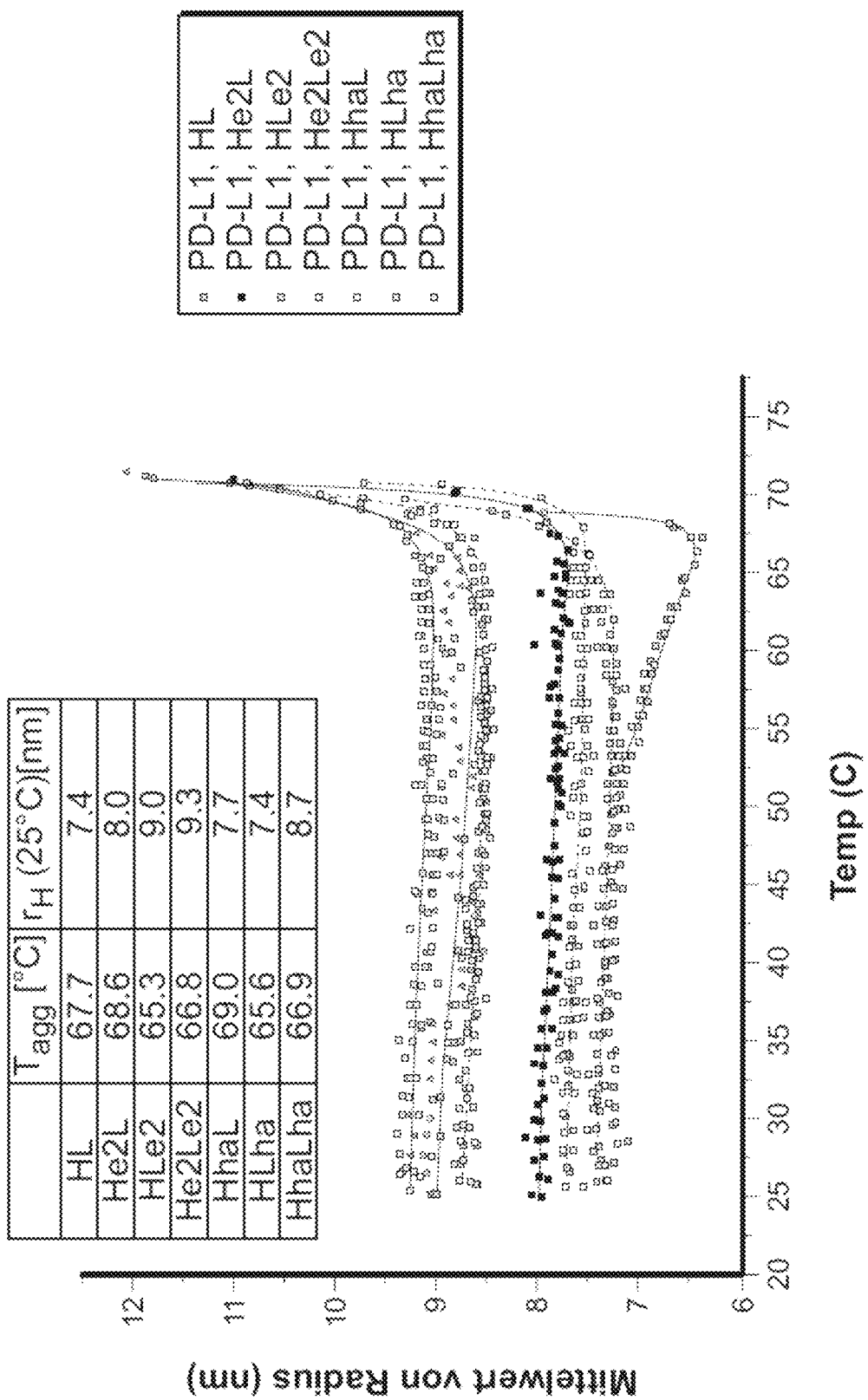

As noted above, Applicants further collected SEC data, including data corresponding to molecular weight determination by right angle scattering (RALS) (see, for example, FIGS. 27A, 27B, and 27C). This data also indicated that all of the tested untagged antibodies and the corresponding epitope-tagged antibodies appeared in solution as monomeric IgGs. Applicants found that the untagged antibodies had a molecular weight ranging from about 140 kDa to about 150 kDa. In some embodiments, those epitope-tagged antibodies having only heavy chain tags or only light chain tags had molecular weights ranging from about 170 kDa to about 210 kDa. In yet other embodiments, those epitope-tagged antibodies having only heavy chain tags or only light chain tags had molecular weights ranging from about 185 kDa to about 205 kDa. In other embodiments, those epitope-tagged antibodies having heavy chain tags or only light chain tags had molecular weights of about 190 kDa. In some embodiments, the epitope-tagged antibodies having both heavy and light chain tags had a molecular weight ranging from between 215 kDa to about 235 kDa. In some embodiments, the epitope-tagged antibodies having both heavy and light chain tags had a molecular weight of between about 220 kDa and about 230 kDa. In addition, SEC data, like the DLS data noted above, suggested that the epitope-tagged antibodies were relatively unstructured and flexible.

When taken together, the results of the DLS, DSC, and SEC experiments indicated that the flexible tags of the epitope-tagged antibodies reduced or prevented the formation of large aggregates, such as when exposed to thermal stresses. It was also able to be concluded that the inclusion of the epitope tags into the antibodies did not disturb the proper folding of the antibody as its whole.

As such, Applicants have shown that epitope-tagged antibodies are stable and, given that they do not exhibit any significant differences in staining as compared with their unmodified, native counterparts, are suitable for use in IHC assays and especially multiplex IHC assays. In addition, Applicants have demonstrated that incorporating epitope tags onto or within the heavy chain of an antibody provides an advantage in terms of thermal stability and quality as compare with incorporating the tags onto the light chain. As will be shown further herein, the epitope-tagged antibodies are believed to be able to be pooled together without cross-reactivity observed with other native antibodies.

Detection of Epitope-Tagged Antibodies

In some embodiments, any epitope-tagged antibody may comprise a detectable moiety and thus the epitope-tagged antibody may be directly detected (e.g. conjugated to a detectable moiety).

In other embodiments, specific reagents are utilized to enable detection of any epitope-tagged antibody, and hence the targets in a tissue sample. In some embodiments, detection reagents are utilized which are specific to the particular epitope tag of the epitope-tagged antibody. In some embodiments, the detection reagents comprise a secondary antibody which is specific for the expressed epitope tags of the epitope-tagged antibody, i.e. the secondary antibody is an anti-epitope or anti-tag antibody. Each anti-tag antibody is designed to detect a specific epitope tag, e.g. one of VSV, V5, HA, etc.

For example, an epitope-tagged antibody expressing one or more VSV epitope tags could be detected by an anti-VSV antibody, i.e. an anti-tag antibody that is specific for expressed VSV epitope tags. Likewise, an epitope-tagged antibody expressing one or more AU5 epitope tags could be detected by an anti-AU5 antibody, i.e. an anti-tag antibody that is specific for expressed AU5 epitope tags.

In some embodiments, the anti-tag antibody may be conjugated to a "detectable moiety" to effectuate detection of the epitope-tagged antibody. A "detectable moiety" is a molecule or material that can produce a detectable (such as visually, electronically or otherwise) signal that indicates the presence (i.e. qualitative analysis) and/or concentration (i.e. quantitative analysis) of the epitope-tagged antibody in a sample. A detectable signal can be generated by any known or yet to be discovered mechanism including absorption, emission and/or scattering of a photon (including radio frequency, microwave frequency, infrared frequency, visible frequency and ultra-violet frequency photons).

In some embodiments, the detectable moiety of the anti-tag antibody includes chromogenic, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Of course, the detectable moieties can themselves also be detected indirectly, e.g. if the detectable moiety is a hapten, then yet another antibody specific to that detectable moiety may be utilized in the detection of the detectable moiety, as known to those of ordinary skill in the art.

In some embodiments, the anti-tag antibody includes a detectable moiety selected from the group consisting of DAB; AEC; CN; BCIP/NBT; fast red; fast blue; fuchsin; NBT; ALK GOLD; CASCADE BLUE acetyl azide; Dapoxylsulfonic acid/carboxylic acid succinimidyl ester; DY-405; ALEXA FLUOR 405 succinimidyl ester; CASCADE YELLOW succinimidyl ester; pyridyloxazole succinimidyl ester (PyMPO); PACIFIC BLUE succinimidyl ester; DY-415; 7-hydroxycoumarin-3-carboxylic acid succinimidyl ester; DYQ-425; 6-FAM phosphoramidite; Lucifer Yellow; iodoacetamide; ALEXA FLUOR 430 succinimidyl ester; Dabcyl succinimidyl ester; NBD chloride/fluoride; QSY 35 succinimidyl ester; DY-485XL; CY2 succinimidyl ester; DY-490; OREGON GREEN 488 carboxylic acid succinimidyl ester; ALEXA FLUOR 488 succinimidyl ester; BODIPY 493/503 C3 succinimidyl ester; DY-480XL; BODIPY FL C3 succinimidyl ester; BODIPY FL C5 succinimidyl ester; BODIPY FL-X succinimidyl ester; DYQ-505; OREGON GREEN 514 carboxylic acid succinimidyl ester; DY-510XL; DY-481XL; 6-carboxy-4',5'-dichloro-2',7'-dimethoxyfluorescein succinimidyl ester (JOE); DY-520XL; DY-521XL; BODIPY R6G C3 succinimidyl ester; erythrosin isothiocyanate; 5-carboxy-2',4',5',7'-tetrabromosulfonefluorescein succinimidyl ester; ALEXA FLUOR 532 succinimidyl ester; 6-carboxy-2',4,4',5'7,7'-hexachlorofluorescein succinimidyl ester (HEX); BODIPY 530/550 C3 succinimidyl ester; DY-530; BODIPY TMR-X succinimidyl ester; DY-555; DYQ-1; DY-556; CY3 succinimidyl ester; DY-547; DY-549; DY-550; ALEXA FLUOR 555 succinimidyl ester; ALEXA FLUOR 546 succinimidyl ester; DY-548; BODIPY 558/568 C3 succinimidyl ester; Rhodamine red-X succinimidyl ester; QSY 7 succinimidyl ester; BODIPY 564/570 C3 succinimidyl ester; BODIPY 576/589 C3 succinimidyl ester; carboxy-X-rhodamine (ROX); succinimidyl ester; ALEXA FLUOR 568 succinimidyl ester; DY-590; BODIPY 581/591 C3 succinimidyl ester; DY-591; BODIPY TR-X succinimidyl ester; ALEXA FLUOR 594 succinimidyl ester; DY-594; carboxynaphthofluorescein succinimidyl ester; DY-605; DY-610; ALEXA FLUOR 610 succinimidyl ester; DY-615; BODIPY 630/650-X succinimidyl ester; erioglaucine; ALEXA FLUOR 633 succinimidyl ester; ALEXA FLUOR 635 succinimidyl ester; DY-634; DY-630; DY-631; DY-632; DY-633; DYQ-2; DY-636; BODIPY 650/665-X succinimidyl ester; DY-635; CY5 succinimidyl ester; ALEXA FLUOR 647 succinimidyl ester; DY-647; DY-648;

DY-650; DY-654; DY-652; DY-649; DY-651; DYQ-660; DYQ-661; ALEXA FLUOR 660 succinimidyl ester; CY5.5 succinimidyl ester; DY-677; DY-675; DY-676; DY-678; ALEXA FLUOR 680 succinimidyl ester; DY-679; DY-680; DY-682; DY-681; DYQ-3; DYQ-700; ALEXA FLUOR 700 succinimidyl ester; DY-703; DY-701; DY-704; DY-700; DY-730; DY-731; DY-732; DY-734; DY-750; CY7 succinimidyl ester; DY-749; DYQ-4; and CY7.5 succinimidyl ester.

Fluorophores belong to several common chemical classes including coumarins, fluoresceins (or fluorescein derivatives and analogs), rhodamines, resorufins, luminophores and cyanines. Additional examples of fluorescent molecules can be found in Molecular Probes Handbook A Guide to Fluorescent Probes and Labeling Technologies, Molecular Probes, Eugene, OR, TheroFisher Scientific, $11^{th}$ Edition. In other embodiments, the fluorophore is selected from xanthene derivatives, cyanine derivatives, squaraine derivatives, naphthalene derivatives, coumarin derivatives, oxadiazole derivatives, anthracene derivatives, pyrene derivatives, oxazine derivatives, acridine derivatives, arylmethine derivatives, and tetrapyrrole derivatives. In other embodiments, the fluorescent moiety is selected from a CF dye (available from Biotium), DRAQ and CYTRAK probes (available from BioStatus), BODIPY (available from Invitrogen), ALEXA FLUOR (available from Invitrogen), Dyight-Flier-DYLIGHT FLUOR (e.g. DYLIGHT 649) (available from Thermo Scientific, Pierce), Atto and Tracy (available from Sigma Aldrich), FLUOPROBES (available from Interchim), ABBERIOR Dyes (available from Abberior), DY and MEGASTOKES Dyes (available from Dyomics), SULFO CY dyes (available from Cyandye), HILYTE FLUOR (available from AnaSpec), SETA, SETAU and SQUARE Dyes (available from SETA BioMedicals), QUASAR and CAL FLUOR dyes (available from Biosearch Technologies), SURELIGHT Dyes (available from APC, RPEPerCP, Phycobilisomes) (Columbia Biosciences), and APC, APCXL, RPE, BPE (available from Phyco-Biotech, Greensea, Prozyme, Flogen).

In some embodiments, the epitope-tagged antibody is an anti-biomarker antibody, and detection of the biomarker is facilitated by contacting the sample with an anti-tag specific binding agent (such as an anti-tag antibody) adapted to deposit a detectable moiety in close proximity to the anti-biomarker antibody when bound to the sample. In some embodiments, the anti-tag antibody is directly conjugated to the detectable moiety (hereafter, "direct method"). In other embodiments, the detectable moiety is indirectly associated with the anti-tag specific binding agent (hereafter, "indirect method"). In some embodiments, the detection reagents are suitable for an indirect method, wherein the detectable moiety is deposited via an enzymatic reaction localized to the biomarker via an anti-biomarker antibody/anti-tag specific binding agent complex. Suitable enzymes for such reactions are well-known and include, but are not limited to, oxidoreductases, hydrolases, and peroxidases. Specific enzymes explicitly included are horseradish peroxidase (HRP), alkaline phosphatase (AP), acid phosphatase, glucose oxidase, β-galactosidase, β-glucuronidase, and β-lactamase. The enzyme may be directly conjugated to the anti-tag antibody, or may be indirectly associated with the anti-tag antibody via a labeling conjugate. As used herein, a "labeling conjugate" comprises:

(a) a specific detection reagent; and
(b) an enzyme conjugated to the specific detection reagent, wherein the enzyme is reactive with the chromogenic substrate, signaling conjugate, or enzyme-reactive dye under appropriate reaction conditions to effect in situ generation of the dye and/or deposition of the dye on the tissue sample.

As used herein, the term "specific detection reagent" shall refer to any composition of matter that is capable of specifically binding to a target chemical structure in the context of a cellular sample. As used herein, the phrase "specific binding," "specifically binds to," or "specific for" or other similar iterations refers to measurable and reproducible interactions between a target and a specific detection reagent, which is determinative of the presence of the target in the presence of a heterogeneous population of molecules including biological molecules. For example, an antibody that specifically binds to a target is an antibody that binds this target with greater affinity, avidity, more readily, and/or with greater duration than it binds to other targets. In one embodiment, the extent of binding of a specific detection reagent to an unrelated target is less than about 10% of the binding of the antibody to the target as measured, e.g., by a radioimmunoassay (RIA). In certain embodiments, a biomarker-specific reagent that specifically binds to a target has a dissociation constant (Kd) of ≤1 µM, ≤100 nM, ≤10 nM, ≤1 nM, or <0.1 nM. In another embodiment, specific binding can include, but does not require exclusive binding. Exemplary specific detection reagents include nucleic acid probes specific for particular nucleotide sequences; antibodies and antigen binding fragments thereof; and engineered specific binding compositions, including ADNECTINs (scaffold based on 10th FN3 fibronectin; Bristol-Myers-Squibb Co.), AFFIBODYs (scaffold based on Z domain of protein A from S. aureus; Affibody AB, Solna, Sweden), AVIMERs (scaffold based on domain A/LDL receptor; Amgen, Thousand Oaks, CA), dAbs (scaffold based on VH or VL antibody domain; GlaxoSmithKline PLC, Cambridge, UK), DARPins (scaffold based on Ankyrin repeat proteins; Molecular Partners AG, Zurich, CH), ANTICALINs (scaffold based on lipocalins; Pieris AG, Freising, DE), NANOBODYs (scaffold based on VHH (camelid Ig); Ablynx N/V, Ghent, BE), TRANS-BODYs (scaffold based on Transferrin; Pfizer Inc., New York, NY), SMIPs (Emergent Biosolutions, Inc., Rockville, MD), and TETRANECTINs (scaffold based on C-type lectin domain (CTLD), tetranectin; Borean Pharma A/S, Aarhus, DK). Descriptions of such engineered specific binding structures are reviewed by Wurch et al., Development of Novel Protein Scaffolds as Alternatives to Whole Antibodies for Imaging and Therapy: Status on Discovery Research and Clinical Validation, Current Pharmaceutical Biotechnology, Vol. 9, pp. 502-509 (2008), the content of which is incorporated by reference. In non-limiting examples, the specific detection reagent of the labeling conjugate may be a secondary detection reagent (such as a species-specific secondary antibody bound to an anti-tag antibody, an anti-tag antibody bound to an epitope-tagged anti-tag antibody specific for the anti-biomarker antibody, an anti-hapten antibody bound to a hapten-conjugated anti-tag antibody, or a biotin-binding protein bound to a biotinylated anti-tag antibody antibody), or other such arrangements. An enzyme thus localized to the sample-bound anti-biomarker antibody can then be used in a number of schemes to deposit a detectable moiety.

In some cases, the enzyme reacts with a chromogenic compound/substrate. Particular non-limiting examples of chromogenic compounds/substrates include 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue, or tetrazolium violet.

In some embodiments, the enzyme can be used in a metallographic detection scheme. Metallographic detection methods include using an enzyme such as alkaline phosphatase in combination with a water-soluble metal ion and a redox-inactive substrate of the enzyme. In some embodiments, the substrate is converted to a redox-active agent by the enzyme, and the redox-active agent reduces the metal ion, causing it to form a detectable precipitate. (see, for example, U.S. patent application Ser. No. 11/015,646, filed Dec. 20, 2004, PCT Publication No. 2005/003777 and U.S. Patent Application Publication No. 2004/0265922; each of which is incorporated by reference herein in its entirety). Metallographic detection methods include using an oxidoreductase enzyme (such as horseradish peroxidase) along with a water soluble metal ion, an oxidizing agent and a reducing agent, again to for form a detectable precipitate. (See, for example, U.S. Pat. No. 6,670,113, which is incorporated by reference herein in its entirety).

In some embodiments, the enzymatic action occurs between the enzyme and the dye itself, wherein the reaction converts the dye from a non-binding species to a species deposited on the sample. For example, reaction of DAB with a peroxidase (such as horseradish peroxidase) oxidizes the DAB, causing it to precipitate.

In yet other embodiments, the detectable moiety is deposited via a signaling conjugate comprising a latent reactive moiety configured to react with the enzyme to form a reactive species that can bind to the sample or to other detection components. These reactive species are capable of reacting with the sample proximal to their generation, i.e. near the enzyme, but rapidly convert to a non-reactive species so that the signaling conjugate is not deposited at sites distal from the site at which the enzyme is deposited. Examples of latent reactive moieties include: quinone methide (QM) analogs, such as those described at WO2015124703A1, and tyramide conjugates, such as those described at, WO2012003476A2, each of which is hereby incorporated by reference herein in its entirety. In some examples, the latent reactive moiety is directly conjugated to a dye, such as N,N'-biscarboxypentyl-5,5'-disulfonato-indodicarbocyanine (Cy5), 4-(dimethylamino) azobenzene-4'-sulfonamide (DABSYL), tetramethylrhodamine (DISCO Purple), and Rhodamine 110 (Rhodamine). In other examples, the latent reactive moiety is conjugated to one member of a specific binding pair, and the dye is linked to the other member of the specific binding pair. In other examples, the latent reactive moiety is linked to one member of a specific binding pair, and an enzyme is linked to the other member of the specific binding pair, wherein the enzyme is (a) reactive with a chromogenic substrate to effect generation of the dye, or (b) reactive with a dye to effect deposition of the dye (such as DAB). Examples of specific binding pairs include:

(1) a biotin or a biotin derivative (such as desthiobiotin) linked to the latent reactive moiety, and a biotin-binding entity (such as avidin, streptavidin, deglycosylated avidin (such as NEUTRAVIDIN), or a biotin binding protein having a nitrated tyrosine at its biotin binding site (such as CAPTAVIDIN)) linked to a dye or to an enzyme reactive with a chromogenic substrate or reactive with a dye (for example, a peroxidase linked to the biotin-binding protein when the dye is DAB);

(2) epitope tags and associated anti-tag antibodies; and (2) a hapten linked to the latent reactive moiety, and an anti-hapten antibody linked to a dye or to an enzyme reactive with a chromogenic substrate or reactive with a dye (for example, a peroxidase linked to the biotin-binding protein when the dye is DAB).

Non-limiting examples of anti-tag antibody and detection reagent combinations are set forth in Table 1:

TABLE 1

| A. Anti-tag antibody linked directly to detectable moiety |
|---|

Anti-tag antibody-Dye conjugate

| B. Anti-tag antibody linked to enzyme reacting with detectable moiety |
|---|

Anti-tag antibody-Enzyme conjugate + DAB
Anti-tag antibody-Enzyme conjugate + Chromogen

| C. Anti-tag antibody linked to Enzyme reacting with detectable moiety |
|---|

| | |
|---|---|
| C1. Signaling conjugate comprises detectable moiety | Anti-tag antibody-Enzyme conjugate + QM-Dye conjugate |
| | Anti-tag antibody-Enzyme conjugate + Tyramide-Dye conjugate |
| C2. Signaling conjugate comprises enzyme that reacts directly with detectable moiety | Anti-tag antibody-Enzyme conjugate + QM-Enzyme conjugate + DAB |
| | Anti-tag antibody-Enzyme conjugate + QM-Enzyme conjugate + Chromogen |
| | Anti-tag antibody-Enzyme conjugate + Tyramide-Enzyme conjugate + DAB |
| | Anti-tag antibody-Enzyme conjugate + Tyramide-Enzyme conjugate + Chromogen |
| C3. Signaling conjugate comprises enzyme that reacts with second signaling conjugate comprising detectable moiety | Anti-tag antibody-Enzyme conjugate + QM-Enzyme conjugate + QM-Dye conjugate |
| | Anti-tag antibody-Enzyme conjugate + QM-Enzyme conjugate + Tyramide-Dye conjugate |
| | Anti-tag antibody-Enzyme conjugate + Tyramide-Enzyme conjugate + QM-Dye conjugate |
| | Anti-tag antibody-Enzyme conjugate + Tyramide-Enzyme conjugate + Tyramide-Dye conjugate |

TABLE 1-continued

| | |
|---|---|
| C4. Signaling conjugate comprises member of a specific binding pair and other member of binding pair is linked to detectable moiety | Anti-tag antibody-Enzyme conjugate + Tyramide-(biotin or epitope tag or hapten) conjugate + Dye-(avidin or anti-tag antibody or anti-hapten antibody) conjugate<br>Anti-tag antibody-Enzyme conjugate + QM-(biotin or epitope tag or hapten) conjugate + Dye-(avidin or anti-tag antibody or anti-hapten antibody) conjugate |
| C5. Signaling conjugate comprises member of a specific binding pair and other member of binding pair is linked to enzyme reactive with detectable moiety | Anti-tag antibody-Enzyme conjugate + QM-(biotin or epitope tag or hapten) conjugate + Enzyme-(avidin or anti-tag antibody or anti-hapten antibody) conjugate + DAB<br>Anti-tag antibody-Enzyme conjugate + QM-(biotin or epitope tag or hapten) conjugate + Enzyme-(avidin or anti-tag antibody or anti-hapten antibody) conjugate + Chromogen<br>Anti-tag antibody-Enzyme conjugate + Tyramide-(biotin or epitope tag or hapten) conjugate + Enzyme-(avidin or anti-tag antibody or anti-hapten antibody) conjugate + DAB<br>Anti-tag antibody-Enzyme conjugate + Tyramide-(biotin or epitope tag or hapten) conjugate + Enzyme-(avidin or anti-tag antibody or anti-hapten antibody) conjugate + Chromogen |
| C6. Signaling conjugate comprises member of a specific binding pair and other member of binding pair is linked to enzyme reactive with second detectable moiety linked to a detectable moiety | Anti-tag antibody-Enzyme conjugate + QM-(biotin or epitope tag or hapten) conjugate + Enzyme-(avidin or anti-tag antibody or anti-hapten antibody) conjugate + Tyramide-Dye conjugate<br>Anti-tag antibody-Enzyme conjugate + QM-(biotin or epitope tag or hapten) conjugate + Enzyme-(avidin or anti-tag antibody or anti-hapten antibody) conjugate + QM-Dye conjugate<br>Anti-tag antibody-Enzyme conjugate + Tyramide-(biotin or epitope tag or hapten) conjugate + Enzyme-(avidin or anti-tag antibody or anti-hapten antibody) conjugate + Tyramide-Dye conjugate<br>Anti-tag antibody-Enzyme conjugate + Tyramide-(biotin or epitope tag or hapten) conjugate + Enzyme-(avidin or anti-tag antibody or anti-hapten antibody) conjugate + QM-Dye conjugate |
| D. Anti-tag antibody linked to member of specific binding pair | |
| D1. Dye linked to other member of specific binding pair | Anti-tag antibody-(biotin or epitope tag or hapten) conjugate + Dye-(avidin or anti-tag antibody or anti-hapten antibody) conjugate |
| D2. Enzyme linked to other member of specific binding pair, wherein the enzyme is reactive with detectable moiety | Anti-tag antibody-(biotin or epitope tag or hapten) conjugate + Enzyme-(avidin or anti-tag antibody or anti-hapten antibody) conjugate + DAB<br>Anti-tag antibody-(biotin or epitope tag or hapten) conjugate + Enzyme-(avidin or anti-tag antibody or anti-hapten antibody) conjugate + Chromogen<br>Anti-tag antibody-(biotin or epitope tag or hapten) conjugate + Enzyme-(avidin or anti-tag antibody or anti-hapten antibody) conjugate + QM-Dye conjugate<br>Anti-tag antibody-(biotin or epitope tag or hapten) conjugate + Enzyme-(avidin or anti-tag antibody or anti-hapten antibody) conjugate + Tyramide-Dye conjugate |
| E. Secondary detection reagent linked directly to detectable moiety | |
| Anti-tag antibody + 2° specific detection reagent-Dye conjugate | |
| F. Secondary detection reagent linked to Enzyme reacting with detectable moiety | |
| Anti-tag antibody + 2° specific detection reagent-Enzyme conjugate + DAB<br>Anti-tag antibody + 2° specific detection reagent-Enzyme conjugate + Chromogen | |
| G. Secondary detection reagent linked to Enzyme reacting with detectable moiety | |
| G1. Signaling conjugate comprises detectable moiety | Anti-tag antibody + 2° specific detection reagent-Enzyme conjugate + QM-Dye conjugate<br>Anti-tag antibody + 2° specific detection reagent-Enzyme conjugate + Tyramide-Dye conjugate |
| G2. Signaling conjugate comprises enzyme that reacts directly with detectable moiety | Anti-tag antibody + 2° specific detection reagent-Enzyme conjugate + QM-Enzyme conjugate + DAB<br>Anti-tag antibody + 2° specific detection reagent-Enzyme conjugate + QM-Enzyme conjugate + Chromogen<br>Anti-tag antibody + 2° specific detection reagent-Enzyme conjugate + Tyramide-Enzyme conjugate + DAB<br>Anti-tag antibody + 2° specific detection reagent-Enzyme |

TABLE 1-continued

| | |
|---|---|
| | conjugate + Tyramide-Enzyme conjugate + Chromogen |
| G3. Signaling conjugate comprises enzyme that reacts with second signaling conjugate comprising detectable moiety | Anti-tag antibody + 2° specific detection reagent-Enzyme conjugate + QM-Enzyme conjugate + QM-Dye conjugate<br>Anti-tag antibody + 2° specific detection reagent-Enzyme conjugate + QM-Enzyme conjugate + Tyramide-Dye conjugate<br>Anti-tag antibody + 2° specific detection reagent-Enzyme conjugate + Tyramide-Enzyme conjugate + QM-Dye conjugate<br>Anti-tag antibody + 2° specific detection reagent-Enzyme conjugate + Tyramide-Enzyme conjugate + Tyramide-Dye conjugate |
| G4. Signaling conjugate comprises member of a specific binding pair and other member of binding pair is linked to detectable moiety | Anti-tag antibody + 2° specific detection reagent-Enzyme conjugate + Tyramide-(biotin or epitope tag or hapten) conjugate + Dye-(avidin or anti-tag antibody or anti-hapten antibody) conjugate<br>Anti-tag antibody + 2° specific detection reagent-Enzyme conjugate + QM-(biotin or epitope tag or hapten) conjugate + Dye-(avidin or anti-tag antibody or anti-hapten antibody) conjugate |
| G5. Signaling conjugate comprises member of a specific binding pair and other member of binding pair is linked to enzyme reactive with detectable moiety | Anti-tag antibody + 2° specific detection reagent-Enzyme conjugate + QM-(biotin or epitope tag or hapten) conjugate + Enzyme-(avidin or anti-tag antibody or anti-hapten antibody) conjugate + DAB<br>Anti-tag antibody + 2° specific detection reagent-Enzyme conjugate + QM-(biotin or epitope tag or hapten) conjugate + Enzyme-(avidin or anti-tag antibody or anti-hapten antibody) conjugate + Chromogen<br>Anti-tag antibody + 2° specific detection reagent-Enzyme conjugate + Tyramide-(biotin or epitope tag or hapten) conjugate + Enzyme-(avidin or anti-tag antibody or anti-hapten antibody) conjugate + DAB<br>Anti-tag antibody + 2° specific detection reagent-Enzyme conjugate + Tyramide-(biotin or epitope tag or hapten) conjugate + Enzyme-(avidin or anti-tag antibody or anti-hapten antibody) conjugate + Chromogen |
| G6. Signaling conjugate comprises member of a specific binding pair and other member of binding pair is linked to enzyme reactive with second detectable moiety linked to a detectable moiety | Anti-tag antibody + 2° specific detection reagent-Enzyme conjugate + QM-(biotin or epitope tag or hapten) conjugate + Enzyme-(avidin or anti-tag antibody or anti-hapten antibody) conjugate + Tyramide-Dye conjugate<br>Anti-tag antibody + 2° specific detection reagent-Enzyme conjugate + QM-(biotin or epitope tag or hapten) conjugate + Enzyme-(avidin or anti-tag antibody or anti-hapten antibody) conjugate + QM-Dye conjugate<br>Anti-tag antibody + 2° specific detection reagent-Enzyme conjugate + Tyramide-(biotin or epitope tag or hapten) conjugate + Enzyme-(avidin or anti-tag antibody or anti-hapten antibody) conjugate + Tyramide-Dye conjugate<br>Anti-tag antibody + 2° specific detection reagent-Enzyme conjugate + Tyramide-(biotin or epitope tag or hapten) conjugate + Enzyme-(avidin or anti-tag antibody or anti-hapten antibody) conjugate + QM-Dye conjugate |
| H. Secondary detection reagent linked to member of specific binding pair | |
| H1. Dye linked to other member of specific binding pair | Anti-tag antibody + 2° specific detection reagent-(biotin or epitope tag or hapten) conjugate + Dye-(avidin or anti-tag antibody or anti-hapten antibody) conjugate |
| H2. Enzyme linked to other member of specific binding pair, wherein the enzyme is reactive with detectable moiety | Anti-tag antibody + 2° specific detection reagent-(biotin or epitope tag or hapten) conjugate + Enzyme-(avidin or anti-tag antibody or anti-hapten antibody) conjugate + DAB<br>Anti-tag antibody + 2° specific detection reagent-(biotin or epitope tag or hapten) conjugate + Enzyme-(avidin or anti-tag antibody or anti-hapten antibody) conjugate + Chromogen<br>Anti-tag antibody + 2° specific detection reagent-(biotin or epitope tag or hapten) conjugate + Enzyme-(avidin or anti-tag antibody or anti-hapten antibody) conjugate + QM-Dye conjugate<br>Anti-tag antibody + 2° specific detection reagent-(biotin or epitope tag or hapten) conjugate + Enzyme- |

TABLE 1-continued (avidin or anti-tag antibody or anti-hapten antibody) conjugate + Tyramide-Dye conjugate As used in Table 1, a "2⁰ specific detection reagent" shall refer to any entity capable of specific binding to the anti-tag antibody. Thus, for example, the 2⁰ specific detection reagent may be an anti-species antibody that binds specifically to the species of immunoglobulin from which the anti-tag antibody is derived, and anti-hapten antibody immunoreactive with a hapten conjugated to the anti-tag antibody, or (where the anti-tag antibody is an epitope-tagged antibody) a second anti-tag antibody reactive with an epitope-tag of the anti-tag antibody. Furthermore, in each example of Table 1, the anti-tag antibody may be substituted with another specific detection agent capable of specific binding to the tag, such as an ADNECTIN, AFFIBODY, AVIMER, dAb, DARPin, ANTICALIN, NANOBODY; TRANSBODY, SMIP, or a TETRANECTIN.

Detection Kits Comprising Epitope-Tagged Antibodies and Detection Reagents for Detecting Epitope-Tagged Antibodies In some embodiments, the epitope-tagged antibodies of the present disclosure may be utilized as part of a "detection kit." In general, any detection kit may include one or more epitope-tagged antibodies and detection reagents for detecting the one or more epitope-tagged antibodies.

The detection kits may include a first composition comprising an epitope-tagged antibody and a second composition comprising detection reagents specific to the first composition, such that the epitope-tagged antibody may be detected via the detection kit. In some embodiments, the detection kit includes a plurality of epitope-tagged antibodies (such is mixed together in a buffer), where the detection kit also includes detection reagents specific for each of the plurality of epitope-tagged antibodies.

By way of example, a kit may include an epitope-tagged antibody specific for a first target, the epitope-tagged antibody having a first epitope tag (e.g. VSV), and an epitope-tagged antibody specific for a second target having a second epitope tag (e.g. HA), wherein the first and second epitope tags are different. The kit may further comprise detection reagents specific for each of the different epitope-tagged antibodies. For example, anti-tag antibodies specific for each of the epitope tags of the different epitope-tagged antibodies may be included. In some embodiments, the anti-tag antibodies may be conjugated to fluorescent detectable moieties (e.g. ALEXA FLUOR IR dyes). In other embodiments, the anti-tag antibodies may be conjugated to an enzyme, and chromogenic substrates for the enzyme may also be included within any kit.

Of course, any kit may include other agents, including buffers; counterstaining agents; enzyme inactivation compositions; deparrafinization solutions, etc. as needed for manual or automated target detection. The detection kits may also comprise other specific binding entities (e.g. nucleic acid probes for ISH; unmodified (native) antibodies, and antibody conjugates) and detection reagents to detect those other specific binding entities. For example, a kit may comprise one or more epitope-tagged antibodies; one or more anti-tag antibodies for detecting the one or more epitope-tagged antibodies; at least one unmodified antibody; and detection reagents for detecting the at least one unmodified antibody. In some embodiments, instructions are provided for using the epitope-tagged antibodies, and other components of the kit, for use in an assay, e.g. a MIHC assay.

Methods of Detecting Targets with Epitope-Tagged Antibodies and Detection Reagents The present disclosure also provides methods of detecting one or more targets within a tissue using any of the epitope-tagged antibodies described herein. In some embodiments, an epitope tagged antibody may be used in a simplex assay to detect a particular target within the tissue sample (e.g. CD68, FoxP3, CD20, etc.), where the epitope-tagged antibody is specific to the target of interest, and where upon application of the epitope-tagged antibody to the tissue sample a target-epitope-tagged antibody complex is formed. Following application of the epitope-tagged antibody, detection reagents (e.g. an anti-tag antibody) are applied such that the target-epitope-tagged antibody complex may be detected. In some embodiments, the detection reagents comprise an anti-tag antibody specific to the particular expressed epitope tag of the epitope-tagged antibody, where the anti-tag antibody comprises a detectable moiety. The single target may then be visualized or otherwise detected.

In some aspects of the present disclosure are provided methods of multiplex detection, including automated multiplex detection. FIG. 15A provides a flowchart illustrating one method for the multiplex detection of targets where a tissue sample is contacted simultaneously with a plurality of epitope-tagged antibodies (step 100), where each epitope-tagged antibody is specific for a particular target, and where each epitope-tagged antibody comprises a different epitope tag (a different expressed epitope tag).

In some embodiments, the sample may be contacted with two epitope-tagged antibodies, where each epitope-tagged antibody is specific for a particular target, and where each epitope-tagged antibody comprises a different epitope tag. In other embodiments, the sample may be contacted with three epitope-tagged antibodies, where each epitope-tagged antibody is specific for a particular target, and where each epitope-tagged antibody comprises a different epitope tag (see, for example, Examples 1 and 2). In yet other embodiments, the sample may be contacted with four or more epitope-tagged antibodies, where each epitope-tagged antibody is specific for a particular target, and where each epitope-tagged antibody comprises a different epitope tag (see, for example, Example 7).

The epitope-tagged antibodies may be supplied to the tissue sample as a "pool" or "cocktail" comprising each of the epitope-tagged antibodies needed for the particular assay. The pooling of epitope-tagged antibodies is believed to be possible since the epitope-tagged antibodies do not show cross-reactivity to each other, at least not to the extent where any cross-reactivity would interfere with staining performance. Each epitope-tagged antibody will bind to their respective targets and form detectable target-epitope-tagged antibody complexes. In some embodiments, and following application of the epitope-tagged antibodies, a blocking step is performed (see, for examples, Examples 1, 2, and 7 herein which illustrate the incorporation of a blockings step and/or other processing steps).

Following the simultaneous application of the epitope-tagged antibodies (step 100), a plurality of anti-tag antibodies is simultaneously applied to the tissue sample (step 110), where each anti-tag antibody is specific to one of the epitope-tagged antibodies initially applied (at step 100), and where each anti-tag antibody comprises a different detectable moiety. In some embodiments, the detectable moiety is a fluorophore. The anti-tag antibodies may be supplied to the tissue sample as a pool or cocktail comprising each of the anti-tag antibodies necessary for detection of the target-epitope-tagged antibody complexes. Following application of the anti-tag antibodies, in some embodiments the tissue sample may be stained with a counterstain. Signals from each of the detectable moieties may be visualized or otherwise detected (e.g. simultaneously visualized or detected).

As an example of a multiplex assay according to one aspect of the present disclosure, a first epitope-tagged antibody comprising a first epitope tag and specific to a first target (e.g. specific to one of CD68, FoxP3, CD20, etc.) is introduced to a tissue sample. In some embodiments, the first epitope-tagged antibody forms a detectable first target-epitope-tagged antibody complex. Simultaneously, a second epitope-tagged antibody comprising a second epitope tag and specific to a second target (e.g. another of CD68, FoxP3, CD20, etc.) is introduced to the sample to form a second target-epitope-tagged antibody complex. Third, fourth, and nth additional epitope-tagged antibodies specific to other targets (forming "n" target-detection probe complexes) and having different epitope tags may be further introduced simultaneously with the first and second epitope-tagged antibody antibodies.

After the epitope-tagged antibodies are deposited, they may be detected, either directly or indirectly depending, of course, on their configuration. In some embodiments, anti-tag antibodies are introduced to enable detection of each of the target-epitope-tagged antibody complex. In some embodiments, the anti-tag antibodies are specific to the different epitope tags of the epitope-tagged antibodies, and where the anti-tag antibodies are each conjugated to a detectable moiety. In some embodiments, the detectable reagents are anti-tag antibodies each conjugated to a fluorophore. In some embodiments, first, second, and nth anti-tag antibodies are simultaneously introduced, where each of the first, second, and nth detection reagents are specific to the different epitope-tagged antibodies, where each of the anti-tag antibodies are conjugated to a fluorophore. In other embodiments, first, second, and nth anti-tag antibodies are sequentially introduced, where each of the first, second, and nth detection reagents are specific to the different epitope-tagged antibodies, and wherein each of the anti-tag antibodies are conjugated to an enzyme.

As a further example of a multiplex assay according to the present disclosure, a first epitope-tagged antibody specific to a first target (e.g. CD3, FoxP3, PD-L1, or an immune cell marker) is introduced to a tissue sample, the first epitope-tagged antibody expressing a first epitope tag. In some embodiments, the first epitope-tagged antibody forms a detectable first target-epitope-tagged antibody conjugate complex. Either simultaneously or subsequently, a second epitope-tagged antibody specific to a second target (e.g. another of CD3, FoxP3, PD-L1) is introduced to the sample to form a second target-epitope-tagged antibody conjugate complex, the second epitope-tagged antibody expressing a second epitope tag. Third, fourth, and nth additional epitope-tagged antibodies each specific to other targets (forming "n" target-epitope-tagged antibody conjugate complexes) may be further introduced, again either sequentially or simultaneously with the first and/or second epitope-tagged antibodies, where the third, fourth and nth epitope-tagged antibodies each express yet further different epitope tags. After the epitope-tagged antibodies are deposited, they may be detected. In some embodiments, additional detection reagents are introduced to enable the detection of the targets and the additional detection reagents include those described herein (e.g. chromogenic detection reagents). In some embodiments, first, second, and nth detection reagents are sequentially introduced, where each of the first, second, and nth detection reagents comprise (i) a secondary antibody, namely an anti-tag antibody, specific to each of the epitope tags of the epitope-tagged antibodies, wherein the secondary antibody is conjugated to an enzyme; and (ii) a chromogenic substrate; wherein each of the first, second, and nth chromogenic substrates are different.

In some embodiments, the multiplex detection method comprises the steps of (i) contacting a biological sample with a first epitope-tagged antibody to form a first target-epitope-tagged antibody conjugate complex; (ii) contacting the biological sample with a first labeling conjugate wherein the first labeling conjugate comprises a first enzyme (where the first labeling conjugate is an anti-tag antibody that specifically binds to the first epitope-tagged antibody and is configured to label the target with an enzyme); (iii) contacting the biological sample with a first signaling conjugate comprising a first latent reactive moiety and a first chromogenic moiety (see, e.g. U.S. patent application Ser. No. 13/849,160, the disclosure of which is incorporated herein by reference for a description of signaling conjugates and their constituent components); (iv) inactivating the first enzyme, such as by contacting the sample with a first enzyme inactivation composition to substantially inactivate or completely inactivate the first enzyme contained in the biological sample.

After the first enzyme is inactivated (optional), the multiplex method further comprises the steps of (v) contacting a biological sample with a second epitope-tagged antibody to form a second target-epitope-tagged antibody conjugate complex; (vi) contacting the biological sample with a second labeling conjugate wherein the second labeling conjugate comprises a second enzyme (where the second labeling conjugate is an anti-tag antibody that specifically binds to the second epitope-tagged antibody and is configured to label the target with an enzyme); (vii) contacting the biological sample with a second signaling conjugate comprising a second latent reactive moiety and a second chromogenic moiety; (viii) inactivating the second enzyme, such as by contacting the sample with a first enzyme inactivation composition to substantially inactivate or completely inactivate the first enzyme contained in the biological sample.

After the second enzyme is inactivated, the method may be repeated such that additional epitope-tagged antibodies may be introduced, along with additional detection reagents, to effectuate detection of other targets. Following introduction of all of the epitope-tagged antibody (and other detection probes) and respective detection reagents or kits, the method further comprises the step of counterstaining the sample and/or detecting signals (manually or via an automated method) from the first, second, and nth chromogenic moieties, wherein each of the first, second, and nth chromogenic moieties are each different. Alternatively, each of the epitope-tagged antibodies may be added simultaneously or sequentially, but before any labeling conjugate is added. As another example, three epitope-tagged antibody may be sequentially applied initially, prior to introduction of any detection reagents, and then each of the detection reagents added sequentially.

In the context of a multiplex assay where multiple targets are detected sequentially, and where the detection employs the use of enzymes, it is desirable to inactivate any reagent or endogenous enzymes between successive detection steps. As a result, it is believed that enzymes present in any one detection step will not interfere with those in a later detection steps. This in turn is believed to improve upon the visualization and detection of the different detectable moieties used in the multiplex assay. Any enzyme inactivation composition known in the art may be used for this purpose. In some embodiments, an enzyme inactivation composition is applied to inactivate the reagent or endogenous enzymes after each detection step. Exemplary enzyme inactivation compositions are disclosed in U.S. 62/159,297, the disclosure of which is incorporated by reference herein in its entirety.

In some embodiments, a denaturation step prevents the enzyme used in a first set of detection reagents from acting on a second substrate. In some embodiments, the denaturant is a substance that denatures the enzyme in the first detection reagent set. In some embodiments, the denaturant is, for example, formamide, an alkyl-substituted amide, urea or a urea-based denaturant, thiourea, guanidine hydrochloride, or derivatives thereof. Examples of alkyl-substituted amides include, but are not limited to, N-propylformamide, N-butylformamide, N-isobutylformamide, and N,N-dipropylaformamide. In some embodiments, the denaturant is provided in a buffer. For example, formamide may be provided in a hybridization buffer comprising 20 mM dextran sulfate (50-57% % formamide (UltraPure formamide stock), 2×SSC (20×SSC stock containing 0.3 M citrate and 3M NaCl), 2.5 mM EDTA (0.5M EDTA stock), 5 mM Tris, pH 7.4 (1 mM Tris, pH 7.4 stock), 0.05% Brij-35 (10% stock containing polyoxyethylene (23) lauryl ether), pH 7.4. In some embodiments, the sample is treated with the denaturant for a period of time and under conditions sufficient to denature the first target probe detection enzyme, for example alkaline phosphatase. In some embodiments, the sample is treated with the denaturant for about 15 to about 30 minutes, preferably about 20 to 24 minutes at about 370° C. In some embodiments, the sample is treated with the denaturant for a period of time and under conditions sufficient to denature the target enzyme while preserving hybridization of the second nucleic acid probe to the target.

For those embodiments employing an anti-tag antibody conjugated to an enzyme, conditions suitable for introducing the signaling conjugates or chromogenic substrates with the biological sample are used, and typically include providing a reaction buffer or solution that comprises a peroxide (e.g., hydrogen peroxide), and that has a salt concentration and pH suitable for allowing or facilitating the enzyme to perform its desired function. In general, this step of the method is performed at temperatures ranging from about 350° C. to about 400° C., although the skilled artisan will be able to select appropriate temperature ranges appropriate for the enzymes and signalizing conjugates selected. For example, it is believed that these conditions allow the enzyme and peroxide to react and promote radical formation on the latent reactive moiety of the signaling conjugate. The latent reactive moiety, and therefore the signaling conjugate as a whole, will deposit covalently on the biological sample, particularly at one or more tyrosine residues proximal to the immobilized enzyme conjugate, tyrosine residues of the enzyme portion of the enzyme conjugate, and/or tyrosine residues of the antibody portion of the enzyme conjugate. The biological sample is then illuminated with light and the target may be detected through absorbance of the light produced by the chromogenic moiety of the signaling conjugate.

Methods of Detection with Epitope-Tagged Antibodies in Conjunction with Other Specific Binding Entities In some aspects of the present disclosure, epitope-tagged antibodies are in conjugation with other specific binding entities to effect multiplex detection of targets in a tissue sample. The skilled artisan will appreciate that any of the above-identified methods and procedures may be adapted accordingly for any assay employing both epitope-tagged antibodies and other specific binding entities.

In some embodiments, the specific binding entities include nucleic acids for in situ hybridization, unmodified antibodies for IHC, and/or antibody conjugates for IHC. As used herein, the terms "unmodified antibody" or "unmodified antibodies" refer to those antibodies that does not comprise an epitope tag or those antibodies which are not conjugated to any other moiety. In essence, "unmodified antibodies" are native antibodies traditionally used in IHC assays, which are specific to a particular target (e.g. an anti-CD3 antibody) and which may be detected, such as with anti-species secondary antibodies. By way of example, a rabbit anti-CD3 antibody may be detected with a goat anti-rabbit antibody.

"Antibody conjugates," as that term is used herein, refers to those antibodies conjugated (either directly or indirectly) to one or more labels, where the antibody conjugate is specific to a particular target and where the label is capable of being detected (directly or indirectly), such as with a secondary antibody (an anti-label antibody). For example, an antibody conjugate may be coupled to a hapten such as through a polymeric linker and/or spacer, and the antibody conjugate, by means of the hapten, may be indirectly detected. As an alternative example, an antibody conjugate may be coupled to a fluorophore, such as through a polymeric linker and/or spacer, and the antibody conjugate may be detected directly. Antibody conjugates are described further in US Publication No. 2014/0147906 and U.S. Pat. Nos. 8,658,389; 8,686,122; 8,618,265; 8,846,320; and 8,445,191.

Figure 15B:
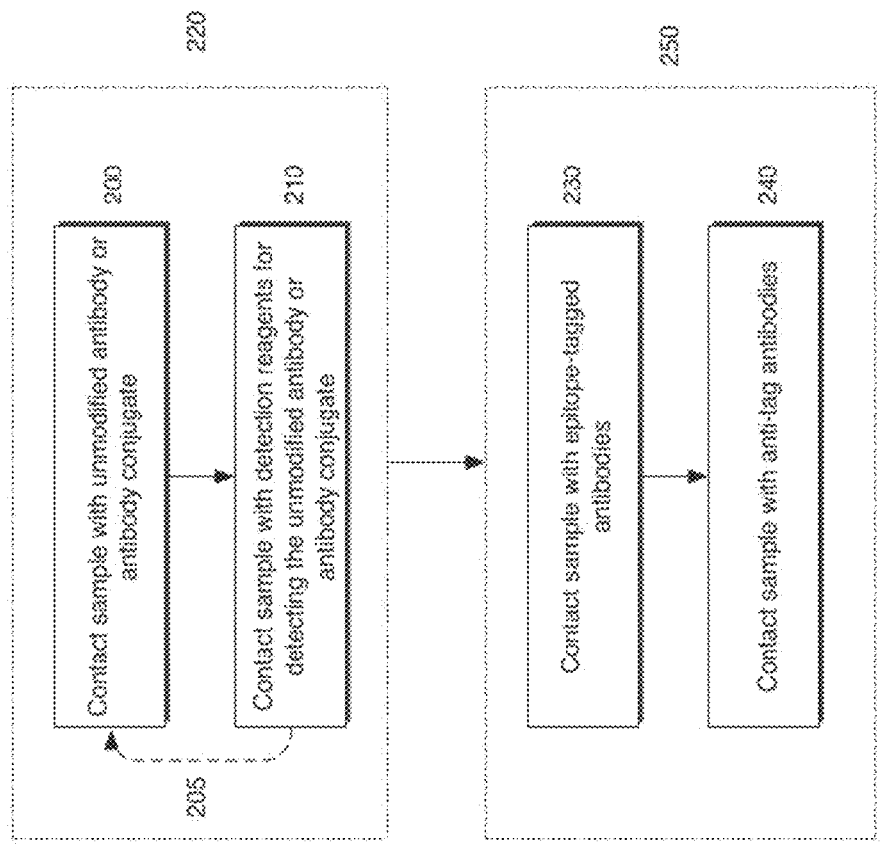
Figure 15C:
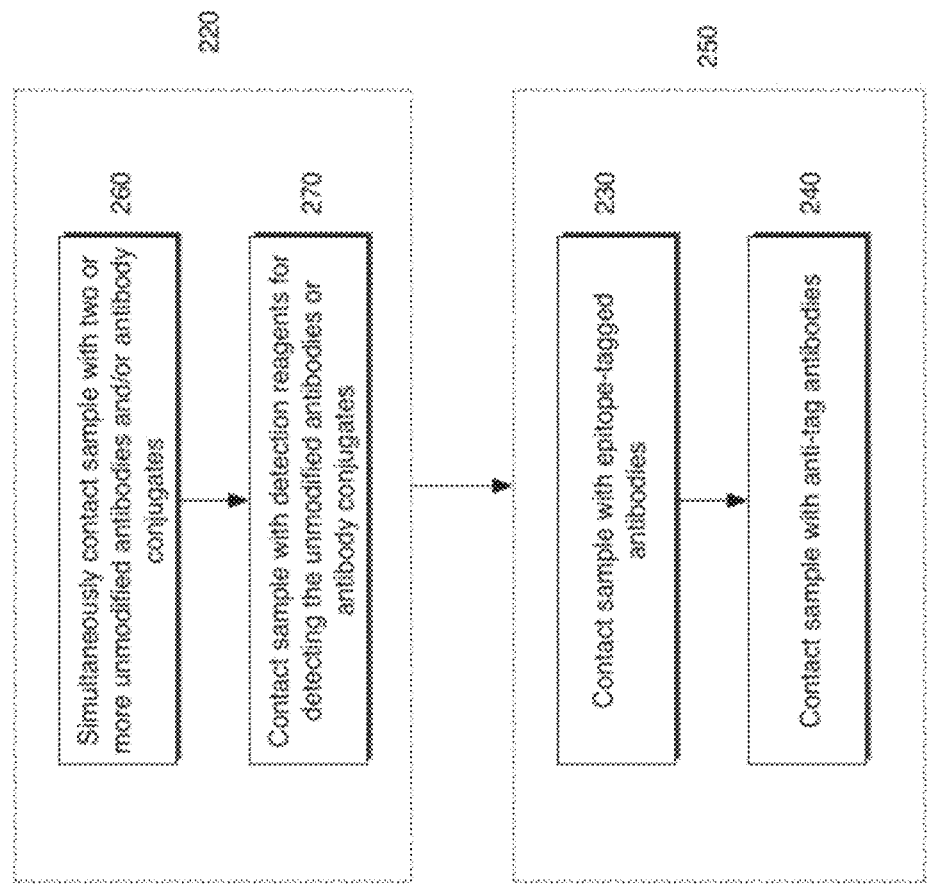
Figure 16A:
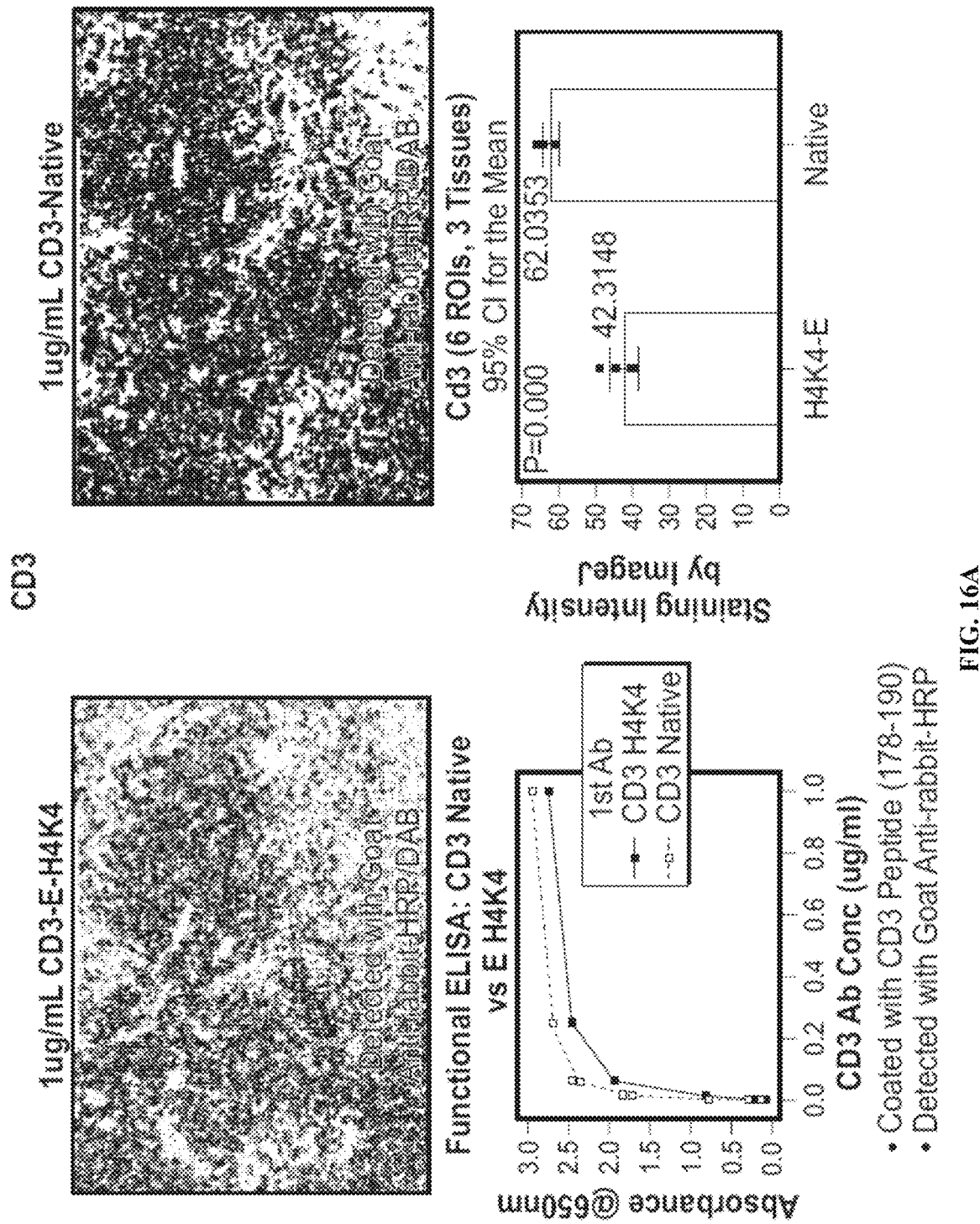
FIG. 16A, FIG. 16B, FIG. 16C, FIG. 16D, and FIG. 16E provide absorbance data corresponding to epitope-tagged antibodies as compared with their corresponding native antibodies (unmodified antibodies).
Figure 16B:
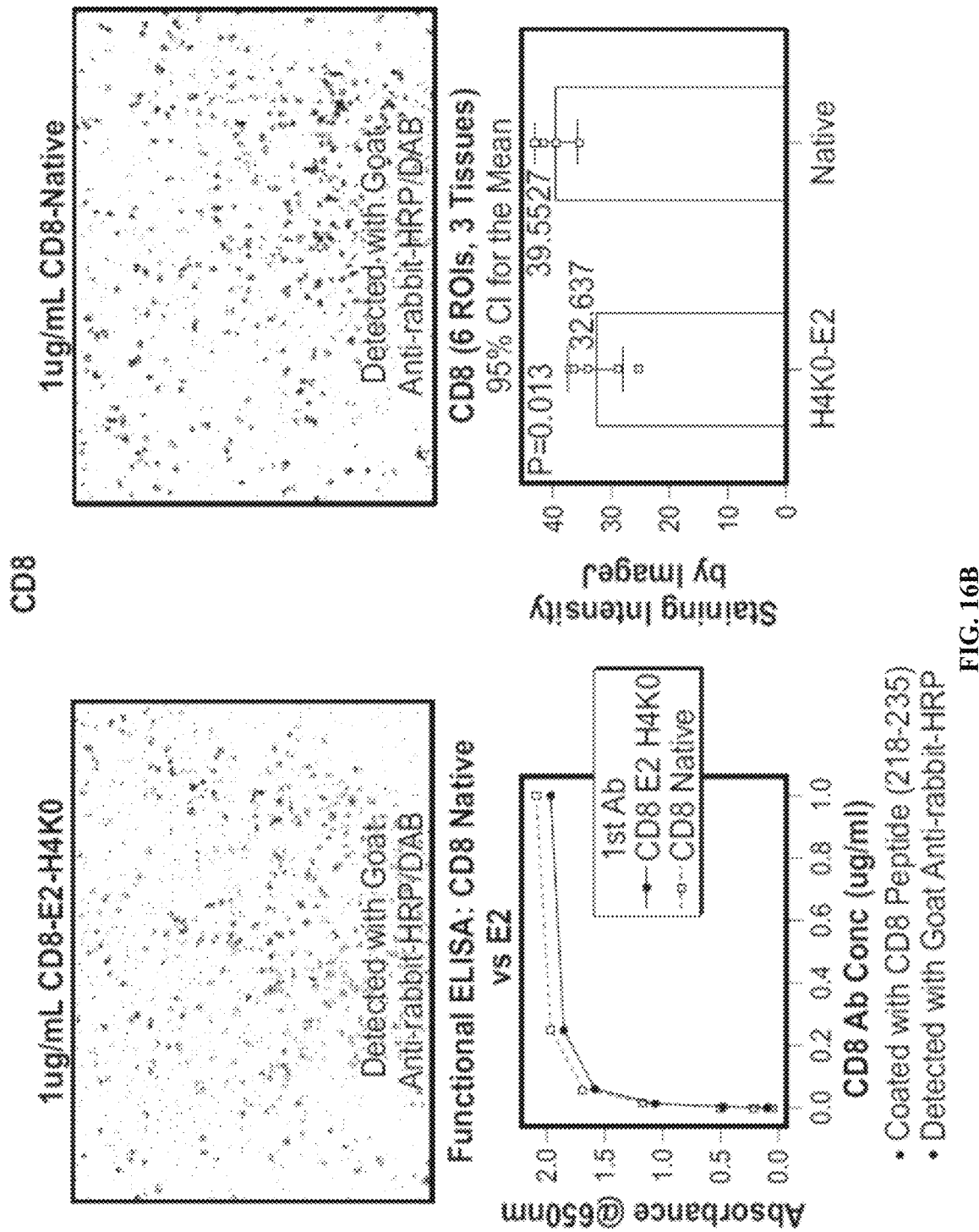
Figure 16C:
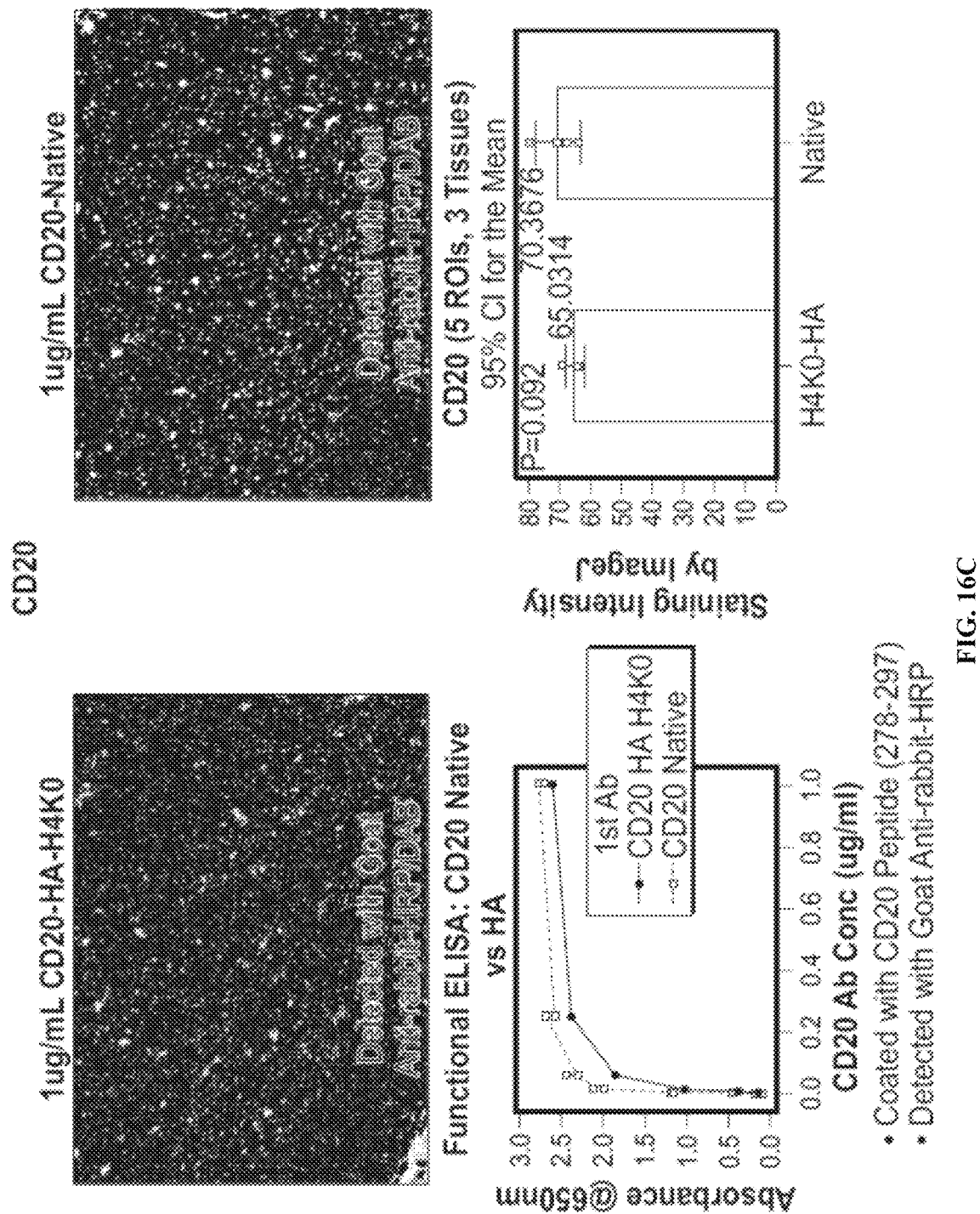
Figure 16D:
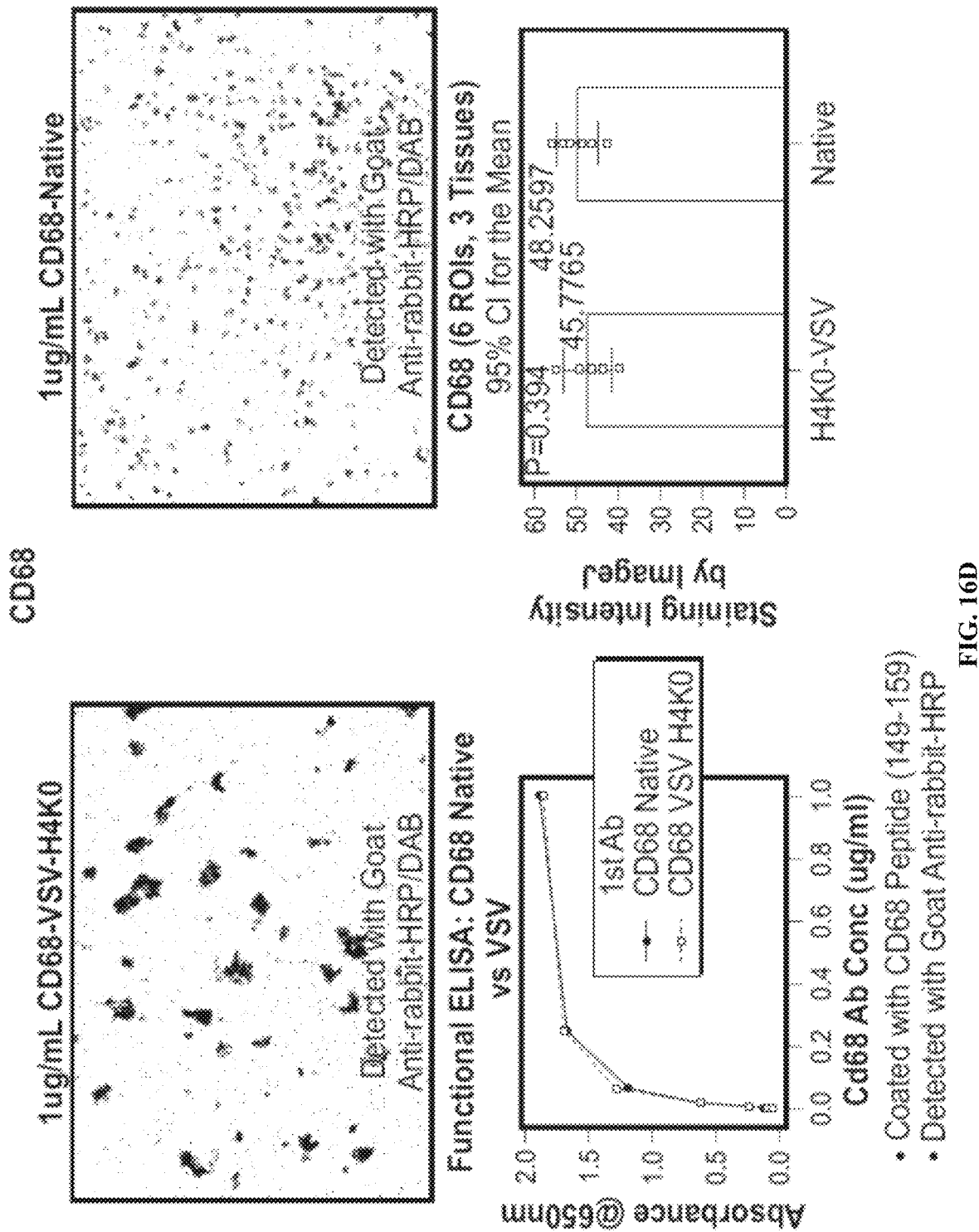
Figure 16E:
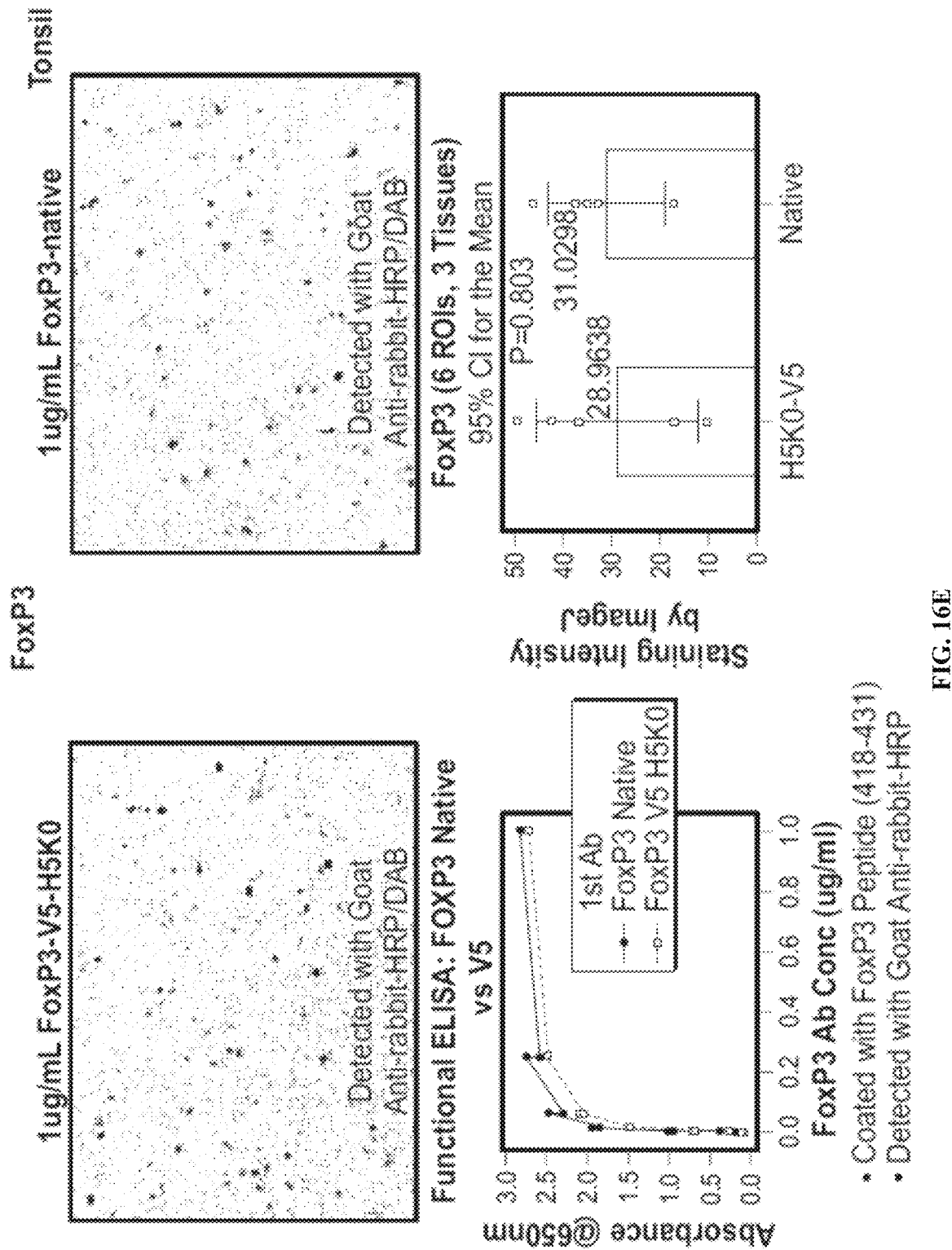

FIGS. 15B and 15C illustrates one method for the multiplex detection of targets where a tissue sample is contacted with one or more unmodified primary antibodies and/or antibody conjugates (simultaneously or sequentially) (first stage, 220) and then subsequently contacted with one or more epitope-tagged antibodies (simultaneously or sequentially) (second stage, 250). Two stage multiplex assays are further illustrated in Examples 3, 4, 5, and 6 herein. The skilled artisan will recognize that the first stage 220 and the second stage 250 may be reversed, such that the epitope-tagged antibodies are applied first to the issue sample followed by application of the unmodified antibodies and/or antibody conjugates. The skilled artisan will also appreciate that appropriate nucleic acid probes may be substituted for the unmodified antibodies and/or antibody conjugates such that the multiplex assay includes both ISH and IHC steps or stages (in any order).

In some embodiments, such as depicted in FIG. 15B, a first unmodified primary antibody or antibody conjugate may be applied to a tissue sample to form a first target-primary antibody complex (step 200). Next, first detection reagents specific to the unmodified primary antibody or antibody conjugate are applied to the tissue sample to detect the first target-primary antibody complex (step 210). Dotted line 205 in FIG. 15B illustrates that steps 200 and 210 of first stage 220 may be repeated one or more times to provide for the sequential multiplex detection of multiple, different targets within the tissue sample with unmodified primary antibodies and/or antibody conjugates. For example, a second unmodified primary antibody or antibody conjugate may be applied to the tissue sample to form a second target-primary antibody complex (200), followed by application of second detection reagents specific to the second unmodified primary antibody or antibody conjugate to detect the second target-primary antibody complex (210).

FIG. 15C represents an alternative method for the multiplex detection of targets using a two stage method similar to that presented in FIG. 15B. In the method depicted in FIG. 15C, each of the unmodified antibodies and/or antibody conjugates are simultaneously introduced to the tissue sample at step 260. Next, the sample is contacted with detection reagents (e.g. anti-species antibodies or anti-label antibodies) at step 270 to effectuate detection of the unmodified antibodies and/or antibody conjugates. In an alternative embodiment, all of the unmodified primary antibodies or antibody conjugates may be sequentially applied (step 260), followed by sequential application of the respective anti-species antibodies (step 270).

The skilled artisan will appreciate that the detection reagents may comprise anti-species antibodies specific to the utilized unmodified antibodies. Alternatively, the detection reagents may comprise anti-label antibodies specific to labels (e.g. haptens) conjugated to the antibody conjugates. The skilled artisan will also appreciate that the anti-species or anti-label antibodies may comprise a detectable moiety and, in embodiments where the detectable moiety is an enzyme, additional chromogenic substrates may be supplied with the first and second detection reagents.

Following the first stage of the multiplex assay 220 (FIG. 15B or 15C), a second stage 250 is performed, where the tissue sample is simultaneously contacted with a plurality of epitope-tagged antibodies (step 230), where each epitope-tagged antibody is specific for a particular target, and where each epitope-tagged antibody comprises a different epitope tag. The epitope-tagged antibodies may be supplied to the tissue sample as a "pool" or "cocktail" comprising each of the epitope-tagged antibodies needed for the particular assay. Each epitope-tagged antibody will form a detectable target-epitope-tagged antibody complex with a specific target. Following the simultaneous application of the epitope-tagged antibodies (primary antibodies) (step 230), anti-tag antibodies (secondary antibodies) are simultaneously applied to the tissue sample (step 240), where each anti-tag antibody is specific to one of the epitope-tagged antibodies applied, and where each anti-tag antibody comprises a different detectable moiety. The anti-tag antibodies may be supplied to the tissue sample as a "pool" or "cocktail" comprising each of the anti-tag antibodies necessary for detection of the target-epitope-tagged antibody complexes.

Following application of the anti-tag antibodies, in some embodiments the tissue sample may be stained with a counterstain (see, for example, Examples 3 through 6 which provide additional processing steps which may be incorporated into any workflow). Signals from each of the detectable moieties (e.g. from the anti-species, anti-label, and/or anti-tag antibodies) may be visualized or otherwise detected (e.g. simultaneously visualized or detected).

As an example of a multiplex assay comprising both (i) unmodified antibodies and/or antibody conjugates, and (ii) epitope-tagged antibodies according to the present disclosure, a first antibody conjugate comprising a hapten label (e.g. an anti-CD3 antibody conjugated indirectly to a happen) is introduced to a tissue sample to form a target-antibody-conjugate complex. Simultaneously, an unmodified antibody (e.g. a rabbit anti-PDL1 antibody) is introduced to the tissue sample to form a target-unmodified-antibody complex. Next, detection reagents are introduced (simultaneously or sequentially) to detect the formed target-antibody-conjugate complex (e.g. an anti-happen antibody) and the formed target-unmodified-antibody complex (e.g. a goat anti-rabbit antibody), where each of the detection reagents are conjugated to a different fluorophore.

In a second stage of the multiplex assay, a first epitope tagged antibody comprising a first epitope tag and specific to a first target (e.g. specific to CD68) is introduced to a tissue sample. In some embodiments, the first epitope-tagged antibody forms a detectable first target-epitope-tagged antibody complex. Simultaneously, a second epitope tagged antibody comprising a second epitope tag and specific to a second target (e.g. specific to FoxP3) is introduced to the sample to form a second target-epitope-tagged antibody complex. Third, fourth, and nth additional epitope-tagged antibodies specific to other targets (forming "n" target-epitope-tags antibody complexes) and having different epitope tags may be further introduced simultaneously with the first and second epitope-tagged antibody antibodies.

After the epitope-tagged antibodies are deposited, they may be detected, either directly or indirectly depending, of course, on their configuration. In some embodiments, anti-tag antibodies are introduced to enable detection of each of the target-epitope-tagged antibody complexes. In some embodiments, first, second, and nth detection reagents are simultaneously introduced, where each of the first, second, and nth detection reagents are specific to the different epitope-tagged antibodies. In some embodiments, first, second, and nth detection reagents are sequentially introduced, where each of the first, second, and nth detection reagents are specific to the different epitope-tagged antibodies. In some embodiments, the detection reagents are anti-tag antibodies that are specific to the different epitope tags of the epitope-tagged antibodies, and where the anti-tag antibodies are each conjugated to a detectable moiety, e.g. a fluorophore or an enzyme. In some embodiments, the detectable reagents are anti-tag antibodies each conjugated to a fluorophore. In other embodiments, the detectable reagents are anti-tag antibodies each conjugated to an enzyme. In yet other embodiments, the detectable reagents are a combination of anti-tag antibodies conjugated to a fluorophore and anti-tag antibodies conjugated to an enzyme. In those embodiments where the anti-tag antibodies are conjugated to an enzyme, substrates for the enzymes are provided to effect detection (as noted previously herein).

In some embodiments, the multiplex detection method comprises the steps of (i) contacting a biological sample with a first detection probe comprising an unmodified antibody to form a first target-antibody conjugate complex; (ii) contacting the biological sample with a first labeling conjugate wherein the first labeling conjugate comprises a first enzyme (where the first labeling conjugate is an anti-species antibody that specifically binds to the first unmodified antibody and is configured to label the target with an enzyme); (iii) contacting the biological sample with a first signaling conjugate comprising a first latent reactive moiety and a first chromogenic moiety; (iv) inactivating the first enzyme, such as by contacting the sample with a first enzyme inactivation composition to substantially inactivate or completely inactivate the first enzyme contained in the biological sample. Alternatively, the first detection probe comprising an unmodified antibody may be detected with an anti-species antibody coupled to a fluorophore.

After the first enzyme is inactivated (optional), the multiplex method further comprises the steps of (v) contacting a biological sample with a second detection probe comprising an epitope-tagged antibody to form a second target-antibody conjugate complex; (vi) contacting the biological sample with a second labeling conjugate wherein the second labeling conjugate comprises a second enzyme (where the second labeling conjugate is an anti-tag antibody that specifically binds to the second detection probe comprising an epitope-tagged antibody and is configured to label the target with an enzyme); (vii) contacting the biological sample with a second signaling conjugate comprising a second latent reactive moiety and a second chromogenic moiety; (viii) inactivating the second enzyme, such as by contacting the sample with a first enzyme inactivation composition to substantially inactivate or completely inactivate the first enzyme contained in the biological sample.

After the second enzyme is inactivated, the method may be repeated such that additional detection probes (unmodified antibodies, antibody conjugates, or epitope-tagged antibodies) may be introduced, along with additional detection reagents, to effectuate detection of other targets. For example, a third detection probe comprising an epitope-tagged antibody expressing a different epitope tag may be introduced and detected, such as with an anti-tag antibody conjugated to one of a fluorophore or an enzyme. Following introduction of all of the detection probes and respective detection reagents or kits, the method further comprises the step of counterstaining the sample and/or detecting signals (manually or via an automated method) from the first, second, and nth chromogenic moieties, wherein each of the first, second, and nth chromogenic moieties are each different.

Automation

The multiplex assays and methods may be semi-automated or automated. For example, the staining processes may be performed on a histochemical staining platform, such as an automated IHC/ISH slide stainer. Automated IHC/ISH slide stainers typically include at least: reservoirs of the various reagents used in the staining protocols, a reagent dispense unit in fluid communication with the reservoirs for dispensing reagent to onto a slide, a waste removal system for removing used reagents and other waste from the slide, and a control system that coordinates the actions of the reagent dispense unit and waste removal system. In addition to performing staining steps, many automated slide stainers can also perform steps ancillary to staining (or are compatible with separate systems that perform such ancillary steps), including: slide baking (for adhering the sample to the slide), dewaxing (also referred to as deparaffinization), antigen retrieval, counterstaining, dehydration and clearing, and coverslipping. Prichard, *Overview of Automated Immunohistochemistry*, Arch Pathol Lab Med., Vol. 138, pp. 1578-1582 (2014), incorporated herein by reference in its entirety, describes several specific examples of automated IHC/ISH slide stainers and their various features, including the intelliPATH (Biocare Medical), WAVE (Celerus Diagnostics), DAKO OMNIS and DAKO AUTOSTAINER LINK 48 (Agilent Technologies), BENCHMARK (Ventana Medical Systems, Inc.), Leica BOND, and Lab Vision Autostainer (Thermo Scientific) automated slide stainers. Additionally, Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Commercially-available staining units typically operate on one of the following principles: (1) open individual slide staining, in which slides are positioned horizontally and reagents are dispensed as a puddle on the surface of the slide containing a tissue sample (such as implemented on the DAKO AUTOSTAINER Link 48 (Agilent Technologies) and intelliPATH (Biocare Medical) stainers); (2) liquid overlay technology, in which reagents are either covered with or dispensed through an inert fluid layer deposited over the sample (such as implemented on VENTANA BenchMark and DISCOVERY stainers); (3) capillary gap staining, in which the slide surface is placed in proximity to another surface (which may be another slide or a coverplate) to create a narrow gap, through which capillary forces draw up and keep liquid reagents in contact with the samples (such as the staining principles used by DAKO TECHMATE, Leica BOND, and DAKO OMNIS stainers). Some iterations of capillary gap staining do not mix the fluids in the gap (such as on the DAKO TECHMATE and the Leica BOND). In variations of capillary gap staining termed dynamic gap staining, capillary forces are used to apply sample to the slide, and then the parallel surfaces are translated relative to one another to agitate the reagents during incubation to effect reagent mixing (such as the staining principles implemented on DAKO OMNIS slide stainers (Agilent)). In translating gap staining, a translatable head is positioned over the slide. A lower surface of the head is spaced apart from the slide by a first gap sufficiently small to allow a meniscus of liquid to form from liquid on the slide during translation of the slide. A mixing extension having a lateral dimension less than the width of a slide extends from the lower surface of the translatable head to define a second gap smaller than the first gap between the mixing extension and the slide. During translation of the head, the lateral dimension of the mixing extension is sufficient to generate lateral movement in the liquid on the slide in a direction generally extending from the second gap to the first gap. See WO 2011-139978 A1. It has recently been proposed to use inkjet technology to deposit reagents on slides. See WO 2016-170008 A1. This list of staining technologies is not intended to be comprehensive, and any fully or semi-automated system for performing biomarker staining may be incorporated into the histochemical staining platform.

Where a morphologically-stained sample is also desired, an automated H&E staining platform may be used. Automated systems for performing H&E staining typically operate on one of two staining principles: batch staining (also referred to as "dip 'n dunk") or individual slide staining. Batch stainers generally use vats or baths of reagents in which many slides are immersed at the same time. Individual slide stainers, on the other hand, apply reagent directly to each slide, and no two slides share the same aliquot of reagent. Examples of commercially available H&E stainers include the VENTANA SYMPHONY (individual slide stainer) and VENTANA HE 600 (individual slide stainer) series H&E stainers from Roche; the Dako CoverStainer (batch stainer) from Agilent Technologies; the Leica ST4020 Small Linear Stainer (batch stainer), Leica ST5020 Multistainer (batch stainer), and the Leica ST5010 Autostainer XL series (batch stainer) H&E stainers from Leica Biosystems Nussloch GmbH.

After the specimens are stained, the stained samples can be manually analyzed on a microscope, and/or digital images of the stained samples can be collected for archiving and/or digital analysis. Digital images can be captured via a scanning platform such as a slide scanner that can scan the stained slides at 20×, 40×, or other magnifications to produce high resolution whole-slide digital images. At a basic level, the typical slide scanner includes at least: (1) a microscope with lens objectives, (2) a light source (such as halogen, light emitting diode, white light, and/or multispectral light sources, depending on the dye), (3) robotics to move glass slides around or to move the optics around the slide or both, (4) one or more digital cameras for image capture, (5) a computer and associated software to control the robotics and to manipulate, manage, and view digital slides. Digital data at a number of different X-Y locations (and in some cases, at multiple Z planes) on the slide are captured by the camera's charge-coupled device (CCD), and the images are joined together to form a composite image of the entire scanned surface. Common methods to accomplish this include:

(1) Tile based scanning, in which the slide stage or the optics are moved in very small increments to capture square image frames, which overlap adjacent squares to a slight degree. The captured squares are then automatically matched to one another to build the composite image; and (2) Line-based scanning, in which the slide stage moves in a single axis during acquisition to capture a number of composite image "strips." The image strips can then be matched with one another to form the larger composite image.

A detailed overview of various scanners (both fluorescent and brightfield) can be found at Farahani et al., *Whole slide imaging in pathology: advantages, limitations, and emerging perspectives*, Pathology and Laboratory Medicine Int'l, Vol. 7, p. 23-33 (June 2015), the content of which is incorporated by reference in its entirety. Examples of commercially available slide scanners include: 3DHistech PANNORAMIC SCAN II; DigiPath PATHSCOPE; Hamamatsu NANOZOOMER RS, HT, and XR; Huron TISSUESCOPE 4000, 4000XT, and HS; Leica SCANSCOPE AT, AT2, CS, FL, and SCN400; Mikroscan D2; Olympus VS120-SL; Omnyx VL4, and VL120; PerkinElmer LAMINA; Philips ULTRA-FAST SCANNER; Sakura Finetek VISIONTEK; Unic PRECICE 500, and PRECICE 600x; VENTANA ISCAN COREO and ISCAN HT; and Zeiss AXIO SCAN.Z1. Other exemplary systems and features can be found in, for example, WO2011-049608) or in U.S. Patent Application No. 61/533,114, filed on Sep. 9, 2011, entitled IMAGING SYSTEMS, CASSETTES, AND METHODS OF USING THE SAME the content of which is incorporated by reference in its entirety.

In some cases, the images may be analyzed on an image analysis system. Image analysis system may include one or more computing devices such as desktop computers, laptop computers, tablets, smartphones, servers, application-specific computing devices, or any other type(s) of electronic device(s) capable of performing the techniques and operations described herein. In some embodiments, image analysis system may be implemented as a single device. In other embodiments, image analysis system may be implemented as a combination of two or more devices together achieving the various functionalities discussed herein. For example, image analysis system may include one or more server computers and a one or more client computers communicatively coupled to each other via one or more local-area networks and/or wide-area networks such as the Internet. The image analysis system typically includes at least a memory, a processor, and a display. Memory may include any combination of any type of volatile or non-volatile memories, such as random-access memories (RAMs), read-only memories such as an Electrically-Erasable Programmable Read-Only Memory (EEPROM), flash memories, hard drives, solid state drives, optical discs, and the like. It is appreciated that memory can be included in a single device, and can also be distributed across two or more devices. Processor may include one or more processors of any type, such as central processing units (CPUs), graphics processing units (GPUs), special-purpose signal or image processors, field-programmable gate arrays (FPGAs), tensor processing units (TPUs), and so forth. It is appreciated that processor can be included in a single device, and can also be distributed across two or more devices. Display may be implemented using any suitable technology, such as LCD, LED, OLED, TFT, Plasma, etc. In some implementations, display may be a touch-sensitive display (a touchscreen). Image analysis system also typically includes a software system stored on the memory comprising a set of instructions implementable on the processor, the instructions comprising various image analysis tasks, such as object identification, stain intensity quantification, and the like. Exemplary commercially-available software packages useful in implementing modules as disclosed herein include VENTANA VIRTUOSO; Definiens TISSUE STUDIO, DEVELOPER XD, and IMAGE MINER; and Visopharm BIOTOPIX, ONCOTOPIX, and STEREOTOPIX software packages.

Automated processes may also include a laboratory information system (LIS). LIS 130 typically performs one or more functions selected from: recording and tracking processes performed on samples and on slides and images derived from the samples, instructing different components of the immune context scoring system to perform specific processes on the samples, slides, and/or images, and track information about specific reagents applied to samples and or slides (such as lot numbers, expiration dates, volumes dispensed, etc.). LIS usually comprises at least a database containing information about samples; labels associated with samples, slides, and/or image files (such as barcodes (including 1-dimensional barcodes and 2-dimensional barcodes), radio frequency identification (RFID) tags, alphanumeric codes affixed to the sample, and the like); and a communication device that reads the label on the sample or slide and/or communicates information about the slide between the LIS and the other components of the immune context scoring system. Thus, for example, a communication device could be placed at each of a sample processing station, automated histochemical stainer, H&E staining platform, and scanning platform. When the sample is initially processed into sections, information about the sample (such as patient ID, sample type, processes to be performed on the section(s)) may be entered into the communication device, and a label is created for each section generated from the sample. At each subsequent station, the label is entered into the communication device (such as by scanning a barcode or RFID tag or by manually entering the alpha-numeric code), and the station electronically communicates with the database to, for example, instruct the station or station operator to perform a specific process on the section and/or to record processes being performed on the section. At scanning platform, the scanning platform may also encode each digital image with a computer-readable label or code that correlates back to the section or sample from which the image is derived, such that when the image is sent to an image analysis system, image processing steps to be performed may be sent from the database of LIS to the image analysis system and/or image processing steps performed on the image by image analysis system are recorded by database of LIS. Commercially available LIS systems useful in the present methods and systems include, for example, VENTANA Vantage Workflow system (Roche).

Counterstaining

Counterstaining is a method of post-treating the samples after they have already been stained with agents to detect one or more targets, such that their structures can be more readily visualized under a microscope. For example, a counterstain is optionally used prior to coverslipping to render the immunohistochemical stain more distinct. Counterstains should be chosen that differ in color from a primary stain. Numerous counterstains are well known, such as hematoxylin, eosin, methyl green, methylene blue, Giemsa, Alcian blue, and Nuclear Fast Red. DAPI (4',6-diamidino-2-phenylindole) is a fluorescent stain that may be used. Counterstains may also be classified according to the structures to which they bind and whether they are suitable for brightfield or fluorescent analysis, for example: brightfield nuclear counterstains, which include hematoxylin (stains from blue to violet), Methylene blue (stains blue), toluidine blue (stains nuclei deep blue and polysaccharides pink to red), nuclear fast red (also called Kernechtrot dye, stains red), and methyl green (stains green); non-nuclear brightfield stains, such as eosin (stains pink); fluorescent nuclear stains, including 4', 6-diamino-2-pheylindole (DAPI, stains blue), propidium iodide (stains red), HOECHST stain (stains blue), nuclear green DCS1 (stains green), nuclear yellow (HOECHST S769121, stains yellow under neutral pH and stains blue under acidic pH), DRAQ5 (stains red), DRAQ7 (stains red); fluorescent non-nuclear stains, such as fluorophore-labelled phalloidin, (stains filamentous actin, color depends on conjugated fluorophore).

In some examples, more than one stain can be mixed together to produce the counterstain. This provides flexibility and the ability to choose stains. For example, a first stain, can be selected for the mixture that has a particular attribute, but yet does not have a different desired attribute. A second stain can be added to the mixture that displays the missing desired attribute. For example, toluidine blue, DAPI, and pontamine sky blue can be mixed together to form a counterstain.

Imaging

Certain aspects, or all, of the disclosed embodiments can be automated, and facilitated by computer analysis and/or image analysis system. In some applications, precise color or fluorescence ratios are measured. In some embodiments, light microscopy is utilized for image analysis. Certain disclosed embodiments involve acquiring digital images. This can be done by coupling a digital camera to a microscope. Digital images obtained of stained samples are analyzed using image analysis software. Color or fluorescence can be measured in several different ways. For example, color can be measured as red, blue, and green values; hue, saturation, and intensity values; and/or by measuring a specific wavelength or range of wavelengths using a spectral imaging camera. The samples also can be evaluated qualitatively and semi-quantitatively. Qualitative assessment includes assessing the staining intensity, identifying the positively-staining cells and the intracellular compartments involved in staining, and evaluating the overall sample or slide quality. Separate evaluations are performed on the test samples and this analysis can include a comparison to known average values to determine if the samples represent an abnormal state.

Samples and Targets

Samples include biological components and generally are suspected of including one or more target molecules of interest. Target molecules can be on the surface of cells and the cells can be in a suspension, or in a tissue section. Target molecules can also be intracellular and detected upon cell lysis or penetration of the cell by a probe. One of ordinary skill in the art will appreciate that the method of detecting target molecules in a sample will vary depending upon the type of sample and probe being used. Methods of collecting and preparing samples are known in the art.

Samples for use in the embodiments of the method and with the composition disclosed herein, such as a tissue or other biological sample, can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Such normal samples are useful, among other things, as controls for comparison to other samples. The samples can be analyzed for many different purposes. For example, the samples can be used in a scientific study or for the diagnosis of a suspected malady, or as prognostic indicators for treatment success, survival, etc.

Samples can include multiple targets that can be specifically bound by a probe or reporter molecule. The targets can be nucleic acid sequences or proteins. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

The skilled artisan will appreciate that epitope-tagged antibodies may be developed which are specific to any of the following targets:

In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, at least a portion of the target molecule is produced by a nucleic acid sequence (e.g., genomic target nucleic acid sequence) amplified or deleted in at least a subset of cells in a sample.

In other examples, a target protein produced from a nucleic acid sequence (e.g., genomic target nucleic acid sequence) that is a tumor suppressor gene that is deleted (lost) in malignant cells. For example, the p16 region (including D9S1749, D9S1747, p16 (INK4A), p14 (ARF), D9S1748, p15 (INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC-000007, nucleotides 55054219-55242525), the C-MYC gene (8q24.21; e.g., GENBANK™ Accession No. NC-000008, nucleotides 128817498-128822856), D5S271 (5p15.2), lipoprotein lipase (LPL) gene (8p22; e.g., GENBANK™ Accession No. NC 000008, nucleotides 19841058-19869049), RB1 (13q14; e.g., GENBANK™ Accession No. NC 000013, nucleotides 47775912-47954023), p53 (17p13.1; e.g., GENBANK™ Accession No. NC-000017, complement, nucleotides 7512464-7531642)), N-MYC (2p24; e.g., GENBANK™ Accession No. NC-000002, complement, nucleotides 151835231-151854620), CHOP (12q13; e.g., GENBANK™ Accession No. NC 000012, complement, nucleotides 56196638-56200567), FUS (16p11.2; e.g., GENBANK™ Accession No. NC 000016, nucleotides 31098954-31110601), FKHR (13p14; e.g., GENBANK™ Accession No. NC-000013, complement, nucleotides 40027817-40138734), as well as, for example: ALK (2p23; e.g., GENBANK™ Accession No. NC-000002, complement, nucleotides 29269144-29997936), Ig heavy chain, CCND1 (11q13; e.g., GENBANK™ Accession No. NC-000011, nucleotides 69165054.69178423), BCL2 (18q21.3; e.g., GENBANK™ Accession No. NC-000018, complement, nucleotides 58941559-59137593), BCL6 (3q27; e.g., GENBANK™ Accession No. NC-000003, complement, nucleotides 188921859-188946169), MALF1, AP1 (1p32-p31; e.g., GENBANK™ Accession No. NC 000001, complement, nucleotides 59019051-59022373), TOP2A (17q21-q22; e.g., GENBANK™ Accession No. NC-000017, complement, nucleotides 35798321-35827695), TMPRSS (21q22.3; e.g., GENBANK™ Accession No. NC 000021, complement, nucleotides 41758351-41801948), ERG (21q22.3; e.g., GENBANK™ Accession No. NC 000021, complement, nucleotides 38675671-38955488); ETV1 (7p21.3; e.g., GENBANK™ Accession No. NC-000007, complement, nucleotides 13897379-13995289), EWS (22q12.2; e.g., GENBANK™ Accession No. NC 000022, nucleotides 27994271-28026505); FLI1 (11q24.1-q24.3; e.g., GENBANK™ Accession No. NC 000011, nucleotides 128069199-128187521), PAX3 (2q35-q37; e.g., GENBANK™ Accession No. NC 000002, complement, nucleotides 222772851-222871944), PAX7 (1p36.2-p36.12; e.g., GENBANK™ Accession No. NC-000001, nucleotides 18830087-18935219), PTEN (10q23.3; e.g., GENBANK™ Accession No. NC 000010, nucleotides 89613175-89716382), AKT2 (19q13.1-q13.2; e.g., GENBANK™ Accession No. NC 000019, complement, nucleotides 45431556-45483036), MYCL1 (1p34.2; e.g., GENBANK™ Accession No. NC 000001, complement, nucleotides 40133685-40140274), REL (2p113-p12; e.g., GENBANK™ Accession No. NC-000002, nucleotides 60962256-61003682) and CSF1R (5q33-q35; e.g., GENBANK™ Accession No. NC-000005, complement, nucleotides 149413051-149473128).

EXAMPLES

The non-limiting examples presented herein each incorporate the use of at least one epitope-tagged antibody. Applicants submit that the epitope-tagged antibodies disclosed herein are suitable for use in IHC assays, including multiplex IHC assays, as demonstrated in the following examples. Applicants also submit that the epitope-tagged antibodies may be used in conjunction with unmodified antibodies or antibody conjugates, as also shown in the following examples. Of course, as detailed herein, the epitope-tagged antibodies may be used in conjunction with other detectable specific binding entities and may be utilized in assays with combine IHC and ISH.

In the embodiments which follow and those noted above, one or more wash steps may be performed, such as to remove unbound antibodies. In some embodiments, a wash step may be performed between each step of the staining procedure to remove excess reagent, etc. Of course, the skilled artisan would understand the processes and procedures associated with any wash steps and be able to apply to those processes and procedures to remove any reagents, unbound antibodies, etc.

Example 1: 3-Plex Immunohistochemical Assay

Example 1 provides a multiplex immunohistochemical assay where three different epitope-tagged antibodies were simultaneously applied to a tissue sample (see FIG. 1). A first epitope-tagged antibody was specific for CD68 (anti-CD68) and comprised the VSV epitope tag (a heavy chain comprising four VSV epitope tags). A second epitope-tagged antibody was specific to FoxP3 (anti-FoxP3) and comprised the V5 epitope tag (a heavy chain comprising five V5 epitope tags). A third epitope-tagged antibody was specific to CD20 (anti-CD20) and comprised the HA epitope tag (a heavy chain comprising four H5 epitope tags). The epitope-tagged antibodies were applied as a "cocktail" comprise 2 µg/mL of each epitope-tagged antibody in diluent 90039.

After the simultaneous application of the three epitope-tagged antibodies, three anti-tag antibodies were simultaneously supplied to the tissue sample (see FIG. 1), where each anti-tag antibody was specific to a different epitope tag of the epitope-tagged antibodies. A first anti-VSV antibody was conjugated with ALEXA 532 (producing an "orange" signal); a second anti-V5 antibody was conjugated with DYLIGHT 649 (producing a "green" signal); and a third anti-HA antibody was conjugated with ALEXA 594 (producing a "purple" signal). The anti-tag antibodies were applied as a "cocktail" comprise 5 µg/mL of each anti-tag antibody in diluent 90040.

The following steps were undertaken for the 3-plex IHC assay (see Table 2):

TABLE 2

| Procedure Step | Selection |
| --- | --- |
| Deparaffinization | Selected |
| Cell Conditioning | CC1, 64 min |
| Tagged 1st Ab cocktail | Incubate - 32 min |
| Blocking with diluent 90040 | 32 min |
| Anti-tag 2nd Ab cocktail | Incubate - 32 min |
| DAPI Counterstain | 4 min |
| ProLong Diamond - -PROLONG DIAMOND anti-fade mounting | |

A complete protocol summary is provided below in Table 3:

TABLE 3

| 1 | Paraffin (Selected) |
| --- | --- |
| 2 | Deparaffinization [Selected] |
| 3 | Warmup Slide to [72 Deg C.] from Medium Temperatures (Deparaffinization) |
| 4 | Cell Conditioning (Selected) |

TABLE 3-continued

| | |
|---|---|
| 5 | Ultra cc 1 [Selected] |
| 6 | Warmup Slide to [100 Deg C.], and Incubate for 4 Minutes (Cell Conditioner #1) |
| 7 | CC1 8 Min [Selected] |
| 8 | CC1 16 Min (Selected) |
| 9 | CC1 24 Min (Selected) |
| 10 | CC1 32 Min (Selected) |
| 11 | CC1 40 Min (Selected) |
| 12 | CC1 48 Min (Selected) |
| 13 | CC1 56 Min (Selected) |
| 14 | CC1 64 Min [Selected |
| 15 | 1st Antibody Manual Application [Selected) |
| 16 | Hand Apply (Primary Antibody). and Incubate for [0 Hr 32 Min] |
| 17 | Blocker (Selected) |
| 18 | Apply One Drop of (OPTION 2) (2nd Option), and Incubate for (32 Minutes) |
| 19 | 3rd Wash after Primary Ab (Selected) |
| 20 | 2nd Antibody Manual Application [Selected] |
| 21 | Hand Apply (Secondary Antibody). and Incubate for (0 Hr 32 Min) |

Figure 2A:
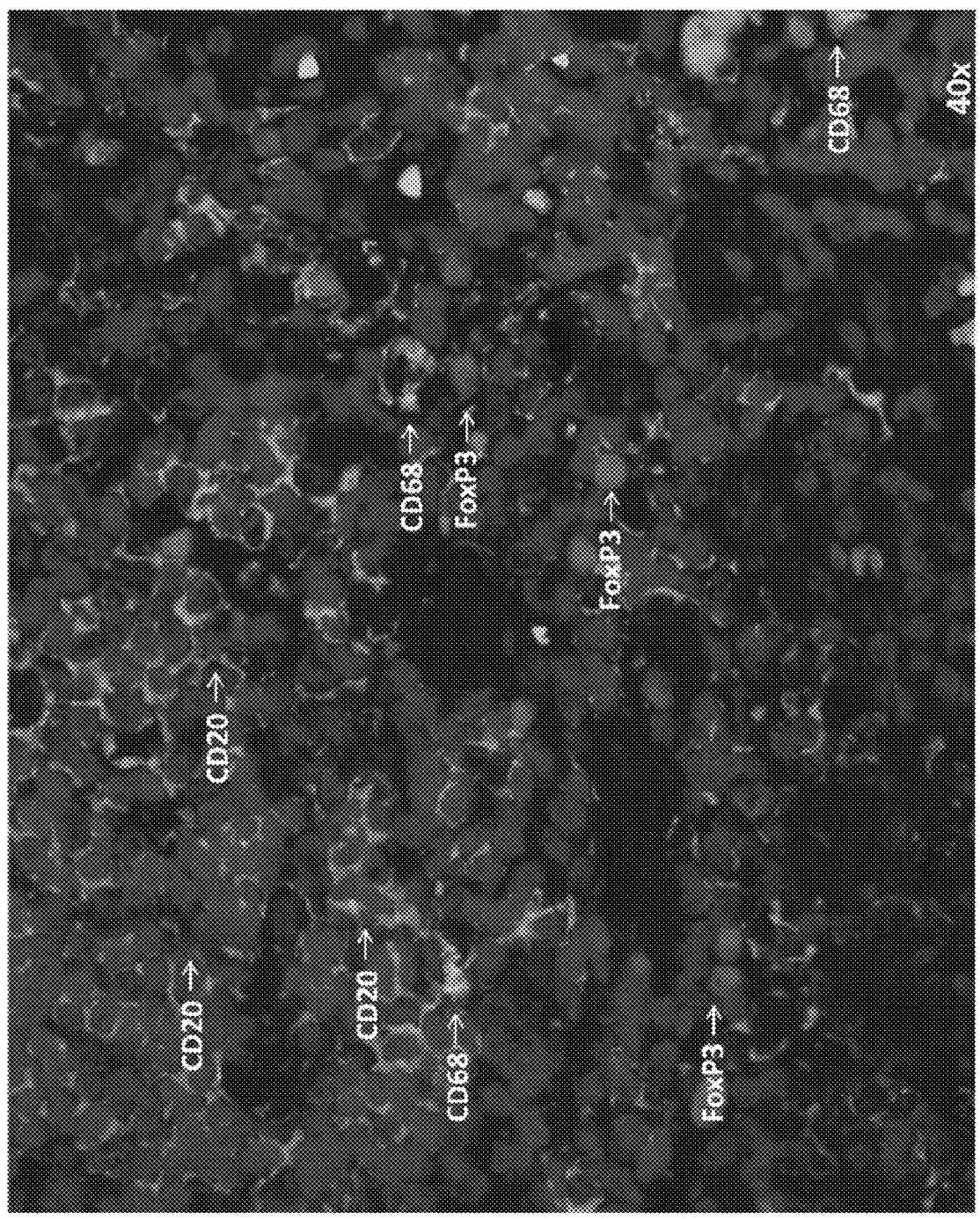
FIG. 2A, FIG. 2B, FIG. 2C, and FIG. 2D are images of tissue samples stained according to a multiplex IHC assay utilizing three different epitope-tagged antibodies.
Figure 2B:
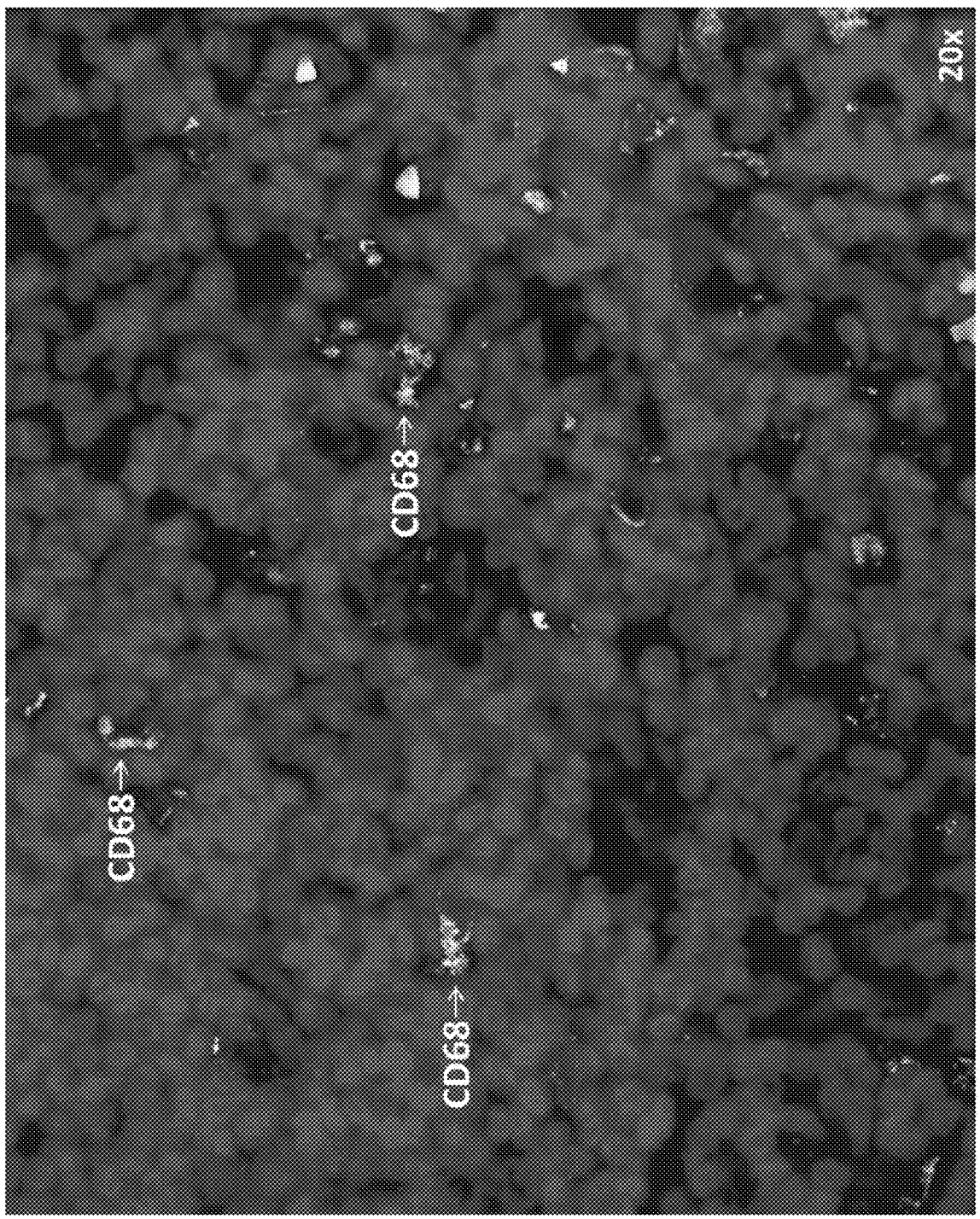
Figure 2C:
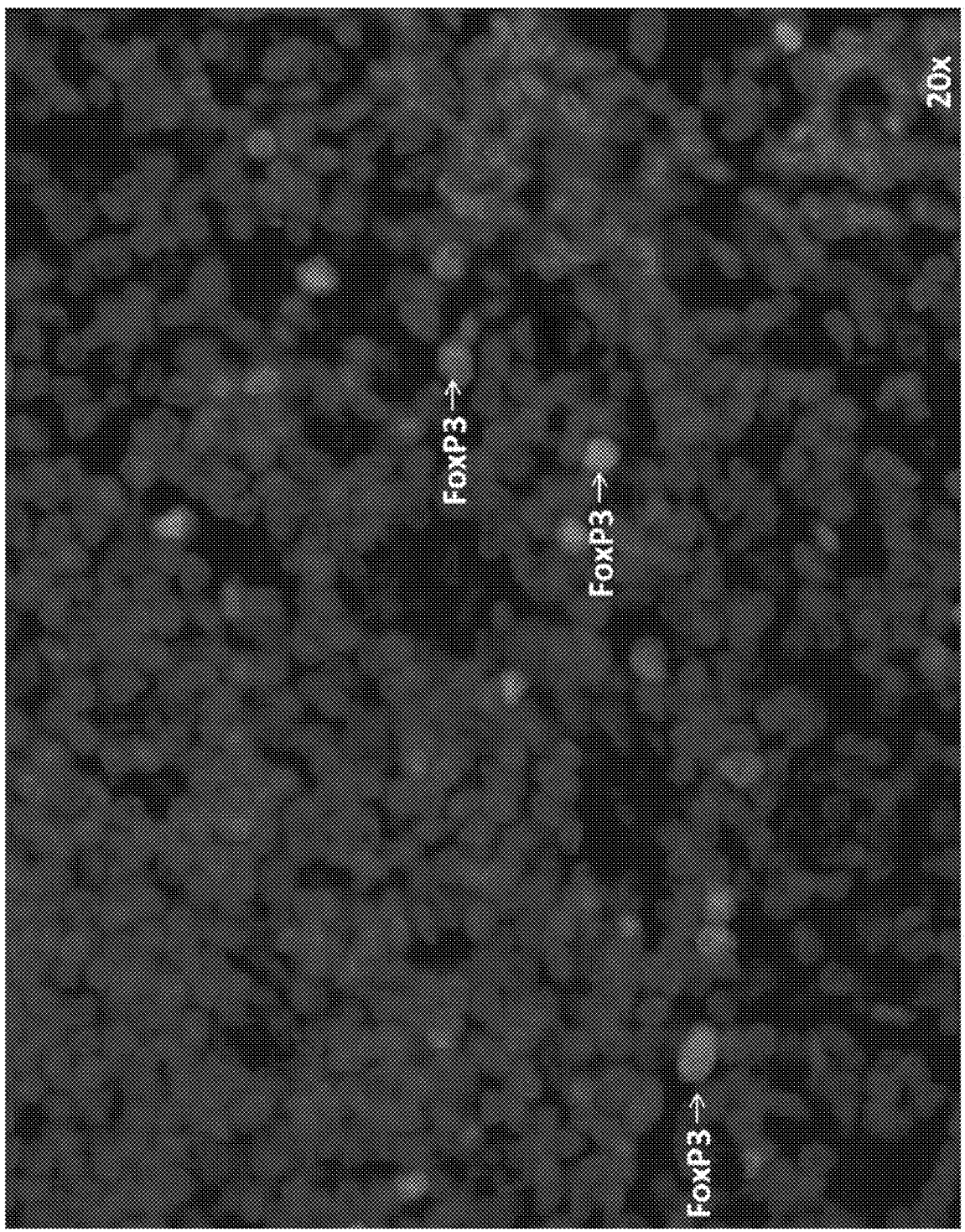
Figure 2D:
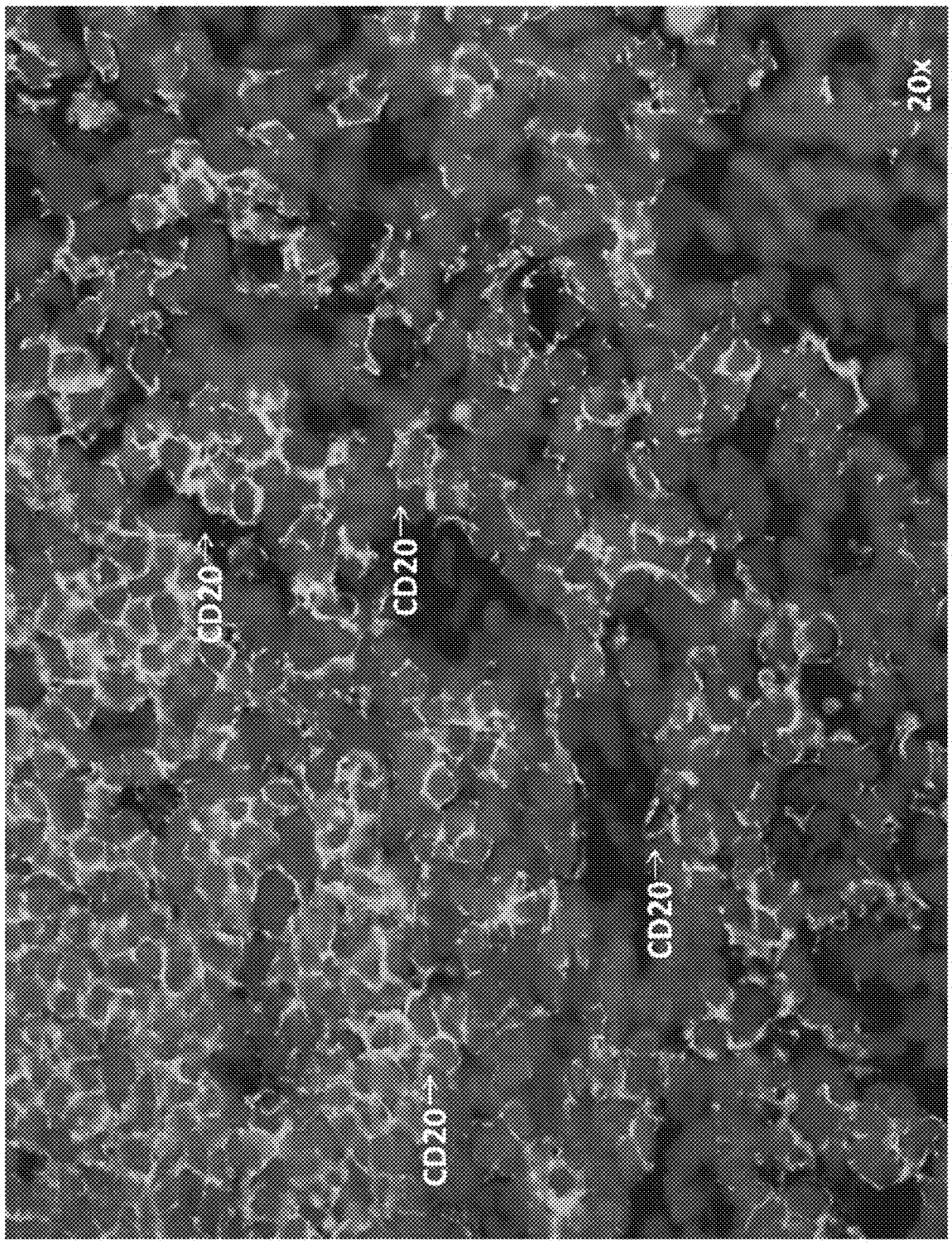

FIGS. 2A through 2D illustrate tissue samples stained with the 3-plex IHC assay noted above. FIG. 2A clearly shows signals from each of the fluorophores conjugated to the anti-tag antibodies, thus revealing locations of each of the target-epitope-tagged antibody complexes, namely CD68-epitope-tagged antibody complexes (orange signals), the CD20-epitope-tagged antibody complexes (green signals), and the Foxp3-epitope-tagged antibody complexes (purple signals). The signal produced from the DAPI counterstain appears blue in each of FIGS. 2A through 2D. FIG. 2B shows only the signals corresponding to the detected CD68-epitope-tagged antibody complexes. FIG. 2C shows only the signals corresponding to the detected Foxp3-epitope-tagged antibody complexes. FIG. 2D shows only signals corresponding to the detected CD20-epitope-tagged antibody complexes. FIGS. 2A through 2D show that the epitope-tagged antibodies of the present disclosure were (1) capable of binding to CD68, CD20, and FoxP3, respectively; (2) capable of being detected by appropriate anti-tag antibodies; and (3) able to be applied to a tissue sample simultaneously (e.g. as a cocktail of antibodies) without interfering with each other. Thus, the epitope-tagged antibodies of the present disclosure were suitable for use in multiple-assays. In addition, the multiplex assay of the present example was able to be completed in less than 4-hours. When compared to traditional multiplex assays, this represents an advancement in the art. In some embodiments, this panel may be used help immune profiling in haematological and solid tumors.

Example 2: 3-Plex Immunohistochemical Assay

Figure 3:
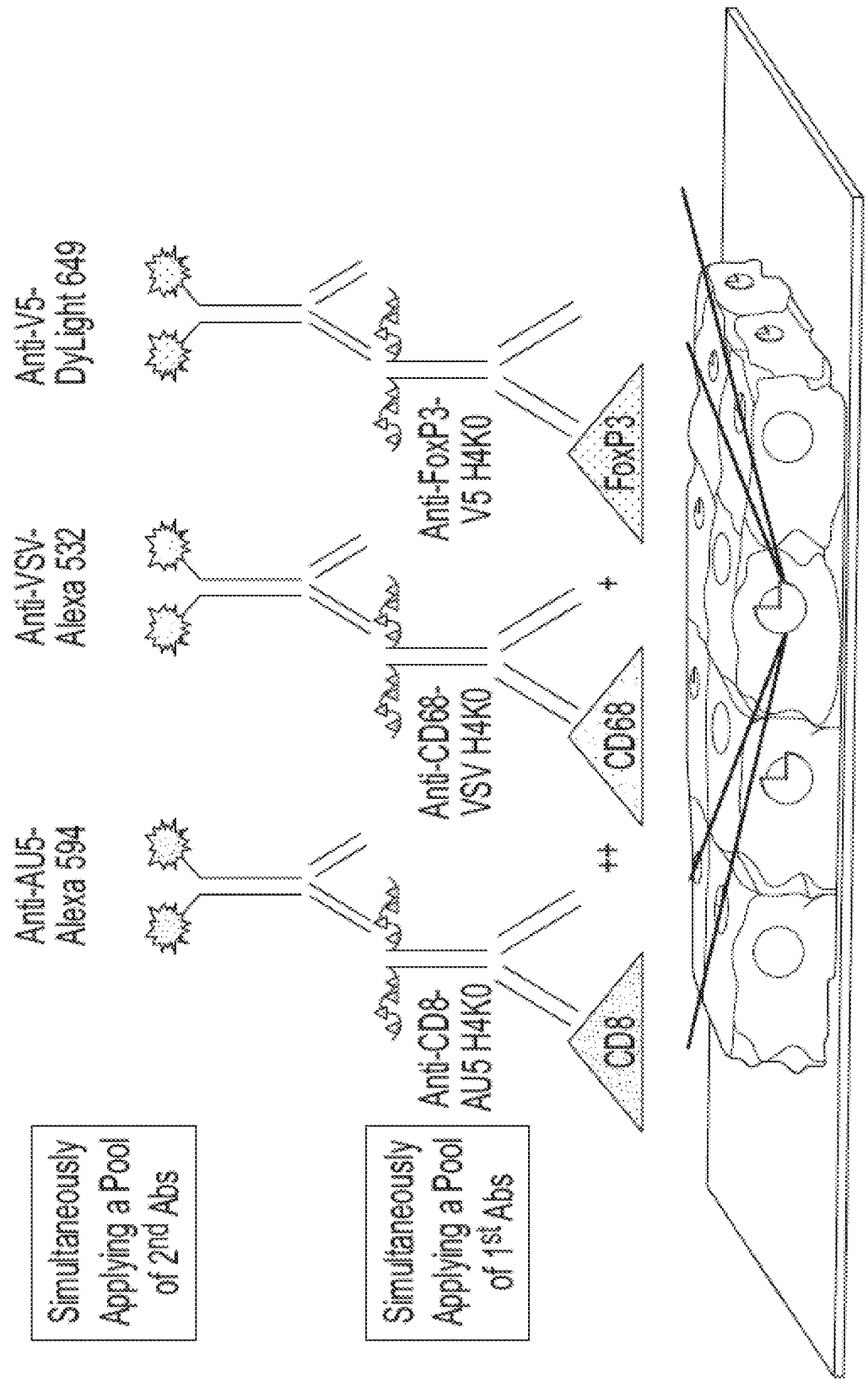
FIG. 3 illustrates a multiplex IHC assay utilizing three different epitope-tagged antibodies.

Example 2 provides a multiplex immunohistochemical assay where three different epitope-tagged antibodies were simultaneously applied to a tissue sample (see FIG. 3). A first epitope-tagged antibody was specific for CD68 (anti-CD68) and comprised the VSV epitope tag (a heavy chain comprising four VSV epitope tags). A second epitope-tagged antibody was specific to FoxP3 (anti-FoxP3) and comprised the V5 epitope tag (a heavy chain comprising five V5 epitope tags). A third epitope-tagged antibody was specific to CD8 (anti-CD8) and comprised the AU5 epitope tag (a heavy chain comprising four AU5 epitope tags). The epitope-tagged antibodies were applied as a "cocktail" comprise 2 µg/mL of each epitope-tagged antibody in diluent 90039.

After the simultaneous application of the three epitope-tagged antibodies, three anti-tag antibodies were simultaneously supplied to the tissue sample (see FIG. 3), where each anti-tag antibody was specific to a different epitope tag of the epitope-tagged antibodies. A first anti-VSV antibody was conjugated with ALEXA 532 (JH) (producing an "orange" signal); a second anti-V5 antibody was conjugated with DYLIGHT 649 (producing a "green" signal); and a third anti-AU5 antibody was conjugated with ALEXA 594 (JH) (producing a "purple" signal). The anti-tag antibodies were applied as a "cocktail" comprise 5 µg/mL of each anti-tag antibody in diluent 90040.

The following steps were undertaken for the 3-plex IHC assay (see Table 4):

TABLE 4

| Procedure Step | Selection |
|---|---|
| Deparaffinization | Selected |
| Cell Conditioning | CC1, 64 min |
| Tagged 1st Ab cocktail | Incubate - 32 min |
| Blocking with diluent 90040 | 32 min |
| Anti-tag 2nd Ab cocktail | Incubate - 32 min |
| DAPI Counterstain | 4 min |
| PROLONG DIAMOND anti-fade mounting | |

A complete protocol summary is also provided at Table 3 above.

Figure 4A:
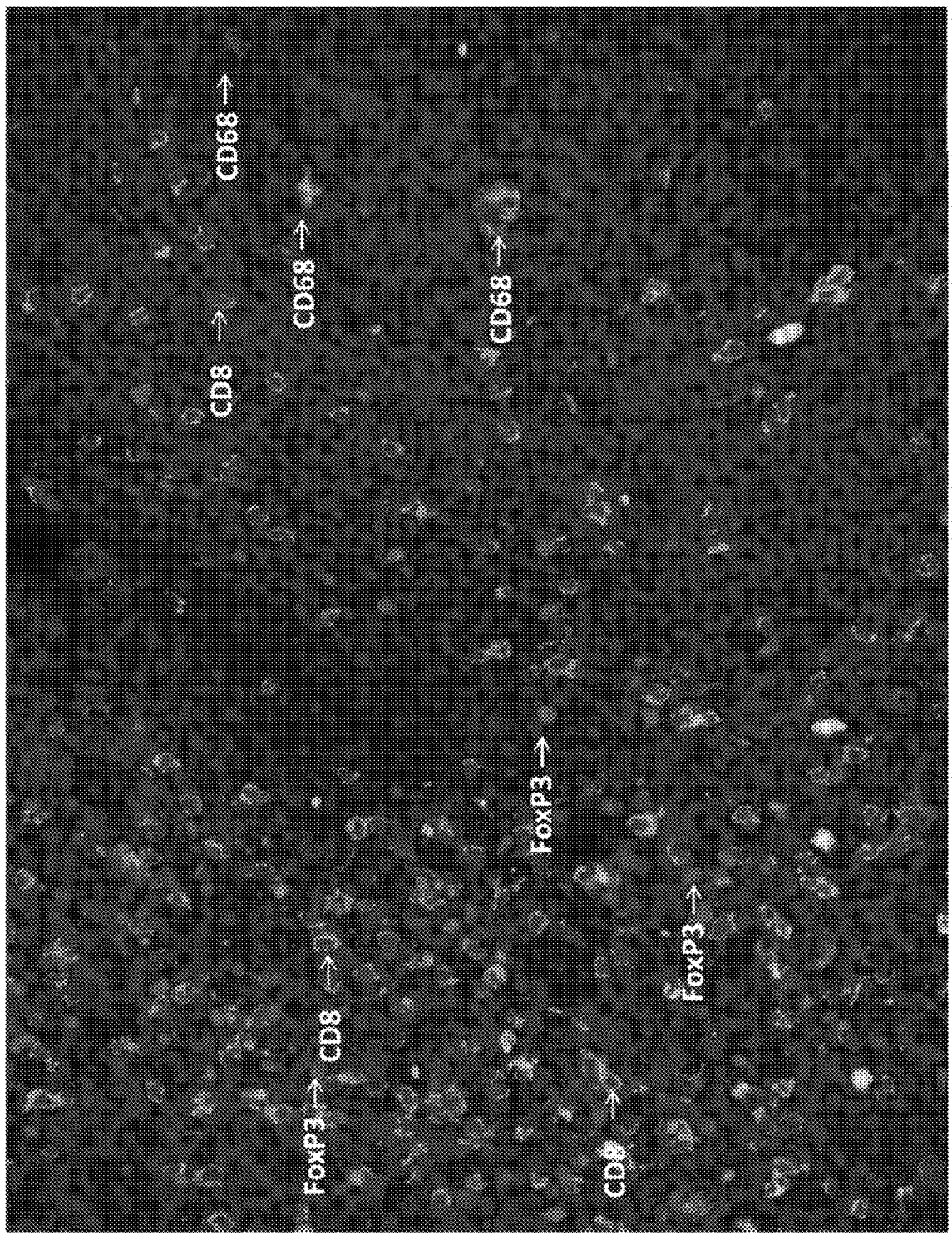
FIG. 4A and FIG. 4B are images of tissue samples stained according to a multiplex IHC assay utilizing three different epitope-tagged antibodies.
Figure 4B:
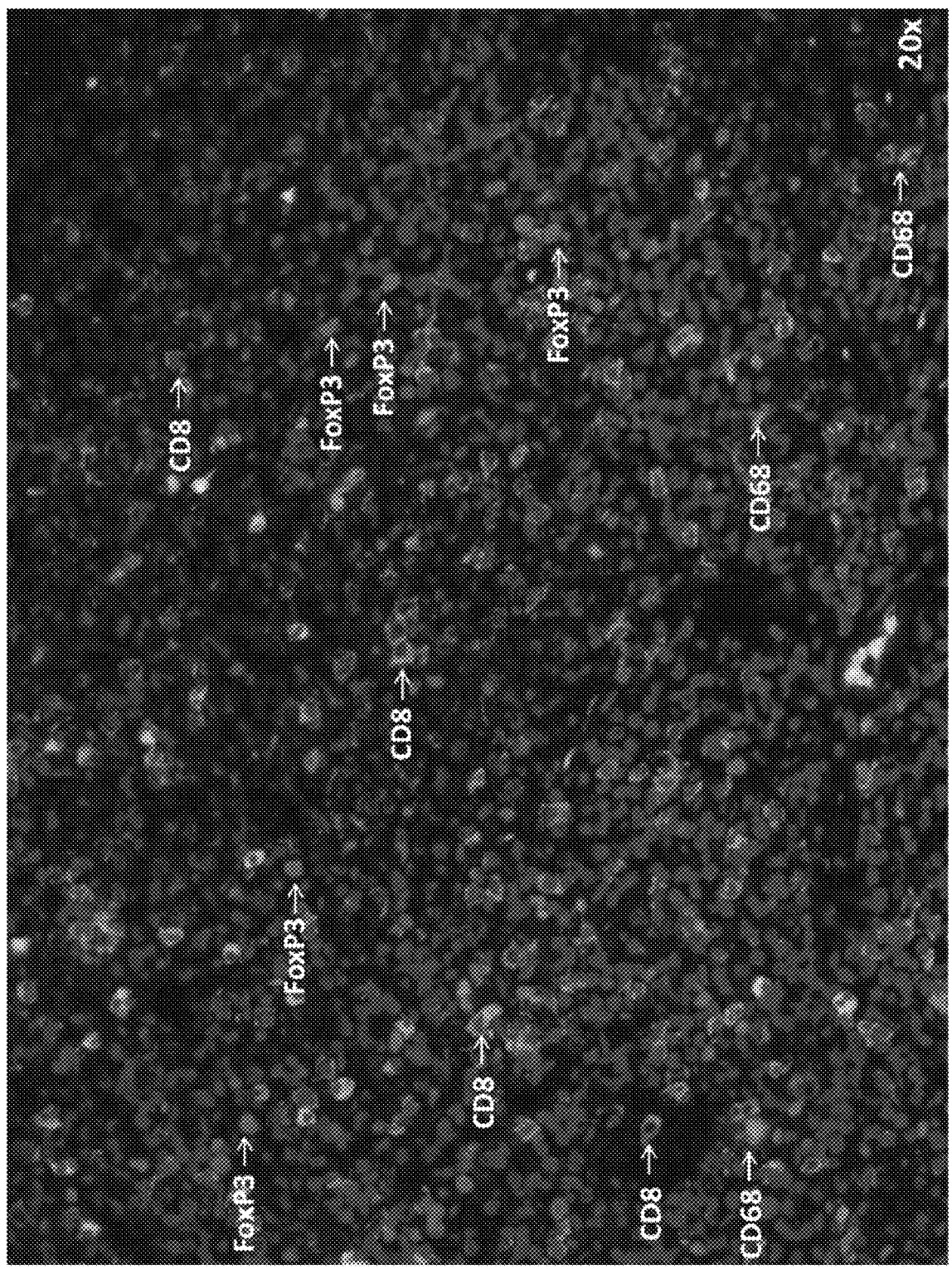

FIGS. 4A and 4B illustrate tissue samples stained with the 3-plex IHC assay noted above. FIGS. 4A and 4B clearly show signals from each of the fluorophores conjugated to the anti-tag antibodies, thus revealing locations of each of the target-epitope-tagged antibody complexes, namely CD68-epitope-tagged antibody complexes (orange signals), the CD8-epitope-tagged antibody complexes (green signals), and the Foxp3-epitope-tagged antibody complexes (purple signals). The signal produced from the DAPI counterstain appears blue in each of FIGS. 4A and 4B. FIGS. 4A and 4B thus show that the epitope-tagged antibodies of the present disclosure were (1) capable of binding to CD68, CD8, and FoxP3, respectively; (2) capable of being detected by appropriate anti-tag antibodies; and (3) able to be applied to a tissue sample simultaneously (e.g. as a cocktail of antibodies) without interfering with each other. Thus, the epitope-tagged antibodies of the present disclosure were suitable for use in multiple-assays. In addition, the multiplex assay of the present example was able to be completed in less than 4-hours. When compared to traditional multiplex assays, this again represents an advancement in the art. This panel of immune markers help immune profiling in hematological and solid tumors.

Example 3: 4-Plex Immunohistochemical Assay Using Combined Anti-Species and Anti-Tag Antibodies Example 3 provides a multiplex immunohistochemical assay where four different epitope-tagged antibodies were applied to a tissue sample (see FIG. 5) in two stages. First, an unmodified antibody, namely an anti-Pan-CK antibody, was contacted with the tissue sample. Following application of the anti-Pan-CK antibody, a goat anti-mouse-ALEXA 488 antibody was applied to detect the target-anti-Pan-CK antibody complex (Goat anti-mouse ALEXA 488 (2 µg/mL) in diluent 90040).

Figure 5:
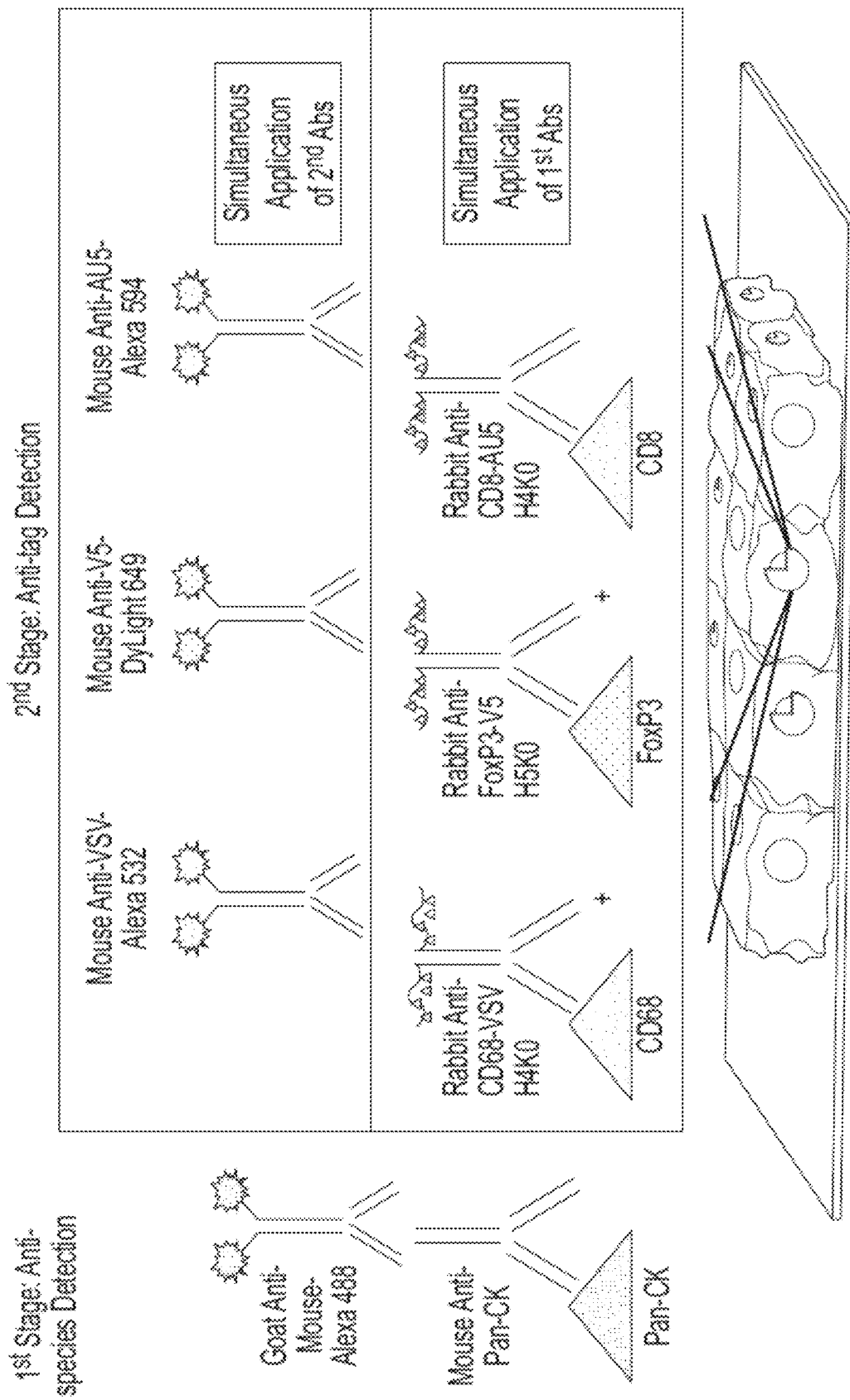
FIG. 5 illustrates a multiplex IHC assay utilizing one unmodified antibody and three different epitope-tagged antibodies.

A second stage was then conducted where three epitope-tagged antibodies were simultaneously supplied to the tissue sample (see FIG. 5). In this second stage, a first epitope-tagged antibody was specific for CD68 (anti-CD68) and comprised the VSV epitope tag (a heavy chain comprising four VSV epitope tags). A second epitope-tagged antibody was specific to FoxP3 (anti-FoxP3) and comprised the V5 epitope tag (a heavy chain comprising five V5 epitope tags). A third epitope-tagged antibody was specific to CD8 (anti-CD8) and comprised the AU5 epitope tag (a heavy chain comprising four AU5 epitope tags). The epitope-tagged antibodies were applied as a "cocktail" comprise 2 µg/mL of each epitope-tagged antibody in diluent 90039.

After the simultaneous application of the three epitope-tagged antibodies, three anti-tag antibodies were simultaneously supplied to the tissue sample (see FIG. 5), where each anti-tag antibody was specific to a different epitope tag of the epitope-tagged antibodies. A first anti-VSV antibody was conjugated with ALEXA 532 (JH); a second anti-V5 antibody was conjugated with DYLIGHT 649; and a third anti-AU5 antibody was conjugated with ALEXA 594 (JH). The anti-tag antibodies were applied as a "cocktail" comprise 5 µg/mL of each anti-tag antibody in diluent 90040.

The following steps were undertaken for the 4-plex IHC assay (see Table 5):

TABLE 5

| Procedure Step | Selection |
| --- | --- |
| Deparaffinization | Selected |
| Cell Conditioning | CC1, 64 min |
| Mouse anti-pan-CK | 32 min |
| Goat anti-mouse-Alexa-ALEXA 488 | 32 min |
| Blocking reagent 90040 | 32 min |
| Tagged 1st Ab cocktail | Incubate - 32 min |
| Blocking with diluent 90040 | 32 min |
| Anti-tag 2nd Ab cocktail | Incubate - 32 min |
| DAPI Counterstain | 4 min |
| PROLONG DIAMOND anti-fade mounting | |

A complete protocol summary is provided at Tables 6B, 6C, and 6D.

Figure 6A:
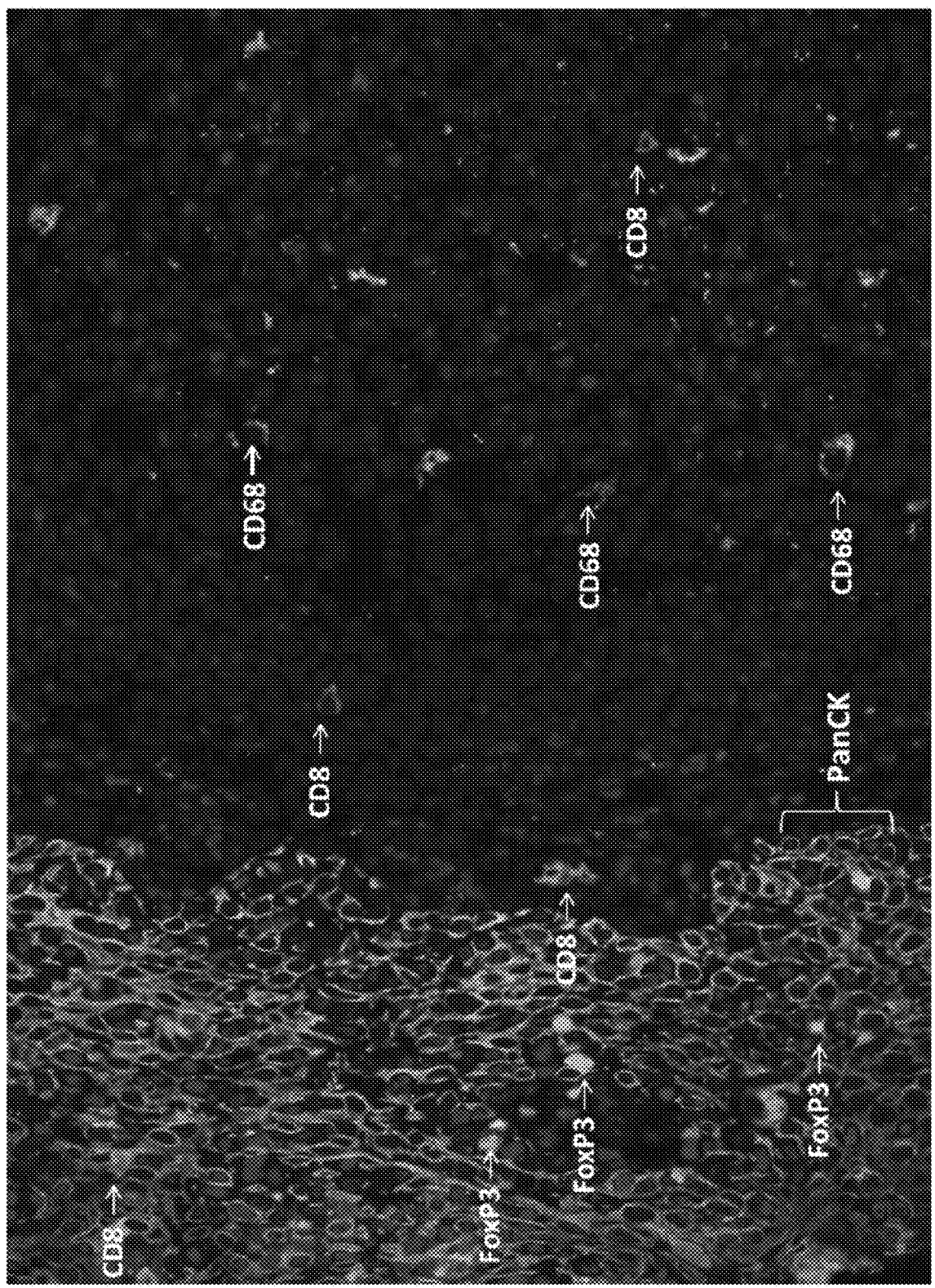
FIG. 6A, FIG. 6B, FIG. 6C, FIG. 6D, FIG. 6E, and FIG. 6F are images of tissue samples stained according to a multiplex IHC assay utilizing one unmodified antibody and three different epitope-tagged antibodies.
Figure 6B:
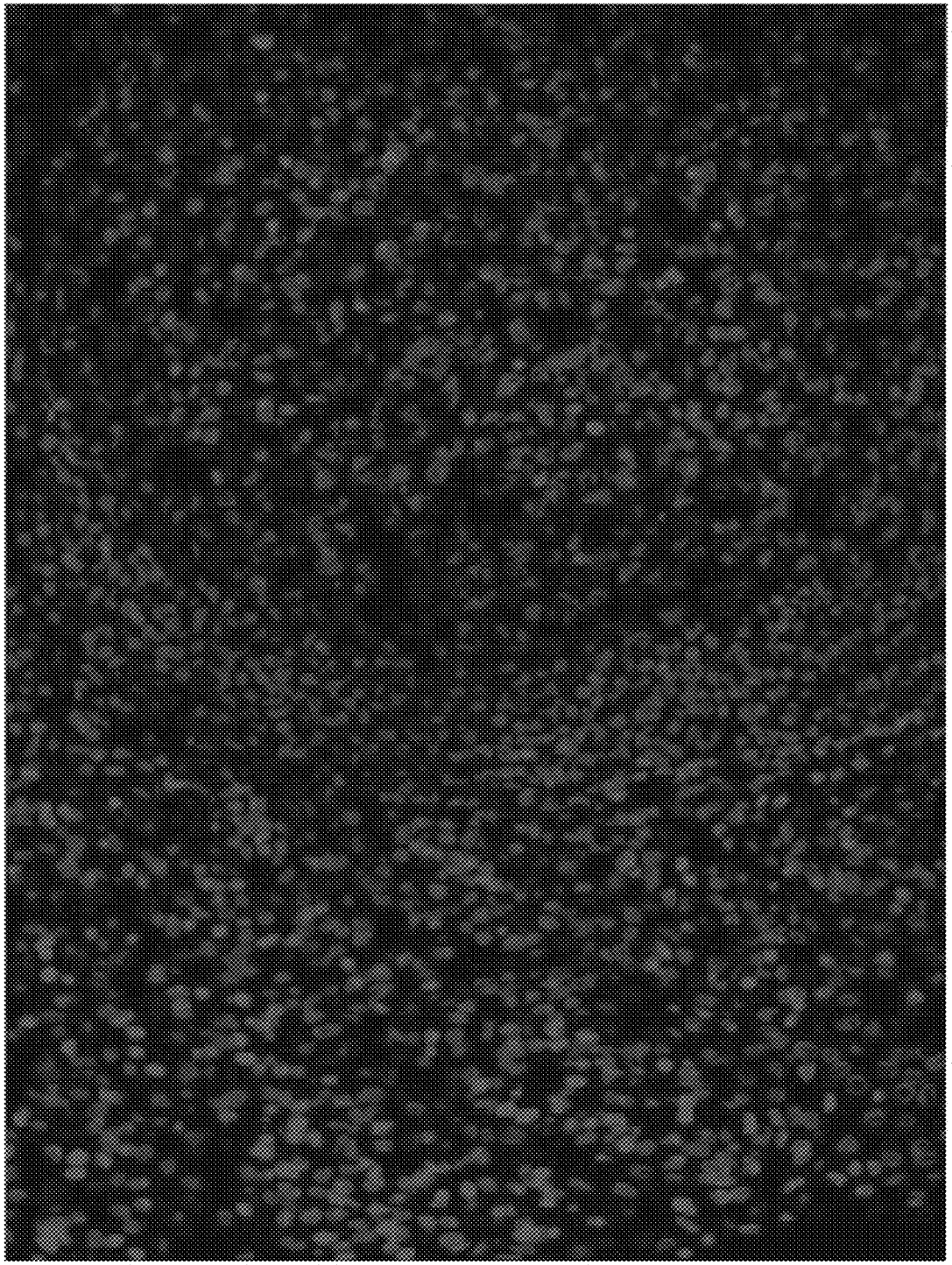
Figure 6C:
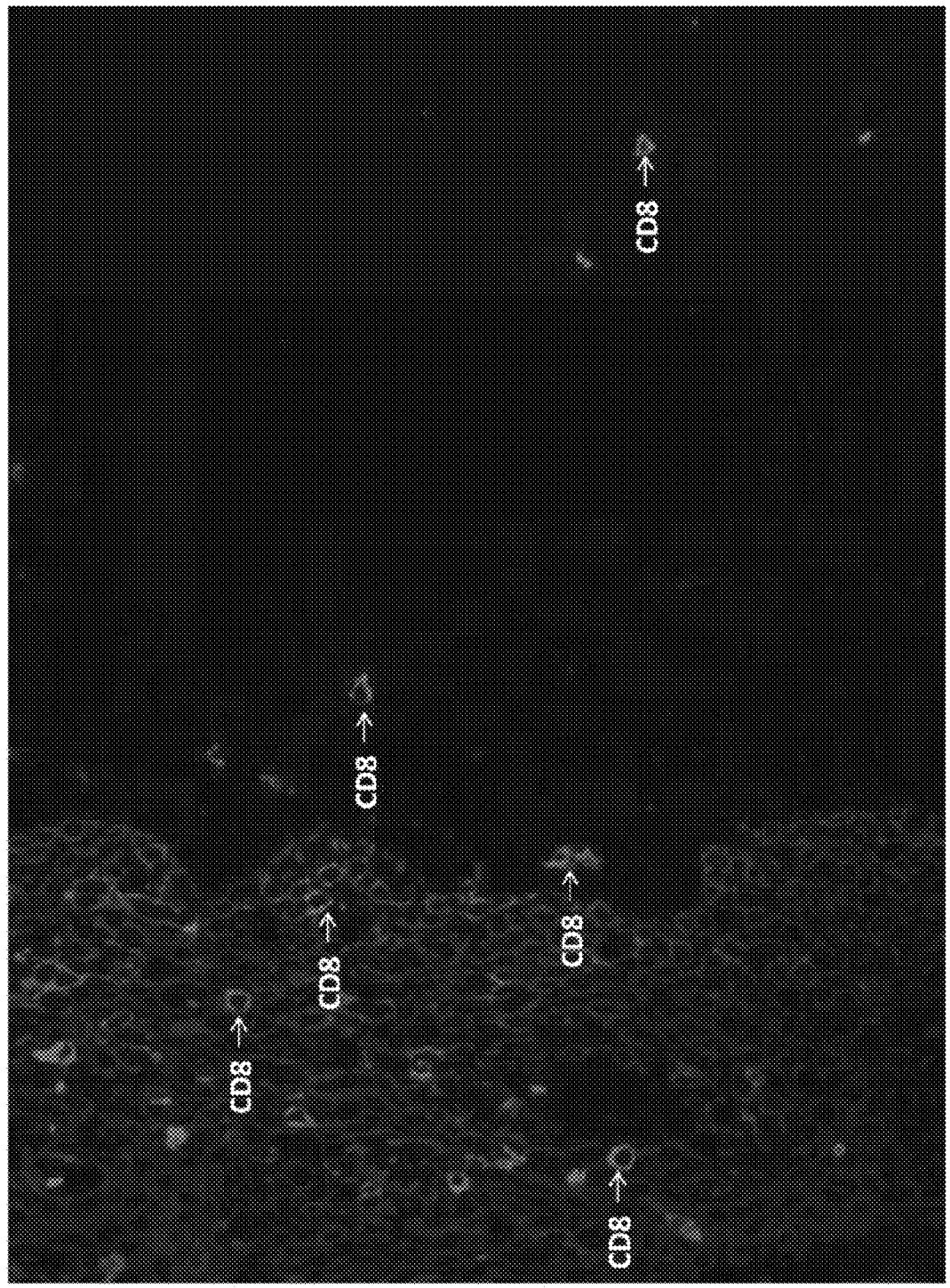
Figure 6D:
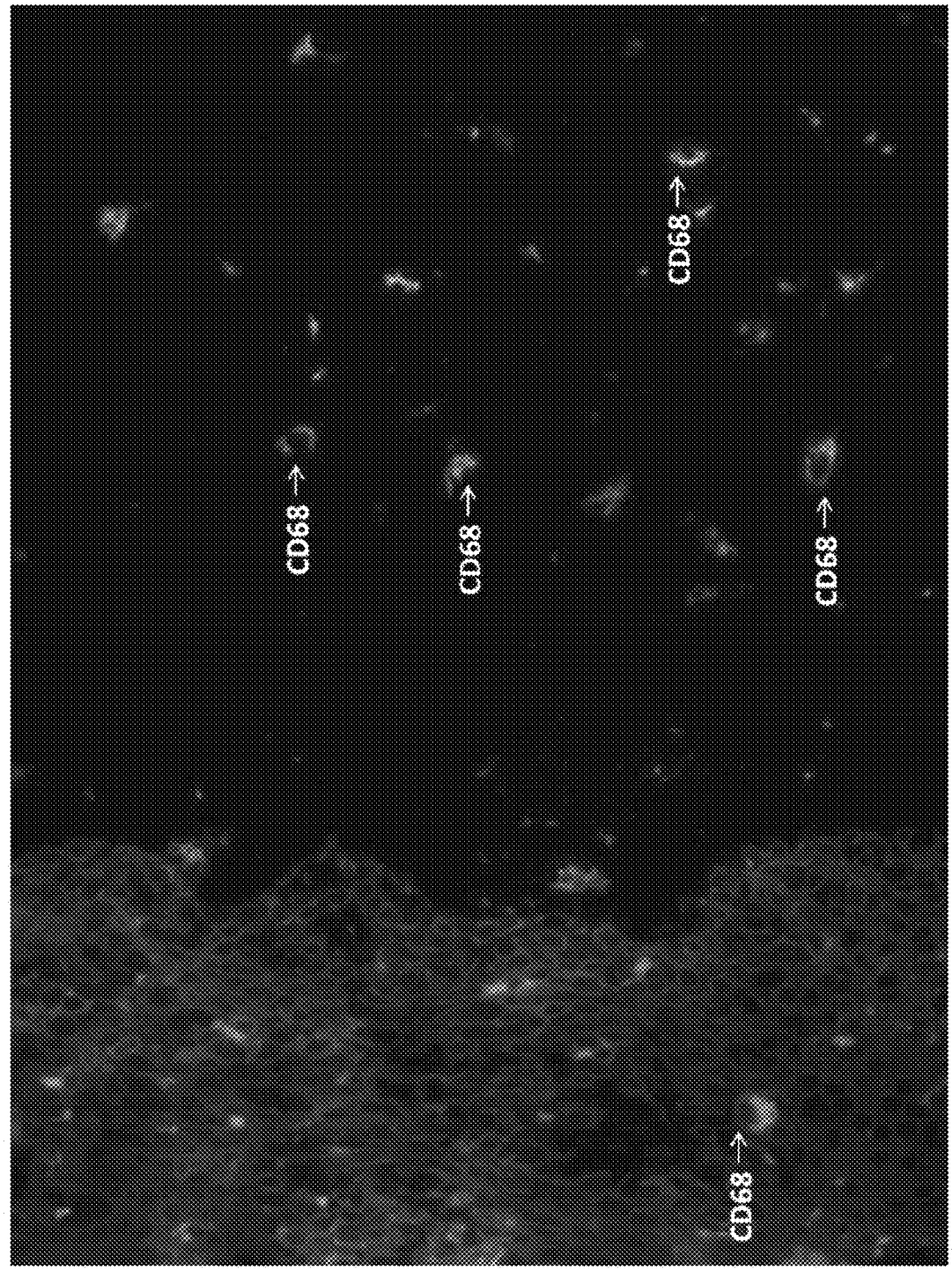
Figure 6E:
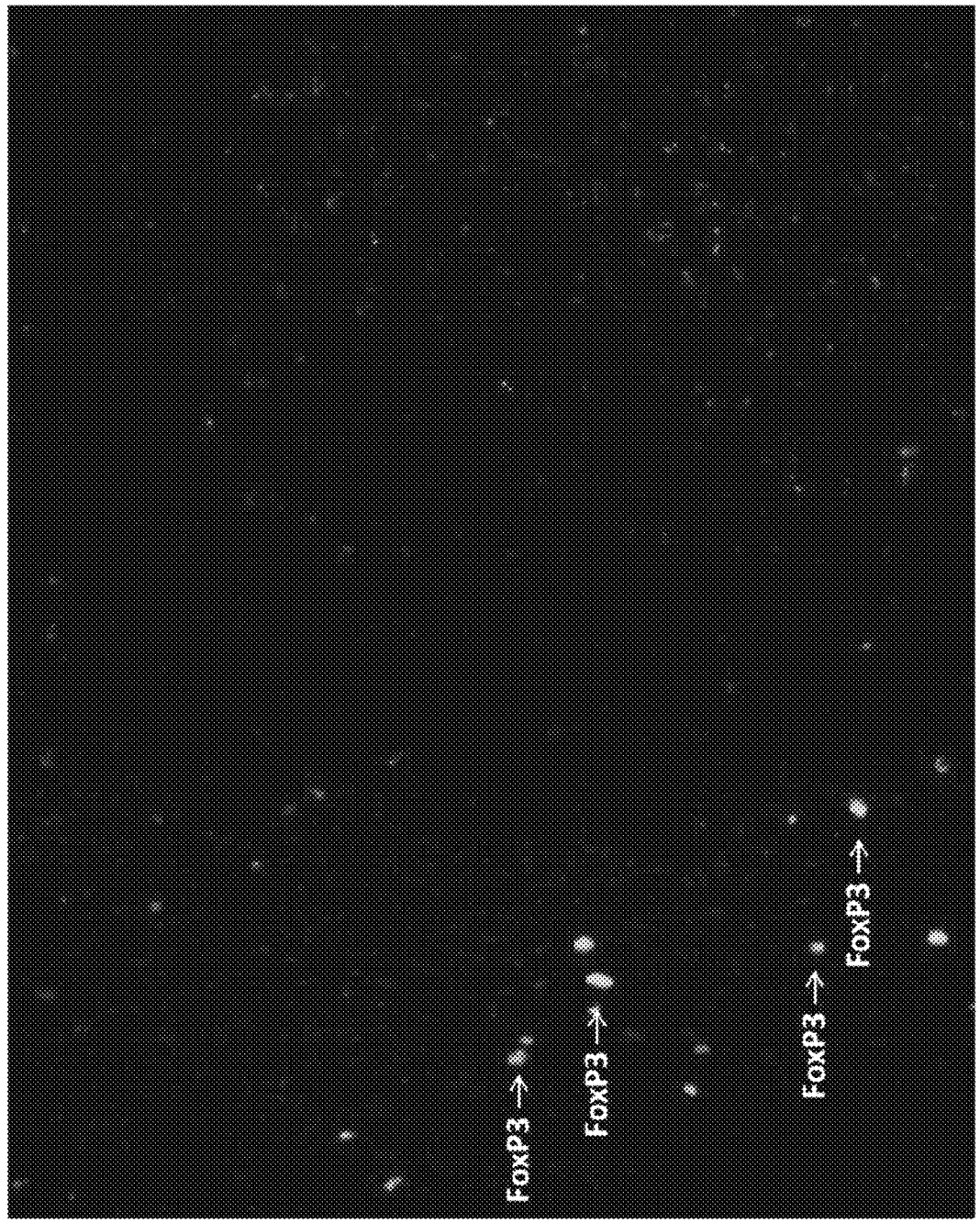
Figure 6F:
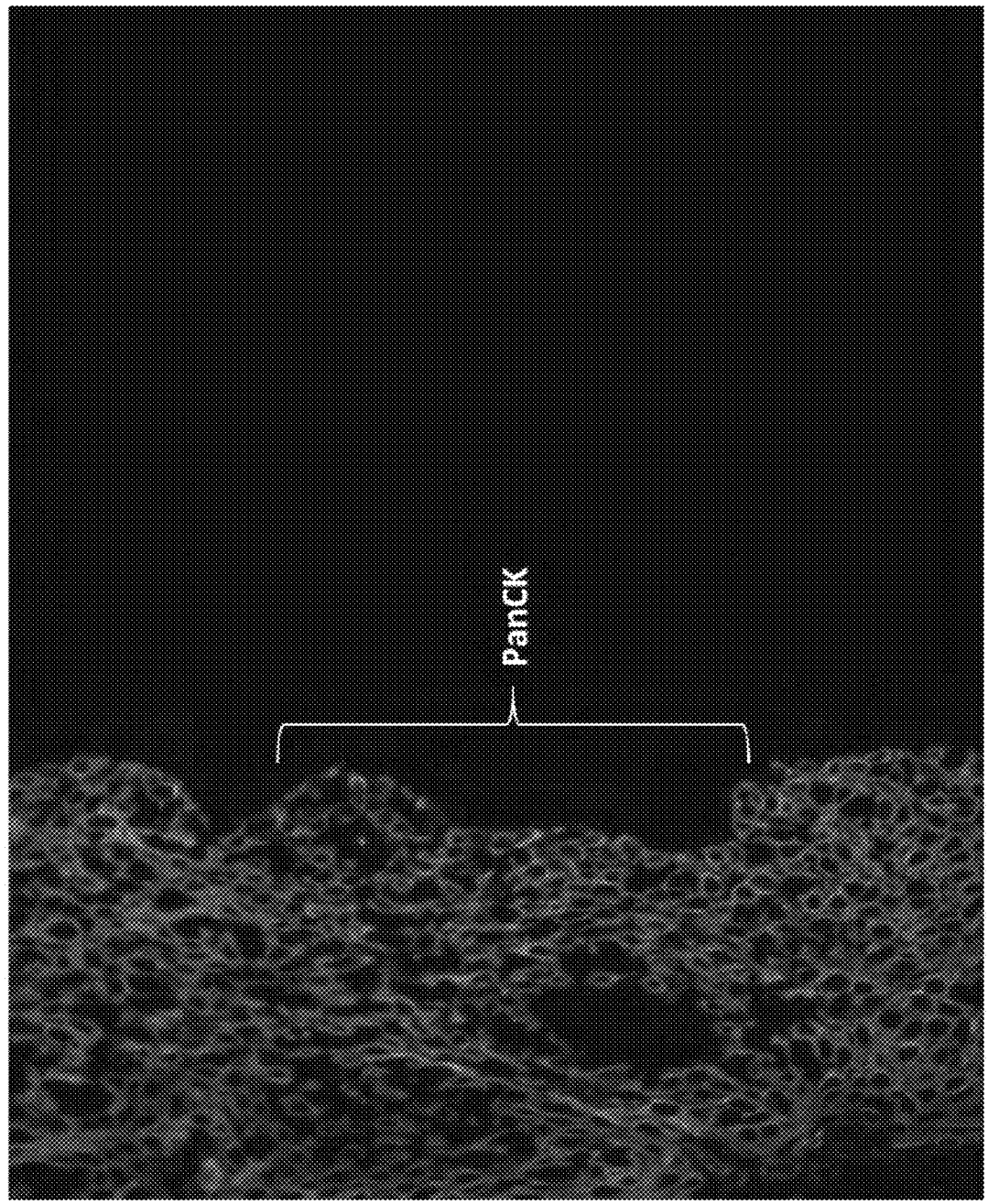

FIGS. 6A through 6F illustrate tissue samples stained with the 4-plex IHC assay noted above. FIG. 6A clearly shows signals from each of the fluorophores conjugated to either the anti-species antibody or anti-tag antibodies, thus revealing locations of each of the target-antibody complexes, namely the Pan-CK-antibody complexes ("green" signals), the CD68-epitope-tagged antibody complexes ("orange" signals), the CD8-epitope-tagged antibody complexes ("red" signals), and the Foxp3-epitope-tagged antibody complexes ("cyan" signals). The signal produced from the DAPI counterstain appears blue in each of FIGS. 6A through 6F. FIG. 6B shows only the signals corresponding to the DAPI counterstain. FIG. 6C shows only the signals corresponding to the detected CD8-epitope-tagged antibody complexes. FIG. 6D shows only the signals corresponding to the detected CD68-epitope-tagged antibody complexes. FIG. 6E shows only signals corresponding to the detected FoxP3-epitope-tagged antibody complexes. FIG. 6F shows only signals corresponding to the detected Pan-CK staining. FIGS. 6A through 6E show that the epitope-tagged antibodies of the present disclosure were (1) capable of binding to CD68, CD8, and FoxP3, respectively; (2) capable of being detected by appropriate anti-tag antibodies; and (3) able to be applied to a tissue sample simultaneously (e.g. as a cocktail of antibodies) without interfering with each other.

FIG. 6A also illustrates that the epitope-tagged antibodies may be combined in an assay with unmodified antibodies or antibody conjugates, such as mouse anti-Pan-CK antibodies, and that such a combination allows for the detection of all fluorophores conjugated to anti-species or anti-tag antibodies. In addition, the multiplex assay of the present example was able to be completed within 4 hours. When compared to traditional multiplex assays, this represents an advancement in the art. This panel of markers may be useful to show the expression and distribution of the above-mentioned immune cell markers and epithelial cell marker within a tumor region.

Example 4: 4-Plex Immunohistochemical Assay Using Combined Anti-Species and Anti-Tau Antibodies Example 4 provides a multiplex immunohistochemical assay where four different epitope-tagged antibodies were applied to a tissue sample (see FIG. 7) in two stages. First, an unmodified antibody, namely an anti-Pan-CK antibody, was contacted with the tissue sample. Following application of the anti-Pan-CK antibody, a goat anti-mouse-ALEXA 488 antibody was applied to detect the target-anti-Pan-CK antibody complex (Goat anti-mouse ALEXA 488 (2 µg/mL) in diluent 90040).

Figure 7:
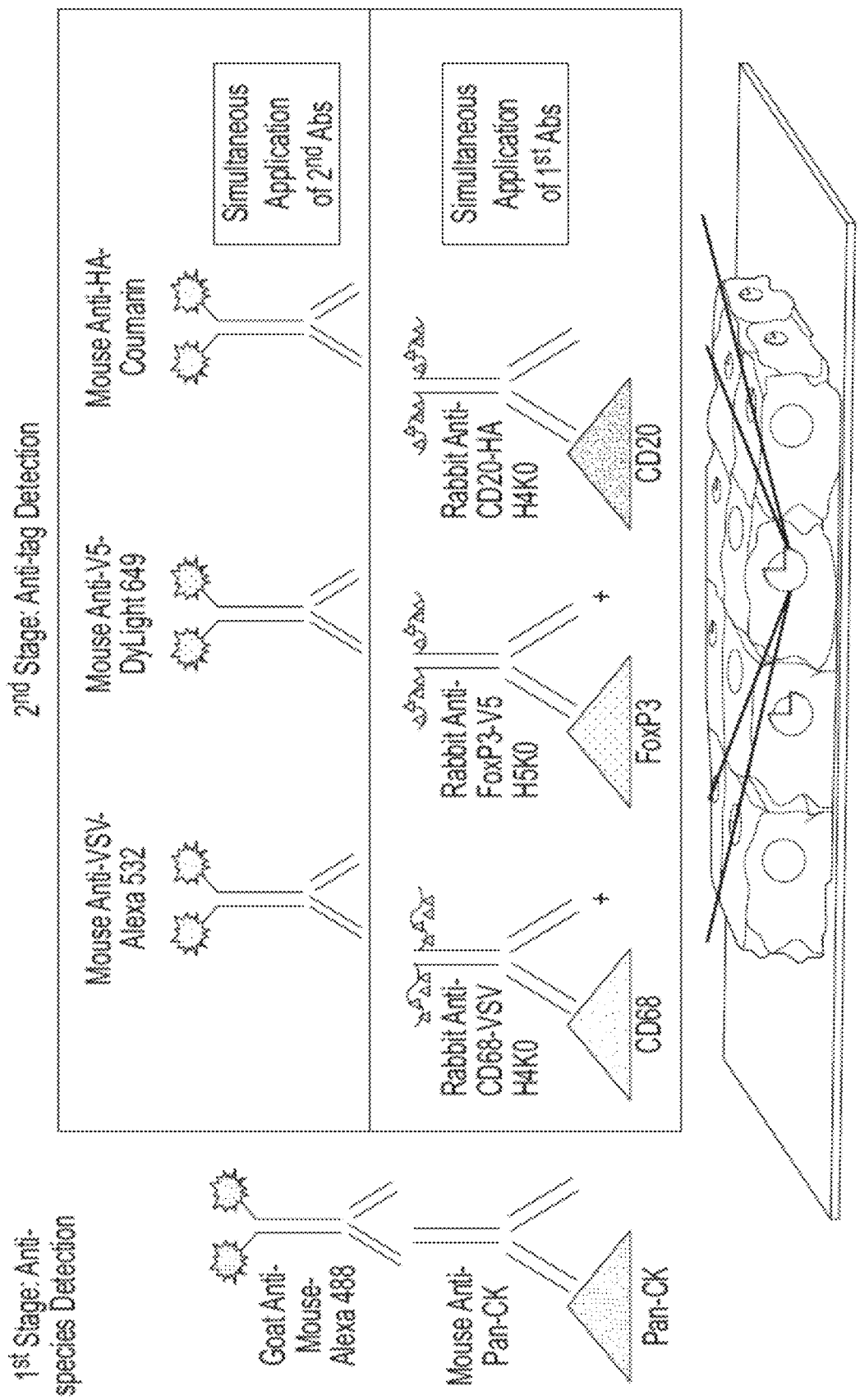
FIG. 7 illustrates a multiplex IHC assay utilizing one unmodified antibody and three different epitope-tagged antibodies.

A second stage was then conducted where three epitope-tagged antibodies were simultaneously supplied to the tissue sample (see FIG. 7). In this second stage, a first epitope-tagged antibody was specific for CD68 (anti-CD68) and comprised the VSV epitope tag (a heavy chain comprising four VSV epitope tags). A second epitope-tagged antibody was specific to FoxP3 (anti-FoxP3) and comprised the V5 epitope tag (a heavy chain comprising five V5 epitope tags). A third epitope-tagged antibody was specific to CD20 (anti-CD20) and comprised the HA epitope tag (a heavy chain comprising four HA epitope tags). The epitope-tagged antibodies were applied as a "cocktail" comprise 2 ag/mL of each epitope-tagged antibody in diluent 90039.

After the simultaneous application of the three epitope-tagged antibodies, three anti-tag antibodies were simultaneously supplied to the tissue sample (see FIG. 7), where each anti-tag antibody was specific to a different epitope tag of the epitope-tagged antibodies. A first anti-VSV antibody was conjugated with ALEXA532 (JH); a second anti-V5 antibody was conjugated with DYLIGHT 649; and a third anti-AU5 antibody was conjugated with Coumarin (JH). The anti-tag antibodies were applied as a "cocktail" comprise 5 µg/mL of each anti-tag antibody in diluent 90040.

The following steps were undertaken for the 4-plex IHC assay (see Table 6A):

TABLE 6A

| Procedure Step | Selection |
| --- | --- |
| Deparaffinization | Selected |
| Cell Conditioning | CC1, 64 min |
| Mouse anti-pan-CK | 32 min |
| Goat anti-mouse- Alexa-ALEXA 488 | 32 min |
| Blocking reagent 90040 | 32 min |
| Tagged 1st Ab cocktail | Incubate - 32 min |
| Blocking with diluent 90040 | 32 min |
| Anti-tag 2nd Ab cocktail | Incubate - 32 min |
| DAPI Counterstain | 4 min |
| PROLONG DIAMOND anti-fade mounting | |

A complete protocol summary is provided at Tables 6B, 6C, and 6D:

TABLE 6B

| | |
|---|---|
| 1 | Enable Mixers |
| 2 | Disable Mixers |
| 3 | [72 C. is the standard temperature] |
| 4 | Warmup Slide m (72 Deg C.) from Medium Temperatures (Deparaffinization) |
| 5 | Incubate for 4 minutes |
| 6 | Apply EZPrep Volume Adjust |
| 7 | Rinse Slide With EZ Prep |
| 8 | Apply EZPrep Volume Adjust |
| 9 | Apply Coverslip |
| 10 | Rinse Slide With EZ Prep |
| 11 | Apply EZPrep Volume Adjust |
| 12 | Apply Coverslip |
| 13 | Enable Mixers |
| 14 | Disable Slide Heater |
| 15 | Pause Point I Landing Zone I |
| 16 | Rinse Slide With EZ Prep |
| 17 | Apply long Cell Conditioner #1 |
| 18 | Apply CC Coverslip Long |
| 19 | [100 C. is the standard temperature] |
| 20 | Warmup Slide ID (100 Deg C. and Incubate for 4 Minutes ( Cell Conditioner #1) |
| 21 | Incubate for4 Minutes |
| 22 | Incubate for 8 minutes |
| 23 | Apply Cell conditioner #1 |
| 24 | Apply CC Medium Coverslip No BB |
| 25 | Incubate for 8 minutes |
| 26 | Incubate for 8 minutes |
| 27 | Apply Cell conditioner #1 |
| 28 | Apply CC Medium Coverslip No BB |
| 29 | Incubate for 8 minutes |
| 30 | incubate for 8 minutes |
| 31 | apply cell conditioner #1 |
| 32 | Apply CC medium Coverslip No BB |
| 33 | Incubate for 8 minutes |
| 34 | Apply Cell conditioner #1 |
| 35 | Apply CC Medium Coverslip No BB |
| 36 | Apply Cell conditioner #1 |
| 37 | Apply CC Medium Coverslip No BB |
| 38 | Apply Cell conditioner #1 |
| 39 | Apply CC Medium Coverslip No BB |
| 40 | Disable Slide Heater |
| 41 | Apply Cell conditioner #1 |
| 42 | Apply CC Medium Coverslip No BB |
| 43 | Rinse Slide with Reaction Buffer |
| 44 | Adjust slide volume with reaction buffer |
| 45 | Apply Coverslip |

TABLE 6C

| | |
|---|---|
| 46 | Rinse Slide With Reaction Buffer |
| 47 | Aqus1 Side Volume With Reaction Buffer |
| 48 | Apply Coverslip |
| 49 | Pause Point Landing Zone |
| 50 | Warmup Slide ID 36 Deg C. |
| 51 | Rinse Slide with reaction Buffer |
| 52 | Adjust Slide Volume with reaction Buffer |
| 53 | Apply one drop of anti-pan keratin (antibody), apply coverslip, and incubate for 0 hr and 16 min |
| 54 | Rinse slide with reaction buffer |
| 55 | Adjust Slide volume with reaction buffer |
| 56 | Apply Coverslip |
| 57 | Rinse slide with reaction buffer |
| 58 | Adjust Slide volume with reaction buffer |
| 59 | Apply Coverslip |
| 60 | Apply one drop of Pretreatment #1 and incubate for 32 minutes |
| 61 | Rinse slide with reaction buffer |
| 62 | Adjust Slide volume with reaction buffer |
| 63 | [blocking buffer] |
| 64 | Apply Coverslip |
| 65 | Rinse slide with reaction buffer |
| 66 | Adjust Slide volume with reaction buffer |
| 67 | Apply Coverslip |
| 68 | Hand Apply (Secondary Antibody), and incubate for 32 minutes |

TABLE 6C-continued

| | |
|---|---|
| 69 | Rinse slide with reaction buffer |
| 70 | Adjust Slide volume with reaction buffer |
| 71 | Apply Coverslip |
| 72 | Rinse Slide With Reaction Buffer |
| 73 | Adjust Slide volume with reaction buffer |
| 74 | Apply Coverslip |
| 75 | Rinse Slide With Reaction Buffer |
| 76 | Adjust Slide volume with reaction buffer |
| 77 | Apply Cover-slip |
| 78 | Hand Apply {Primary antibody). and Incubate for 32 minutes |
| 79 | (Ab w/Tags) |
| 80 | Rinse slide with reaction buffer |
| 81 | Adjust Slide volume with reaction buffer |
| 82 | Apply Coverslip |
| 83 | Rinse slide with reaction buffer |
| 84 | Adjust Slide volume with reaction buffer |
| 85 | Apply Coverslip |
| 86 | Apply One Drop of [OPTION 2] (2nd option) and Incubate for 32 minutes |
| 87 | Rinse Slide With Reaction Buffer |
| 88 | Adjust Slide volume with reaction buffer |
| 89 | [Blocking Buffer] |
| 90 | Apply Coverslip |

TABLE 6D

| | |
|---|---|
| 91 | Rinse slide with reaction buffer |
| 92 | Adjust Slide volume with reaction buffer |
| 93 | Apply Coverslip |
| 94 | Hand Apply (Secondary Antibody), and incubate for 32 minutes |
| 95 | Rinse slide with reaction buffer |
| 96 | Adjust Slide volume with reaction buffer |
| 97 | Apply Coverslip |
| 98 | Rinse Slide With Reaction Buffer |
| 99 | Adjust Slide volume with reaction buffer |
| 100 | Apply Coverslip |

Figure 8A:
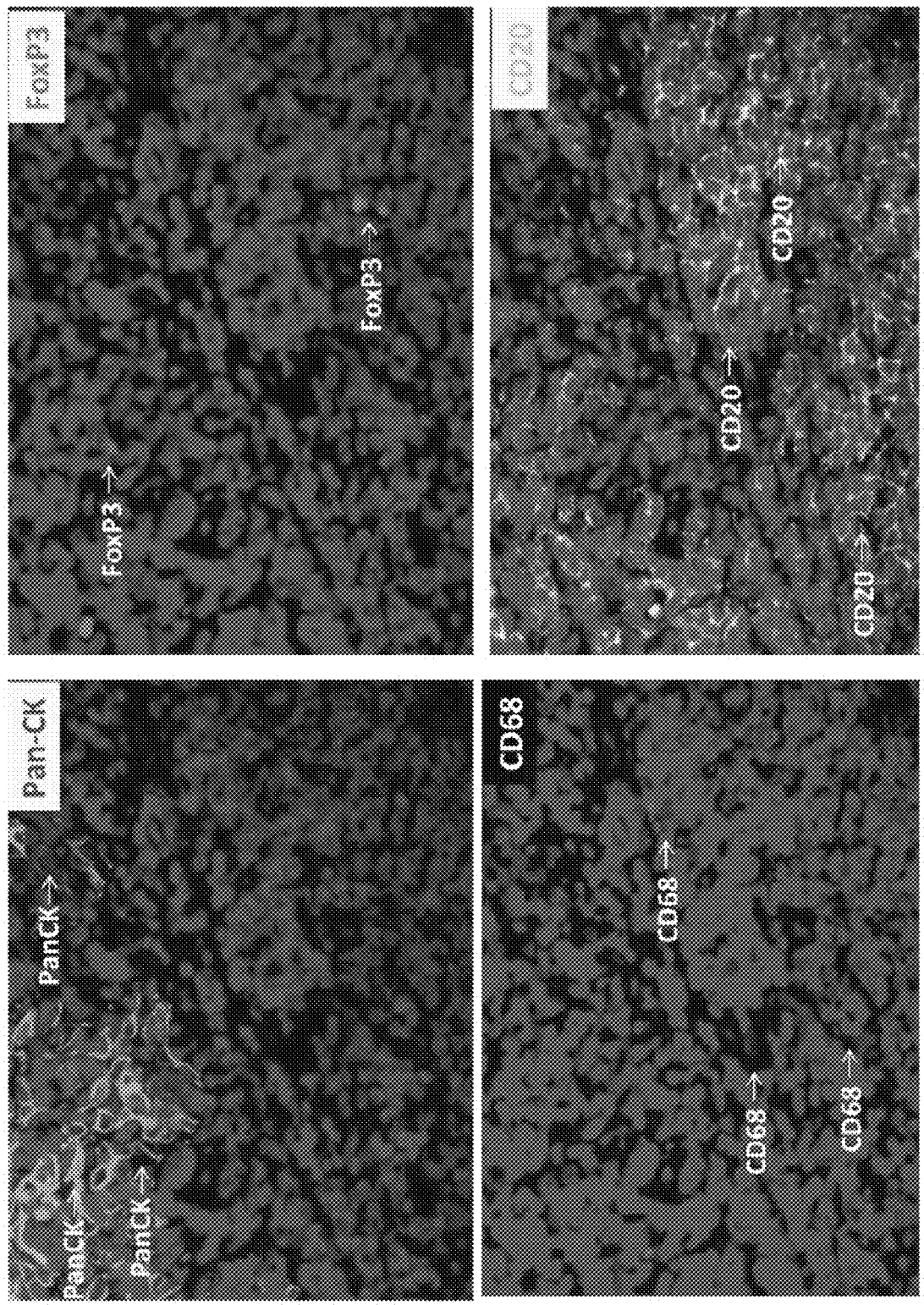
FIG. 8A and FIG. 8B are images of tissue samples stained according to a multiplex IHC assay utilizing one unmodified antibody and three different epitope-tagged antibodies.
Figure 8B:
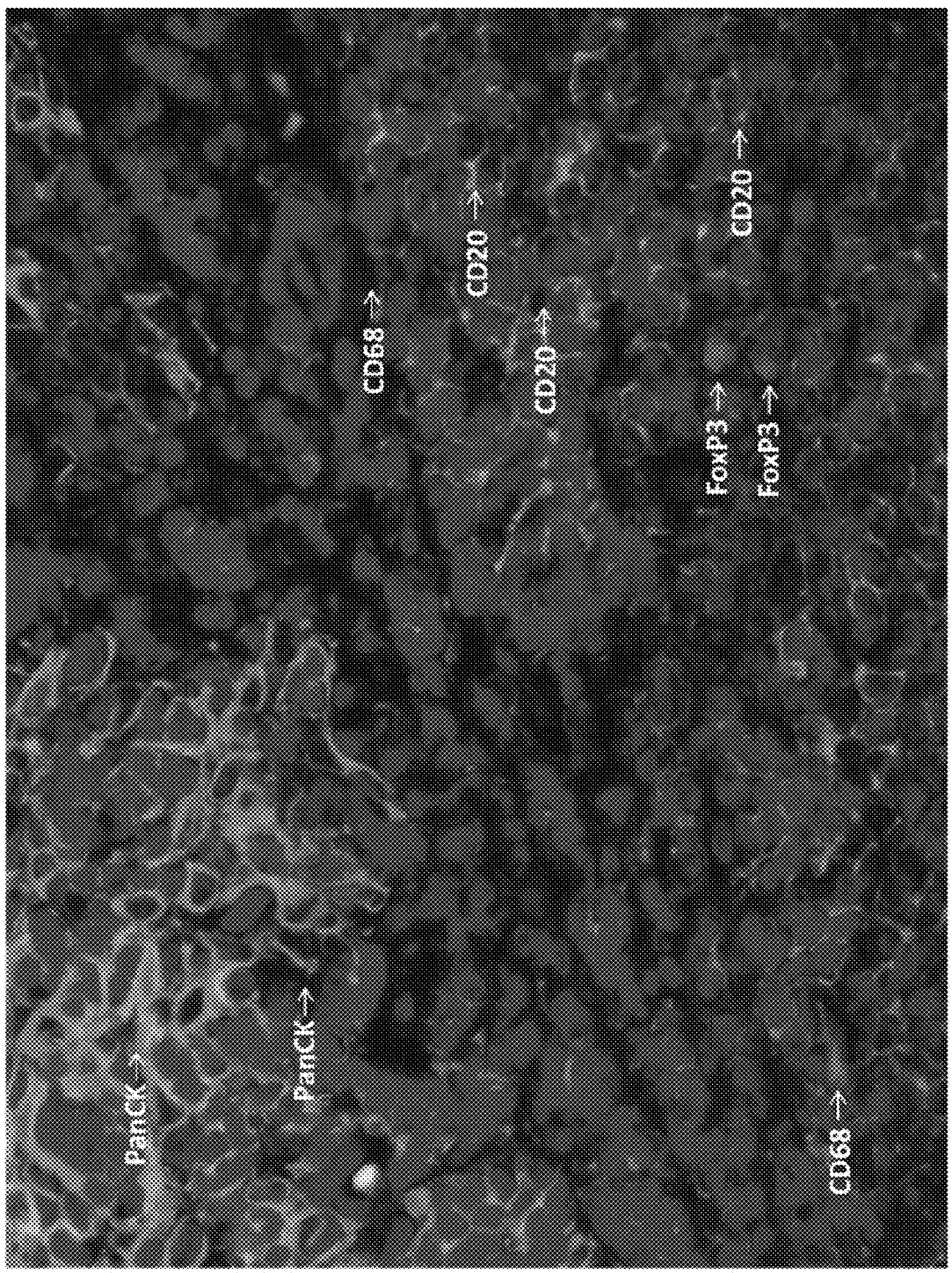

FIGS. 8A and 8B illustrate tissue samples stained with the 4-plex IHC assay noted above. FIG. 8A provides four images, each image showing signals corresponding to detected Pan-CK, FoxP3, CD68, and CD20. FIG. 8B provides an image where each of the signals corresponding to detected Pan-CK, FoxP3, CD68, and CD20, the image derived from a tissue sample onto which all four of the above-identified antibodies were applied. Once again, FIGS. 8A and 8B show that the epitope-tagged antibodies of the present disclosure were (1) capable of binding to CD68, CD20, and FoxP3, respectively; (2) capable of being detected by appropriate anti-tag antibodies; and (3) able to be applied to a tissue sample simultaneously (e.g. as a cocktail of antibodies) without interfering with each other. FIG. 8B also illustrates that the epitope-tagged antibodies may be combined in an assay with unmodified antibodies or antibody conjugates, such as mouse anti-Pan-CK antibodies and that such a combination allows for the detection of all fluorophores conjugated to anti-species or anti-tag antibodies. In addition, the multiplex assay of the present example was able to be completed within 4 hours. When compared to traditional multiplex assays, this represents an advancement in the art. This panel of markers may be useful to show the expression and distribution of the above-mentioned immune cell markers and epithelial cell marker for tumor region.

Example 5: 4-Plex Immunohistochemical Assay Using Combined Anti-Species and Anti-Tag Antibodies Example 5 provides a multiplex immunohistochemical assay where four different epitope-tagged antibodies were applied to a tissue sample (see FIG. 9) in two stages. As compared with Examples 3 and 5, Example 5 provides two antibodies in a first stage and another two epitope-tagged antibodies in a second stage.

Figure 9:
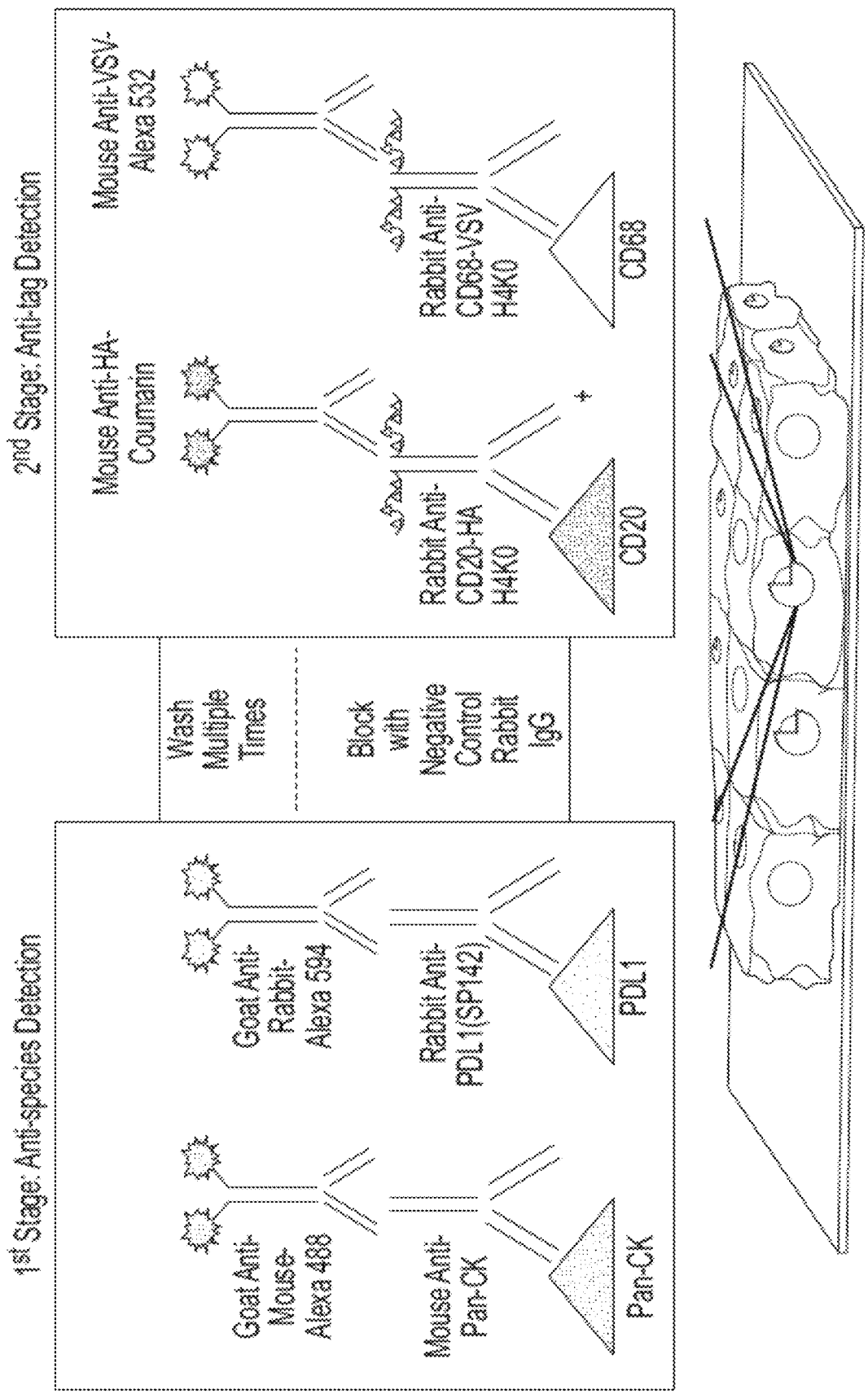
FIG. 9 illustrates a multiplex IHC assay utilizing two unmodified antibodies and two different epitope-tagged antibodies.

With regard to the first stage depicted in FIG. 9, a first unmodified antibody, namely an anti-Pan-CK antibody, was contacted with the tissue sample. Simultaneously or subsequent to the application of the first unmodified antibody, a second unmodified antibody, namely an anti-PDL1 (SP142) antibody, was contacted with the tissue sample. Following application of the first and second unmodified antibodies, a goat anti-mouse ALEXA 488 antibody was applied to detect the target-anti-Pan-CK antibody complexes (Goat anti-mouse ALEXA 488 (2 µg/mL) in diluent 90040) and a goat anti-rabbit-ALEXA 594 antibody was applied to detect the target-anti-PDL1 (SP142) antibody complexes (Goat anti-Rabbit-ALEXA 594 (2 g/ml) in 90040).

A second stage was then conducted where two epitope-tagged antibodies were simultaneously supplied to the tissue sample (see FIG. 9). In this second stage, a first epitope-tagged antibody was specific for CD20 (anti-CD20) and comprised the HA epitope tag (a heavy chain comprising four HA epitope tags). A second epitope-tagged antibody was specific to CD68 (anti-CD68) and comprised the VSV epitope tag (a heavy chain comprising four VSV epitope tags). The epitope-tagged antibodies were applied as a "cocktail" comprise 2 µg/mL of each epitope-tagged antibody in diluent 90039.

After the simultaneous application of the two epitope-tagged antibodies, two anti-tag antibodies were simultaneously supplied to the tissue sample (see FIG. 9), where each anti-tag antibody was specific to a different epitope tag of the epitope-tagged antibodies. A first anti-HA antibody was conjugated with Coumarin; and a second anti-VSV antibody was conjugated with ALEXA 532. The anti-tag antibodies were applied as a "cocktail" comprise 5 µg/mL of each anti-tag antibody in diluent 90040.

The following steps were undertaken for the 4-plex IHC assay (see Table 7):

TABLE 7

| Procedure Step | Selection |
| --- | --- |
| Deparaffinization | Selected |
| Cell Conditioning | CC1, 64 min |
| Mouse anti-pan-CK and Rabbit anti-PDL1 | 32 min |
| Blocking reagent 90040 | 32 min |
| Goat anti-mouse-ALEXA 488 and Goat anti-Rabbit ALEXA 594 | 32 min |
| Negative Control Rabbit IgG | 32 min |
| Blocking with diluent 90040 | 32 min |
| Tagged 1st Ab cocktail | Incubate-32 min |
| Blocking with diluent 90040 | 32 min |
| Anti-tag 2nd Ab cocktail | Incubate-32 min |
| DAPI Counterstain | 4 min |
| PROLONG DIAMOND anti-fade mounting | |

A complete protocol summary is provided at Table 8:

1 Paraffin [Selected]
2 Deparaffinization [Selected]
3 Warmup Slide to [72 Deg C.] from Medium Temperatures (Deparaffinization)
4 Cell Conditioning [Selected]
5 Ultra CC1 [Selected]
6 Warmup Slide to (100 Deg C.], and Incubate for 4 Minutes (Cell Conditioner #1)
7 CC1 8 Min (Selected)
8 CC1 16 Min (Selected]
9 CC1 24 Min (Selected]
10 CC1 32 Min (Selected)
11 CC1 40 Min (Selected)
12 CC1 48 Min (Selected]
13 CC1 56 Min (Selected)
14 CC1 64 Min (Selected
15 Research Fork #1 (Selected)
16 Hand Apply (Antibody) and Incubate for [0 Hr 16 Min]
17 Blocker [Selected]
18 Apply One Drop of [OPTION 2] (Option 1), and Incubate for [32 Minutes]
19 3rd wash after Primary Ab (Selected)
20 Research Fork #2 (Selected)
21 Hand Apply (Secondary Antibody), and Incubate for [0 Hr 32 Min]
22 Research Fork #9 (Selected)
23 Apply Three Drops of (NEG CTL Rbt Ig] (Antibody) and Incubate for (32 Minutes]
24 Research Fork #3 (Selected)
25 Apply One Drop of [OPTION 2] (Option 2) and Incubate for (32 Minutes]
26 Research Fork #4 (Selected)
27 Hand Apply (Primary Antibody), and Incubate for (0 Hr 32 Min]
28 Research Fork #5 (Selected)
29 Research Fork #6 (Selected)
30 Apply One Drop of (OPTION 2] (Option 3) and Incubate for (32 Minutes]
31 Research Fork #7 (Selected)
32 Research Fork #8 (Selected)
33 Counterstain Options [Selected]
34 Apply One Drop of [HEMATOXYLIN II] (Counterstain), Apply Coverslip, and Incubate for (4 Minutes]

Figure 10A:
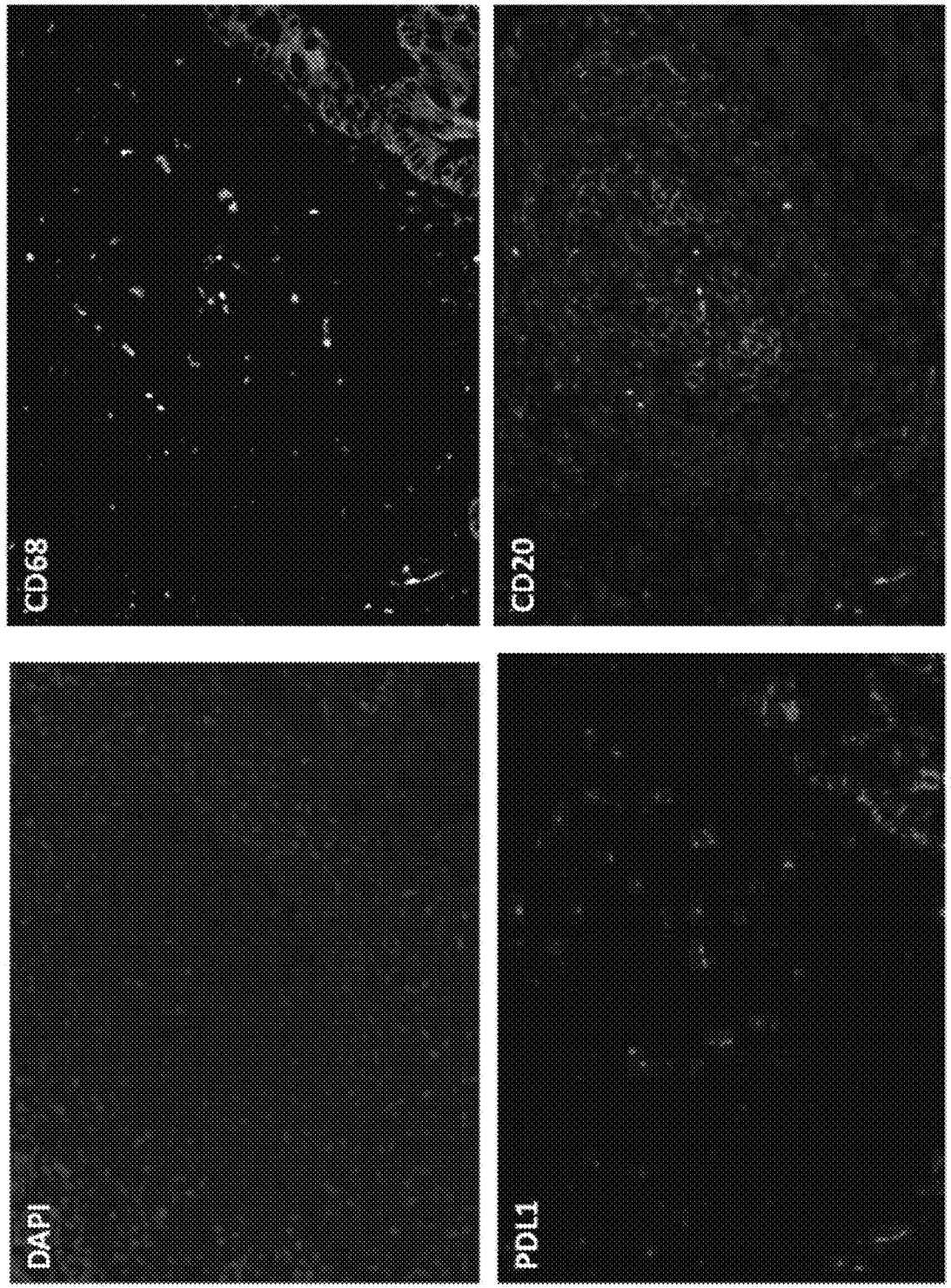
Figure 10B:
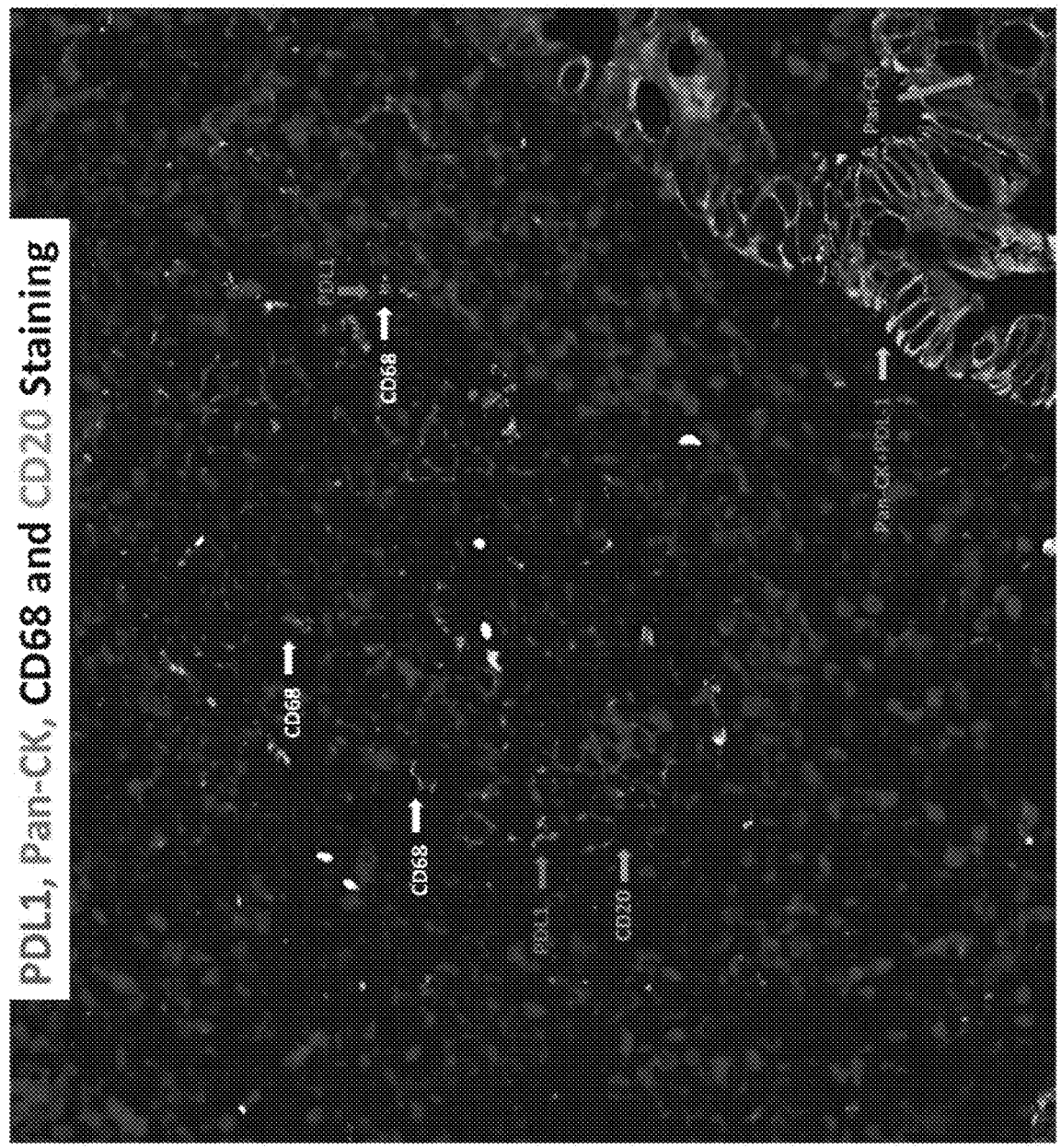
Figure 10D:
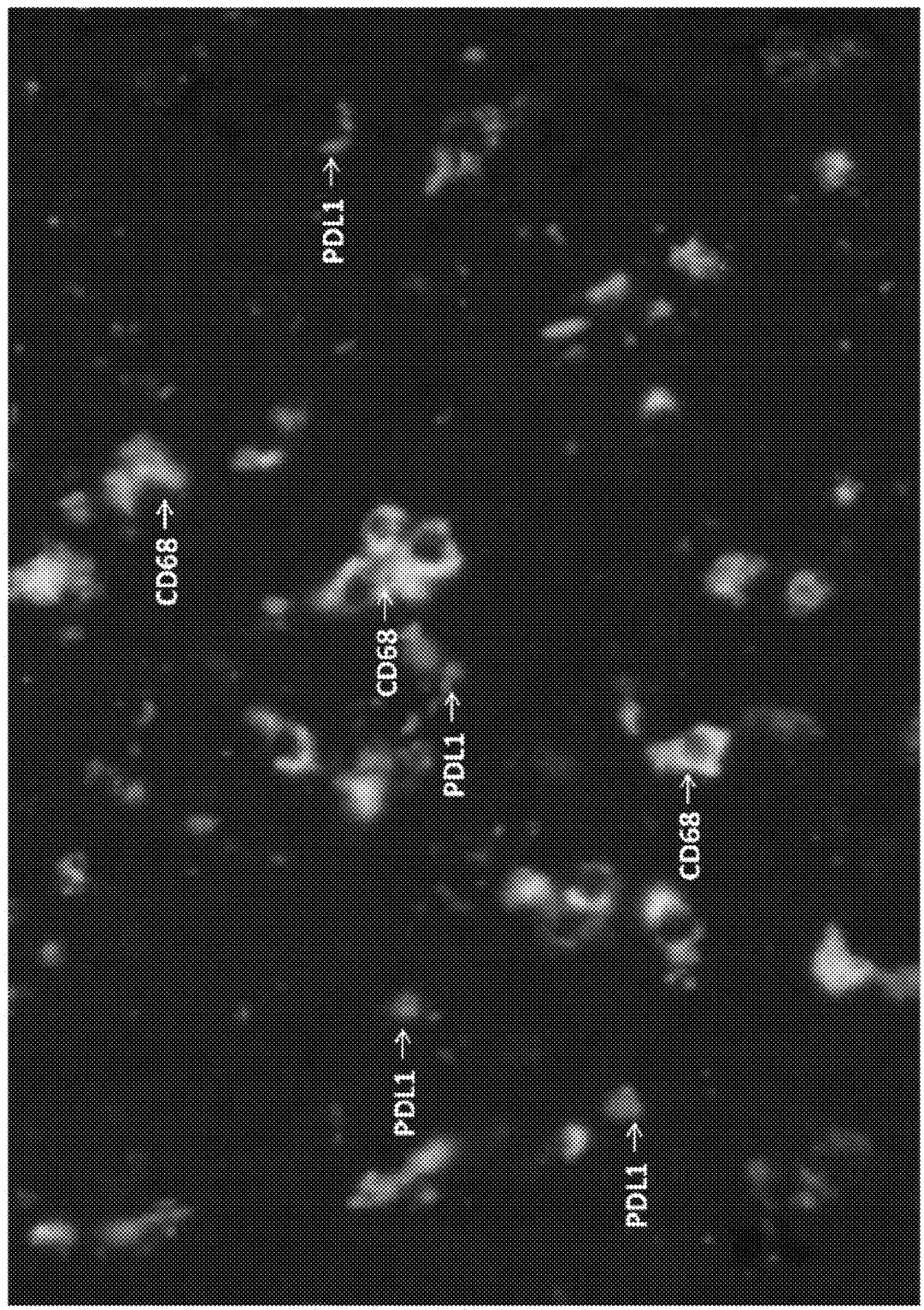
Figure 10E:
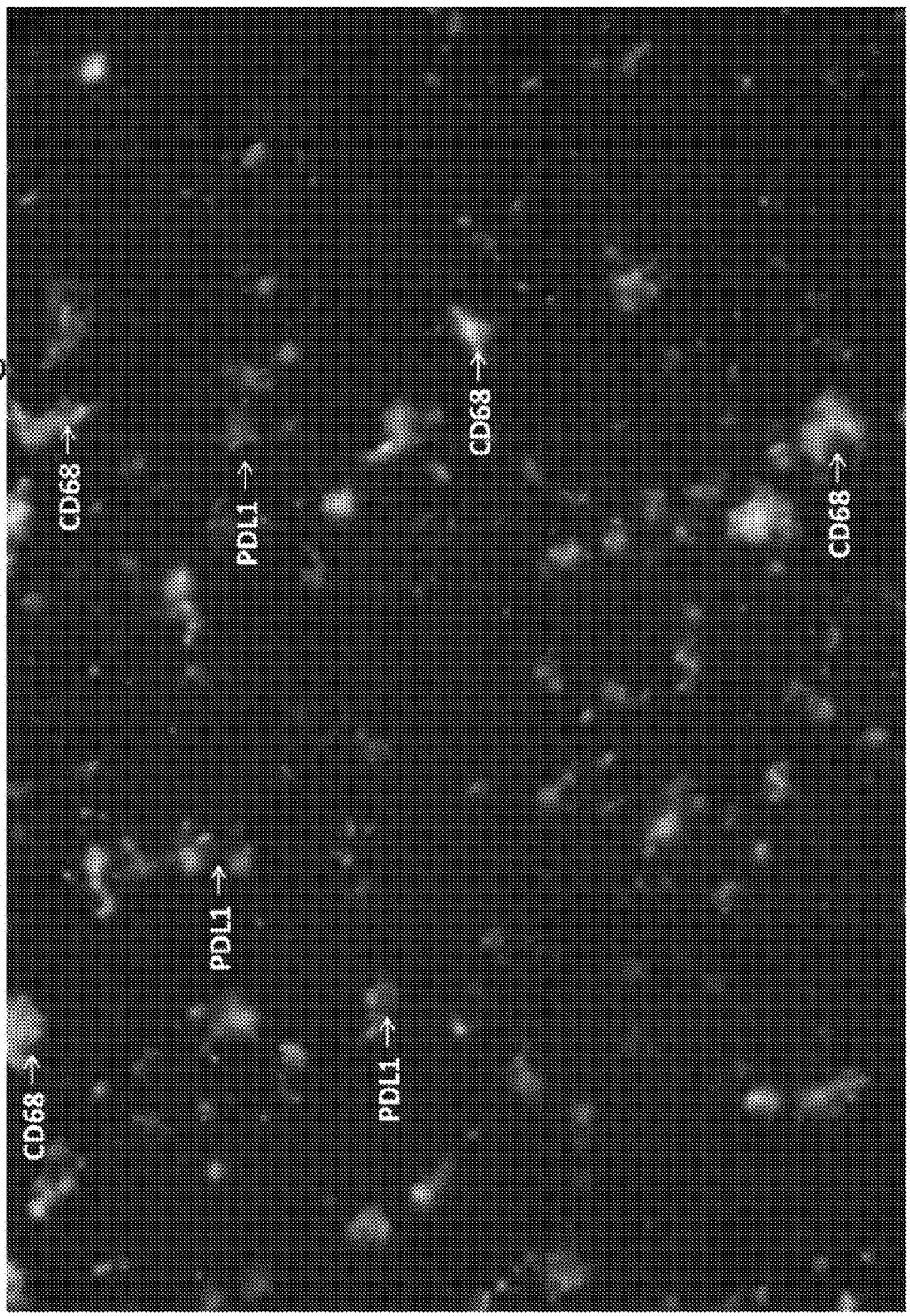
Figure 10F:
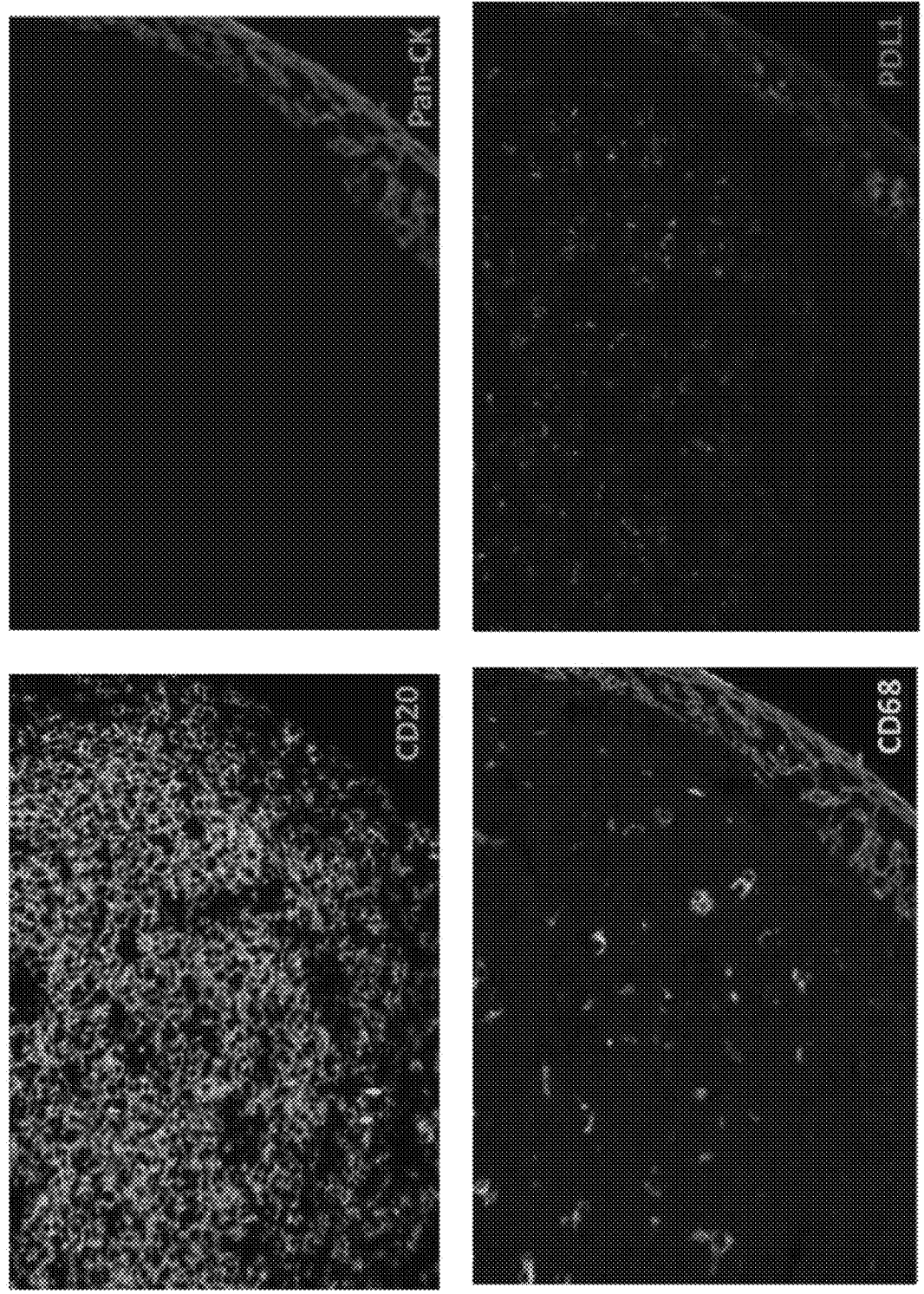
Figure 10G:
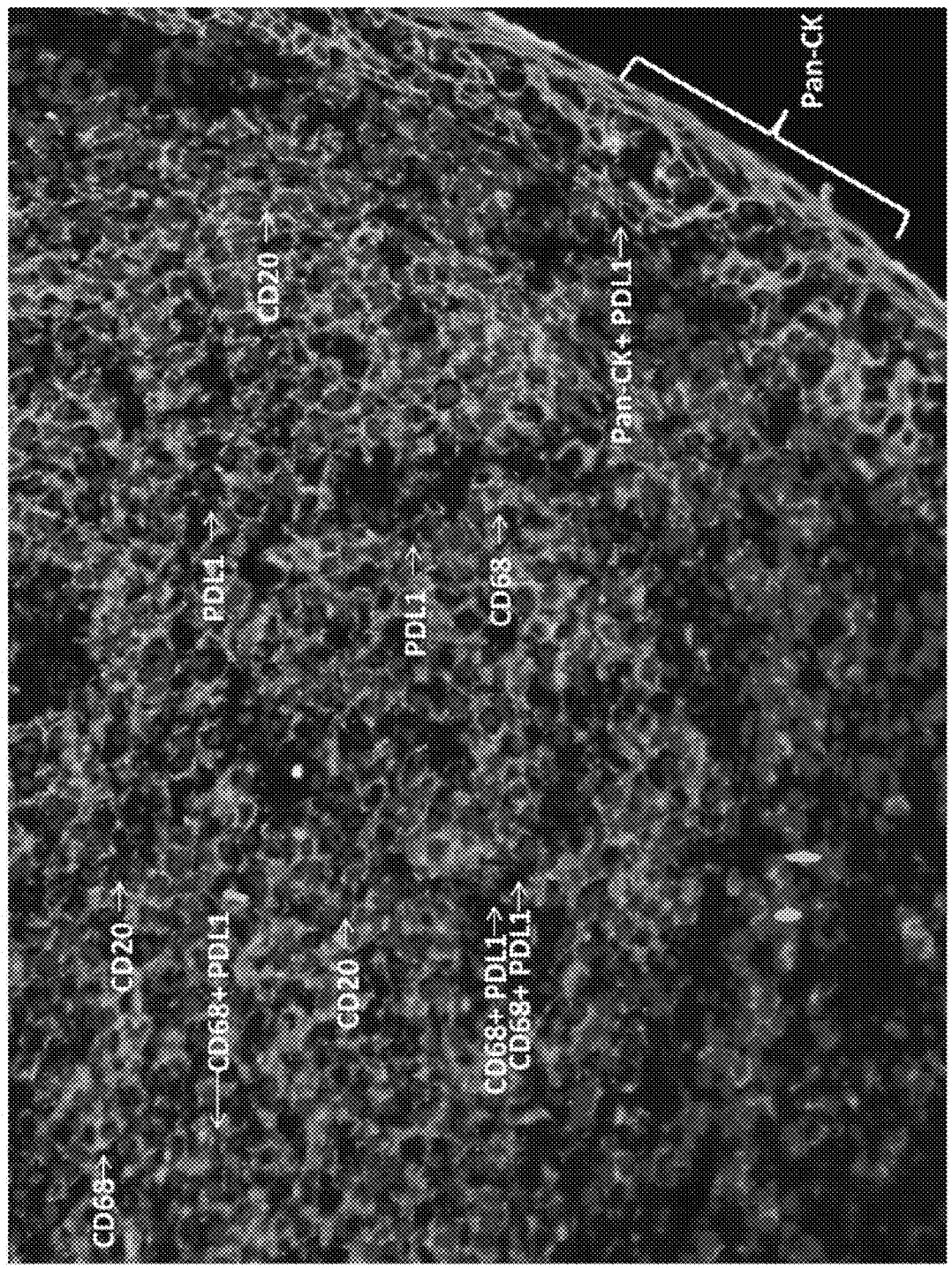

FIGS. 10A through 10G illustrate tissue samples stained with the 4-plex IHC assay noted above. FIG. 10A provides images showing DAPI staining, PDL1 staining, CD20 staining, and CD68 staining, each individually. FIG. 10B provides an image showing signals corresponding to DAPI staining, PDL1 staining, CD20 staining, CD68 staining, and Pan-CK staining. FIG. 10C provides individual images showing each of Pan-CK staining and PDL1 staining; and an image showing signals corresponding to Pan-CK staining and PDL1 staining. FIG. 10C illustrates that two unmodified antibodies raised from different species may be combined and detected using anti-species antibodies, where the signals allow to show tumor region (Pan-CK positive tumor epithelial cells) and PDL1 expressing tumor cells (co-localization of Pan-CK and PDL1) or PDL1 expressing immune cells. FIGS. 10D and 10E each provide images showing CD68 and PDL1 co-staining, where macrophages (CD68 positive) express PDL1, a known phenomenon. In some embodiments, this particular assay may be used to identify tumor infiltrating lymphocytes. FIGS. 10D and 10E thus illustrates that unmodified antibodies and epitope-tagged antibodies may be successfully combined, across two stages of application, and that each of the antibodies may be detected by anti-species or anti-tag antibodies. FIGS. 10D and 10E also illustrate the co-localization of cell membranes expressing both PDL1 and having the CD68 marker. FIGS. 10F and 10G illustrate a tissue sample stained with PDL1, Pan-CK, CD68, and CD20.

Once again, FIGS. 10A through 10G show that the epitope-tagged antibodies of the present disclosure were (1) capable of binding to CD20 and CD68, respectively; (2) capable of being detected by appropriate anti-tag antibodies; and (3) able to be applied to a tissue sample simultaneously (e.g. as a cocktail of antibodies) without interfering with each other. FIGS. 10A through 10G also illustrate that the epitope-tagged antibodies may be combined in an assay with two unmodified antibodies or antibody conjugates, such as mouse anti-Pan-CK antibodies or rabbit anti-PDL1 (SP142) antibodies and that such a combination allows for the detection of all fluorophores conjugated to anti-species or anti-tag antibodies. In addition, the multiplex assay of the present example was able to be completed within 4 hours. When compared to traditional multiplex assays, this represents an advancement in the art. This panel of markers allow for the identification of the expression of PD-L1 in tumor cells and infiltrating immune cells in tumor microenvironment on patients with anti-PD-L1 treatment].

Example 6: 4-Plex Immunohistochemical Assay Using Combined Anti-Species and Anti-Tag Antibodies Example 6 provides a multiplex immunohistochemical assay where four different epitope-tagged antibodies were applied to a tissue sample (see FIG. 11) in two stages. As compared with Examples 3 and 5, Example 5 provides two antibodies in a first stage and another two epitope-tagged antibodies in a second stage.

Figure 11:
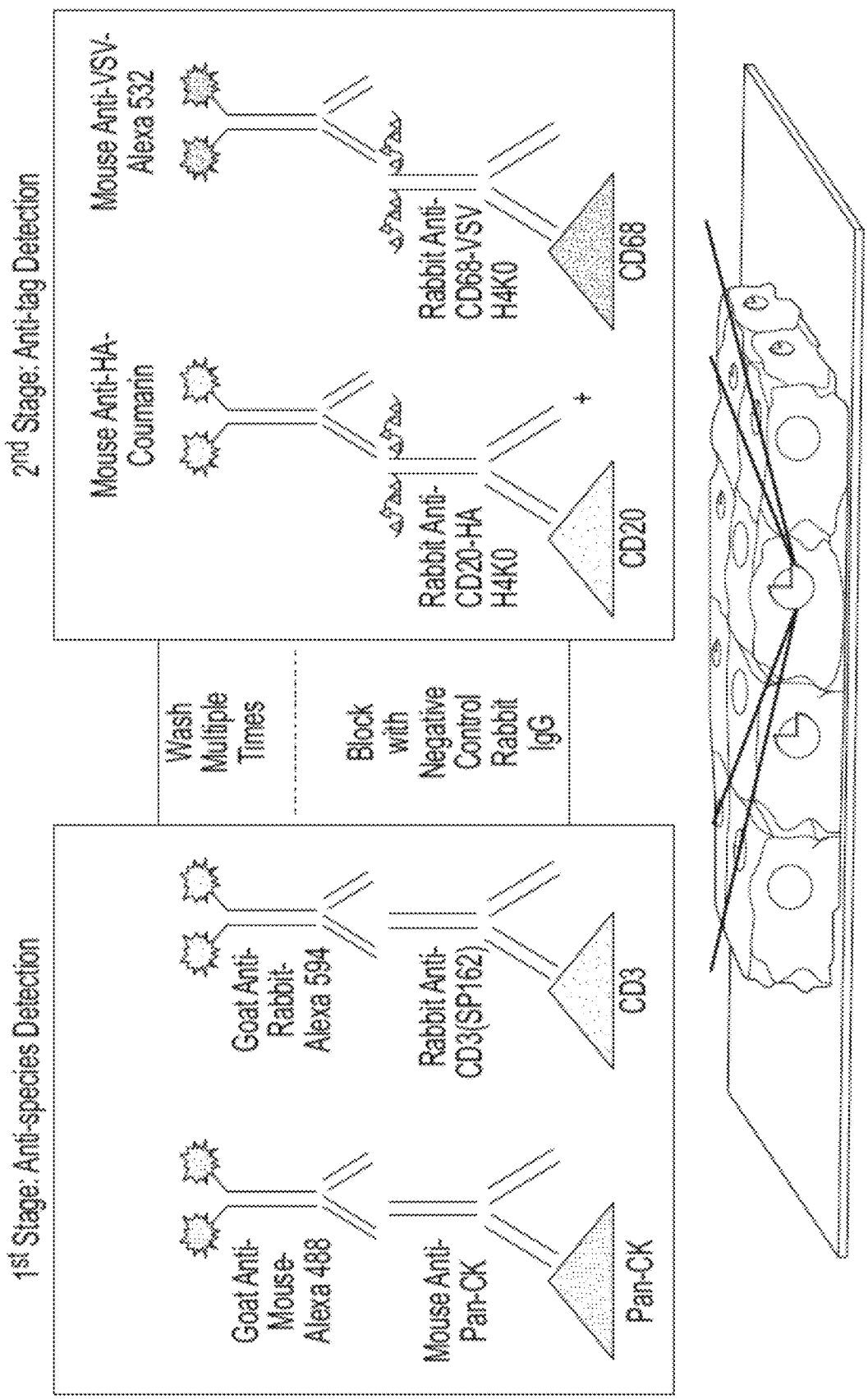
FIG. 11 illustrates a multiplex IHC assay utilizing two unmodified antibodies and two different epitope-tagged antibodies.

With regard to the first stage depicted in FIG. 11, a first unmodified antibody, namely an anti-Pan-CK antibody, was contacted with the tissue sample. Simultaneously or subsequent to the application of the first unmodified antibody, a second unmodified antibody, namely an anti-CD3 (SP162) antibody, was contacted with the tissue sample. Following application of the first and second unmodified antibodies, a goat anti-mouse-ALEXA 488 antibody was applied to detect the target-anti-Pan-CK antibody complexes (Goat anti-mouse-ALEXA 488 (2 µg/mL) in diluent 90040) and a goat anti-rabbit-ALEXA 594 antibody was applied to detect the target-anti-PDL1 (SP142) antibody complexes (Goat anti-Rabbit-ALEXA 594 (2 ug/ml) in 90040).

A second stage was then conducted where two epitope-tagged antibodies were simultaneously supplied to the tissue sample (see FIG. 11). In this second stage, a first epitope-tagged antibody was specific for CD20 (anti-CD20) and comprised the HA epitope tag (a heavy chain comprising four HA epitope tags). A second epitope-tagged antibody was specific to CD68 (anti-CD68) and comprised the VSV epitope tag (a heavy chain comprising four VSV epitope tags). The epitope-tagged antibodies were applied as a "cocktail" comprise 2 µg/mL of each epitope-tagged antibody in diluent 90039.

After the simultaneous application of the two epitope-tagged antibodies, two anti-tag antibodies were simultaneously supplied to the tissue sample (see FIG. 11), where each anti-tag antibody was specific to a different epitope tag of the epitope-tagged antibodies. A first anti-HA antibody was conjugated with Coumarin; and a second anti-VSV antibody was conjugated with ALEXA 532. The anti-tag antibodies were applied as a "cocktail" comprise 5 µg/mL of each anti-tag antibody in diluent 90040.

The following steps were undertaken for the 4-plex IHC assay (Table 9):

TABLE 9

| Procedure Step | Selection |
| --- | --- |
| Deparaffinization | Selected |
| Cell Conditioning | CC1, 64 min |
| Mouse anti-pan-CK and Rabbit anti-CD3 | 32 min |
| Blocking reagent 90040 | 32 min |
| Goat anti-mouse-ALEXA 488 and Goat anti-Rabbit ALEXA 594 | 32 min |
| Negative Control Rabbit IgG | 32 min |

TABLE 9-continued

| Procedure Step | Selection |
| --- | --- |
| Blocking with diluent 90040 | 32 min |
| Tagged 1st Ab cocktail | Incubate-32 min |
| Blocking with diluent 90040 | 32 min |
| Anti-tag 2nd Ab cocktail | Incubate-32 min |
| DAPI Counterstain | 4 min |
| PROLONG DIAMOND anti-fade mounting | |

A complete protocol summary is provided at Table 8.

Figure 12A:
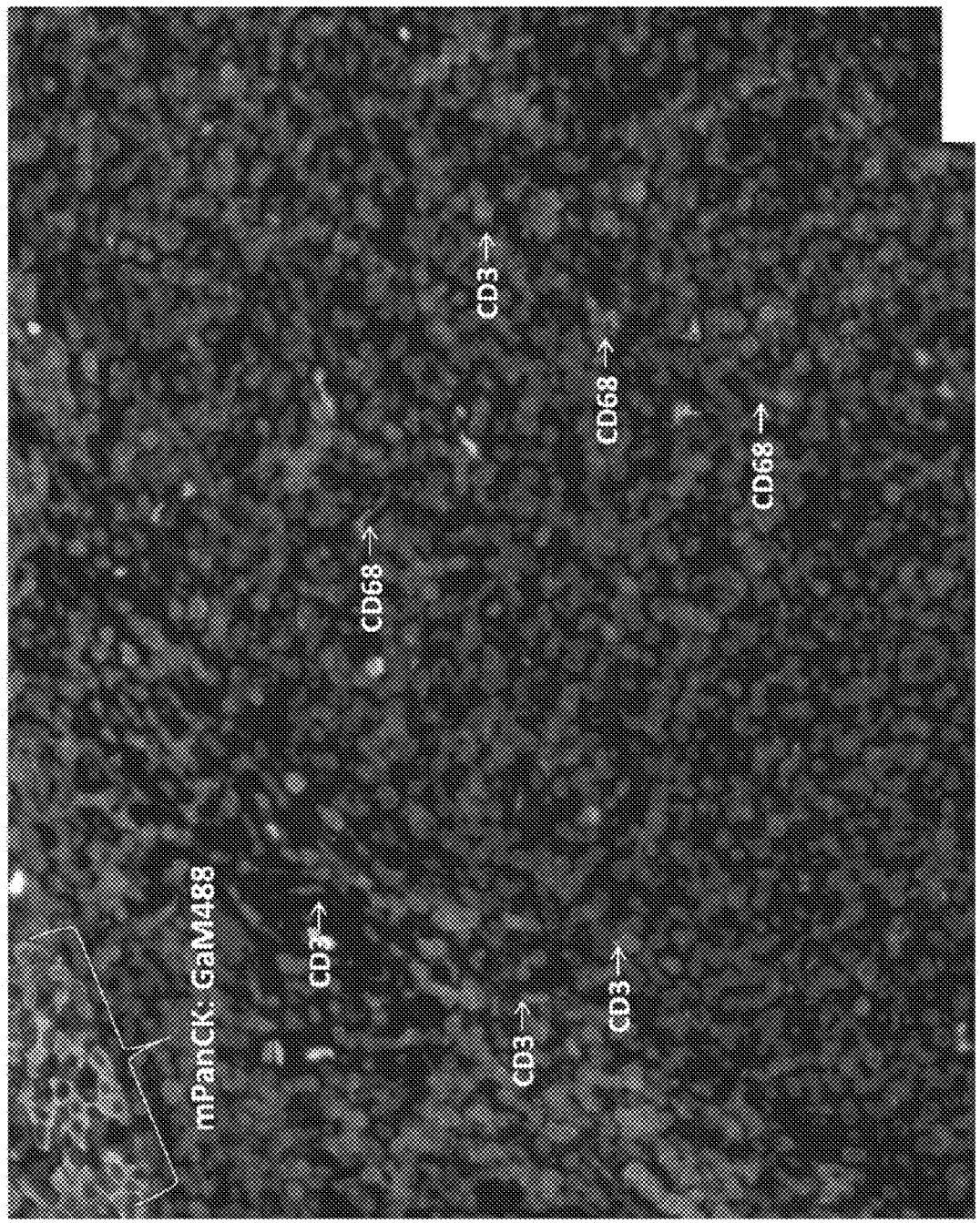
FIG. 12A, FIG. 12B, FIG. 12C, and FIG. 12D, are images of tissue samples stained according to a multiplex IHC assay utilizing two unmodified antibodies and two different epitope-tagged antibodies.
Figure 12B:
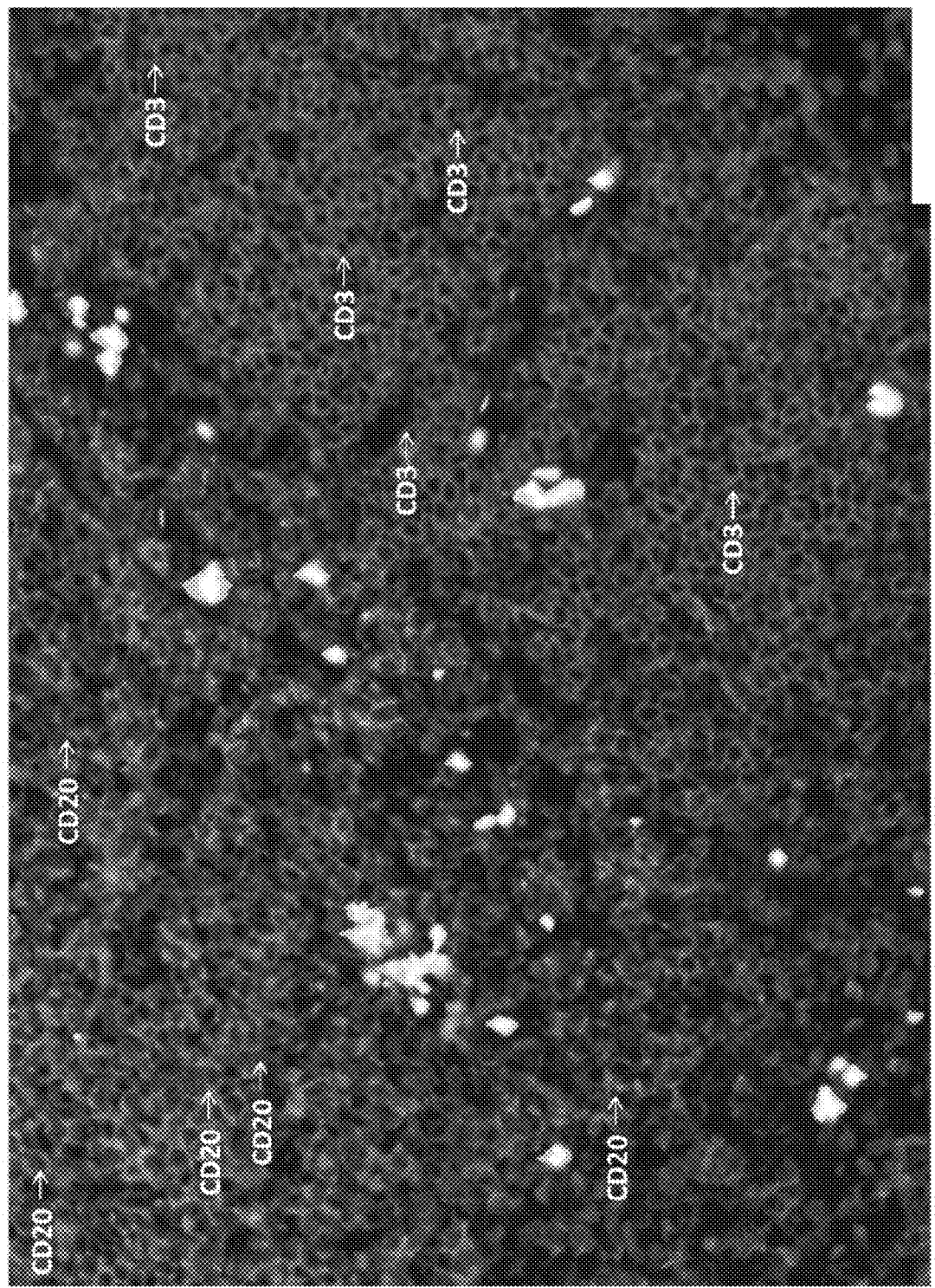
Figure 12C:
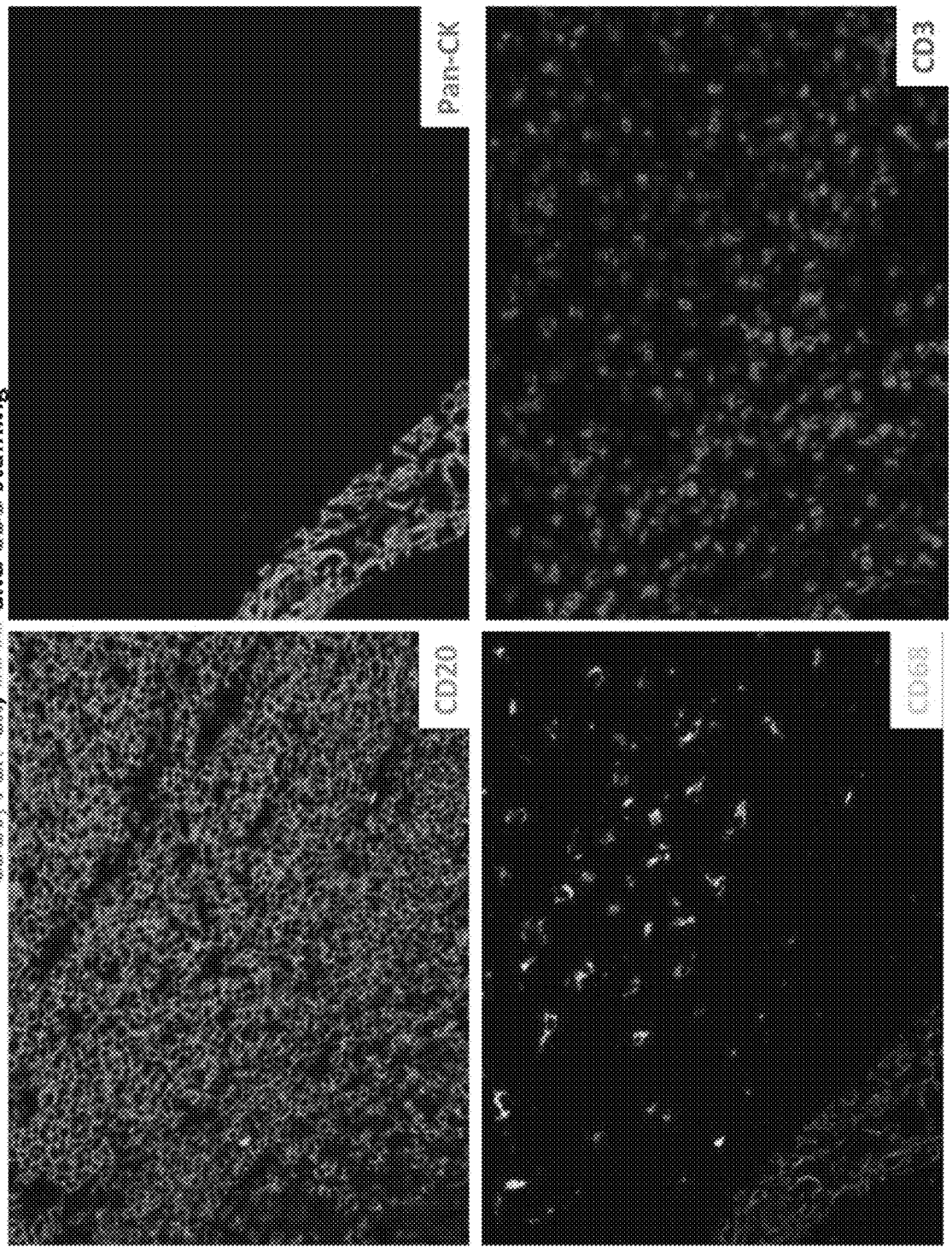
Figure 12D:
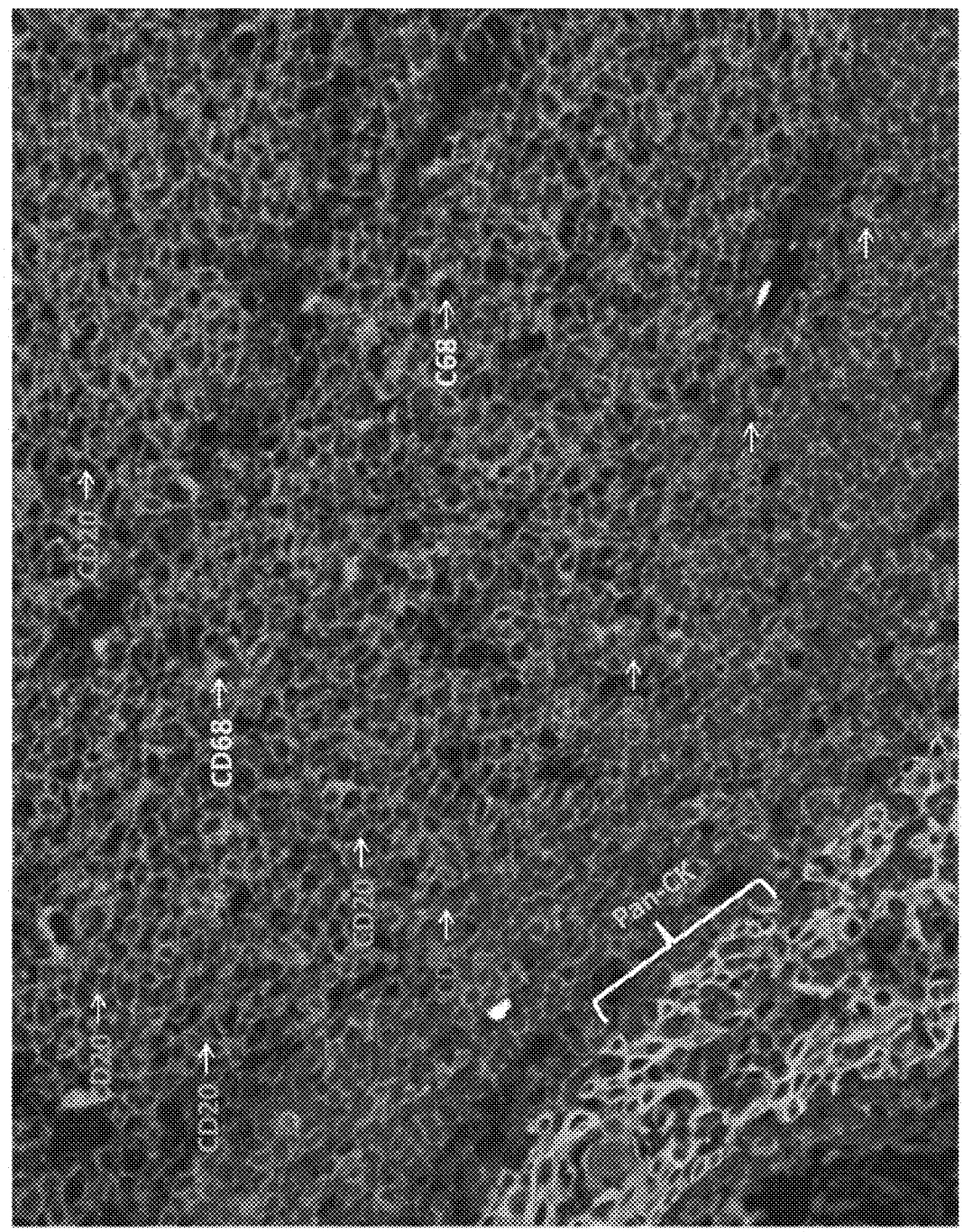

FIGS. 12A through 12D illustrate tissue samples stained with the 4-plex IHC assay noted above. FIG. 12A provides images showing DAPI staining, CD3 staining, PanCK staining, and CD68 staining. FIG. 12B provides an image showing signals corresponding to CD20 staining and CD3 staining, which represent the two distinct B cell and T cell populations. FIG. 12B illustrates that unmodified antibodies (anti-CD3) and epitope-tagged antibodies (anti-CD68) may be successfully combined, across two stages of application, and that each of the antibodies may be detected by anti-species or anti-tag antibodies, respectively. FIGS. 12C and 12D illustrate a tissue sample stained with CD3, Pan-CK, CD68, and CD20.

FIGS. 12A through 12D show that the epitope-tagged antibodies of the present disclosure were (1) capable of binding to CD20 and CD68, respectively; (2) capable of being detected by appropriate anti-tag antibodies; and (3) able to be applied to a tissue sample simultaneously (e.g. as a cocktail of antibodies) without interfering with each other. FIGS. 12A through 12D also illustrate that the epitope-tagged antibodies may be combined in an assay with two unmodified antibodies or antibody conjugates, such as mouse anti-Pan-CK antibodies or rabbit-anti-CD3 (SP162) antibodies and that such a combination allows for the detection of all fluorophores conjugated to anti-species or anti-tag antibodies. In addition, the multiplex assay of the present example was able to be completed within 4 hours. When compared to traditional multiplex assays, this represents an advancement in the art. This panel of markers illustrates the immune cell markers and tumor cell marker, which help illustrate an immune profile in tumor microenvironment.

Example 7: 5-Plex Immunohistochemical Assay

Figure 13:
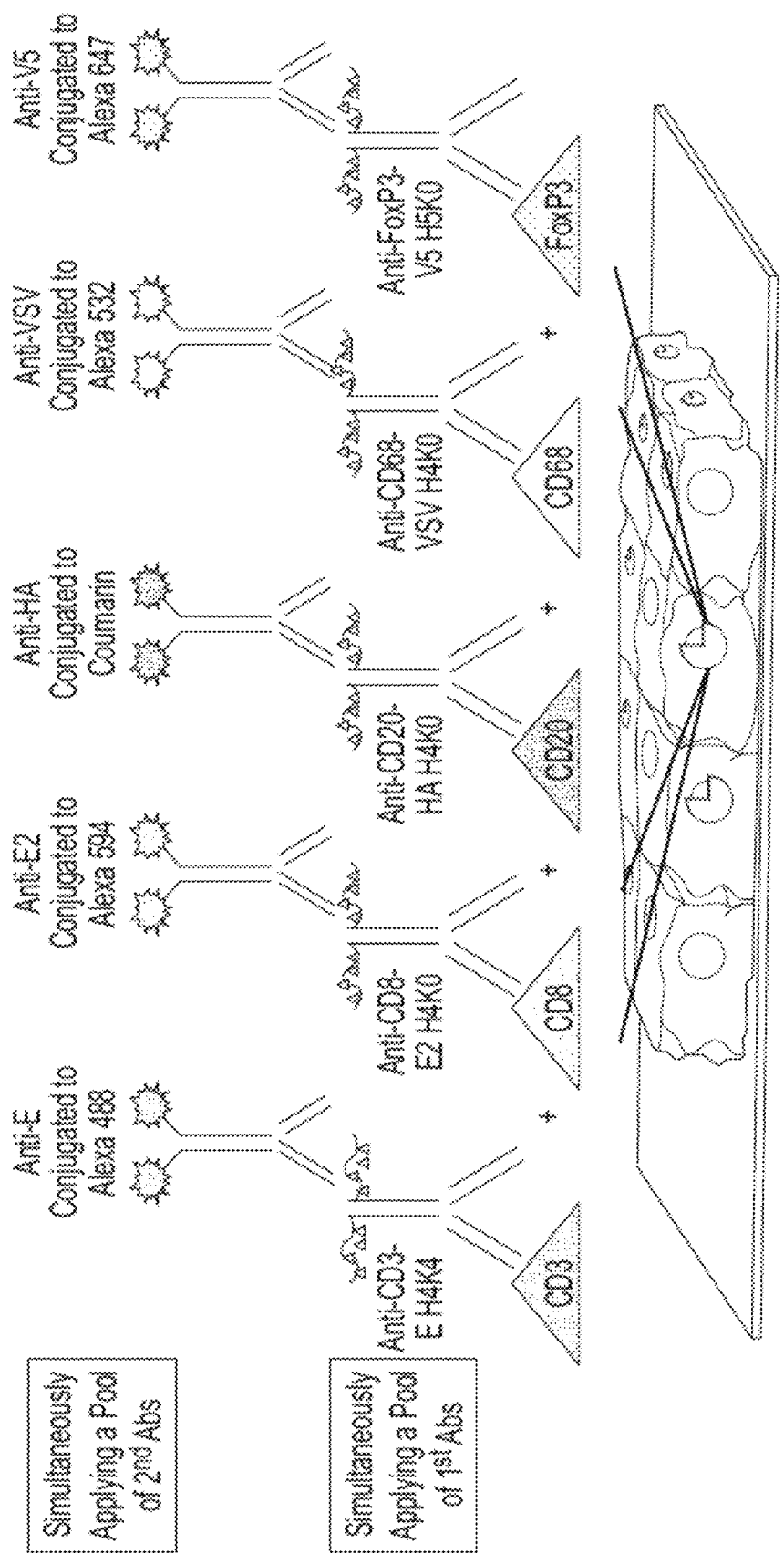
FIG. 13 illustrates a multiplex IHC assay utilizing five different epitope-tagged antibodies.

Example 7 provides a multiplex immunohistochemical assay where five different epitope-tagged antibodies were simultaneously applied to a tissue sample (see FIG. 13). A first epitope-tagged antibody was specific for CD3 (anti-CD3) and comprised the E epitope tag (a heavy chain comprising four E epitope tags). A second epitope-tagged antibody was specific to CD8 (anti-CD8) and comprised the E2 epitope tag (a heavy chain comprising four E2 epitope tags). A third epitope-tagged antibody was specific to CD20 (anti-CD20) and comprised the HA epitope tag (a heavy chain comprising four HA epitope tags). A fourth epitope-tagged antibody was specific to CD68 (anti-CD68) and comprised the VSV epitope tag (a heavy chain comprising four VSV epitope tags). A fifth epitope-tagged antibody was specific to FoxP3 (anti-FoxP3) and comprised the V5 epitope tag (a heavy chain comprising five V5 epitope tags). The epitope-tagged antibodies were applied as a "cocktail" comprise 2 µg/mL of each epitope-tagged antibody in diluent 90039.

After the simultaneous application of the three epitope-tagged antibodies, five anti-tag antibodies were simultaneously supplied to the tissue sample (see FIG. 13), where each anti-tag antibody was specific to a different epitope tag of the epitope-tagged antibodies. A first anti-E antibody was conjugated with ALEXA 488; a second anti-E2 antibody was conjugated with ALEXA 594; a third anti-HA antibody was conjugated with Courmarin; a fourth anti-VSV antibody was conjugated to ALEXA 532; and a fifth anti-V5 antibody was conjugated to ALEXA 647. The anti-tag antibodies were applied as a "cocktail" comprise 5 µg/mL of each anti-tag antibody in diluent 90040.

The following steps were undertaken for the 3-plex IHC assay (Table 10):

TABLE 10

| Procedure Step | Selection |
| --- | --- |
| Deparaffinization | Selected |
| Cell Conditioning | CC1, 64 min |
| Tagged 1st Ab cocktail | Incubate-32 min |
| Blocking with diluent 90040 | 32 min |
| Anti-tag 2nd Ab cocktail | Incubate-32 min |
| DAPI Counterstain | 4 min |
| PROLONG DIAMOND anti-fade mounting | |

A complete protocol summary is provided at Table 3.

Figure 14A:
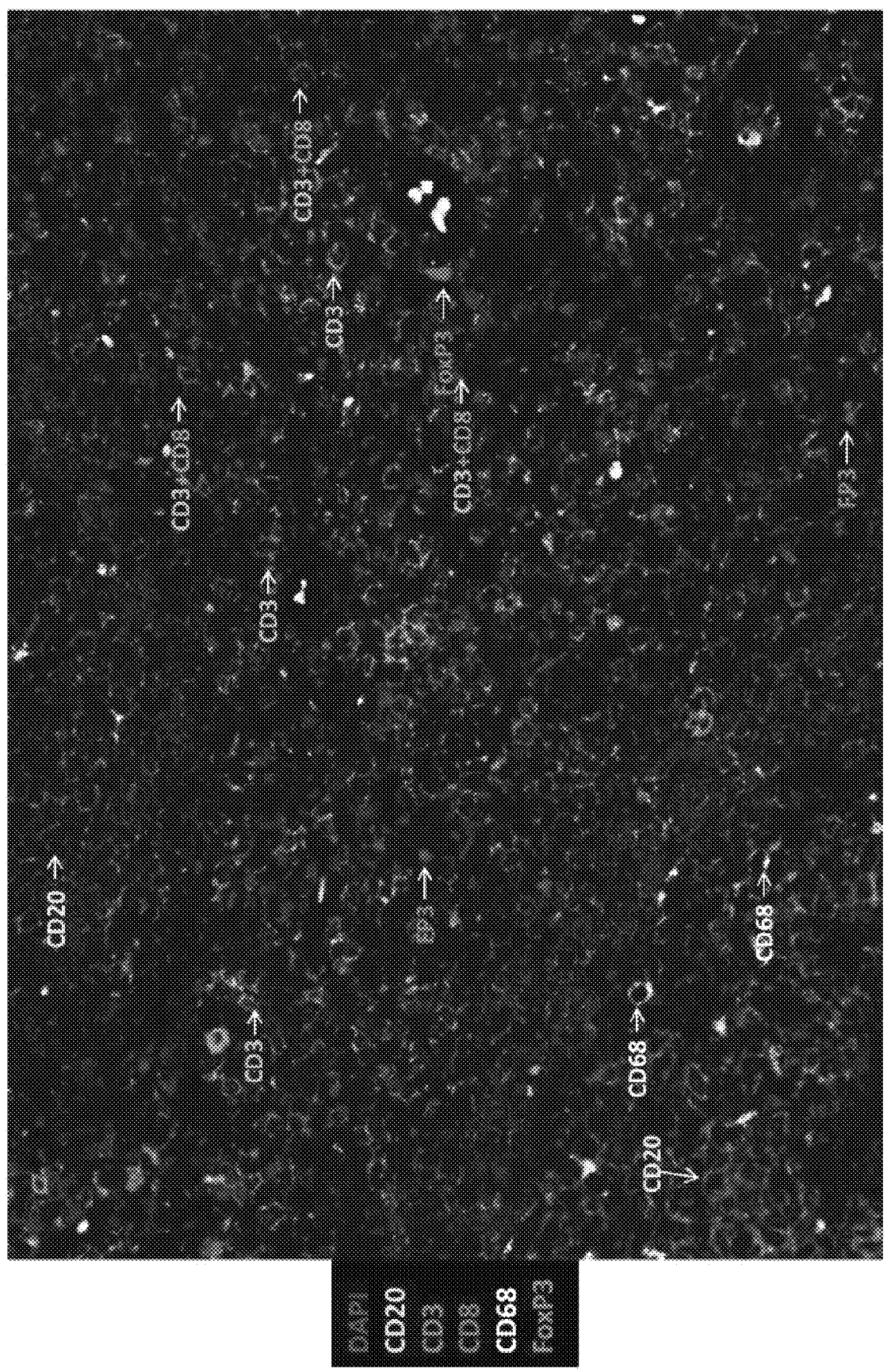
FIG. 14A, FIG. 14B, FIG. 14C, FIG. 14D, FIG. 14E, FIG. 14F, FIG. 14G, FIG. 14H, FIG. 14I, and FIG. 14J are images of tissue samples stained according to a multiplex IHC assay utilizing five different epitope-tagged antibodies.
Figure 14B:
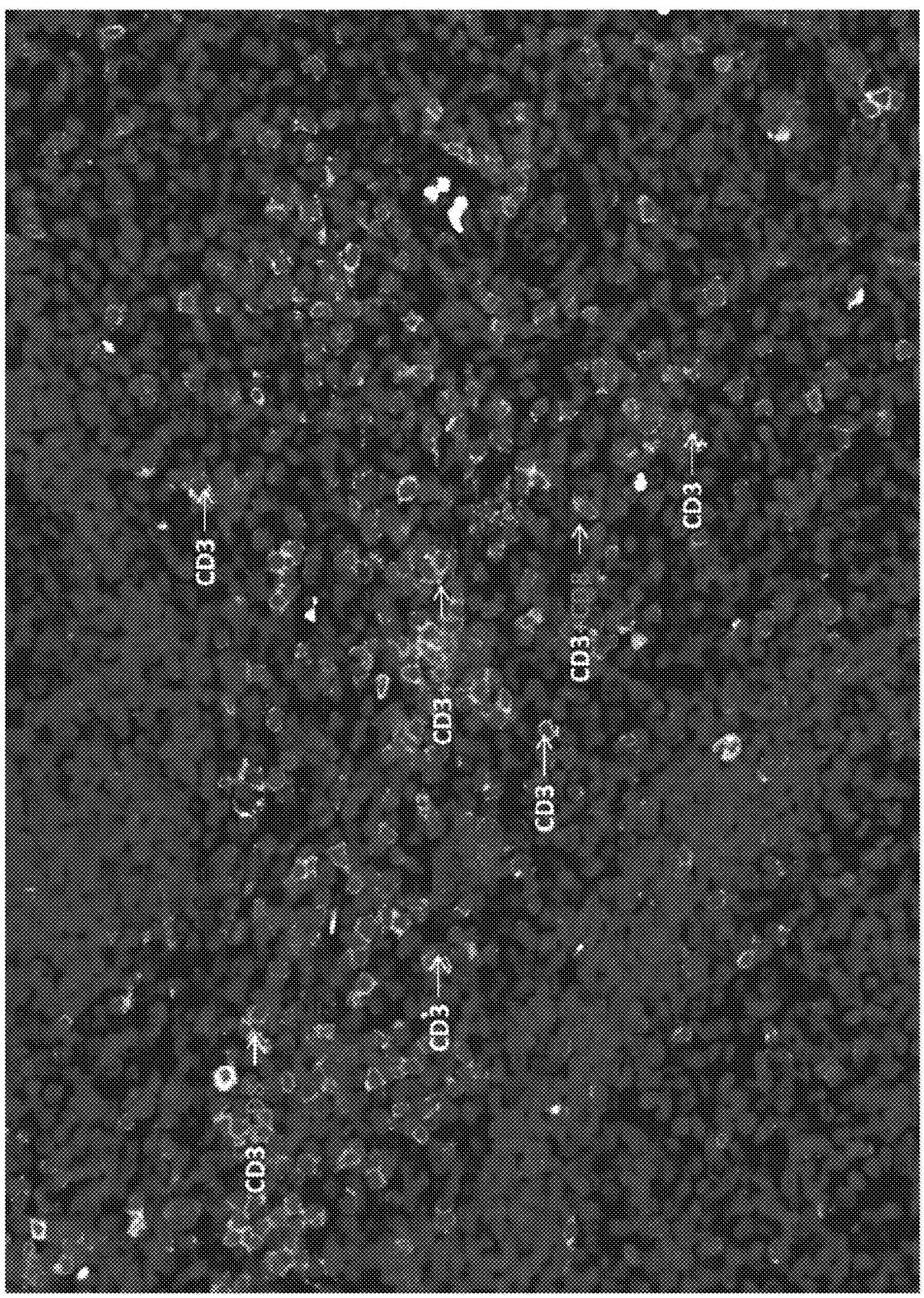
Figure 14C:
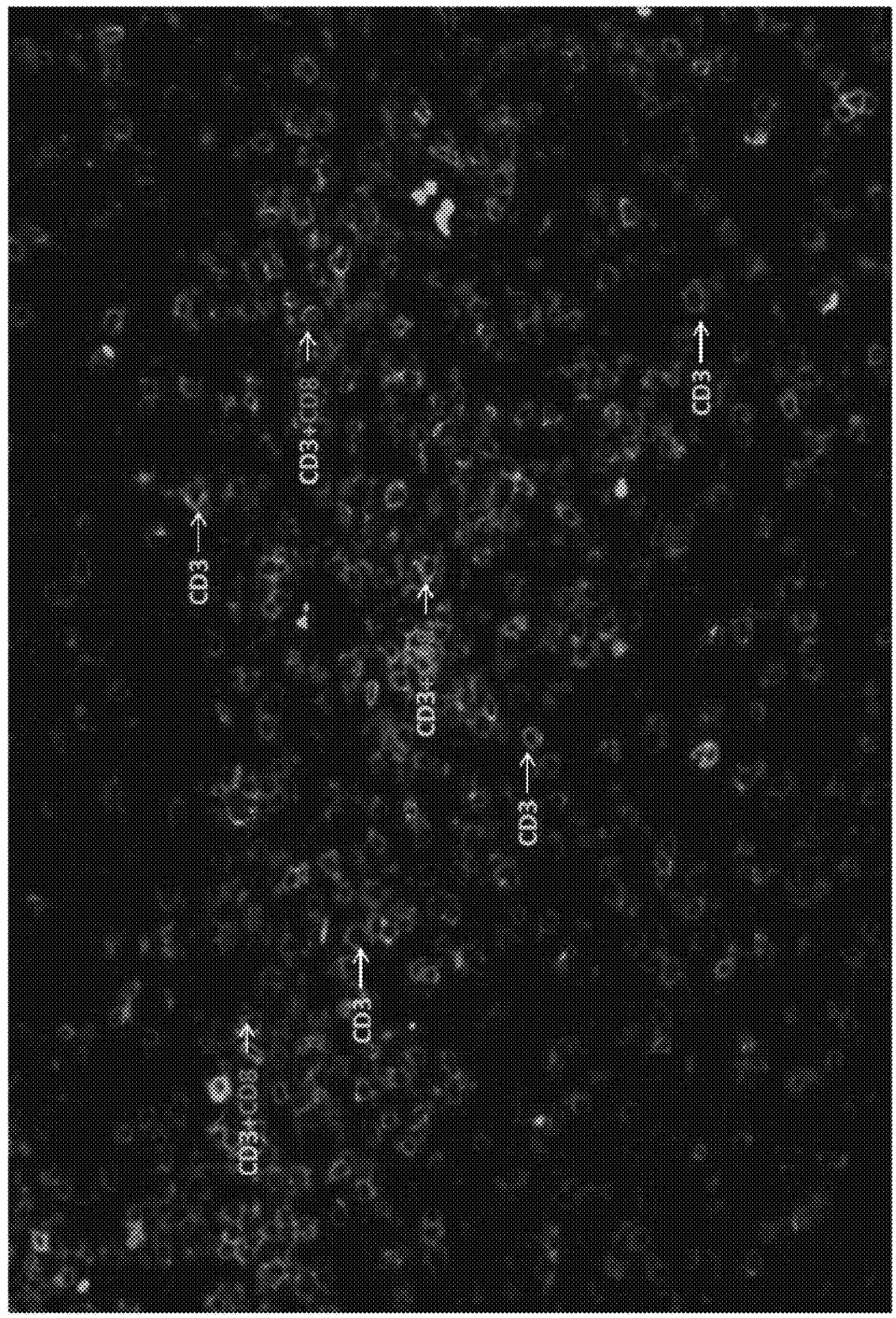

FIG. 14A provides an image showing signals corresponding to DAPI, CD20, CD3, CD8, CD68, and FoxP3 staining. FIG. 14B provides an image showing DAPI, CD3 and CD8 staining. Notably, FIG. 14B illustrates locations where the CD3 and CD8 signals are co-registered (in the presence of the DAPI counterstain) such that the CD3 white signals and CD8 red signals overlap to provide co-registered magenta signals. Similarly, FIG. 14C illustrates co-registration of CD3 (green) and CD8 (red) signals, without the presence of the DAPI counterstain.

Figure 14D:
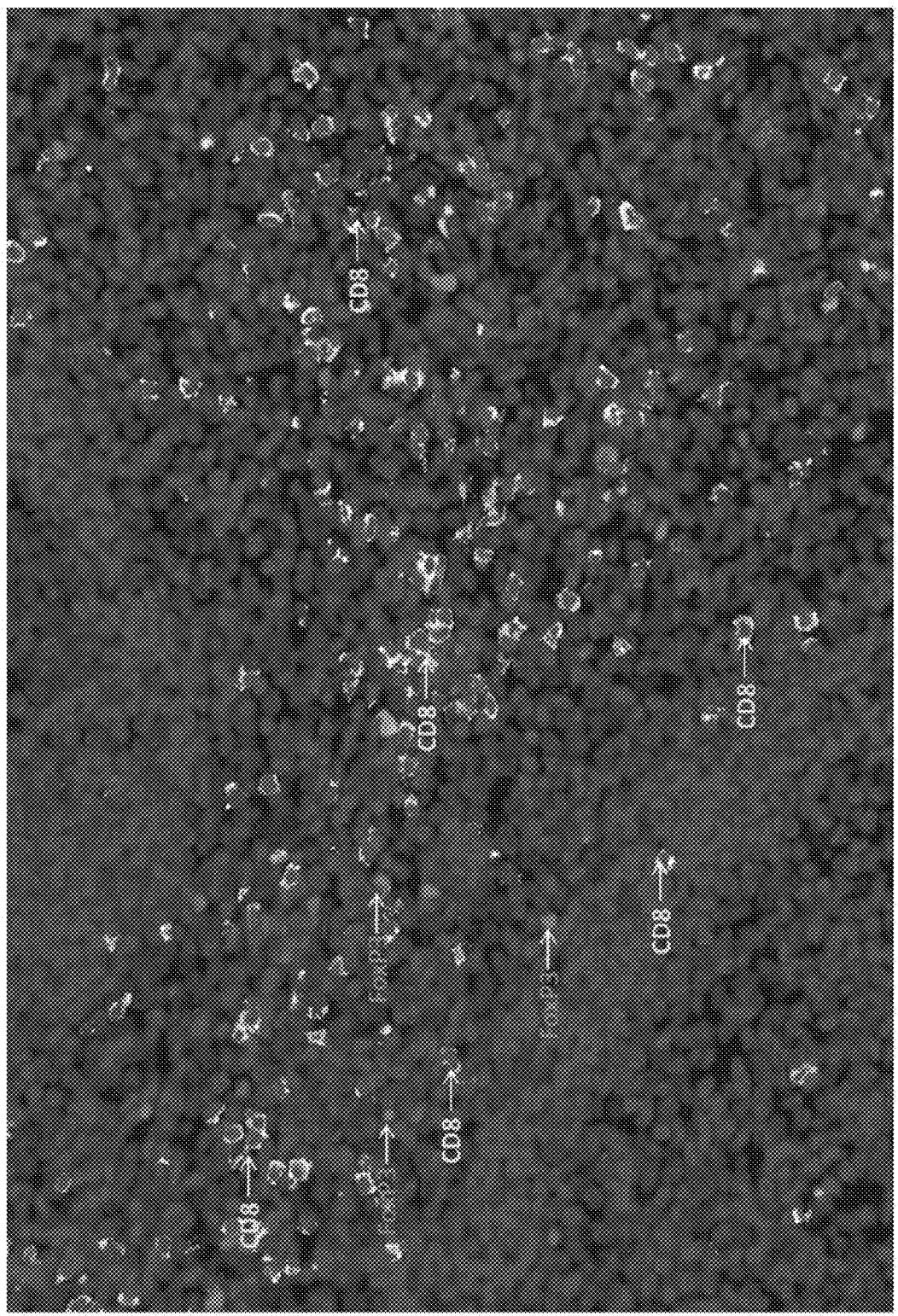
Figure 14E:
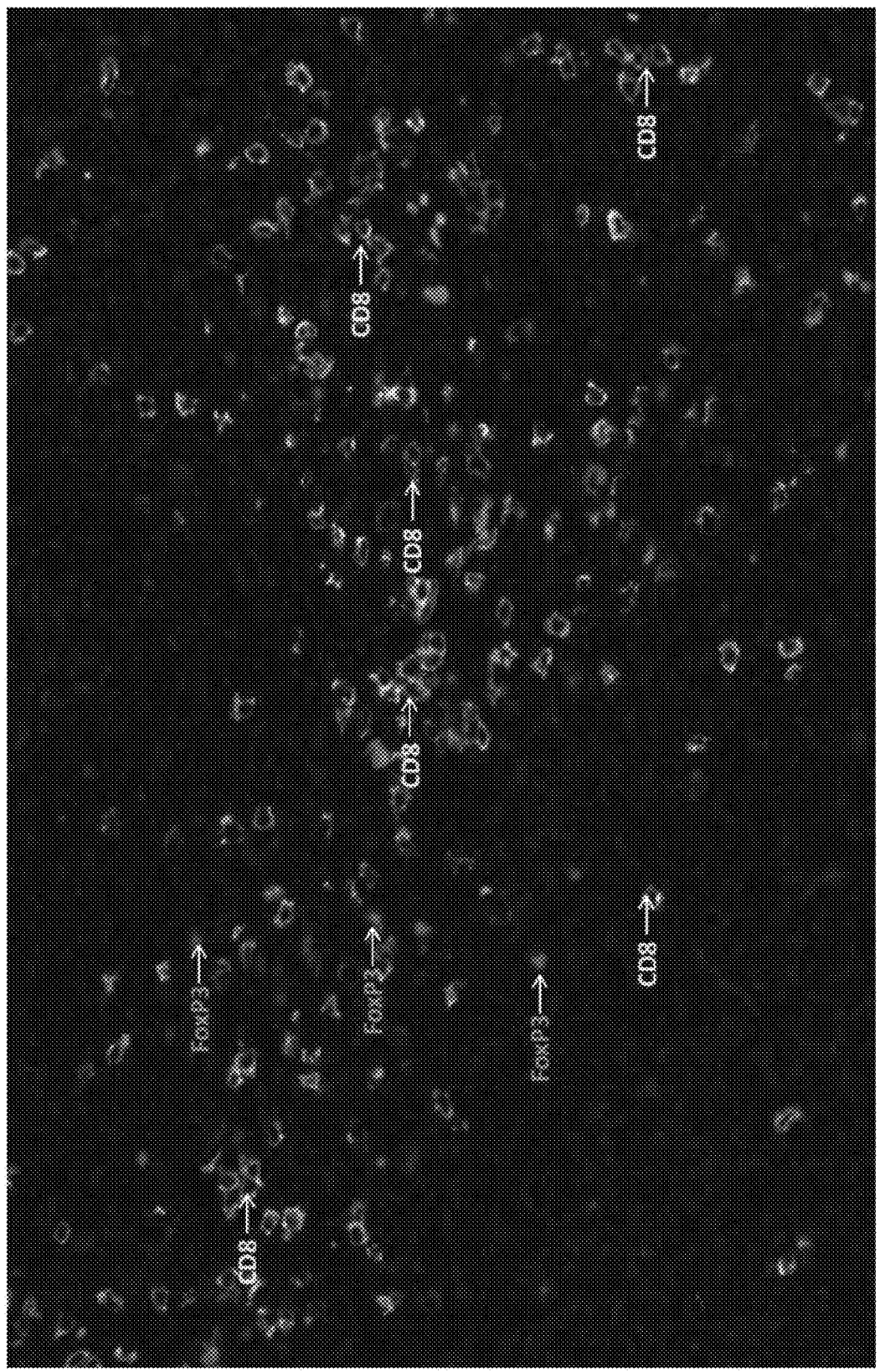
Figure 14F:
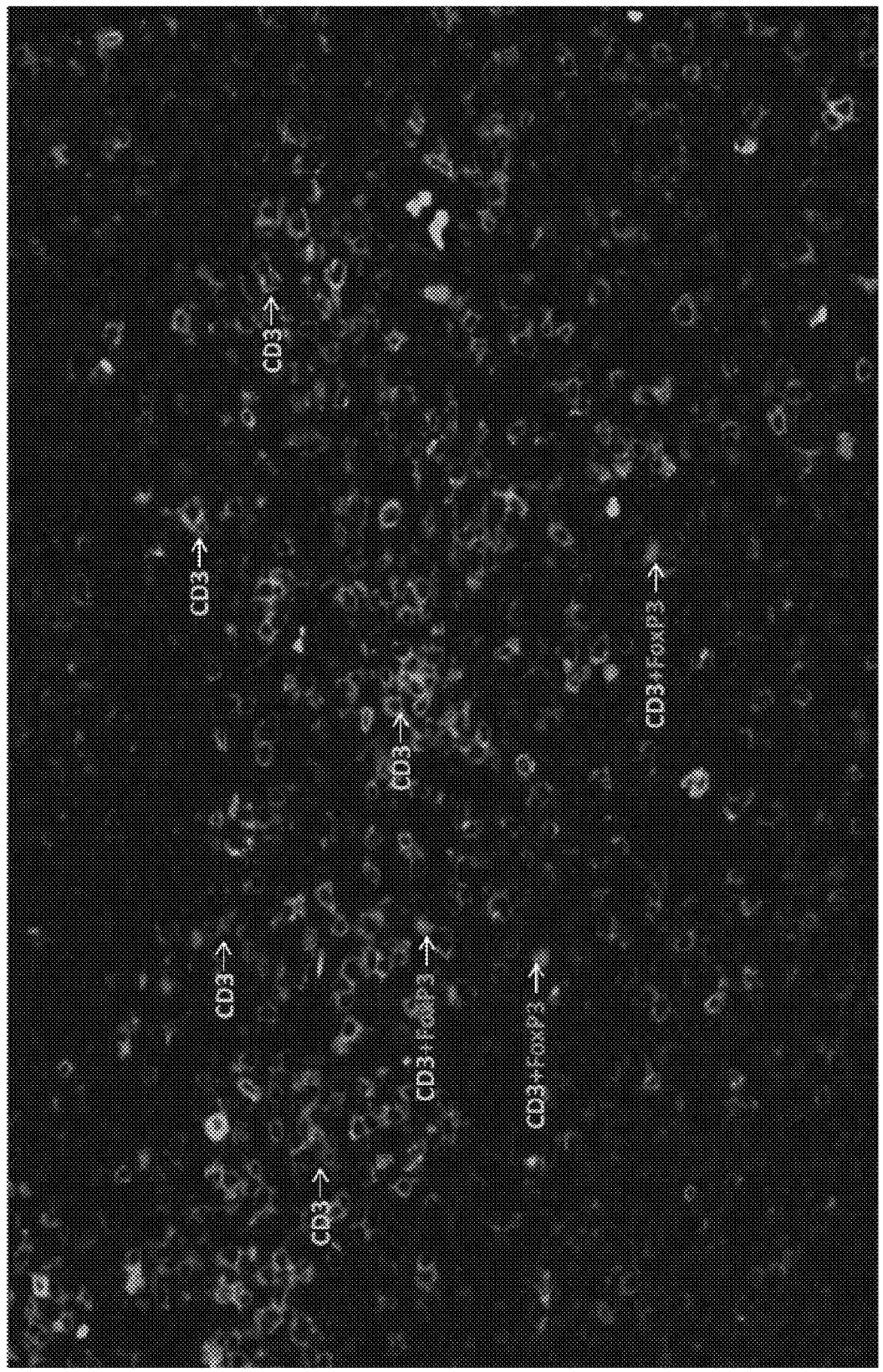
Figure 14G:
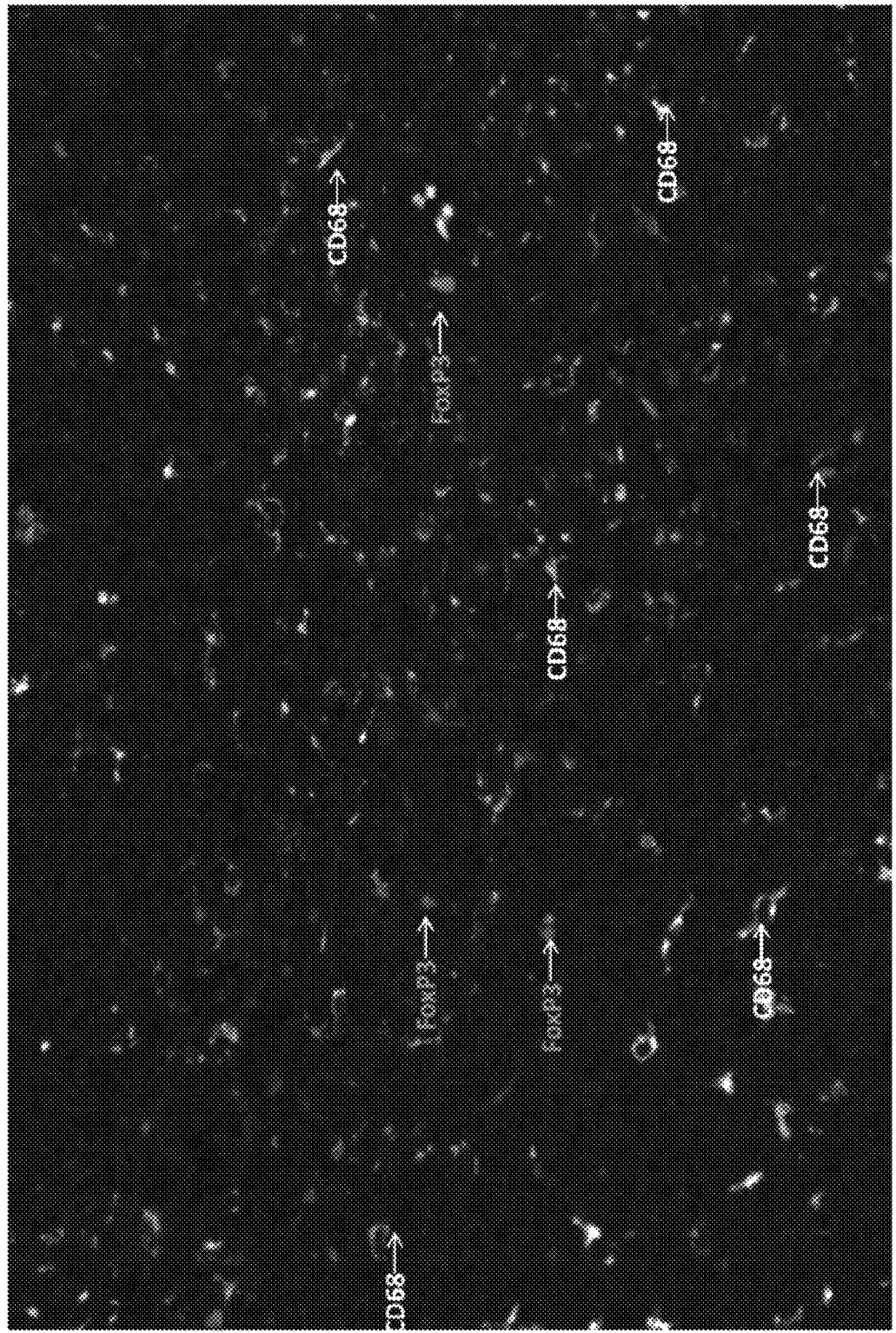
Figure 14H:
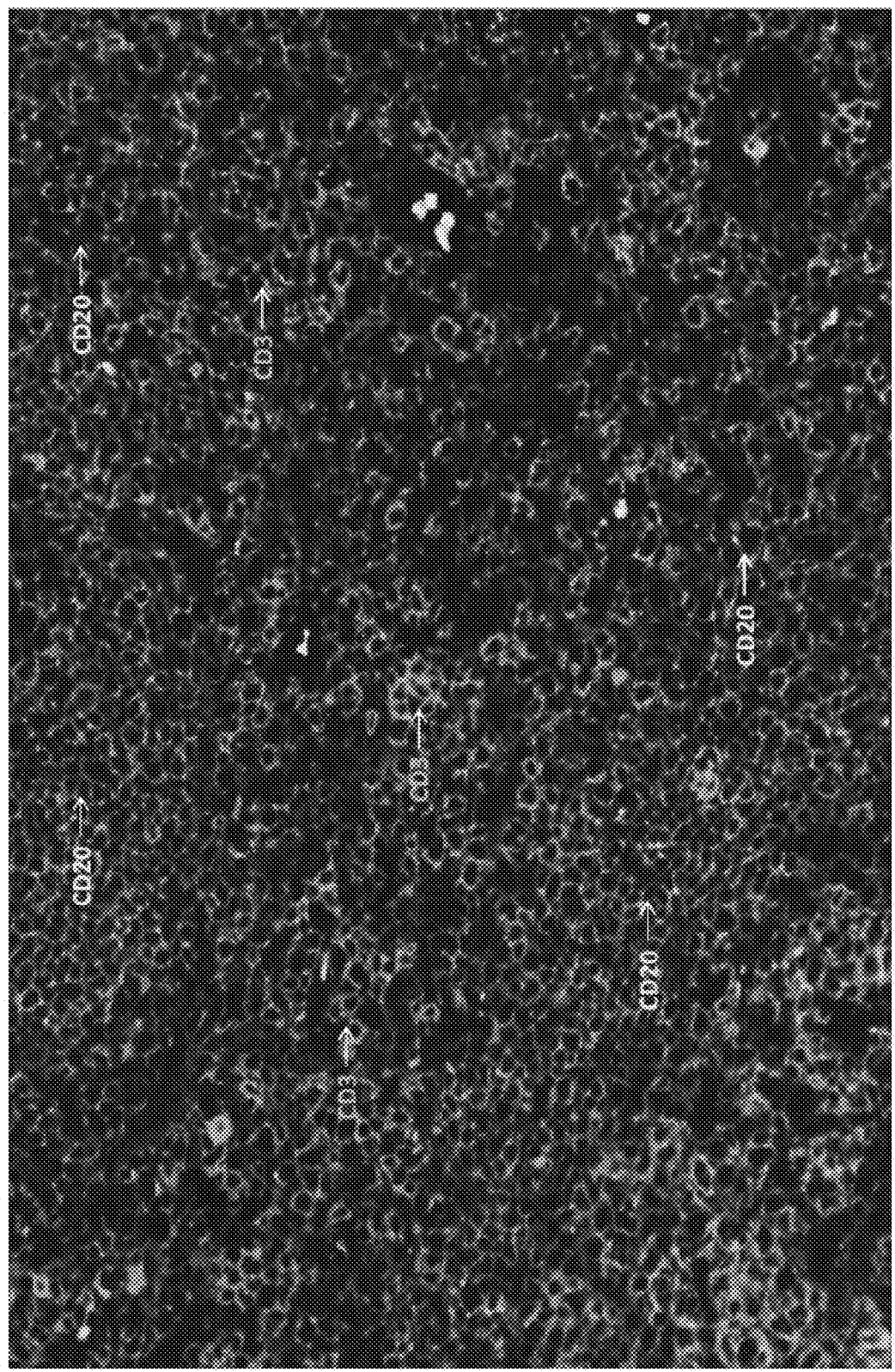
Figure 14I:
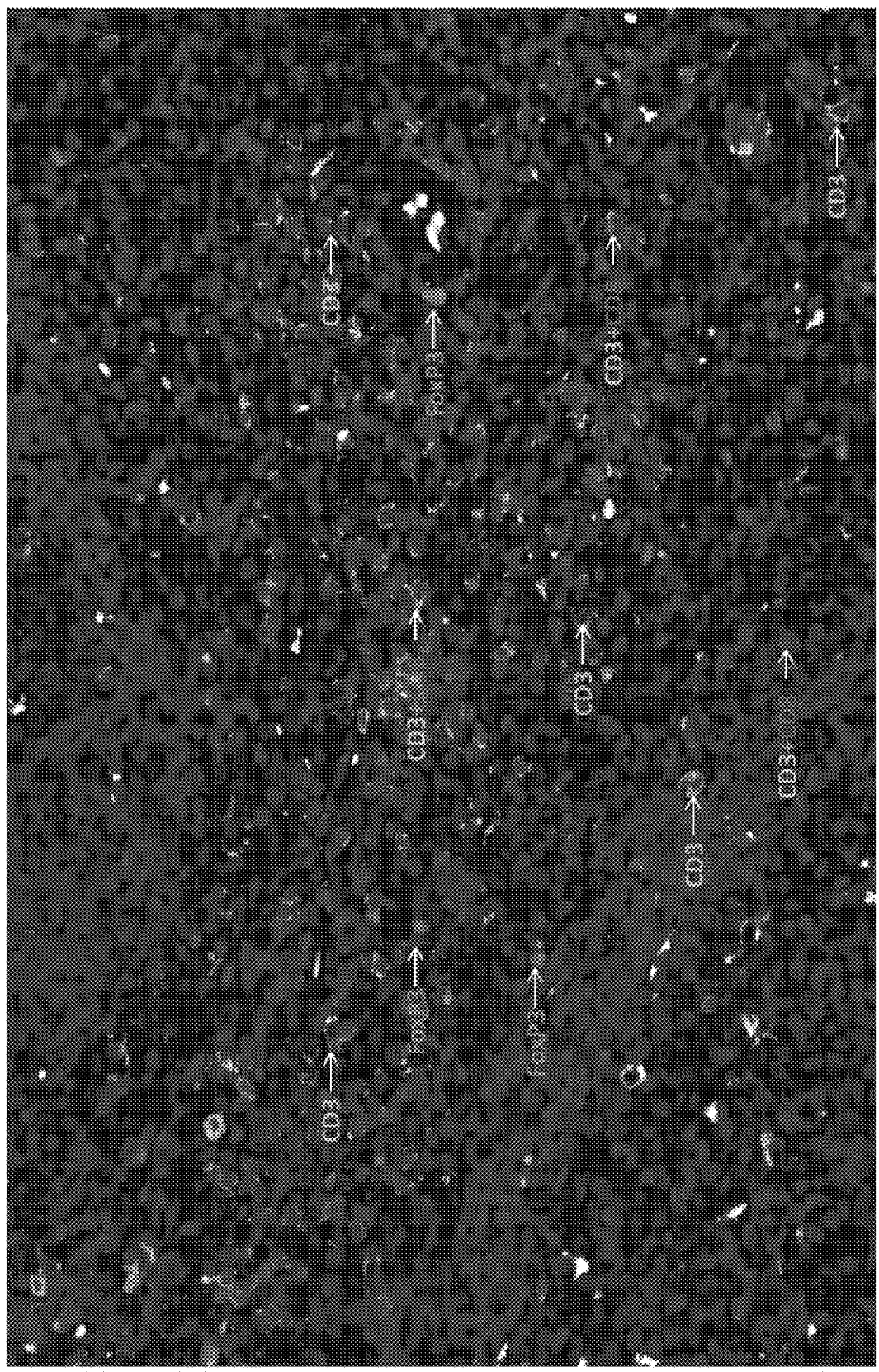
Figure 14J:
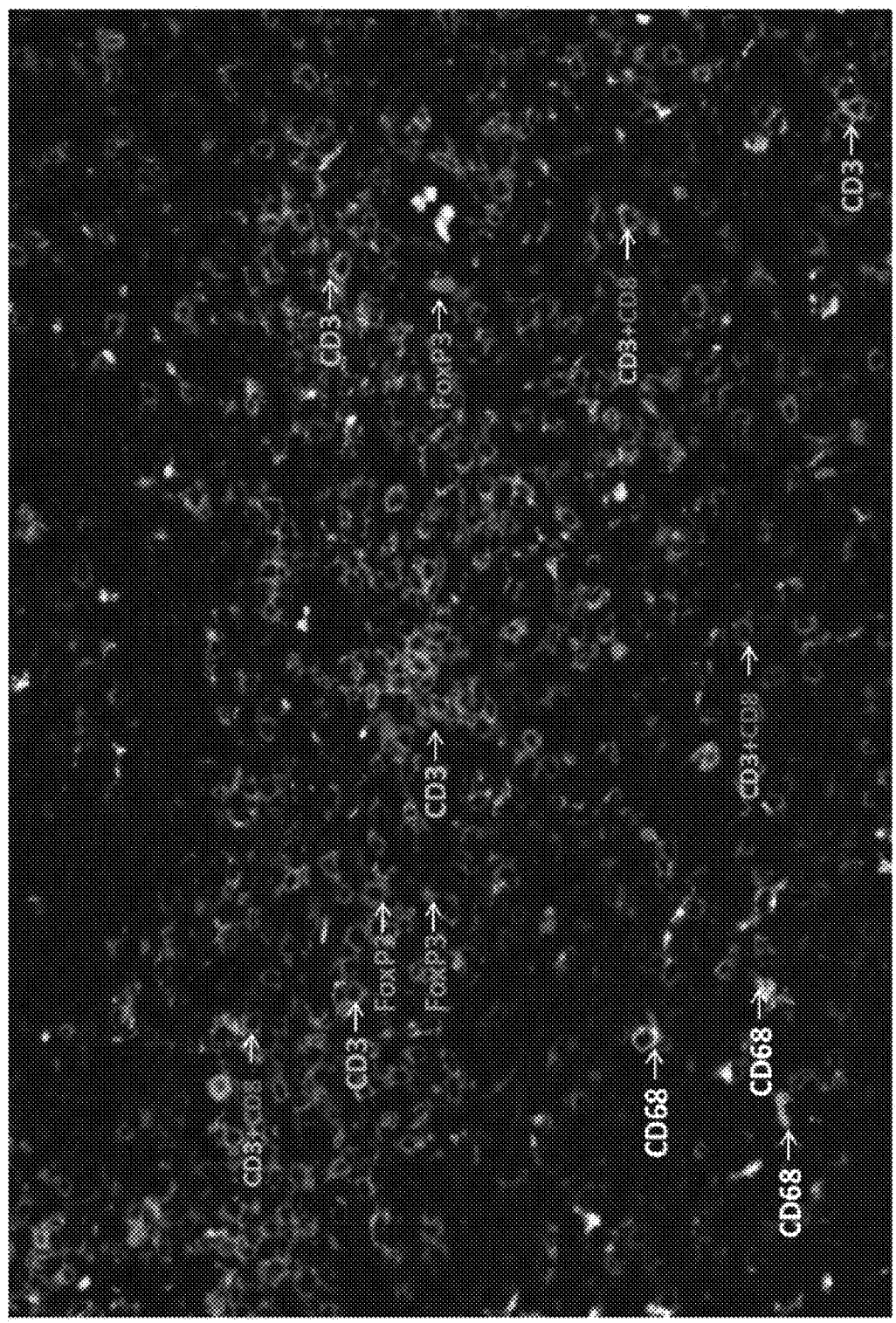

FIG. 14D provides an image showing DAPI, CD8 (cytotoxic T cell marker) and FoxP3 (regulatory T cell marker) staining, where no co-registration is observed. FIG. 14E provides an image showing CD8 (cytotoxic T cell marker) and FoxP3 (regulatory T cell marker) staining, where no co-registration is observed. FIG. 14F provides an image showing CD3 (T cell marker) and FoxP3 (regulatory T cell marker) staining, where co-registration is observed. FIG. 14G provides an image showing CD68 and FoxP3 staining; while FIG. 14H provides an image showing CD20 (B cell marker) and CD3 (T cell marker) staining. FIG. 14I provides an image showing CD3, FoxP3, and CD8 staining, where CD8 (cytotoxic T cell marker) and FoxP3 (regulatory T cell marker) are co-localized to CD3 (T cell marker). FIG. 14J provides an image showing CD3, FoxP3, CD8, and CD68 staining. These staining patterns illustrate different populations of immune cells and their relationship to one another.

FIGS. 14A through 14I show that the five epitope-tagged antibodies of the present disclosure were (1) capable of binding to CD20, CD3, CD8, CD68, and FoxP3; (2) capable of being detected by appropriate anti-tag antibodies; and (3) able to be applied to a tissue sample simultaneously (e.g. as a cocktail of antibodies) without interfering with each other. The 5-plex MIHC assay was able to be completed in less than four hours. This assay is useful for immune profiling in in hematological and solid tumors.

Example 8: Evaluation of HER2/neu (4B5) Antibody—V5 Peptide Conjugates on HER2+4 nl Cell Line Models and Breast Cancer Tissue This example demonstrates the visualization of HER2/neu (4B5) antibody V5 peptide conjugates on HER2+4 nl cell line models and HER2+ breast cancer tissue. Slides containing tonsil tissue sections were developed using a standard protocol for an automated stainer [BenchMark® XT, Ventana Medical Systems, Inc, (VMSI) Tucson, AZ]. A typical automated protocol is as follows: The paraffin-coated tissue on the slides was heated to 75° C. for 4 minutes and treated once with EZPrep (VMSI #950-102), volume adjusted at 75° C. before application of the Liquid Cover Slip (LCS, VMSI #650-010). After the slide was incubated for 4 minutes at 75° C., the slide was rinsed and EZPrep volume was adjusted, followed with LCS to deparaffinize the tissue (process repeated three times—4 total cycles). The slides were cooled to 37° C. and incubated for 4 minutes. The slides were thoroughly rinsed with cell condition solution (CCI, VMSI #950-124), followed by application of LCS. The slides were heated to 95° C. for 8 minutes. The slides were then heated to 100° C. and incubated for 8 minutes. The slides were rinsed with CCI followed by application of LCS and incubated for 8 minutes at 100° C. Every 4 minutes, for 16 minutes, CCI and LCS were applied in order to prevent slide drying.

The slides were cooled to 37° C. and rinsed twice with reaction buffer (VMSI #950-300), 100 µL of UV Inhibitor (a component of the VMSI ultra View DAB Detection Kit #760-500) was applied to the slide and incubated for 4 minutes. The slides were rinsed once with reaction buffer before the application of 100 µL of HER2/neu antibody-VS peptide conjugate (1 µg/mL) in Ventana Antibody Diluent with Casein (VMSI #760-219) for 16 minutes at 37° C. The slides were rinsed 3 times with reaction buffer before the addition of 100 µL of Pierce MsAntiV5 Antibody (Clone EIO/V4RR, Pierce #MAS-15253) at 1 g/mL in Ventana Avidin Diluent with B5 Blocker (VMSI #90040). The MsAntiV5 antibody was incubated at 37° C. for 8 minutes. The slides were rinsed 3 times with reaction buffer before the addition of 100 µL of ultra View HRP universal multimer (a component of the VMSI ultra View DAB Detection Kit #760-500). After 3 rinses with reaction buffer, 100 µL of both the ultra View DAB and ultra View H20 2 were applied to the slide and co-incubated for 8 minutes with LCS at 37° C. The slides were rinsed once in reaction buffer before 100 L of the Ultra View Copper was applied to the slide and incubated for 4 minutes at 37° C. The slides then underwent 2 rinses with reaction buffer before counterstaining with Hematoxylin II (VMSI #750-2021) which was incubated on the slide for 4 minutes with LCS. After 2 rinses with reaction buffer, the bluing reagent (VMSI #760-2037) was applied and incubated for 4 minutes for the counterstain to be complete. The slides were removed from the instrument and treated to a detergent wash, rinsed with water, dehydrated with an alcohol rundown and xylene before manual application of a solid cover slip. Results discussed below are for IHC staining of a 2+HER2+ breast cancer tissue case. The slides were viewed through a brightfield microscope. The results shown in Table 11 were a subjective score of the DAB IHC signal strength (e.g., the intensity of the staining) with 2 being the most the DAB intensity observed for the HER2/neu (4B5) standard slide.

TABLE 11

| Subjective score of the DAB IHC signal strength | |
| --- | --- |
| Antibody | IHC Intensity |
| 4B5 Control | 2 |
| H0K4 | 2 |

TABLE 11-continued

Subjective score of the DAB IHC signal strength

| Antibody | IHC Intensity |
|---|---|
| H0K3 | 1.5 |
| H0K2 | 1.5 |
| H0K1 | 1 |
| H5K0 | 2 |
| H4K0 | 2 |
| H3K0 | 2.25 |
| H2K0 | 2 |
| H1K0 | 1.75 |
| H4K4 | 2.25 |
| H3K3 | 2.5 |
| H2K2 | 2.25 |

The H0K4 HER2-V5 conjugate provided comparable IHC DAB staining to the HER2/neu (4B5) standard control on the 2+ breast cancer case. The H0K1 to H0K3 HER2-V 5 conjugates demonstrated slightly inferior IHC staining. The H2KO to H5KO HER2-V5 conjugates provided comparable to the HER2/neu (4B5) standard control on the 2+ breast cancer case. The H1KO HER2-V5 conjugate also demonstrated slightly inferior IHC tissue staining.

Example 9: Evaluation of HER2/Neu (4B5) Antibody—V5 Peptide Conjugates HER2+4111 Cell Line Models and Breast Cancer Tissue This example demonstrates the visualization of HER2/neu (4B5) antibody-V5 peptide conjugates on HER2+4 n1 cell line models and HER2+ breast cancer tissue. Slides containing tonsil tissue sections were developed using a standard protocol for an automated stainer [BenchMark® XT, Ventana Medical Systems, Inc, (VMSI) Tucson, AZ]. A typical automated protocol is as follows: The paraffin-coated tissue on the slides was heated to 75° C. for 4 minutes and treated once with EZPrep (VMSI #950-102), volume adjusted at 75° C. before application of the Liquid Cover Slip (LCS, VMSI #650-010). After the slide was incubated for 4 minutes at 75° C., the slide was rinsed and EZPrep volume was adjusted, followed with LCS to deparaffinize the tissue (process repeated three times—4 total cycles). The slides were cooled to 37° C. and incubated for 4 minutes. The slides were thoroughly rinsed with cell condition solution (CCl, VMSI #950-124), followed by application of LCS. The slides were heated to 95° C. for 8 minutes. The slides were then heated to 100° C. and incubated for 8 minutes. The slides were rinsed with CCl followed by application of LCS and incubated for 8 minutes at 100° C. Every 4 minutes, for 16 minutes, CCI and LCS were applied in order to prevent slide drying.

The slides were cooled to 37° C. and rinsed twice with reaction buffer (VMSI #950-300), 100 µL of UV Inhibitor (a component of the VMSI ultra View DAB Detection Kit #760-500) was applied to the slide and incubated for 4 minutes. The slides were rinsed once with reaction buffer before the application of 100 µL of HER2/neu antibody -V5 peptide conjugate (1 µg/mL) in Ventana Antibody Diluent with Casein (VMSI #760-219) for 16 minutes at 37° C. The slides were rinsed 3 times with reaction buffer before the addition of 100 µL of Pierce MsAntiV5 Antibody (Clone E10N4RR, Pierce #MA5-15253) at 1 µg/mL in Ventana Avidin Diluent with B5 Blocker (VMSI #90040). The MsAntiV5 antibody was incubated at 37° C. for 8 minutes. The slides were rinsed 3 times with reaction buffer before the addition of 100 µL of ultra View HRP universal multimer (a component of the VMSI ultra View DAB Detection Kit #760-500). After 3 rinses with reaction buffer, 100 µL of both the ultra View DAB and ultra View H20 2 were applied to the slide and co-incubated for 8 minutes with LCS at 37° C. The slides were rinsed once in reaction buffer before 100 µL of the Ultra View Copper was applied to the slide and incubated for 4 minutes at 37° C. The slides then underwent 2 rinses with reaction buffer before counterstaining with Hematoxylin II (VMSI #750-2021) which was incubated on the slide for 4 minutes with LCS. After 2 rinses with reaction buffer, the bluing reagent (VMSI #760-2037) was applied and incubated for 4 minutes for the counterstain to be complete. The slides were removed from the instrument and treated to a detergent wash, rinsed with water, dehydrated with an alcohol rundown and xylene before manual application of a solid cover slip.

Results discussed below are for IHC staining of a 2+HER2+ breast cancer tissue case. The slides were viewed through a brightfield microscope. The results shown in Table 12 were a subjective score of the DAB IHC signal strength (e.g., the intensity of the staining) with 2 being the most the DAB intensity observed for the HER2/neu (485) standard slide.

TABLE 12

Subjective score of the DAB IHC signal strength

| Antibody | IHC Intensity |
|---|---|
| 4B5 Control | 2 |
| H0K4 | 2 |
| H0K3 | 1.5 |
| H0K2 | 1.5 |
| H0K1 | 1 |
| H5K0 | 2 |
| H4K0 | 2 |
| H3K0 | 2.25 |
| H2K0 | 2 |
| H1K0 | 1.75 |
| H4K4 | 2.25 |
| H3K3 | 2.5 |
| H2K2 | 2.25 |

The H0K4 HER2-V5 conjugate provided comparable IHC DAB staining to the HER2/neu (4B5) standard control on the 2+ breast cancer case. The H0K1 to H0K3 HER2-V5 conjugates demonstrated slightly inferior IHC staining. The H2KO to H5KO HER2-V 5 conjugates provided comparable to the HER2/neu (4B5) standard control on the 2+ breast cancer case. The H1KO HER2-V5 conjugate also demonstrated slightly inferior IHC tissue staining.

Example 10: BioLayer Interferometry (BL]) Evaluation of HER2/Neu (4B5) Antibody—VS Peptide Conjugates: Conjugate Recognition of HER2 Peptide Antigen and Subsequent Conjugate Recognition by AntiVS Antibody All BioLayer Interferometry experiments were performed on a ForteBio Octet Red BU instrument using ForteBio Amine Reactive Sensors (ForteBio #18-5001) in Greiner Bio-one black flat well 96-well polypropylene microplates (Greiner Bio-one #655209). All BLI assays were performed at 37° C.

BLI analyses were performed as followed:
ForteBio Amine-reactive biosensors (ForteBio) were hydrated in 200 µL of 0.1 MMES pH 5.0 [2-(N-morpholino ethanesulfonic acid)]. Biosensors were activated for 5 minutes by treatment in a 200 µL mixture of 0.4 M EDC (1-ethyl-3-[3-dimethylaminopropyl]carbodiimide hydrochloride), 0.1 M NHS (N-hydrosulfosuccinimide) in ddi water. BSA-HER2 peptide immunogen loading was performed by treating the sensors for 20 minutes with 200 μL of BSA-HER2 peptide immunogen (25 μg/mL) in O.IM MES pH 5.0. The sensors were quenched with 1M ethanolamine (pH=8.5) for 5 minutes followed by equilibruim in 10 mM phosphate (pH=7.4), 134 mM NaCl containing ForteBio Kinetics Buffer Additive (ForteBio #18-5032 diluted to 1×) for 5 minutes. HER2-V5 antibodypeptide conjugate binding was performed by treating sensors for approximately 45 minutes with a 3 g/mL solution of the conjugate in 10 mM phosphate (pH=7.4), 134 mM NaCl containing ForteBio Kinetics Buffer Additive (ForteBio #18-5032 diluted to 1×). The HER2-V5 antibody-peptide antibody conjugate was allowed to dissociate from the sensor for 20 minutes in in 10 mM phosphate (pH=7.4), 134 mM NaCl containing ForteBio Kinetics Buffer Additive (ForteBio #18-5032 diluted to 1×). MsAntiV5 antibody recognition of the biosensor was performed by treating sensors for approximately 45 minutes with a 3 μg/mL solution of Pierce MsAntiV5 Antibody (Clone E10/V4RR, Pierce #MAS-15253) in 10 mM phosphate (pH 7.4), 134 mM NaCl containing ForteBio Kinetics Buffer Additive (ForteBio #18-5032 diluted to 1×). The HER2-V5 antibody-peptide antibody conjugate was allowed to dissociate from the sensor for approximately 45 minutes in 10 mM phosphate (pH=7.4), 134 mM NaCl containing ForteBio Kinetics Buffer Additive (ForteBio #18-5032 diluted to 1×).

Figure 24A:
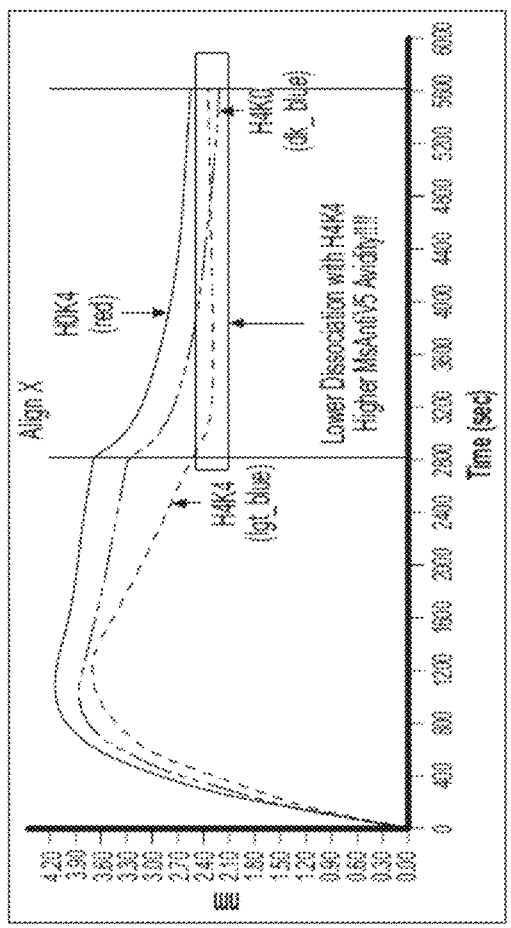
FIG. 24A provides kinetic data from a BLI assay indicating that the antibodies with four tags on both the heavy and light chains dissociate at a much slower rate than the same antibody with four tags only on the heavy chain or only on the light chain.
Figure 24B:
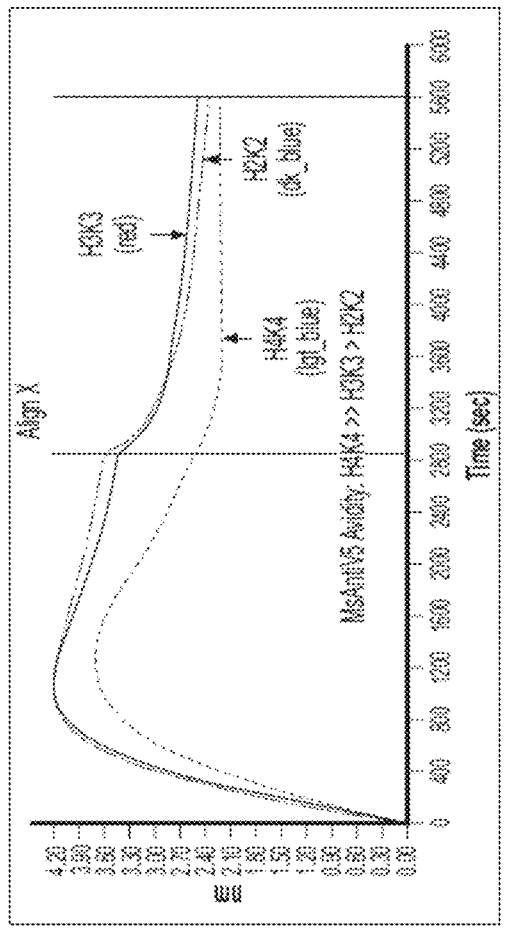
FIG. 24B provides an avidity effect comparison illustrating the advantage of antibodies with four tags on both the heavy and light chains.
Figure 24C:
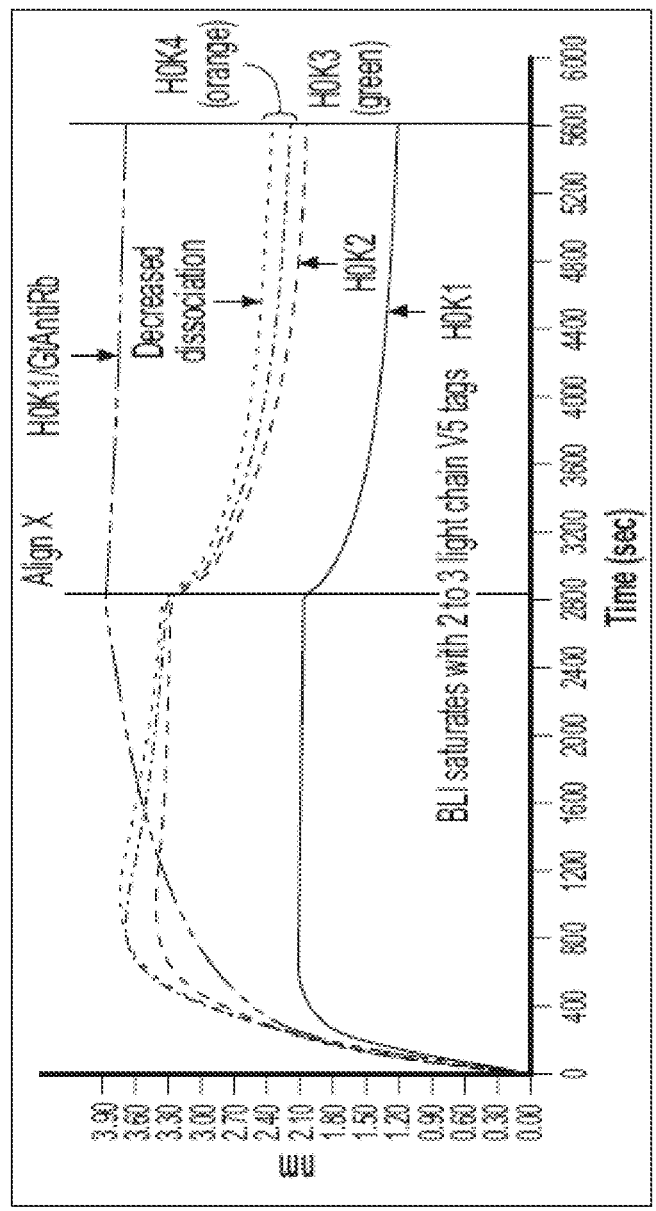
FIG. 24C illustrates MsAntiV5 recognition with HER2 H0KX, where light chain tags show a similar BLI response to heavy chain tags; MsAntiV5 showed faster on-rate and similar BLI response to GtAntiRb with H0K3; and the figure further illustrates that BLI response became saturated with approximately two to three V5 tags (which matched tissue staining results). There was also an observed decreased anti-V5 dissociation with higher V5-tag loading.

Results:

BioLayer Interferometry experiments were performed to demonstrate the peptide labeling impact on antibody-peptide conjugate/antigen recognition and then subsequently secondary anti-peptide antibody/antibody-peptide conjugate recognition. BLI studies demonstrated that peptide labeling of the antibody heavy and light chains minimally impacted antibody recognition of the requisite antigen. Further studies showed that increased peptide labeling changed the mode of secondary antibody recognition from affinity to avidity interactions. Increased labeling of both heavy and light chains caused at least some assay layer compression and increased avidity, whereas secondary antibody dissociation was greatly minimized (see FIGS. 24A and 24B).

BLI analysis showed (1) good signal/noise for all antibody recognition steps; (2) consistent assay response with replicate data points; and (3) no cross-reactivity was observed for MsAntiV5 with native HER2(4B5).

Example 11: DLS/DSC Testing

Methods

DLS: hydrodynamic radius, aggregates, temperature induced aggregation

DSC: influence of E4 tag on melting temperature IgG domains (see

TABLE 13

| Sample | Conc [mg/ml] | Amount [mg] |
|---|---|---|
| CD3(SP162), E, H4K4 | 0.61 | 1.8 |
| CD3(SP162), E, H0K4 | 1.34 | 4.0 |
| CD3(SP162), E, H4K0 | 0.91 | 1.8 |
| CD3(SP162), native | 0.96 | 1.0 |

Figure 25A:
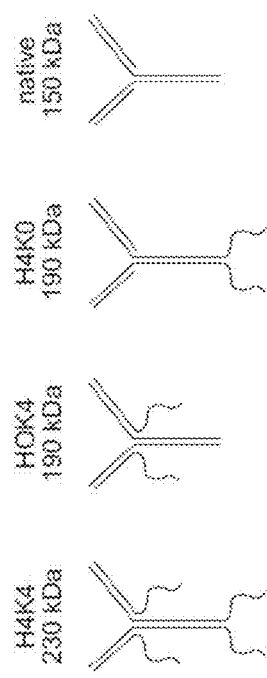
FIG. 25A illustrates the structure of certain epitope-tagged antibodies used for DLS/DSC testing.

All samples were in PBS with 0.1% sodium azide and 1% BSA; the E4 tag was fused at C-terminus of H and/or K chain (see FIG. 25A). The molecular weight of the E4 tag was 20 kDa.

BSA removal with Protein A chromatography:
(1) Protein A chromatography—Column: HiTrap MabSelect SuRe (1 ml); Buffer A: 50 mM KP, 150 mM NaCl pH 7.5; Buffer B: 50 mM Natriumcitrat pH 4.0
(2) Dialysis for 16 h at 4° C. against 50 mM KP-Puffer 150 mM KCl pH 7.4
(3) concentrate to 0.5 mg protein/ml with Pall Macrosep Advance 10 kDa Yield (see Table 14):

TABLE 14

| Sample | H4K4 | H0K4 | H4K0 | native |
|---|---|---|---|---|
| Start amount (specified by Ventana) [mg] | 1.8 | 4.0 | 1.8 | 1.0 |
| Amount after concentration [mg] | 0.7 | 1.5 | 0.5 | 0.3 |
| % yield | 39 | 38 | 29 | 32 |

Figure 25B:
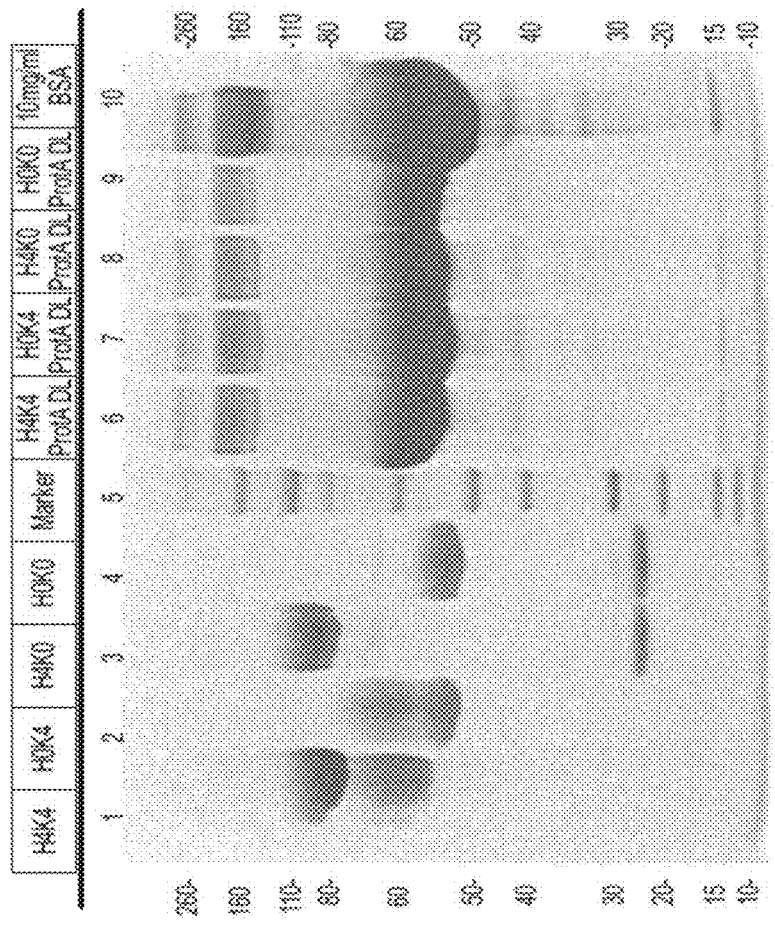
FIG. 25B shows that BSA was quantitatively removed from the samples (SDS page).
Figure 25C:
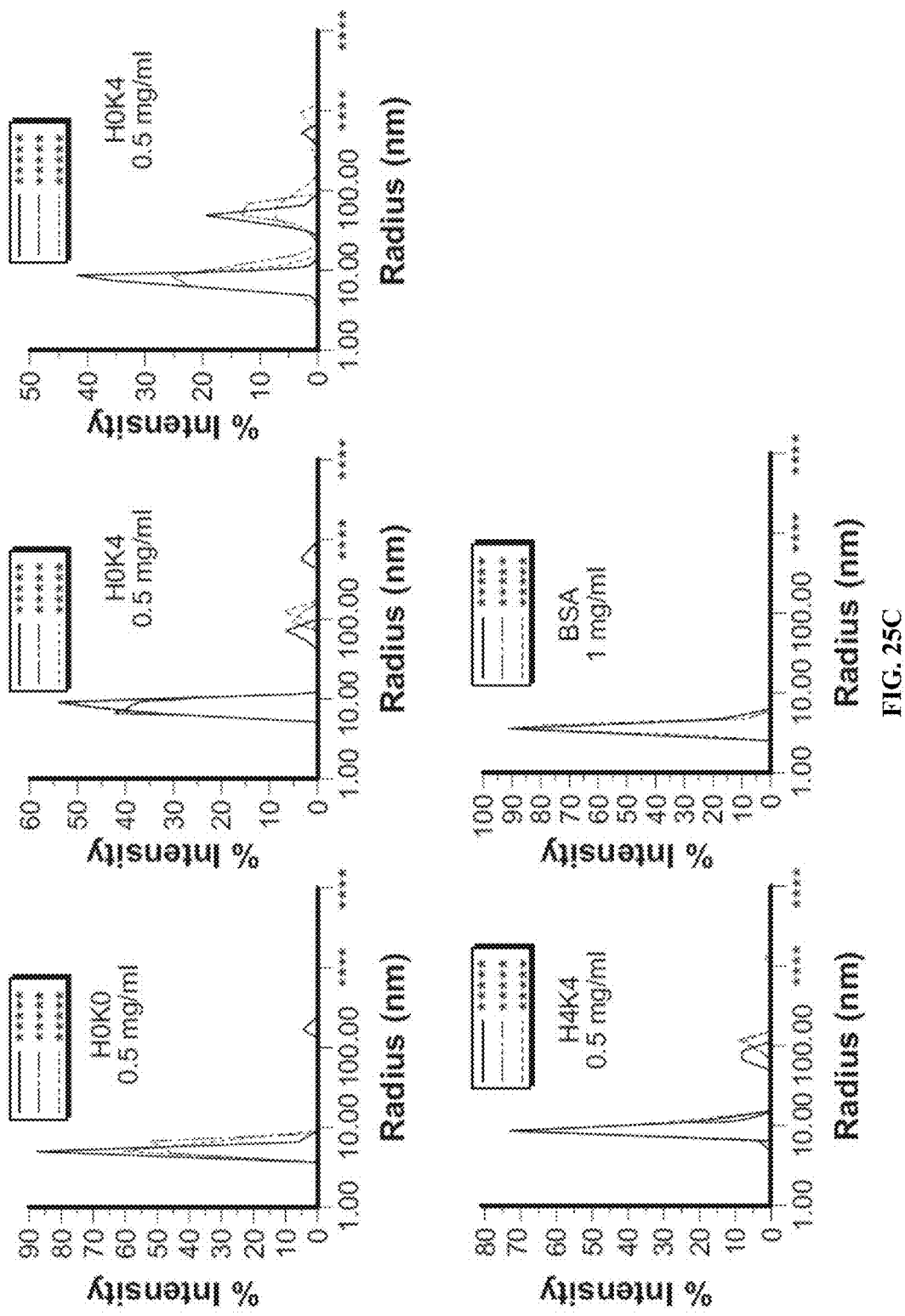
FIG. 25C provides DLS measurement data.

FIG. 25B shows that BSA was quantitatively removed from the samples (SDS page).

SEC Chromatography—Molecular weight calculated from refractive index and right angel light scattering detector in combination with SEC (YMC 200) (see Table 15):

TABLE 15

| Sample | Mw-(kDa) |
|---|---|
| H0K0 | 154 |
| H0K4 | 205 |
| H4K0 | 205 |
| H4K4 | 252 |

SEC chromatography indicated that molecular weights were as expected.

DLS Measurements—Analysis and Interpretation (see Tables 16A and 16B):

TABLE 16A

Hydrodynamic Radius Peak 1 (Regularization Fit)

| Sample | N | rH [nm] mean | SD |
|---|---|---|---|
| BSA 10 mg/ml | 3 | 4.0 | 0.1 |
| BSA 1 mg/ml | 3 | 3.8 | 0.1 |
| V184 H0K0 | 3 | 5.4 | 0.4 |
| V184 H0K4 | 3 | 7.8 | 0.2 |
| V184 H4K0 | 3 | 8.3 | 0.5 |
| V184 H4K4 | 3 | 9.3 | 0.3 |

TABLE 16B

Polydispersity of Peak 1

| Sample | N | Pd [%] mean | SD |
|---|---|---|---|
| BSA 10 mg/ml | 3 | 15.2 | 3.3 |
| BSA 1 mg/ml | 3 | 10.7 | 2.1 |
| V184 H0K0 | 3 | 12.5 | 3.6 |
| V184 H0K4 | 3 | 15.5 | 2.3 |
| V184 H4K0 | 3 | 21.6 | 7.5 |
| V184 H4K4 | 3 | 12.7 | 1.1 |

Reproducibility of the measurements is good;

H0K0 had a rH (5.4 nm) as expected for an IgG, only little amount of aggregates were detectable;

C-terminal fusion of E4 tag caused a significant increase in rH, that could be explained by the unstructured nature of the E4 tag;

Slightly more aggregates were detectable in the samples with E4 tag; and

H4K0 had significantly more aggregates (approx. 2% (w/w)) than the others and a higher polydispersity in Peak1, indicating a higher content on oligomers (dimer to tetramer).

Figure 25D:
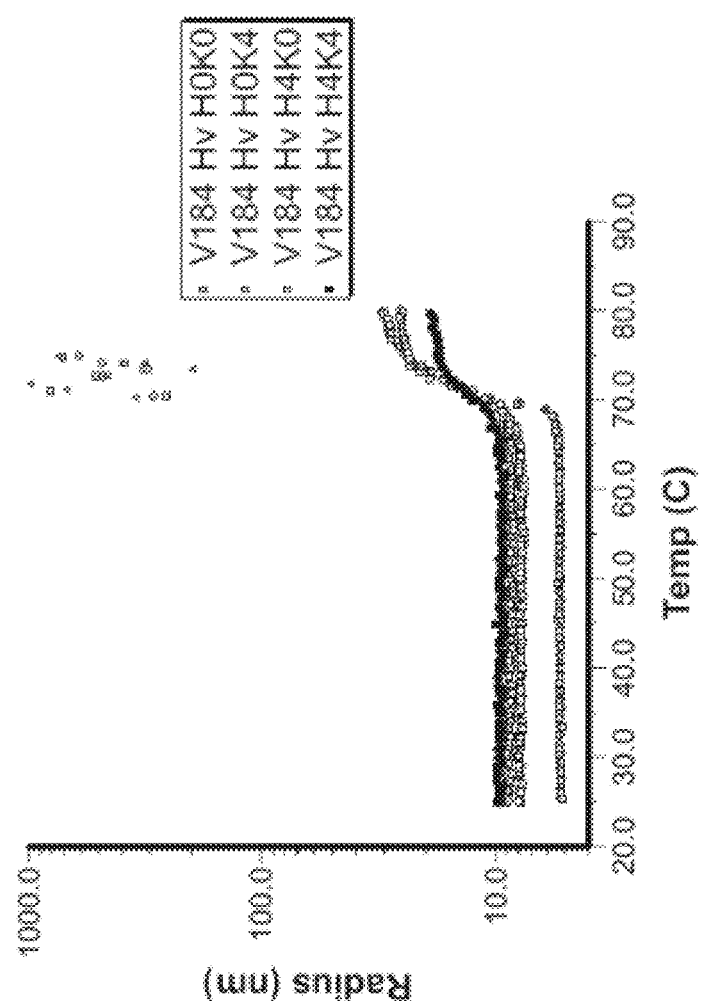
FIGS. 25D and 25E illustrate various DLS temperature ramps.
Figure 25E:
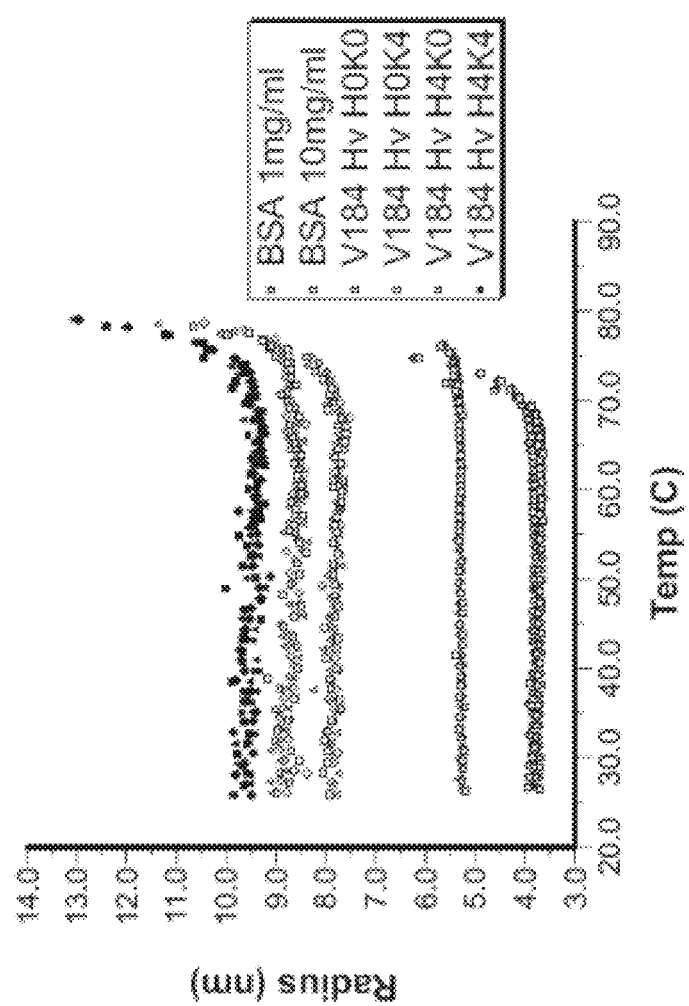

DLS Temperature ramp (see FIGS. 25D and 25E)

Hydrodynamic Radius (Cumulative fit) is followed over the temperature range from 25° C. to 80° C. with a ramp rate of 0.1 K/min (approx. 10 h); the native IgG (H0K0) forms very large (~1 μm) aggregates at 70° C.; and the temperature curves suggest, that the E4 tag reduces the formation of this temperature induced aggregates.

With OnsetTemp the starting point of aggregation was determined. OnsetTemp is a measure for the stability of the protein structure; Fusion of E4 tag to the C-terminus of the H chain has no significant influence on OnsetTemp; Fusion of E4 tag to the C-terminus of the K chain causes a decrease of OnsetTemp by 2 K; this effect could be observed at H0K4 and H4K4. The K4 fusion had a destabilizing effect on the IgG.

Figure 25F:
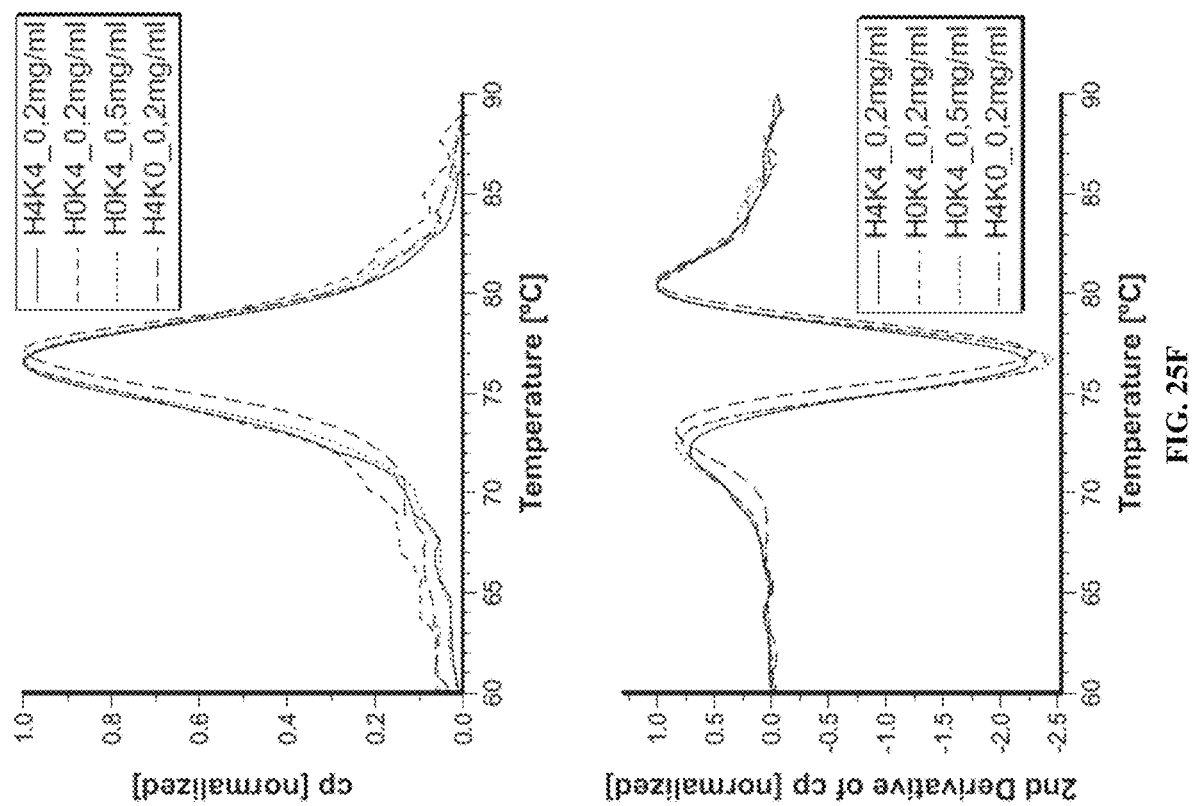
FIG. 25F illustrates the results of a DLS analysis.

DSC analysis (see FIG. 25F)—Due to the limited amount of sample, the DSC experiments had to performed at very low concentrations as single measurements; fusion of E4 tag to the C-terminus of the K chain caused a significant decrease of Tm compared to H4K0; the destabilizing effect of the K4 fusion on IgG shown in the DLS experiment could be verified by DSC.

DLS/DSC Summary

All experiments were performed in 50 mM potassium phosphate buffer, 150 mM potassium chloride pH 7.4. Evaluation of the effect of buffer, pH, salt concentration was not the aim of this study.

Observed effects of the E4 tag:

Increase of molecular weight was determined by RALS from 154 kDa (H0K0) to 205 kDa (H4K0 and H0K4) and 252 kDa (H4K4)

Increase of rH from 5.4 nm (H0K0) to 8 nm (H4K0 and H0K4) and 9 nm (H4K4)

E4 tag at the K chain but not at the H chain reduced the stability of the IgG as shown by DLS OnsetTemp determination and by DSC E4 tag reduced the tendency to form large aggregates at high temperature.

Example 12-Kinetics and Association/Dissociate Rate Studies

Overview of Surface Plasmon Resonance Spectroscopy

Surface plasmon resonance (SPR) spectroscopy is a technique for the study of ligand binding interactions. SPR is capable of measuring real-time quantitative binding affinities and kinetics for antibodies interacting with ligand molecules using relatively small quantities of materials. The conventional SPR technique requires one binding component to be immobilized on a sensor chip whilst the other binding component in solution is flowed over the sensor surface; a binding interaction is detected using an optical method that measures small changes in refractive index at the sensor surface. This exploits the phenomenon of surface plasmon generation in thin metal films and the total internal reflection of light at a surface-solution interface to produce an electromagnetic film or evanescent wave that extends a short distance (up to 300 nm) into the solution.

Figure 30A:
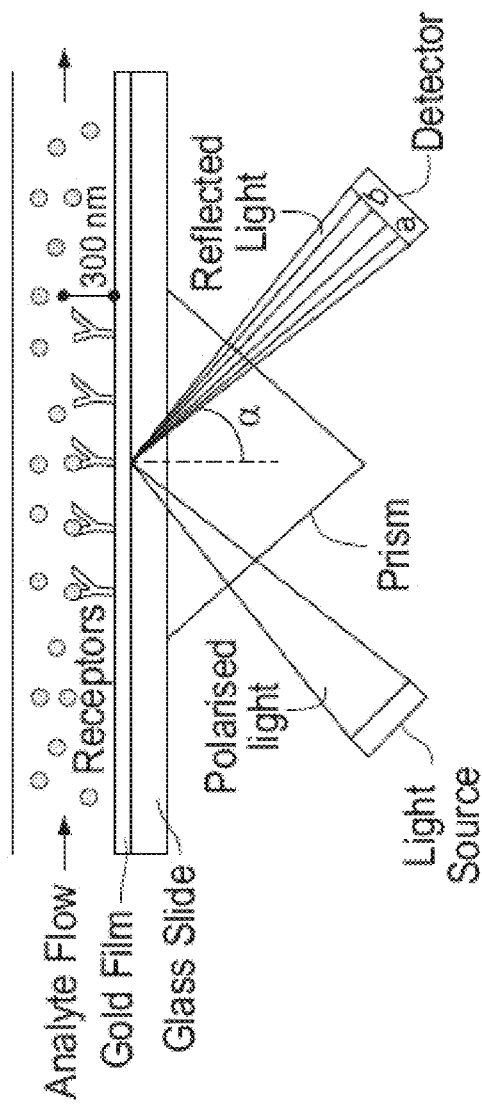
FIG. 30A, FIG. 30B, and FIG. 30C provide a schematic illustration of the basic SPR experiment for measuring the binding of an analyte molecule to a receptor molecule.
Figure 30B:
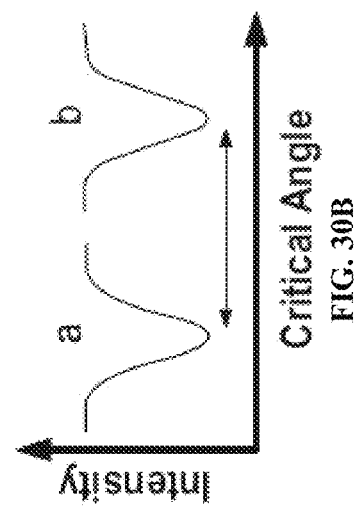
Figure 30C:
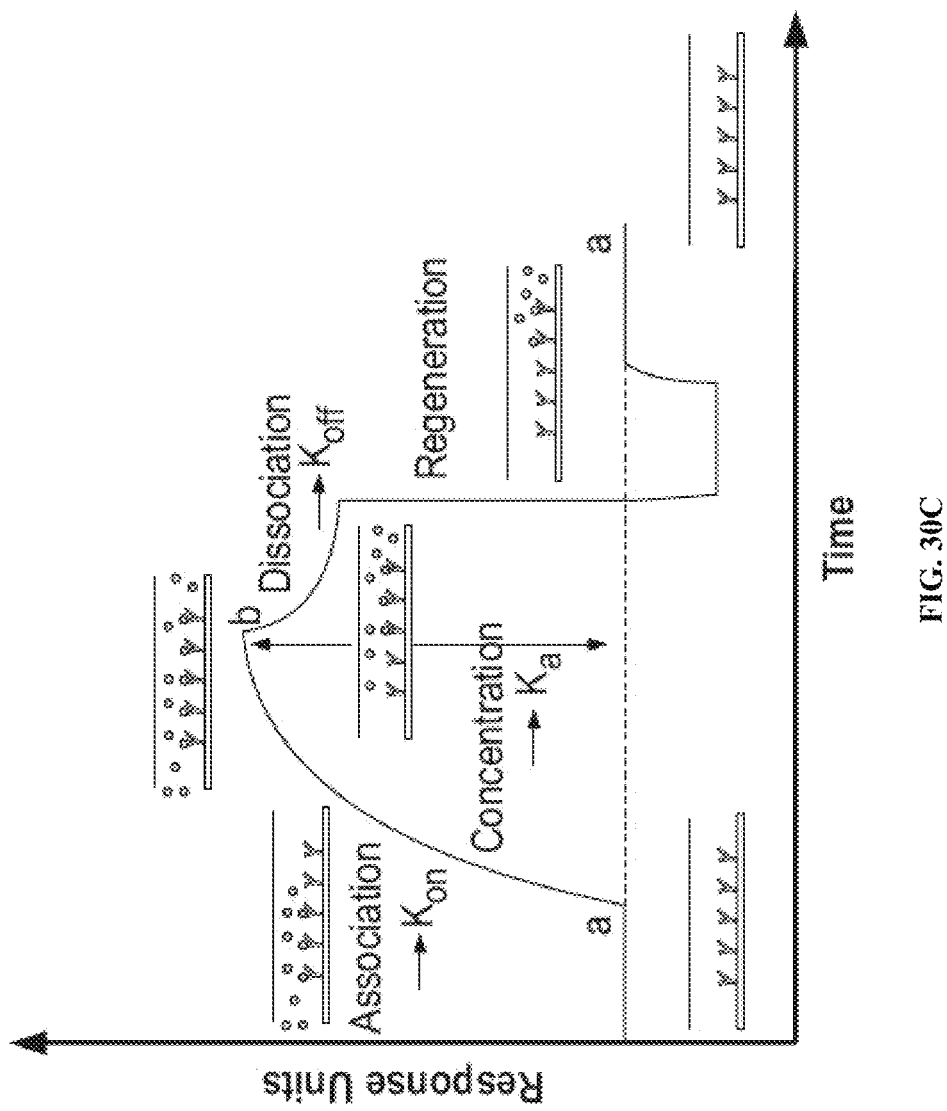

FIG. 30 denotes a schematic illustration of the basic SPR experiment for measuring the binding of an analyte molecule to a receptor molecule. By way of example: A. Instrument set up for an SPR experiment based on BIAcore™ technology. SPR uses an optical method to measure the refractive index near to a sensor surface; this exploits total internal reflection of light at a surface-solution interface to produce an electromagnetic field or evanescent wave that extends a short distance (up to 300 nm) into the solution. The surface is a thin film of gold on a glass support that forms the floor of a small-volume (less than 100 nl) flow cell through which an aqueous solution is continuously passed. In order to detect the binding of an analyte molecule to a receptor molecule, the receptor molecule is usually immobilized on the sensor surface and the analyte molecule is injected in the aqueous solution through the flow cell. Polarized light from a laser source is directed through a prism to the under surface of the gold film where surface plasmons are generated at a critical angle of the incident light. This absorption of light is seen as a decrease in intensity of the reflected light. The critical angle is dependent on the refractive index of the medium within 300 nm of the gold surface and changes when molecules bind to the surface, e.g. when analyte molecules bind to immobilized receptor molecules. B. Change in the critical angle of incident light from angle a to angle b on binding of an analyte molecule to a receptor molecule. C. Response of the SPR experiment in the form of a sensorgram. If interaction between the immobilized receptor molecule and the analyte molecule occurs, the refractive index at the surface of the gold film changes and this is seen as an increase in signal intensity. Resonance or response units (RU) are used to describe the increase in the signal, where 1 RU is equal to a critical angle shift of 10-4 deg. At the start of the experiment all immobilized receptor molecules have not been exposed to analyte molecules and the RU correspond to the starting critical angle a. Analyte molecules are injected into the flow cell; if they bind to the immobilized receptor molecules, there is an association phase during which binding sites become occupied and the shape of this curve can be used to measure the rate of association (kon). When a steady-state is achieved (all binding sites occupied in this example) the RU correspond to the changed final critical angle b. This maximum RU relates to the concentrations of immobilized receptor and analyte molecules and so can be used to measure the binding affinity (KD). When analyte molecules are removed from the continuous flow there is a dissociation phase during which binding sites become unoccupied and the shape of this curve can be used to measure the rate of dissociation (koff). The surface can then be regenerated and returned to the critical angle a to start the experiment again.

Kinetics Studies

A Biacore T200 instrument (GE Healthcare) was used to kinetically assess the binding behavior of rabbit monoclonal antibodies towards singly chemically biotinylated peptidic 2 kDa analytes: E_Tag (1-13)[Glu(Bi-PEG)-1]amid, and E_Tag (1-13)[Glu(Bi-PEG)-13]amid; E2_Tag (1-12)[Glu(Bi-PEG)-1]amid, and E2_Tag (1-12)[Glu(Bi-PEG)-12]amid; V5_Tag (1-14)[Glu(Bi-PEG)-1]amid, and V5_Tag (1-14)[Glu(Bi-PEG)-14]amid; VSV-G_Tag (1-11)[Glu(Bi-PEG)-11]amid; HA_Tag (1-9)[Glu(Bi-PEG)-1]amid, and HA_Tag (1-9)[Glu(Bi-PEG)-9]amid.

The rabbit IgG (150 kDa) monoclonal antibodies mAb<E>rRb-J26_wt-IgG and mAb<E>rRb-J26_H2L5, mAb<E2>rRb-J78_wt-IgG and mAb<E2>rRb-J78_H5L3, mAb<V5>rRb-J53_wt-IgG and mAb<V5>rRb-J53_H1L2, mAb<HA>rRb-J15_H2L2, mAb<VSV-G>rRb-J110_H5L2, and Rb—N-IgG (rabbit normal IgG, Sigma) were investigated for their binding kinetics and binding stoichiometries. A CM5 series sensor was mounted into the system and was normalized in HBS-ET buffer (10 mM HEPES pH 7.4, 150 mM NaCl, 3 mM EDTA, 0.005% w/v Tween 20) according to the manufacturer's instructions. The sample buffer was the system buffer supplemented with 1 mg/ml CMD (Carboxymethyldextran, Sigma #86524). The system operated at 37° C. 13000 RU GARbFcγ (goat anti rabbit Fcγ), Code Nr.: 111-005-046, Jackson Immuno Research were immobilized according to the manufacturer's instructions using EDC/NHS chemistry on all four flow cells. The sensor was deactivated using 1M ethanolamine. The binding activities of the respective antibodies against the analytes were kinetically tested. Antibodies were captured at 30 nM concentration by a 2 min injection at 10 μl/min. The flow rate was set to 60 μl/min. Analytes were injected for 3 min at different concentration steps of 0 nM buffer control, 22 nM, 67 nM, 200 nM twice, 600 nM and 1800 nM. The dissociation was monitored for 5 min. After each analyte injection the antibody capture system was fully regenerated by a 1 min 25 sec injection of HBS-ET buffer at 20 μl/min, followed by a 1 min injection at 20 μl/min with 10 mM glycine buffer pH 1.5 and two injections for 1 min at 20 μl/min with 10 mM glycin pH 1.7. Where possible, kinetic signatures were evaluated according to a Langmuir fit with RMAX local. In cases, where the dissociation rate was not apparent a steady state algorithm was applied according to the manufacturer's evaluation software.

Figure 31A:
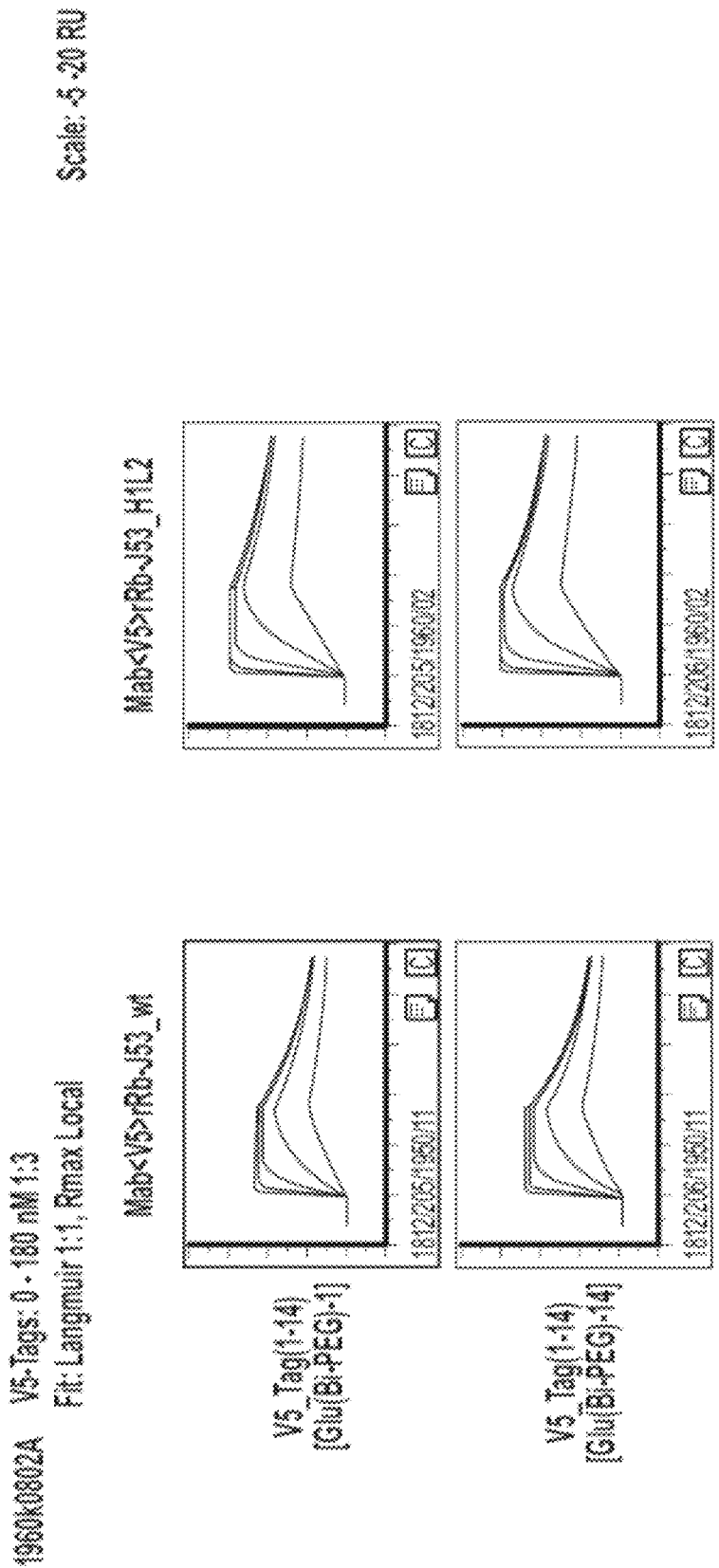
FIG. 31A, FIG. 31B, FIG. 31C, FIG. 31D, and FIG. 31E illustrate kinetic assessments of the binding behavior of rabbit monoclonal antibodies towards singly chemically biotinylated peptidic 2 kDa analytes. Mab<V5>rRb-J53_wt and Mab<V5>rRb-J53_H1L2 show a 1:1 binding stoichiometry. There were no kinetic differences observable between peptide analytes with biotin position in bi-1 or bi-14 (FIG. 31A). Mab<E>rRb-J26_wt and Mab<E>rRb-J26_H2L5 show three digit nanomolar affinities and 1:2 binding stoichiometry MR=2 (FIG. 31B). Mab<E2>rRb-J78_wt and Mab<E2>rRb-J78_H5L show two to three digit nanomolar affinities and 1:1 binding stoichiometry MR=1. Peptides with biotin in position bi-1 were recognized with higher affinity than with biotinylation in position bi-12 (FIG. 31C). Mab<HA>rRb-J15_H2L2 showed affinity in the three digit nanomolar range with 1:1 binding stoichiometry. No kinetic difference was observed between peptide analytes with biotin at position bi-1 or at position bi-9 (FIG. 31D). Mab<VSV-G>rRb-J110_H5L2 shows three digit nanomolar affinity and 1:2 binding stoichiometry (FIG. 31E).

FIG. 31A illustrates the results of a SPR experiment in accordance with the method described above. In particular, FIG. 31A illustrates the difference in kinetics between Mab<V5>rRb-J53_wt and Mab<V5>rRb-J53_H1L2, where MR was about 1.4, therefore indicating about a 1:1 binding stoichiometry. There were no observable kinetic difference between peptides analytes labeled with biotin at position bi-1 or at position bi-14. J53 H1L2 (one V5 tag on a heavy chain and two V5 tags on the light chain) showed slightly higher affinity than J53 wt.

Figure 31B:
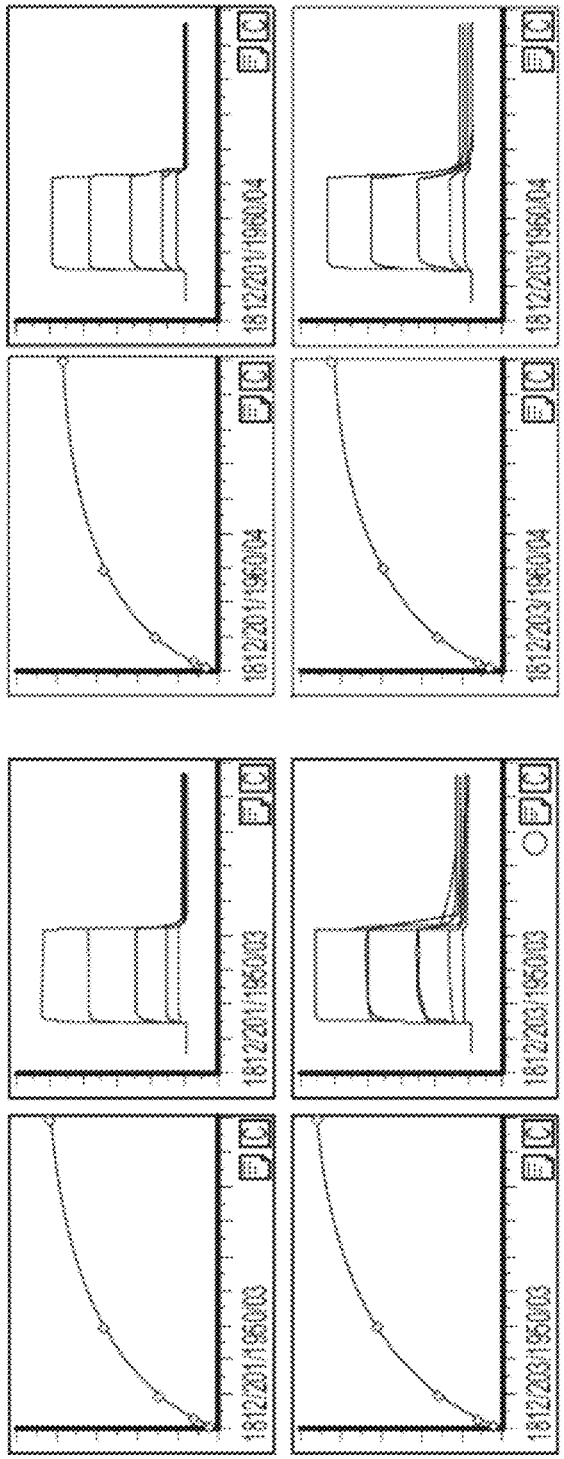

FIG. 31B illustrates the results of a SPR experiment in accordance with the method described above. In particular, FIG. 31B illustrates the difference in kinetics between Mab<E>rRb-J26_wt and Mab<E>rRb-J26_H2L5, where MR was determined to be up to about 2, which means an approximate 1:2 binding stoichiometry. Here, no determinable kd complex stability was observed, but steady state affinity was noted. The E epitope tag with biotin at position bi-1 possessed regular fast on/fast off kinetics, while the E epitope tag with biotin at position bi-13 had unspecific binding in the dissociation phase, and this was believed to be due to weak complex stability the antibodies.

Figure 31C:
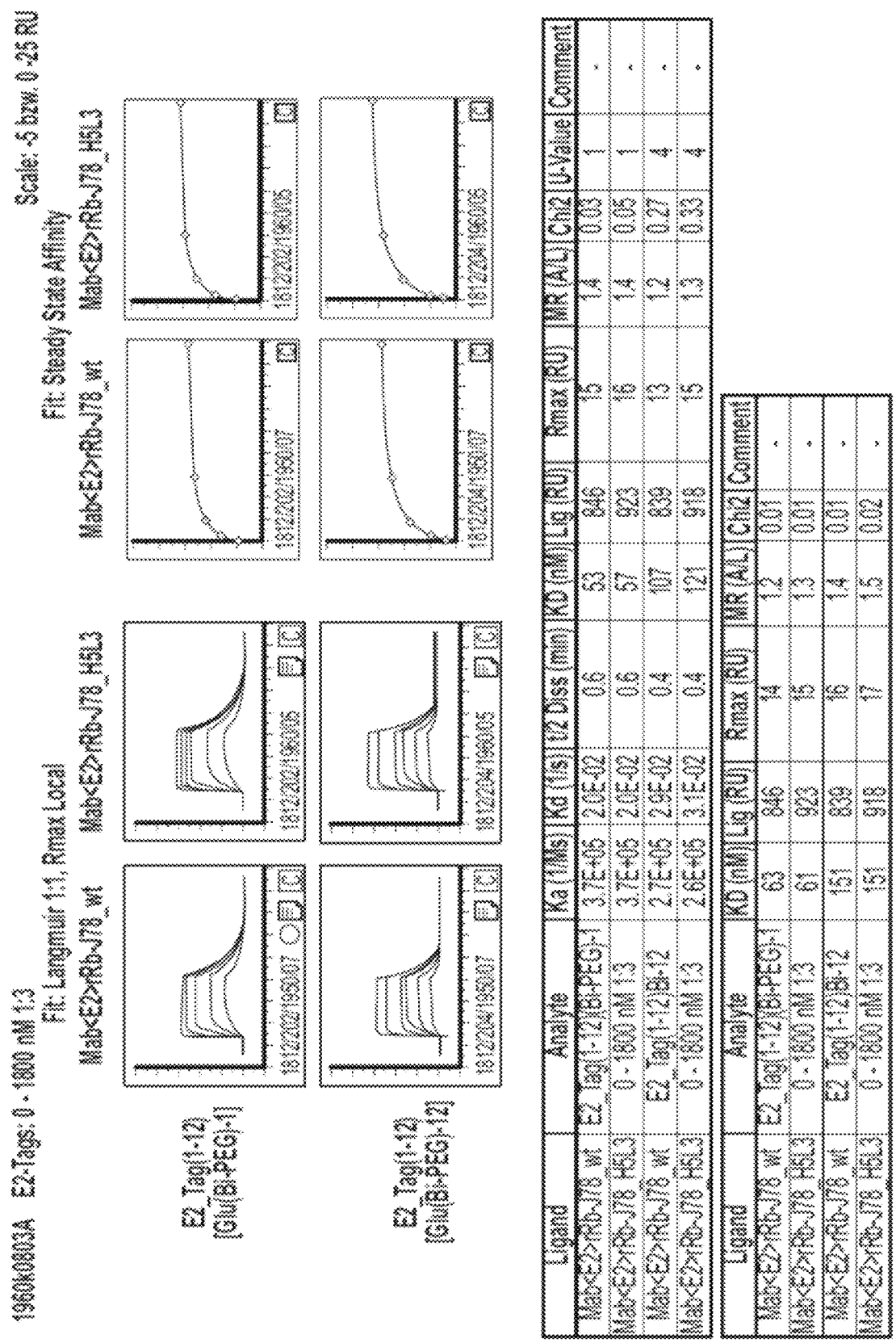

FIG. 31C illustrates the results of a SPR experiment in accordance with the method described above. In particular, FIG. 31C illustrates the difference in kinetics between Mab<E2>rRb-J78_wt and Mab<E2>rRb-J78_H5L, where MR was about 1.4, therefore indicating about a 1:1 binding stoichiometry. There were no observable kinetic differences between the peptides with biotin at position bi-1 or at position bi-12.

Figure 31D:
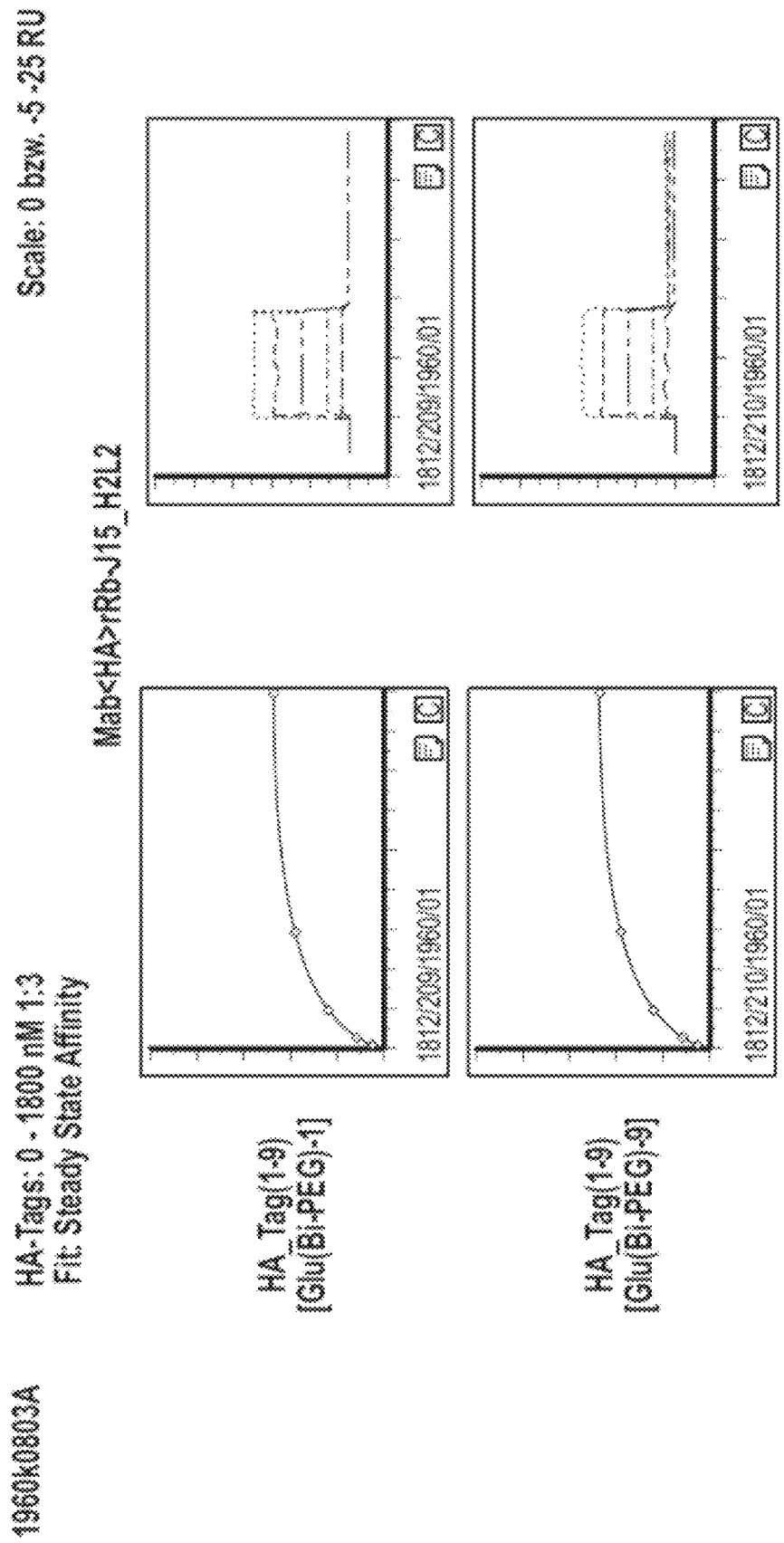

FIG. 31D illustrates the results of a SPR experiment in accordance with the method described above. In particular, FIG. 31D illustrates the difference in kinetics between Mab<HA>rRb-J15_H2L2, where MR was about 1.4, therefore indicating about a 1:1 binding stoichiometry. There were no observable kinetic differences between peptide analytes with biotin at position bi-1 or at position bi-9.

Figure 31E:
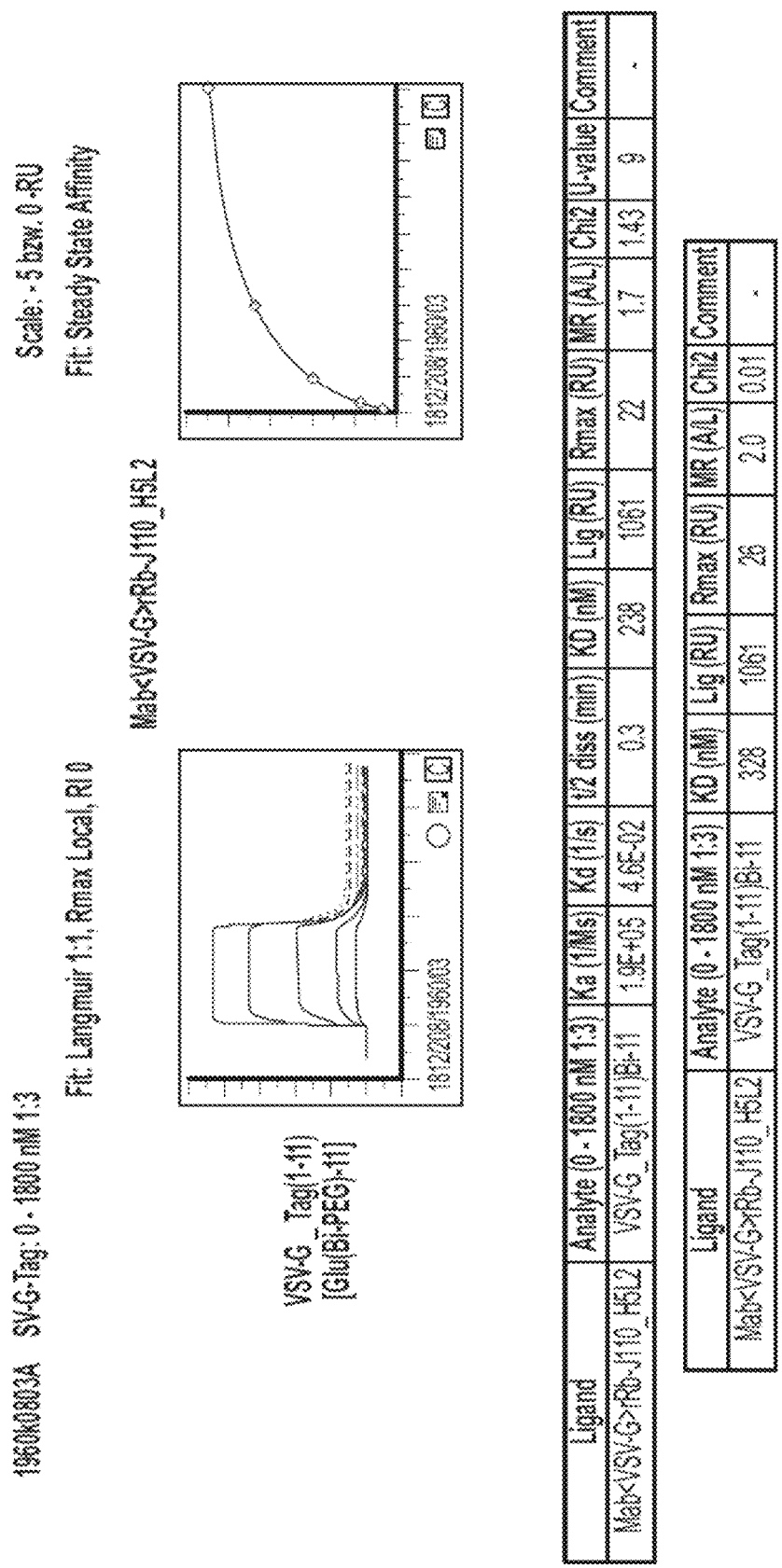
Figure 32A:
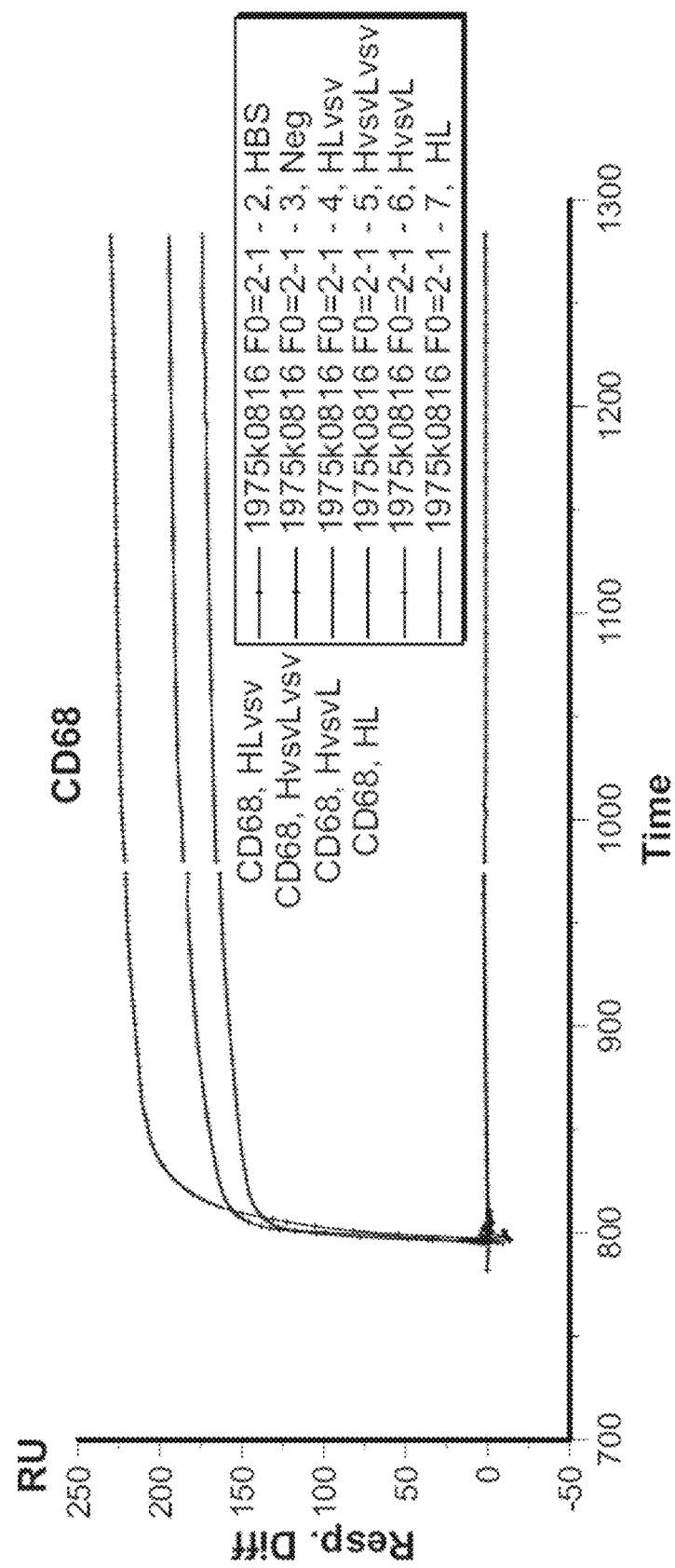
FIG. 32A, FIG. 32B, FIG. 32C, and FIG. 32D illustrate kinetic assessments of the binding behavior of rabbit monoclonal anti-tag antibodies towards the respective tagged antibody analytes: CD68 HLvsv, CD68 HvsvLvsv, CD68 HvsvL, CD68 HL (FIG. 32A); CD8 HL, CD8 He2L (FIG. 32B top); PD-L1 SP63 He2L, PD-L1 SP63 HLe2, PD-L1 SP63 He2Le2, PD-L1 SP63 HL (FIG. 32B bottom); CD20 HL, CD20 HhaL, CD20 HLha, CD20 HhaLha (FIG. 32C top); PD-L1 SP63 HhaL, PD-L1 SP63 HLha, PD-L1 SP63 HhaLha, PD-L1 SP63 HL (FIG. 32C bottom); FoxP3 HL, FoxP3 H5v5L, FoxP3 HL5v5, FoxP3 H5v5L5v5, FoxP3 H4v5L, FoxP3 HL4v5, FoxP3 H4v5L4v5 (FIG. 32D).
Figure 32B:
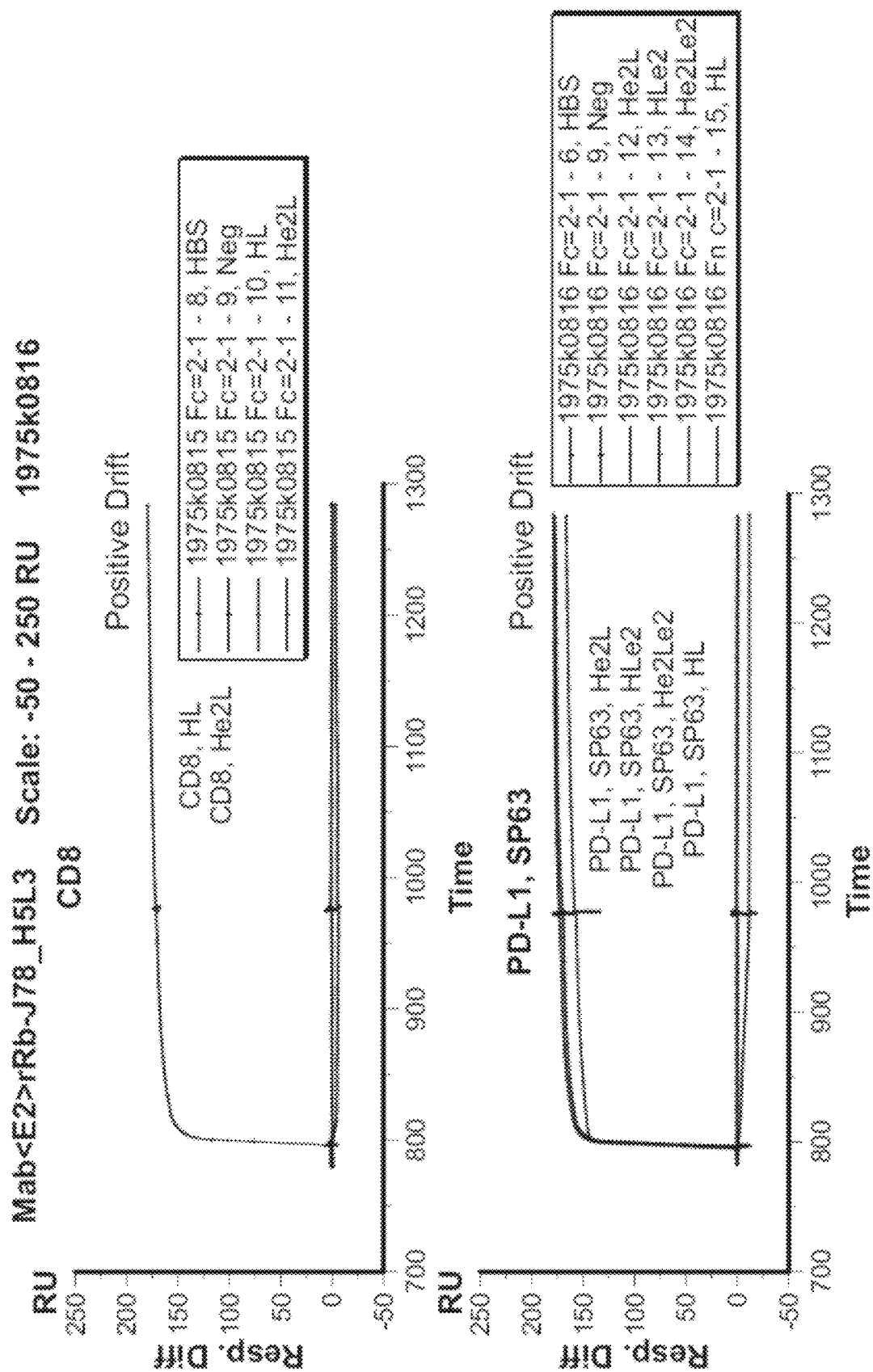
Figure 32C:
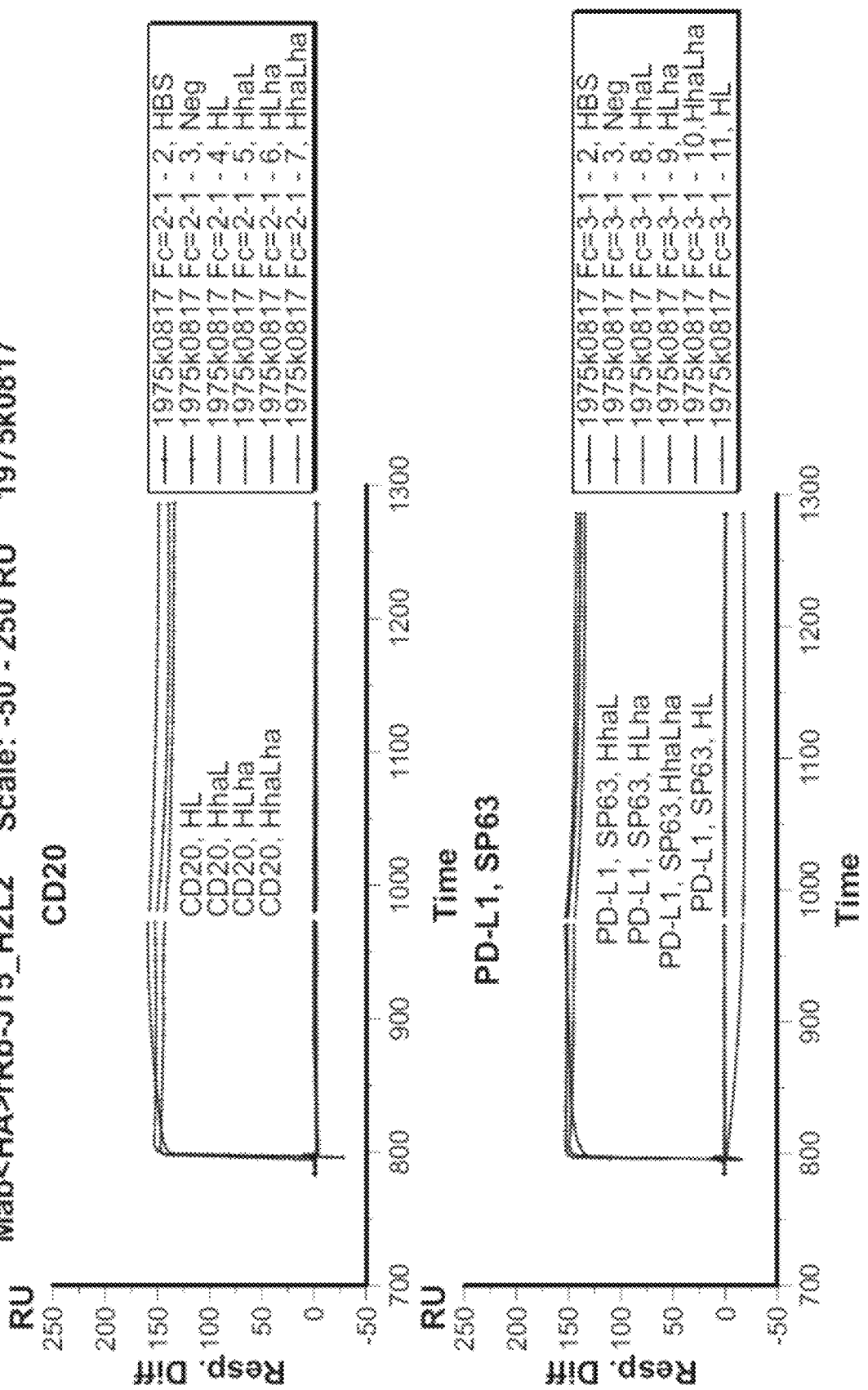
Figure 32D:
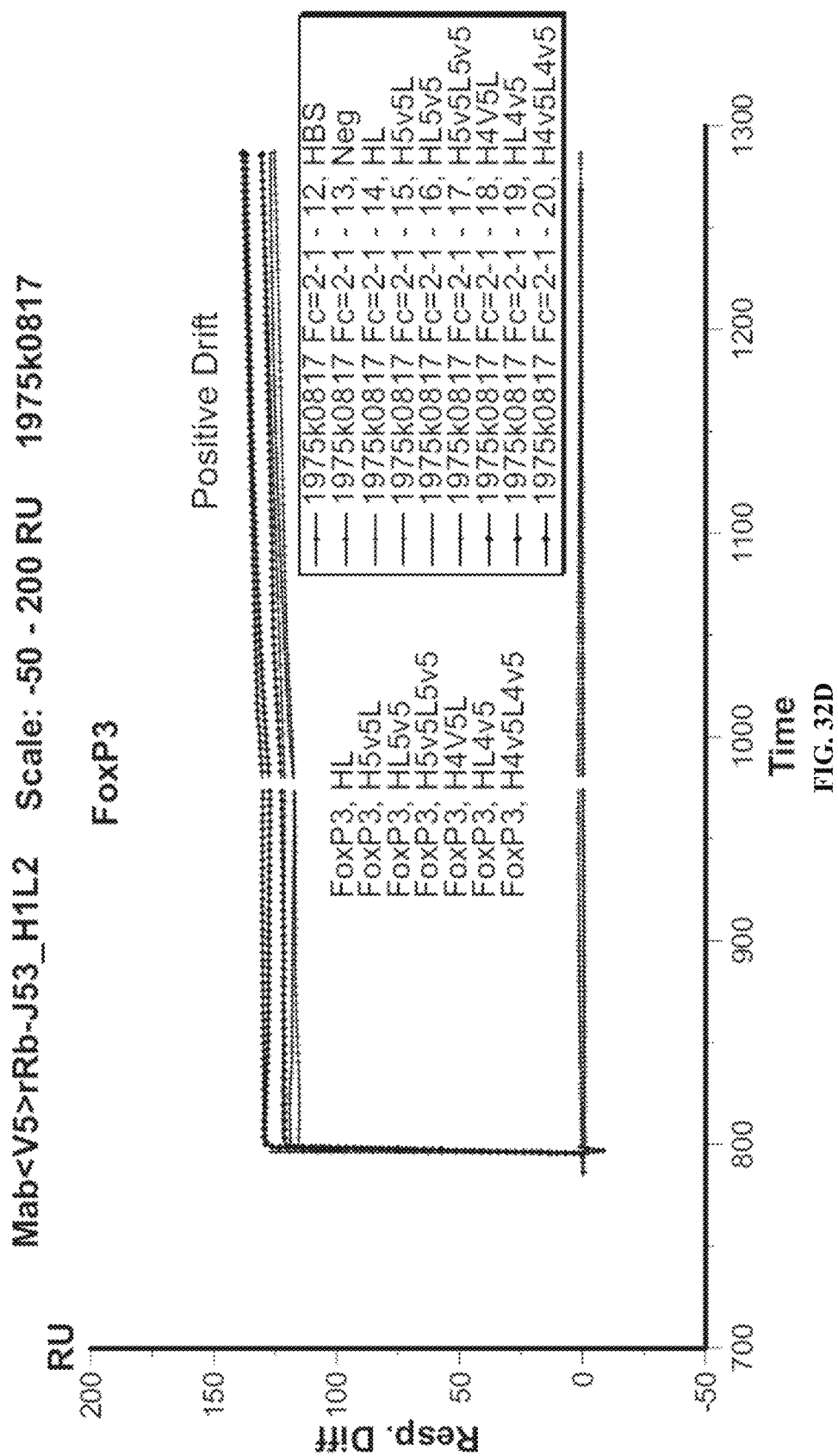

FIG. 31E illustrates the results of a SPR experiment in accordance with the method described above. In particular, FIG. 31E illustrates the difference in kinetics between Mab<VSV-G>rRb-J110_H5L2, where MR was up to about 2, therefore indicating about a 1:2 binding stoichiometry.

Association/Dissociation Rate Study

A Biacore T200 instrument (GE Healthcare) was used to kinetically assess the binding behavior of rabbit monoclonal antibodies towards the respective tagged antibody analytes: CD68 HLvsv, CD68 HvsvLvsv, CD68 HvsvL, CD68 HL; CD8 HL, CD8 He2L; PD-L1 SP63 He2L, PD-L1 SP63 HLe2, PD-L1 SP63 He2Le2, PD-L1 SP63 HL; CD20 HL, CD20 HhaL, CD20 HLha, CD20 HhaLha; PD-L1 SP63 HhaL, PD-L1 SP63 HLha, PD-L1 SP63 HhaLha, PD-L1 SP63 HL; FoxP3 HL, FoxP3 H5v5L, FoxP3 HL5v5, FoxP3 H5v5L5v5, FoxP3 H4v5L, FoxP3 HL4v5, FoxP3 H4v5L4v5.

The rabbit IgG (150 kDa) monoclonal antibodies mAb<E>rRb-J26_wt-IgG and mAb<E>rRb-J26_H2L5, mAb<E2>rRb-J78_wt-IgG and mAb<E2>rRb-J78_H5L3, mAb<V5>rRb-J53_wt-IgG and mAb<V5>rRb-J53_H1L2, mAb<HA>rRb-J15_H2L2, mAb<VSV-G>rRb-J110_H5L2, and Rb—N-IgG (rabbit normal IgG, Sigma) were investigated for their binding kinetics and binding stoichiometries. A CM5 series sensor was mounted into the system and was normalized in HBS-ET buffer (10 mM HEPES pH 7.4, 150 mM NaCl, 3 mM EDTA, 0.005% w/v Tween 20) according to the manufacturer's instructions. The sample buffer was the system buffer supplemented with 1 mg/ml CMD (Carboxymethyldextran, Sigma #86524). The system operated at 37° C. 13000 RU GARbFcγ (goat anti rabbit Fcγ), Code Nr.: 111-005-046, Jackson Immuno Research were immobilized according to the manufacturer's instructions using EDC/NHS chemistry on all four flow cells. The sensor was deactivated using 1M ethanolamine. The binding activities of the respective antibodies against the analytes were kinetically tested. Antibodies were captured at about a 30 nM concentration by a 2 min injection at 10 μl/min. The flow rate was set to 60 μl/min. Analytes were injected for 3 min at different concentration steps of 0 nM buffer control, 22 nM, 67 nM, 200 nM twice, 600 nM and 1800 nM. The dissociation was monitored for 5 min. After each analyte injection the antibody capture system was fully regenerated by a 1 min 25 sec injection of HBS-ET buffer at 20 μl/min, followed by a 1 min injection at 20 μl/min with 10 mM glycine buffer pH 1.5 and two injections for 1 min at 20 μl/min with 10 mM glycin pH 1.7. Where possible, kinetic signatures were evaluated according to a Langmuir fit with RMAX local. In cases, where the dissociation rate was not apparent a steady state algorithm was applied according to the manufacturer's evaluation software.

According to this study, Applicants have found that the epitope-tagged antibodies are all specifically bound by the anti-tag antibodies. As noted in FIGS. 32A through 32D, the association rates were rapid and the dissociation rates were either out of the instrument's specification range or were drifting positively. The kd (1/s) was therefore set to 1E-05 1/s.

When compared to the kinetics study noted above (see, for example, FIGS. 31A through 31E) it was apparent that the kinetics between the epitope-tagged antibodies and the anti-tag antibodies were avidity catalyzed. The epitope-tagged antibodies displayed two epitopes and mediated affinity. Therefore, a kinetic quantification would give avidity but not affinity. Applicants also found that the avidity factor could be calculated by comparing the data with from the kinetic studies set forth above. For example, as shown in FIG. 31A, Mab<V5>rRb-J53_H1L2 versus bi-14 tag (kd=2.4E-03 1/s) was at least 240-fold avidity catalyzed (2.4E-03 1/s/1E-05 1/s=240). Similarly, FIG. 31C indicates that Mab<E2>rRb-J78_H5L3 (kd=2.0E-02 1/s) was at least 2000-fold avidity catalyzed (2.0E-02 1/s/1E-05 1/s=2000).

Example 13—a Flexible and Versatile Toolbox for Parallel Multiplex Immunohistochemical Detection Using Recombinant Epitope-Tagged Antibodies and Monoclonal Anti-Tag Antibodies (See FIGS. 33A Through 33E)

Introduction

Contextual detection of multiple biomarkers on single formalin-fixed, paraffinembedded (FFPE) slides for clinical applications remains an unmet need. Current multiplex immunohistochemistry (IHC) procedures entail successive rounds of antibody application and fluorophore attachment followed by antibody inactivation. We have developed an automated and largely parallel multiplex IHC approach using series of epitope-tagged antibodies and anti-epitope antibodies conjugated to fluorophores, haptens, or enzymes, and demonstrated feasibility by 5-plex fluorescent and duplex brightfield assays of markers relevant for immuno-oncology.

Methods

DNA sequences corresponding to peptide epitope tags were fused in-frame to rabbit monoclonal antibody cDNAs for production of anti-CD3, CD8, CD68, FoxP3, and PDL1 antibodies in mammalian cells. Recombinant tagging bypasses the potential antibody inactivation associated with chemical-based tagging. Epitope-tagged primary antibodies produced identical diaminobenzidine (DAB) staining intensity and pattern as untagged native antibodies (data not shown). Conjugation of fluorophores or haptens to anti-tag or anti-hapten antibodies was performed using NHS ester precursors. Horseradish peroxidase (HRP) and alkaline phosphatase (AP) were conjugated to reduced antibodies via NHS-maleimide linkers. Affinity of antiepitope antibodies was assessed using biolayer interferometry. Automated IHC of FFPE tissue sections including tumor samples from non-small cell lung cancer (NSCLC) patients was performed on VENTANA BenchMark ULTRA platform.

Results

Figure 33A:
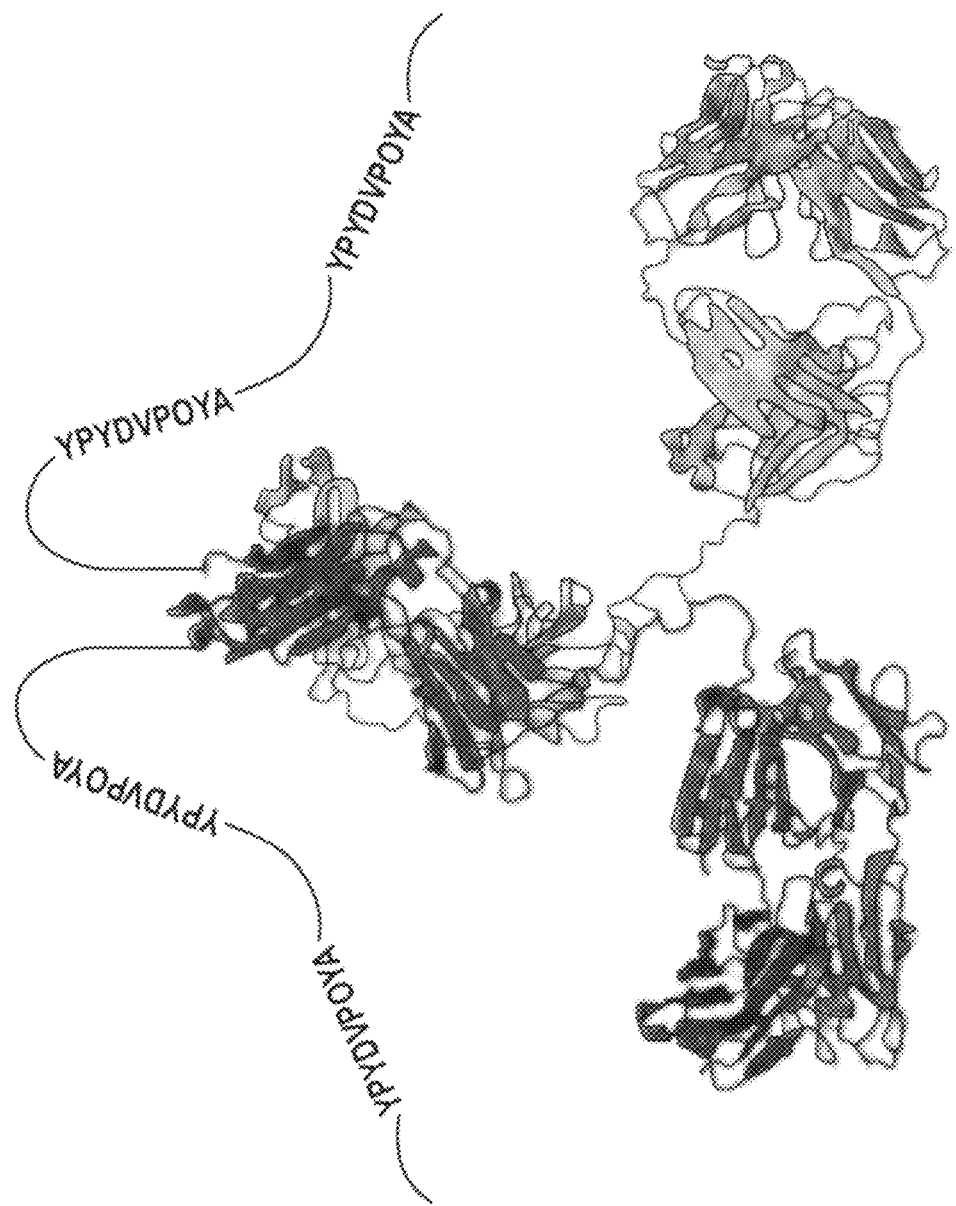
FIG. 33A (A) Schematic representation of recombinant epitope-tagged antibody and (B) detection strategy of 5-plex fluorescent multiplex detection without successive removal of serially deposited primary antibodies and anti-species antibody conjugates. In addition to enzyme-mediated fluorophore deposition, an additional signal amplification configuration involves using hapten-conjugated anti-tag and fluorophore-conjugated anti-hapten antibodies as described in (C).
Figure 33A:
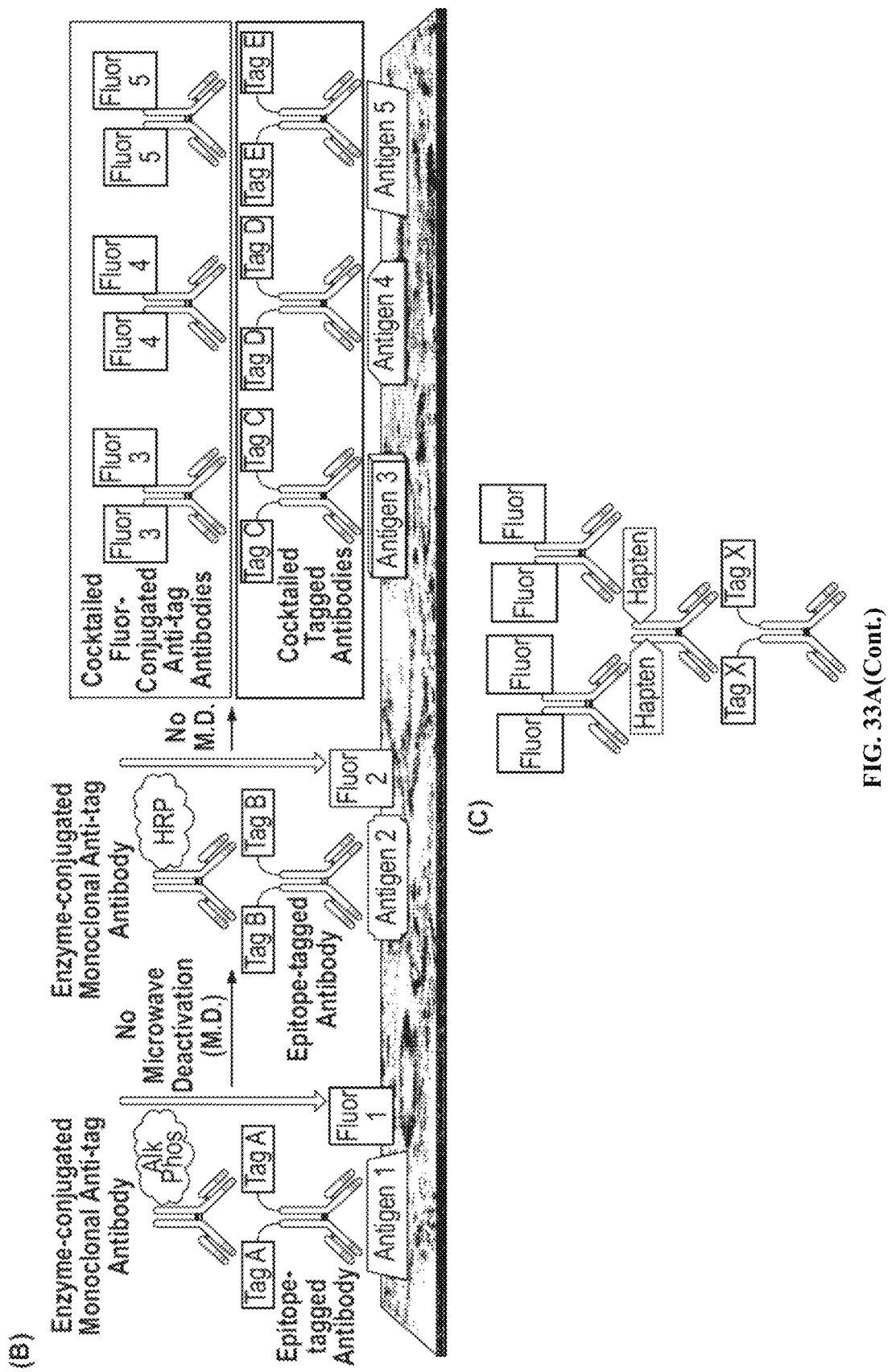
Figure 33B:
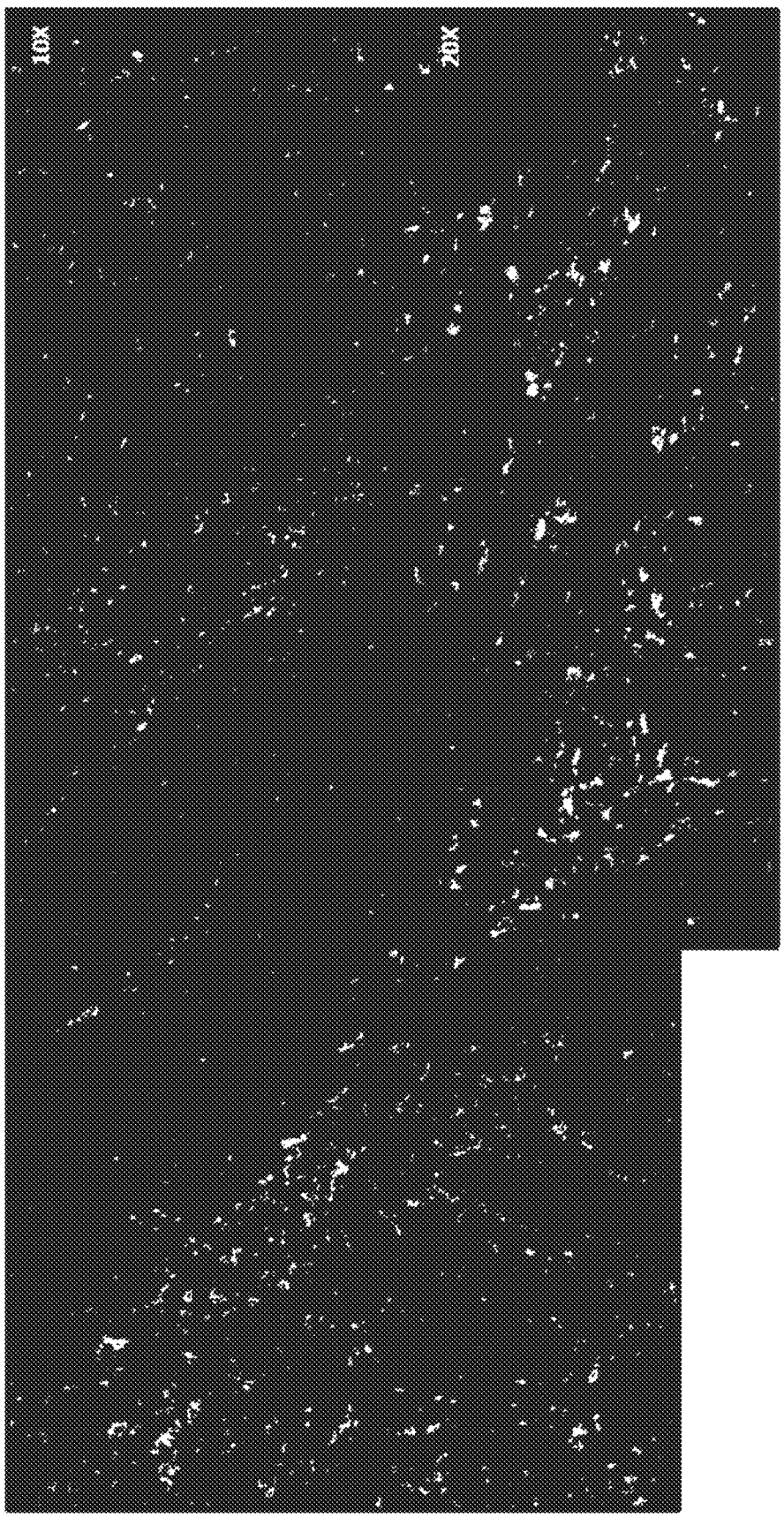
FIG. 33B provides a FFPE NSCLC section probed with epitope-tagged antibodies against PD-L1 (cyan), CD3 (gold), CD8 (green), FoxP3 (red), and CD68 (purple). The markers were detected by fluorophore-conjugated anti-tag antibodies and antibody-enzyme conjugate-mediated deposition of fluorophores onto tissue components as described in FIG. 1. Slides were scanned using Zeiss Axio Scan.Z1 equipped with six cube filters and visualized in Zen software following pseudo-coloring. Colors were assigned based on fluorophore emission wavelength in the color spectrum with exception of CD68. Cell nuclei were marked by DAPI stain (Blue). The salmon colored objects are red blood cells (RBC) that auto-fluoresce in multiple channels.
Figure 33C:
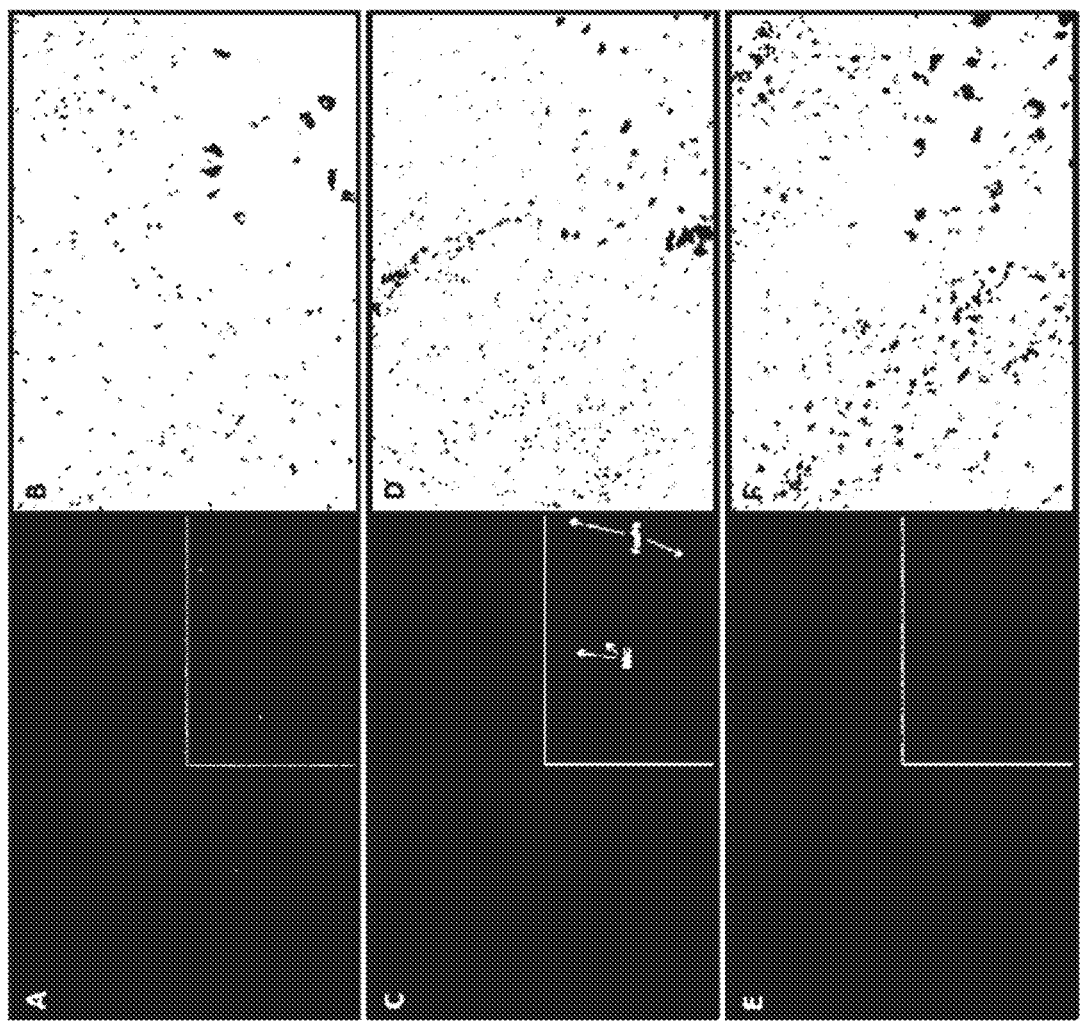
FIG. 33C provides FFPE lung tumor sections probed with (A) tagged and (B) native anti-CD8 antibodies, (C) tagged and (D) native anti-FoxP3 antibodies, and (E) tagged and (F) native anti-CD68 antibodies. The markers were detected using (A, C, and E) fluorophore-conjugated anti-tag antibodies or (B, D, and F) VENTANA ultraView Universal DAB Detection Kit. Fluorescently stained slides were co-stained with VENTANA DISCOVERY QD DAPI.
Figure 33D:
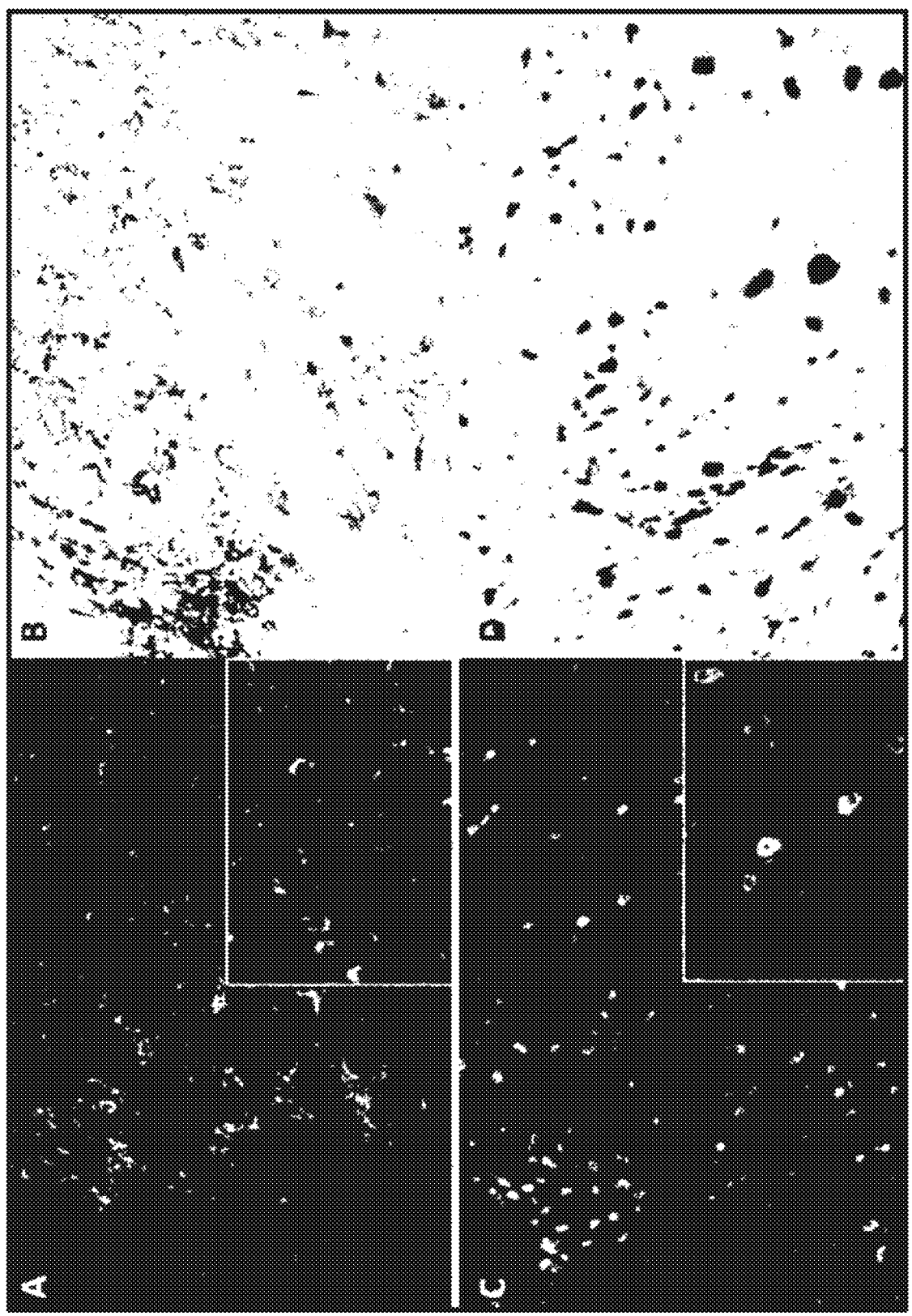
FIG. 33D provides a FFPE lung tumor sections probed with (A) tagged and (B) native anti-PD-L1 (SP263) antibodies or with (C) tagged and (D) native anti-CD3 antibodies. The markers were detected using (A and C) enzyme-conjugated anti-tag antibodies and QM- and TSA-fluor deposition, (B) VENTANA OptiView DAB IHC, or (D) VENTANA ultraView Universal DAB detection kits.
Figure 33E:
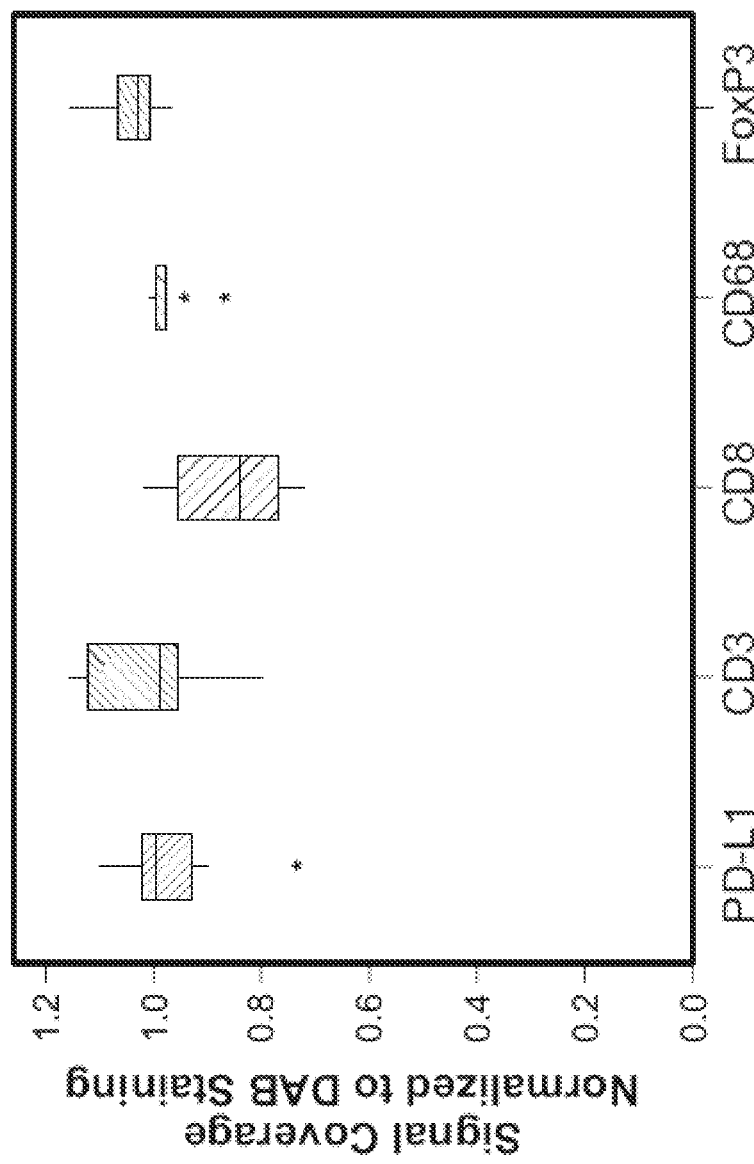
FIG. 33E provides a boxplot of 10 NSCLC cases showing coverage of each marker stained using 5-plex fluorescent assay compared against DAB. The markers were detected as described in FIGS. 33A through 33D. Scanned fluorescent and DAB whole slide images were evaluated by pathologist after brightness adjustment and without further processing. The few cases that exhibited discordance between PD-L1 and CD8 fluorescence and DAB staining had unusually high autofluorescence associated with extensive connective tissue in the lung. Connective autofluorescence could be removed digitally using signal unmixing procedures.

Multiple clones of rabbit monoclonal antibodies against each of the five epitope tags were conjugated and screened for retention of affinity, stability, and appropriate staining intensity and pattern. At least one clone of each anti-epitope antibody met the functional requirements and these were used to stain FFPE lung sections in conjunction with cocktailed epitope-tagged antibodies. Epitope-tagged antibodies were detected using one of three detection configurations in order of sensitivity: 1) fluor-conjugated anti-epitope antibodies, 2) hapten-conjugated anti-tag antibodies and fluor-conjugated anti-hapten antibodies, and 3) attachment of tyramide- or quinone methide-fluors to tissue specimens with HRP- or AP-conjugated antiepitope antibodies (FIG. 33A). Titration of antibodies and assay optimization enabled pairings of particular biomarkers with detection configurations to generate specific fluorescence patterns and relative intensities comparable to those produced by DAB stains using untagged antibodies and HRP-conjugated anti-species antibodies (FIGS. 33B through 33E). Two-color brightfield stains were generated using enzyme-conjugated anti-tag antibodies and HRP- and AP-activated chromogens (data not shown).

Conclusion

We have demonstrated feasibility of automated parallel multiplex IHC using a series of epitope-tagged antibodies and fluor-, hapten-, or enzyme-conjugated anti-tag antibodies. The approach has following advantages: Streamlining workflow—applying tagged antibodies and anti-tag antibody probes as cocktails significantly shortens assay time. Flexibility and versatility—a library of haptens, epitope tags, fluorophores, and enzymes can be matched to properly detect low and high abundance markers (e.g. pairing low abundance markers with the more sensitive enzyme-mediated fluor deposition) and accommodate increasing numbers of biomarkers beyond 5-plex. Epitope preservation—unlike approaches based on serially applied antibodies, using tagged and anti-tag antibodies avoids the damaging effects of multiple cycles of antibody inactivation on tissue integrity.

Example 14—Biochemical Analysis of Binding Stoichiometry Between Peptide Epitope-Tagged Antibody and Anti-Epitope Tag Antibody This study was initiated to determine the stoichiometry of anti-tag secondary antibodies binding to tagged primary antibodies. This information was useful in understanding the sensitivity and degree of signal amplification afforded by the use of fluorophore- or enzyme-conjugated anti-tag antibodies for detection of tagged primary antibodies. Anti-tag antibodies were incubated with antibodies tagged at C-termini of immunoglobulin heavy chains (IgH) with 4 to 5 tandem peptide epitope tags separated by hydrophilic spacer segments at increasing molar ratios from 0.5:1 to 8:1. The bound complexes were separated from unbound antibodies using size exclusion chromatography. For primary antibodies with 4 tandem peptide epitope tags per IgH, no unbound anti-tag antibodies were observed until a molar ratio of 6 anti-tag antibodies to 1 tagged antibody was reached. For the anti-FoxP3 antibody with 5 V5 epitope tags per IgH, no unbound anti-V5 antibodies were observed until a molar ratio of 8 anti-tag antibodies to 1 tagged antibody was reached. The data indicated that at least 4 anti-tag immunoglobulins (IgGs) could stably associate with each IgG with 4 peptide epitope tags per IgH (8 tags per entire IgG). Coupled with the surface plasmon resonance (SPR) results, which showed that anti-tag antibodies have significantly higher affinity for tagged antibodies than free and non-tandem tag peptides, the current study provided compelling evidence that the specific tandem arrangement of peptide epitope tags and spacers found in the tagged primary antibodies disclosed herein could adopt a spatial conformation that mediates strong bivalent binding of multiple anti-tag antibodies with no steric hindrance.

To understand the biochemical basis driving the sensitivity of the technology as well as its limitations, it was important to characterize how tagged antibodies interacted with anti-tag antibodies. Previous SPR experiments have shown tighter binding between anti-tag and tagged antibodies than between anti-tag antibodies and free peptides, suggesting avidity-mediated binding between anti-tag and tagged antibodies. However, these studies did not reveal the number of anti-tag antibodies that could become bound to each tagged antibody, and thus fell short of providing a definitive answer regarding valency of anti-tag antibody binding to tagged antibody. As shown in FIGS. 32A-32D, the anti-tag antibodies bound tagged antibodies with rapid association kinetics and dissociation was non-existent or too slow for an instrument to measure reliably. Such tight binding enabled size exclusion chromatography (SEC) to be used for separation of stable tagged and anti-tag antibody complexes from free tagged antibodies or free anti-tag antibodies. The objective of this study was to determine how many fold excess anti-tag antibodies could engage tagged antibodies in stable complexes until no additional anti-tag antibodies could bind and elute as free antibodies in SEC. It was believed that the stoichiometry of binding between anti-tag and tagged antibodies could address the valency question more definitively. In addition, this information offered insight into the degree of signal amplification that anti-tag antibodies could provide as detection reagents.

MATERIALS

The following peptide epitope-tagged antibodies dissolved in PBS were produced and purified by Protein A resin at Spring Bioscience (see Table 17):

TABLE 17

| Tagged Antibody | Peptide Tag | Tag Configuration* |
|---|---|---|
| xCD8(SP239) | E2 | H4K0 |
| xFoxP3(SP97) | V5 | H5K0 |
| xFoxP3(SP97) | V5 | H4K0 |
| xPDL1(SP263) | E2 | H4K0 |
| xCD3(SP162) | E | H4K0 |
| xCD8(SP239) | AU5 | H4K0 |
| xCD68(SP251) | VSV-G | H4K0 |

*Letters in tag configuration referred to Ig heavy (H) or kappa light (K) chain while numbers following the letters referred to number of tandem tag repeats fused to the C-terminus of heavy or light chains. For example, H4K0 referred to 4 tandem tag repeats on the heavy chain with no tags on the light chain.

The following anti-tag antibodies dissolved in PBS were produced and purified by Protein A resin at Spring Bioscience (see Table 18):

TABLE 18

| Anti-Tag Antibody |
|---|
| XE2 J78_H5L3 |
| xV5 J53_H1L2 |
| xVSV-G |
| J110_H5L2 |
| xE J26_H2L5 |
| XE2 J78_H5L3 |
| xV5 J53_H1L2 |
| xAU5 J66_H3L1 |

EQUIPMENT—AKTA Explorer FPLC (asset tag XX, no calibration required); Superose 6 Increase 10/300 GL size exclusion column; Hybridization oven (asset tag XX, no calibration required).

Anti-tag antibodies were incubated with tagged antibodies in about 0.75×PBS and about 0.25×Reaction Buffer (RB, P/N 950-300) for about 30 min at about 37° C. prior to sample loading. Reaction mixture volume was about 0.1 mL and entire samples were loaded. Concentration of tagged antibodies was kept constant at about 0.5 µM while concentrations of anti-tag antibodies varied from about 0.25 µM to about 4 µM to achieve molar anti-tag to tagged antibody ratios of about 0.5:1, about 1:1, about 2:1, about 4:1, about 6:1, and when necessary about 8:1. As controls, anti-tag or tagged antibodies at about 0.5 µM in about 0.75×PBS and about 0.25× RB were separately prepared, incubated for about 30 min at about 37° C., and loaded. Fractionation in Superose 6 column was performed at ambient room temperature. Protein elution was monitored using UV absorbance at about 210, about 230, and about 280 nm.

STATISTICAL ANALYSES—It was believed that there was no need for statistical analyses in the execution of this study.

Peptide epitope-tagged antibodies were incubated with anti-tag antibodies at varying molar ratios to determine stoichiometry of binding between them. In general, as molar ratios of tagged antibodies to anti-tag antibodies increased from 0.5:1 to 6:1, increasingly larger antibody complexes with SEC elution volumes between 13.5 and 12 mLs were observed (FIGS. 34A through 34G). For all of the tag and anti-tag pairs tested (V5, E2, E, VSV-G, and AU5) in which 4 tandem tags and spacer segments were fused to the C-termini of each heavy chain, no free anti-tag antibodies were observed at anti-tag:tagged antibody molar ratios of 4:1 or less (FIGS. 34A through 34F). Free anti-tag antibodies became visible only at molar ratios of 6:1 (FIGS. 34A through 34F). These results indicate that the highest stoichiometry of stable binding was approximately 4 anti-tag antibodies per tagged antibody containing a total of 8 peptide tags (4 tags and spacers per heavy chain) regardless of the amino acid sequence of the peptide epitope tags. When considered together with data showing stronger interaction between anti-tag and tagged antibodies than between anti-tag antibodies and free peptide tags (see FIGS. 32A-32D), these results suggested that each anti-tag antibody could interact with a tagged antibody in a bivalent fashion by binding 2 peptide tags.

Figure 34B:
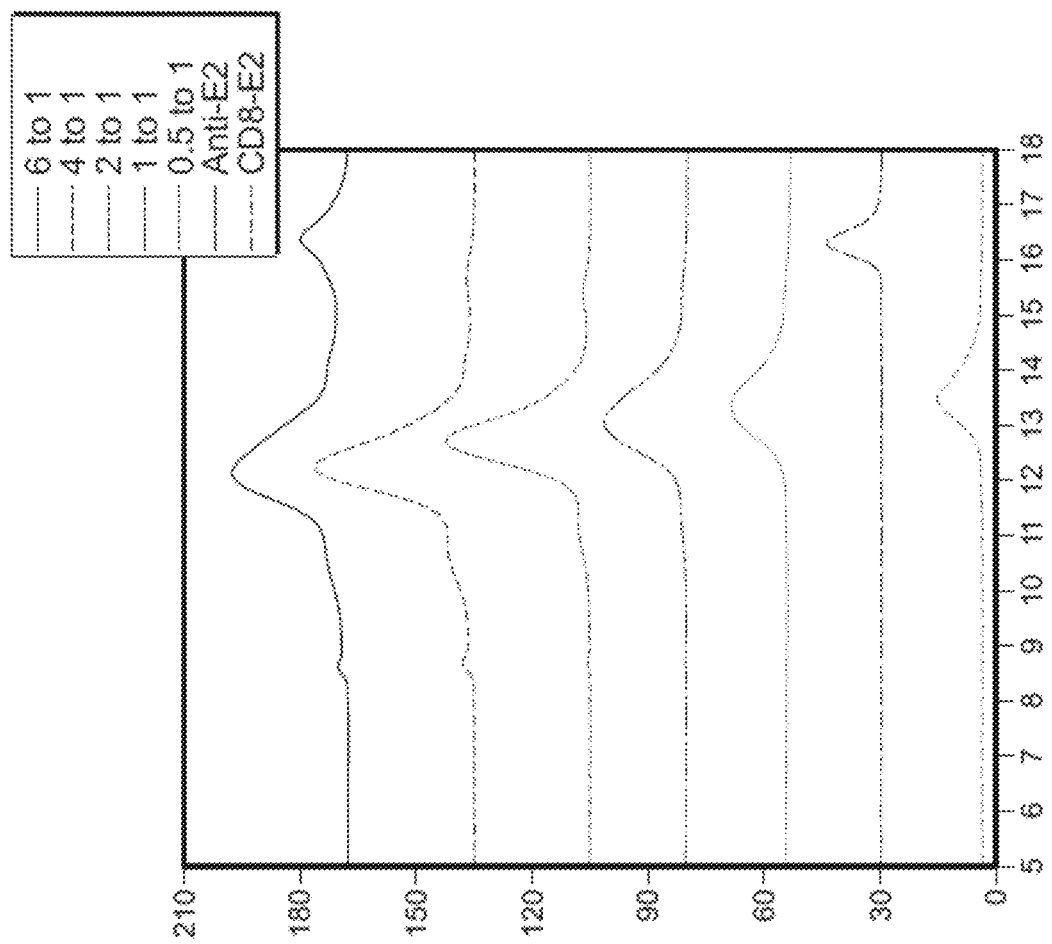
FIG. 34B sets forth size exclusion chromatography elution profiles of 0.5 µM anti-CD8-E2 (H4K0), 0.5 µM anti-E2, and anti-E2 mixed with 0.5 µM anti-CD8-E2 at varying molar ratios from 0.5:1 to 6:1.
Figure 34C:
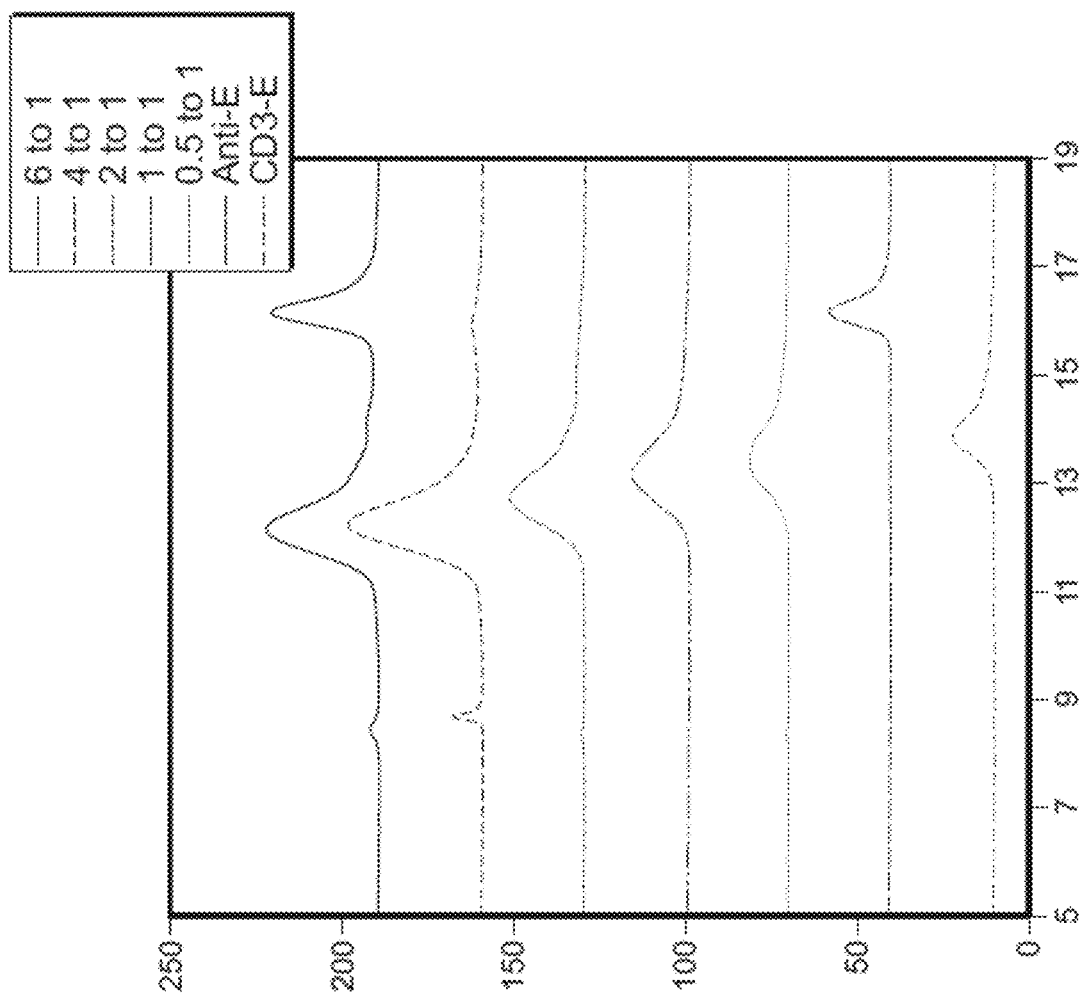
FIG. 34C sets forth size exclusion chromatography elution profiles of 0.5 µM anti-CD3-E (H4K0), 0.5 µM anti-E, and anti-E mixed with 0.5 µM anti-CD3-E at varying molar ratios from 0.5:1 to 6:1.
Figure 34D:
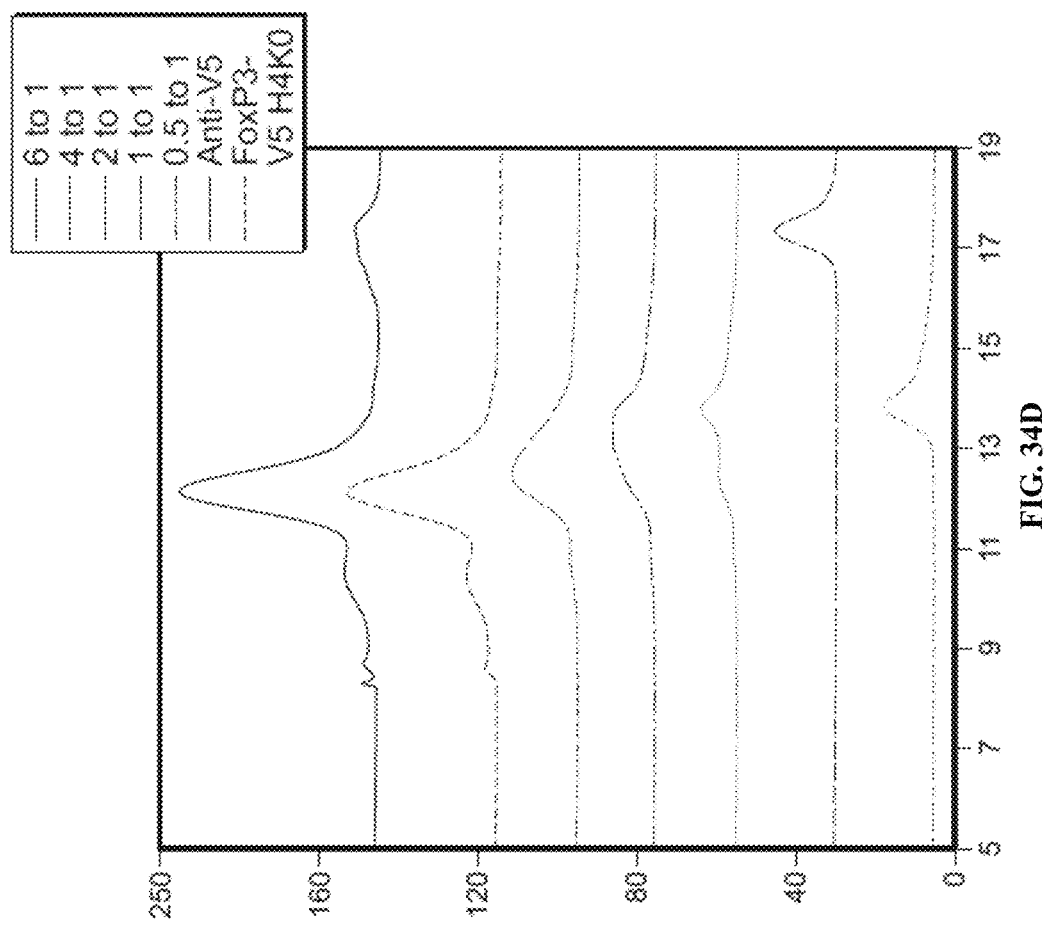
FIG. 34D sets forth size exclusion chromatography elution profiles of 0.5 µM anti-FoxP3-V5 (H4K0), 0.5 µM anti-V5, and anti-V5 mixed with 0.5 µM anti-FoxP3-V5 at varying molar ratios from 0.5:1 to 6:1.
Figure 34E:
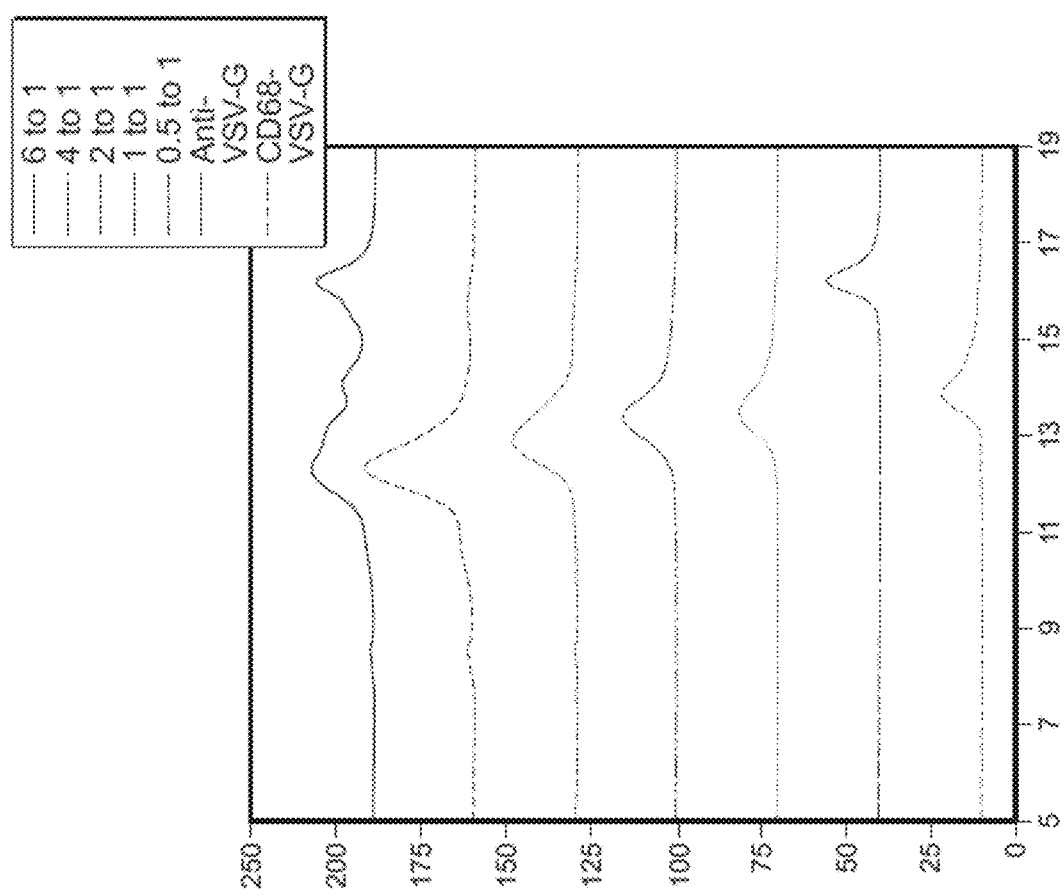
FIG. 34E sets forth size exclusion chromatography elution profiles of 0.5 µM anti-CD68-VSV-G (H4K0), 0.5 µM anti-VSV-G, and anti-VSV-G mixed with 0.5 µM anti-C68-VSV-G at varying molar ratios from 0.5:1 to 6:1.
Figure 34F:
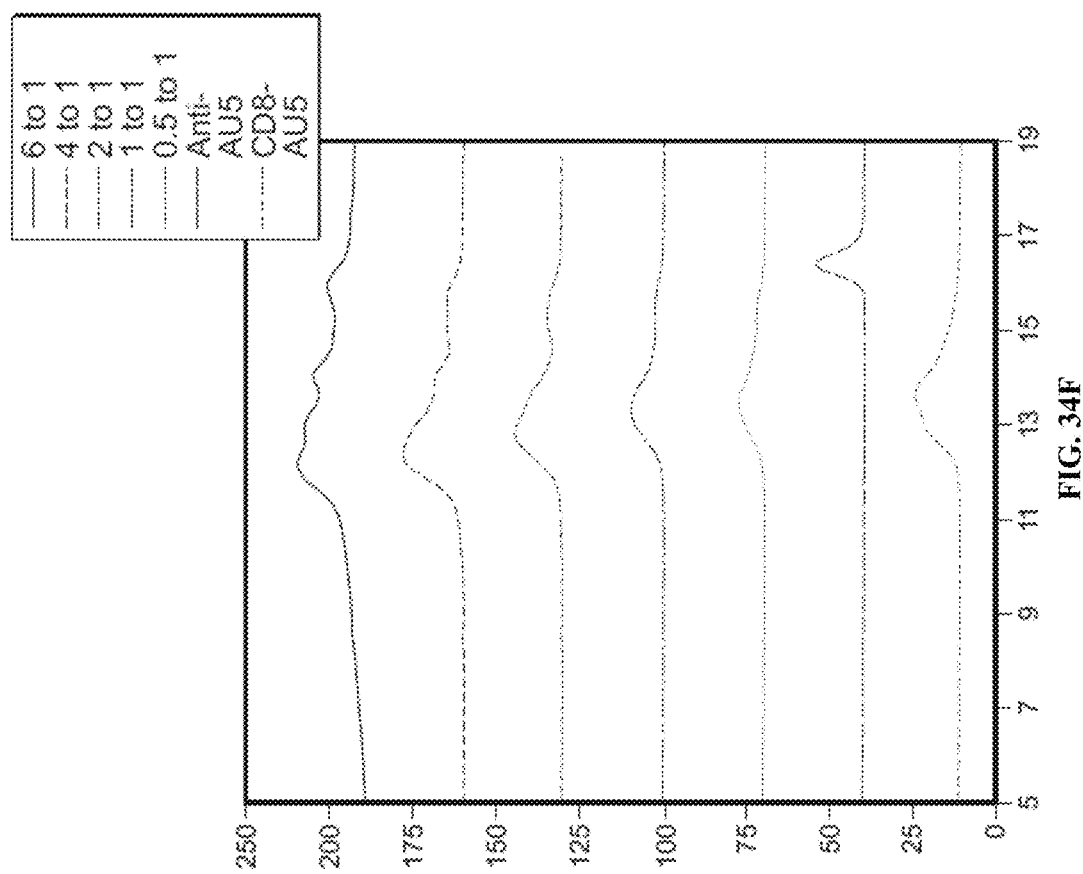
FIG. 34F sets forth size exclusion chromatography elution profiles of 0.5 µM anti-CD8-AU5 (H4K0), 0.5 µM anti-AU5, and anti-AU5 mixed with 0.5 µM anti-CD8-AU5 at varying molar ratios from 0.5:1 to 6:1.
Figure 34G:
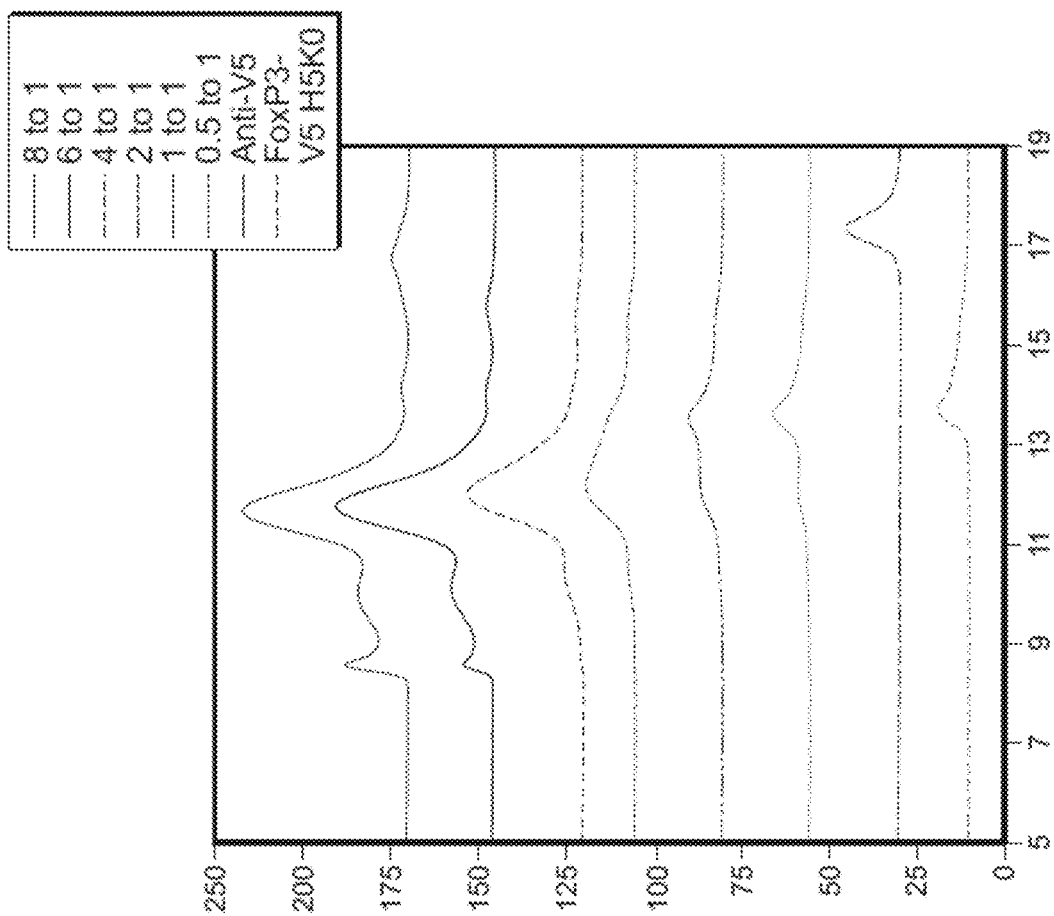
FIG. 34G sets forth size exclusion chromatography elution profiles of 0.5 µM anti-FoxP3-V5 (H5K0), 0.5 µM anti-V5, and anti-V5 mixed with 0.5 µM anti-FoxP3-V5 at varying molar ratios from 0.5:1 to 8:1.

At 6:1 molar ratios of anti-VSV-G to CD68-VSV-G and anti-AU5 to CD8-AU5, significant amounts of slower-eluting peaks were observed that trailed the peaks corresponding to the largest protein complexes were observed (FIGS. 34F and 34G). These slower-eluting peaks likely represented complexes that consisted of less than 4 anti-tag antibodies per tagged antibody. The fact that these smaller complexes were observed only at high ratios of anti-tag antibodies to tagged antibodies was consistent with competition among anti-tag antibodies for limited number of epitope tags resulting in weaker monovalent interaction between tagged and anti-tag antibodies.

For tagged antibody with 5 tandem tags and spacers, no free anti-tag antibodies were observed until molar ratios of anti-tag antibody to tagged antibody reached 8:1 (FIG. 34G). In addition, unlike binding between anti-tag antibodies and tagged antibodies with 4 tags per IgH (H4K0) in which the complexes consisted of one predominant peak (FIGS. 34A through 34D for E, E2, and V5 tags) or several minor peaks that trailed the major peak (FIGS. 34F and 34G for VSV-G and AU5 tags), that between anti-V5 and anti-FoxP3-V5 with 5 tags per IgH (H5K0) resulted in at least two complexes that were significantly larger than the major complex that eluted at 11.7 mL (FIG. 34G). It is believed that the peak at 8.5 mL could have represented more than one species of protein complexes as it corresponded to the void volume of the Superose 6 Increase column. These results suggested that while the most stable complex between anti-V5 and H5K0-tagged anti-FoxP3-V5 antibodies consisted of 5 to 6 anti-tag antibodies per tagged antibody, even larger complexes were able to form. It is possible the larger complexes could only form between V5-tagged antibody and anti-V5 antibody clone J53_H1L2 because the affinity of this particular antibody clone for its cognate tag was the highest of all anti-tag antibodies (see FIGS. 31A-31E). The high affinity of J53_H1L2 for the V5 tag could mediate stable monovalent binding or cross-linking of two V5-tagged antibodies.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

Although the disclosure herein has been described with reference to particular embodiments, it is to be understood that these embodiments are merely illustrative of the principles and applications of the present disclosure. It is therefore understood that numerous modifications may be made to the illustrative embodiments and that other arrangements may be devised without departing from the spirit and scope of the present disclosure as defined by the appended claims.

The invention claimed is:

1. A multiplex immunohistochemical method for detecting a plurality of targets in a sample, wherein the method comprises the steps of:
   (a) simultaneously contacting the sample with:
      (a1) a first epitope-tagged primary antibody, wherein the first epitope-tagged primary antibody comprises:
         (i) a first antibody specific to a first target, and
         (ii) at least a first epitope tag construct, wherein the first epitope tag construct comprises alternating spacers and a first epitope tag; and
      (a2) a second epitope-tagged primary antibody, wherein the second epitope-tagged primary antibody comprises:
         (i) a second antibody specific to a second target that is different from the first target and wherein the first antibody and the second antibody are same-species antibodies; and
         (ii) at least a second epitope tag construct, wherein the second epitope tag construct comprises alternating spacers and a second epitope tag, and wherein the second epitope tag is different from the first epitope tag; and
   (b) contacting the sample with a first set of detection reagents for detecting binding of the first epitope-tagged primary antibody to the sample, wherein the first set of detection reagents comprises a first anti-tag antibody, wherein the first anti-tag antibody is specific for the first epitope tag; and
   (c) contacting the sample with a second set of detection reagents for detecting binding of the second epitope-tagged primary antibody to the sample, wherein the set of detection reagents comprises a second anti-tag antibody, wherein the second anti-tag antibody is specific for the second epitope tag.

2. The method of claim 1, wherein the sample is simultaneously contacted with the first and second anti-tag antibodies.

3. The method of claim 1, wherein the first epitope-tagged primary antibody and the second epitope-tagged prim ay antibody are applied as a first mixture; and wherein the first and second anti-tag antibodies are applied as a second mixture.

4. The method of claim 1, wherein the epitope tag construct has the structure (-[Spacer]-[Epitope Tag]-), wherein the structure is repeated from 1 to 12 times.

5. The method of claim 1 or 4, wherein the method further comprises the steps of:
   (d) contacting the sample with a third primary antibody specific to a third target; and
   (e) contacting the sample with a third set of detection reagents for detecting binding of the third primary antibody to the sample, wherein the third set of detection reagents comprises an antibody specific for the third antibody.

6. The method of claim 5, wherein the third primary antibody is a third epitope-tagged antibody, wherein the third epitope-tagged primary antibody comprises:
   (i) a third antibody specific to the third target, and
   (ii) a third epitope tag construct, wherein the third epitope tag construct comprises at least 2 repeats of a third epitope tag, wherein the repeats of the third epitope tag are separated by a spacer; and wherein the antibody specific for the third antibody is a third anti-tag antibody, wherein the third anti-tag antibody is specific for the third epitope tag.

7. The method of claim 6, wherein the sample is simultaneously contacted with the first epitope-tagged primary antibody, the second epitope-tagged primary antibody, and the third epitope-tagged primary antibody.

8. The method of claim 7, wherein the sample is simultaneously contacted with the anti-tag antibodies.

9. The method of claim 8, wherein the first epitope-tagged primary antibody, the second epitope-tagged primary antibody, and the third primary antibody are applied as a first mixture; and wherein the anti-tag antibodies are applied as a second mixture.

10. The method of claim 5, wherein the third primary antibody does not comprise an epitope tag and has a species that is different from the first antibody and the second antibody, and wherein the antibody specific for the third antibody is an anti-species secondary antibody.

11. The method of claim 1, wherein the first epitope tag construct is expressed at a C-terminus of a heavy chain of the first antibody; and the second epitope tag construct is expressed at a C-terminus of a heavy chain of the second antibody.

12. The method of claim 11, wherein:
the first epitope-tagged antibody further comprises the first epitope tag construct expressed at a C-terminus of a light chain of the first antibody; and
the second antibody further comprises the second epitope tag construct expressed at a C-terminus of the light chain.

13. The method of claim 11, wherein:
the first epitope tag construct comprises at least 2 epitope tags; and
the second epitope tag construct comprises at least 2 epitope tags.

14. The method of claim 13, wherein:
the first epitope-tagged antibody has a configuration selected from the group consisting of H2K0, H3K0, H4K0, H5K0, H2K2, H3K3, and H4K4; and
the second epitope-tagged antibody has a configuration selected from the group consisting of H2K0, H3K0, H4K0, H5K0, H2K2, H3K3, and H4K4.

15. The method of claim 1, wherein the first epitope tag construct is expressed at a C-terminus of a light chain of the first antibody; and the second epitope tag construct is expressed at a C-terminus of a light chain of the second antibody.

16. The method of claim 15, wherein the first epitope-tagged antibody has a configuration H0K4; and the second epitope-tagged antibody has a configuration H0K4.

* * * * *

SEQUENCE LISTING

```
<160> NUMBER OF SEQ ID NOS: 32

<210> SEQ ID NO 1
<211> LENGTH: 11
<212> TYPE: PRT
<213> ORGANISM: Artificial Sequence
<220> FEATURE:
<223> OTHER INFORMATION: Synthetic:  VSV Epitope tag

<400> SEQUENCE: 1

Tyr Thr Asp Ile Glu Met Asn Arg Leu Gly Lys
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic:  AU5 Epitope tag

<400> SEQUENCE: 2

Thr Asp Phe Tyr Leu Lys
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetic:  E Epitope tag

<400> SEQUENCE: 3

Gly Ala Pro Val Pro Tyr Pro Asp Pro Leu Glu Pro Arg
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic:  V5 Epitope tag

<400> SEQUENCE: 4

Gly Lys Pro Ile Pro Asn Pro Leu Leu Gly Leu Asp Ser Thr
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic:  HA Epitope tag

<400> SEQUENCE: 5

Tyr Pro Tyr Asp Val Pro Asp Tyr Ala
1               5

<210> SEQ ID NO 6
<211> LENGTH: 12
```

```
<212> TYPE: PRT
<213> ORGANISM: Artificial Sequence
<220> FEATURE:
<223> OTHER INFORMATION: Synthetic: E2 Epitope tag

<400> SEQUENCE: 6

Gly Val Ser Ser Thr Ser Ser Asp Phe Arg Asp Arg
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic: KT3 Epitope tag

<400> SEQUENCE: 7

Lys Pro Pro Thr Pro Pro Pro Glu Pro Glu Thr
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Synthetic: AU1 Epitope tag

<400> SEQUENCE: 8

Asp Thr Tyr Arg Tyr Ile
1               5

<210> SEQ ID NO 9
<211> LENGTH: 14
<212> TYPE: PRT
<213> ORGANISM: Artificial Sequence
<220> FEATURE:
<223> OTHER INFORMATION: Synthetic: OLLAS Epitope tag

<400> SEQUENCE: 9

Ser Gly Phe Ala Asn Glu Leu Gly Pro Arg Leu Met Gly Lys
1               5                   10

<210> SEQ ID NO 10
<211> LENGTH: 31
<212> TYPE: PRT
<213> ORGANISM: Artificial Sequence
<220> FEATURE:
<223> OTHER INFORMATION: Synthetic: Repeated portion of AA sequence of
      spacer

<400> SEQUENCE: 10

Gly Arg Ser Ser Gly Gln Pro Lys Ala Pro Ser Val Pro Asn Ser Ala
1               5                   10                  15

Ser His Ser Gly Ser Ala Pro Asn Thr Ser Ser Ala Pro Gly Ser
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic: Repeated portion of AA sequence of
      spacer

<400> SEQUENCE: 11

Ser Ala Ser Ser Gly Gln Pro Lys Ala Pro Ser Val Pro Asn Ser Ala
1               5                   10                  15
```

Ser His Ser Gly Ser Ala Pro Asn Thr Ser Ser Ala Pro Gly Ser
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic: Repeated portion of AA sequence of
      spacer

<400> SEQUENCE: 12

Ser Arg Ser Val Gly Gln Pro Lys Ala Pro Ser Val Pro Asn Ser Ala
1               5                   10                  15

Ser His Ser Gly Ser Ala Pro Asn Thr Ser Ser Ala Pro Gly Ser
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Synthetic: Repeated portion of AA sequence of
      spacer

<400> SEQUENCE: 13

Asp Ile Ser Ser Gly Gln Pro Lys Ala Pro Ser Val Pro Asn Ser Ala
1               5                   10                  15

Ser His Ser Gly Ser Ala Pro Asn Thr Ser Ser Ala Pro Gly Ser
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Synthetic: Repeated portion of AA sequence of
      spacer

<400> SEQUENCE: 14

Gly Ala Ser Ser Gly Gln Pro Lys Ala Pro Ser Val Pro Asn Ser Ala
1               5                   10                  15

Ser His Ser Gly Ser Ala Pro Asn Thr Ser Ser Ala Pro Gly Ser
            20                  25                  30

<210> SEQ ID NO 15
<211> LENGTH: 631
<212> TYPE: DNA
<213> ORGANISM: Artificial Sequence
<220> FEATURE:
<223> OTHER INFORMATION: Synthetic: 4 VSV nucleic acid sequence

<400> SEQUENCE: 15
agcggccgca gcagtggaca accaaaagca ccatcagtac cgaactccgc ctcgcactct     60
ggcagcgcgc ctaatacaag ttcagctccg ggtcctata ctgatattga atgaatcgg     120 cttggcaaaa gcgcttctag cggccagcct aaagctccga gtgtccccaa ttcagcgtcc    180
cattcggggt ctgccccaaa cacgtcgtcc gcacccggtt catacaccga catcgagatg    240
aaccgcctcg ggaagtcgcg aagcgttgga caaccgaaag caccctcggt gccaaactcc    300
gcatcacata gtggcagcgc ccccaataca agttcagcgc cagggtccta tacagatatt    360
gaaatgaata gactgggaaa agatatctct agcgggcagc ctaaggctcc ctcagttccc    420

```
aactctgctt cccactcggg gtctgcgcca aataccctcta gcgccctgg ctcttacaca    480 gacattgaga tgaatcggct tggcaagggc gccagtagcg ccaacctaa agcaccttca     540 gtgccaaatt ccgcatcgca ttctgggtcg gcccccaata cttcctcagc gccagggagc    600
agcagtggcg cctagtaggg ccggcaaggc c                                   631
```

```
<210> SEQ ID NO 16
<211> LENGTH: 209
<212> TYPE: PRT
<213> ORGANISM: Artificial Sequence
<220> FEATURE:
<223> OTHER INFORMATION: Synthetic: 4 VSV amino acid sequence
<220> FEATURE:
<221> NAME/KEY: misc_feature
<222> LOCATION: (204)..(205)
<223> OTHER INFORMATION: Location of stop codon

<400> S

```
ccaaacacgt cgtccgcacc cggttcaacc gacttctacc tcaagtcgcg aagcgttgga    240
caaccgaaag caccctcggt gccaaactcc gcatcacata gtggcagcgc ccccaataca    300
agttcagcgc cagggtccac agattttat ctgaaagata tctctagcgg gcagcctaag     360
gctccctcag ttcccaactc tgcttccac tcggggtctg cgccaaatac ctctagcgcc     420
cctggctcta cagattttta cttgaagggc gccagtagcg gccaacctaa agcaccttca    480
gtgccaaatt ccgcatcgca ttctgggtcg gcccccaata cttcctcagc gccagggagc    540
agcagtggcg cctagtaggg ccggcaaggc c                                    571
```

```
<210> SEQ ID NO 18
<211> LENGTH: 188
<212> TYPE: PRT
<213> ORGANISM: Artificial Sequence
<220> FEATURE:
<223> OTHER INFORMATION: Synthetic:  4 AU5 amino acid sequence
<220> FEATURE:
<221> NAME/KEY: misc_feature
<222> LOCATION: (184)..(185)
<223> OTHER INFORMATION: Location of stop codon

<400> SEQUENCE: 18

Ser Gly Arg Ser Ser Gly Gln Pro Lys Ala Pro Ser Val Pro Asn Ser
1               5                   10                  15

Ala Ser His Ser Gly Ser Ala Pro Asn Thr Ser Ser Ala Pro Gly Ser
            20                  25                  30

Thr Asp Phe Tyr Leu Lys Ser Ala Ser Ser Gly Gln Pro Lys Ala Pro
        35                  40                  45

Ser Val Pro Asn Ser Ala Ser His Ser Gly Ser Ala Pro Asn Thr Ser
    50                  55                  60

Ser Ala Pro Gly Ser Thr Asp Phe Tyr Leu Lys Ser Arg Ser Val Gly
65                  70                  75                  80

Gln Pro Lys Ala Pro Ser Val Pro Asn Ser Ala Ser His Ser Gly Ser
                85                  90                  95

Ala Pro Asn Thr Ser Ser Ala Pro Gly Ser Thr Asp Phe Tyr Leu Lys
            100                 105                 110

Asp Ile Ser Ser Gly Gln Pro Lys Ala Pro Ser Val Pro Asn Ser Ala
        115                 120                 125

Ser His Ser Gly Ser Ala Pro Asn Thr Ser Ser Ala Pro Gly Ser Thr
    130                 135                 140

Asp Phe Tyr Leu Lys Gly Ala Ser Ser Gly Gln Pro Lys Ala Pro Ser
145                 150                 155                 160

Val Pro Asn Ser Ala Ser His Ser Gly Ser Ala Pro Asn Thr Ser Ser
                165                 170                 175

Ala Pro Gly Ser Ser Ser Gly Ala Gly Arg Gln Gly
            180                 185
```

```
<210> SEQ ID NO 19
<211> LENGTH: 655
<212> TYPE: DNA
<213> ORGANISM: Artificial Sequence
<220> FEATURE:
<223> OTHER INFORMATION: Synthetic:  4 E nucleic acid sequence

<400> SEQUENCE: 19
agcggccgca gcagtggaca accaaaagca ccatcagtac cgaactccgc ctcgcactct     60
ggcagcgcgc ctaatacaag ttcagctccg gggtccggcg ctcctgttcc ttatcccgat    120
ccattggaac ctcgcagcgc ttctagcggc cagcctaaag ctccgagtgt ccccaattca    180
```

```
gcgtcccatt cggggtctgc cccaaacacg tcgtccgcac ccggttcagg ggcaccagtg      240
ccctaccctg atccactcga accccggtcg cgaagcgttg acaaccgaa agcaccctcg       300 gtgccaaact ccgcatcaca tagtggcagc gccccaata caagttcagc gccagggtcc      360
ggggcccccg tccttatcc agatcccctg aacctaggg atatctctag cgggcagcct       420
aaggctccct cagttcccaa ctctgcttcc cactcggggt ctgcgccaaa tacctctagc     480
gcccctggct ctggagctcc agttccctat cctgacccac tggagcctag aggcgccagt     540
agcggccaac ctaaagcacc ttcagtgcca aattccgcat cgcattctgg gtcggccccc     600
aatacttcct cagcgccagg gagcagcagt ggcgcctagt agggccggca aggcc          655
```

```
<210> SEQ ID NO 20
<211> LENGTH: 216
<212> TYPE: PRT
<213> ORGANISM: Artificial Sequence
<220> FEATURE:
<223> OTHER INFORMATION: Synthetic:  4 E amino acid sequence
<220> FEATURE:
<221> NAME/KEY: misc_feature
<222> LOCATION: (212)..(213)
<223> OTHER INFORMATION: Location of stop codon

<400> SEQUENCE: 20
```

```
Ser Gly Arg Ser Gly Gln Pro Lys Ala Pro Ser Val Pro Asn Ser
1               5                   10                  15

Ala Ser His Ser Gly Ser Ala Pro Asn Thr Ser Ser Ala Pro Gly Ser
            20                  25                  30

Gly Ala Pro Val Pro Tyr Pro Asp Pro Leu Glu Pro Arg Ser Ala Ser
            35                  40                  45

Ser Gly Gln Pro Lys Ala Pro Ser Val Pro Asn Ser Ala Ser His Ser
    50                  55                  60

Gly Ser Ala Pro Asn Thr Ser Ser Ala Pro Gly Ser Gly Ala Pro Val
65                  70                  75                  80

Pro Tyr Pro Asp Pro Leu Glu Pro Arg Ser Arg Ser Val Gly Gln Pro
                85                  90                  95

Lys Ala Pro Ser Val Pro Asn Ser Ala Ser His Ser Gly Ser Ala Pro
                100                 105                 110

Asn Thr Ser Ser Ala Pro Gly Ser Gly Ala Pro Val Pro Tyr Pro Asp
            115                 120                 125

Pro Leu Glu Pro Arg Asp Ile Ser Ser Gly Gln Pro Lys Ala Pro Ser
    130                 135                 140

Val Pro Asn Ser Ala Ser His Ser Gly Ser Ala Pro Asn Thr Ser Ser
145                 150                 155                 160

Ala Pro Gly Ser Gly Ala Pro Val Pro Tyr Pro Asp Pro Leu Glu Pro
                165                 170                 175

Arg Gly Ala Ser Ser Gly Gln Pro Lys Ala Pro Ser Val Pro Asn Ser
                180                 185                 190

Ala Ser His Ser Gly Ser Ala Pro Asn Thr Ser Ser Ala Pro Gly Ser
            195                 200                 205

Ser Ser Gly Ala Gly Arg Gln Gly
    210                 215
```

```
<210> SEQ ID NO 21
<211> LENGTH: 709
<212> TYPE: DNA
<213> ORGANISM: Artificial Sequence
<220> FEATURE:
```

<223> OTHER INFORMATION: Synthetic: 5 V5 nucleic acid sequence

<400> SEQUENCE: 21

```
agcggccgca gcagtggaca accaaaagca ccatcagtac cgaactccgc ctcgcactct    60
ggcagcgcgc ctaatacaag ttcagctccg gggtccggta agccaatacc caacccgctc   120
ctaggactgg attcgaccag cgcttctagc ggccagccta aagctccgag tgtccccaat   180
tcagcgtccc attcggggtc tgccccaaac acgtcgtccg cacccggttc agggaagccg   240
atccctaatc ctcttttagg cttggatagt acttcgcgaa gcgttggaca accgaaagca   300
ccctcggtgc caaactccgc atcacatagt ggcagcgccc ccaatacaag ttcagcgcca   360
gggtccggta agcctattcc aaacccactc cttggtctcg actcgaccga tatctctagc   420
gggcagccta aggctccctc agttcccaac tctgcttccc actcggggtc tgcgccaaat   480
acctctagcg cccctggctc tggaaaacca attcccaacc cgttgcttgg attagattca   540
acgggcgcca gtagcggcca acctaaagca ccttcagtgc caattccgc atcgcattct    600
gggtcggccc ccaatacttc ctcagcgcca gggagcggaa agccgatccc aaacccacta   660
ctcggcctgg acagtacgag cagtggcgcc tagtagggcc ggcaaggcc               709
```

<210> SEQ ID NO 22
<211> LENGTH: 234
<212> TYPE: PRT
<213> ORGANISM: Artificial Sequence
<220> FEATURE:
<223> OTHER INFORMATION: Synthetic: 5 V5 amino acid sequence
<220> FEATURE:
<221> NAME/KEY: misc_feature
<222> LOCATION: (230)..(231)
<223> OTHER INFORMATION: Location of stop codon

<400> SEQUENCE: 22

```
Ser Gly Arg Ser Ser Gly Gln Pro Lys Ala Pro Ser Val Pro Asn Ser
1               5                   10                  15

Ala Ser His Ser Gly Ser Ala Pro Asn Thr Ser Ser Ala Pro Gly Ser
            20                  25                  30

Gly Lys Pro Ile Pro Asn Pro Leu Leu Gly Leu Asp Ser Thr Ser Ala
        35                  40                  45

Ser Ser Gly Gln Pro Lys Ala Pro Ser Val Pro Asn Ser Ala Ser His
    50                  55                  60

Ser Gly Ser Ala Pro Asn Thr Ser Ser Ala Pro Gly Ser Gly Lys Pro
65                  70                  75                  80

Ile Pro Asn Pro Leu Leu Gly Leu Asp Ser Thr Ser Arg Ser Val Gly
                85                  90                  95

Gln Pro Lys Ala Pro Ser Val Pro Asn Ser Ala Ser His Ser Gly Ser
            100                 105                 110

Ala Pro Asn Thr Ser Ser Ala Pro Gly Ser Gly Lys Pro Ile Pro Asn
        115                 120                 125

Pro Leu Leu Gly Leu Asp Ser Thr Asp Ile Ser Ser Gly Gln Pro Lys
    130                 135                 140

Ala Pro Ser Val Pro Asn Ser Ala Ser His Ser Gly Ser Ala Pro Asn
145                 150                 155                 160

Thr Ser Ser Ala Pro Gly Ser Gly Lys Pro Ile Pro Asn Pro Leu Leu
                165                 170                 175

Gly Leu Asp Ser Thr Gly Ala Ser Ser Gly Gln Pro Lys Ala Pro Ser
            180                 185                 190

Val Pro Asn Ser Ala Ser His Ser Gly Ser Ala Pro Asn Thr Ser Ser
```

```
                195                 200                 205
Ala Pro Gly Ser Gly Lys Pro Ile Pro Asn Pro Leu Leu Gly Leu Asp
    210                 215                 220

Ser Thr Ser Ser Gly Ala Gly Arg Gln Gly
225                 230

<210> SEQ ID NO 23
<211> LENGTH: 607
<212> TYPE: DNA
<213> ORGANISM: Artificial Sequence
<220> FEATURE:
<223> OTHER INFORMATION: Synthetic:  4 HA nucleic acid sequence

<400> SEQUENCE: 23
agcggccgca gcagtggaca accaaaagca ccatcagtac cgaactccgc ctcgcactct      60
ggcagcgcgc ctaatacaag ttcagctccg gggtcctatc cttacgatgt tcccgattac     120
gcttctgctt ctagcggcca gcctaaagct ccgagtgtcc ccaattcagc gtcccattcg     180
gggtctgccc caaacacgtc gtccgcaccc ggttcatacc cctatgacgt cccagattat     240
gcatcgcgaa gcgttggaca accgaaagca ccctcggtgc caaactccgc atcacatagt     300
ggcagcgccc caatacaag ttcagcgcca gggtcctatc cctacgacgt tcctgattat     360
gccgatatct ctagcgggca gcctaaggct ccctcagttc caactctgc ttcccactcg     420 gggtctgcgc caaataccte tagcgccct ggctcttatc cctacgacgt gccagattac     480
gcaggcgcca gtagcggcca acctaaagca ccttcagtgc caaattccgc atcgcattct     540
gggtcggccc ccaatacttc ctcagcgcca gggagcagca gtggcgccta gtagggccgg     600
caaggcc                                                               607

<210> SEQ ID NO 24
<211> LENGTH: 200
<212> TYPE: PRT
<213> ORGANISM: Artificial Sequence
<220> FEATURE:
<223> OTHER INFORMATION: Synthetic:  4 HA amino acid sequence
<220> FEATURE:
<221> NAME/KEY: misc_feature
<222> LOCATION: (196)..(197)
<223> OTHER INFORMATION: Location of stop codon

<400> SEQUENCE: 24

Ser Gly Arg Ser Ser Gly Gln Pro Lys Ala Pro Ser Val Pro Asn Ser
1               5                   10                  15

Ala Ser His Ser Gly Ser Ala Pro Asn Thr Ser Ser Ala Pro Gly Ser
            20                  25                  30

Tyr Pro Tyr Asp Val Pro Asp Tyr Ala Ser Ala Ser Ser Gly Gln Pro
        35                  40                  45

Lys Ala Pro Ser Val Pro Asn Ser Ala Ser His Ser Gly Ser Ala Pro
    50                  55                  60

Asn Thr Ser Ser Ala Pro Gly Ser Tyr Pro Tyr Asp Val Pro Asp Tyr
65                  70                  75                  80

Ala Ser Arg Ser Val Gly Gln Pro Lys Ala Pro Ser Val Pro Asn Ser
                85                  90                  95

Ala Ser His Ser Gly Ser Ala Pro Asn Thr Ser Ser Ala Pro Gly Ser
            100                 105                 110

Tyr Pro Tyr Asp Val Pro Asp Tyr Ala Asp Ile Ser Ser Gly Gln Pro
        115                 120                 125

Lys Ala Pro Ser Val Pro Asn Ser Ala Ser His Ser Gly Ser Ala Pro
```

```
                    130                 135                 140
Asn Thr Ser Ser Ala Pro Gly Ser Tyr Pro Tyr Asp Val Pro Asp Tyr
145                 150                 155                 160

Ala Gly Ala Ser Ser Gly Gln Pro Lys Ala Pro Ser Val Pro Asn Ser
                165                 170                 175

Ala Ser His Ser Gly Ser Ala Pro Asn Thr Ser Ser Ala Pro Gly Ser
            180                 185                 190

Ser Ser Gly Ala Gly Arg Gln Gly
        195                 200

<210> SEQ ID NO 25
<211> LENGTH: 643
<212> TYPE: DNA
<213> ORGANISM: Artificial Sequence
<220> FEATURE:
<223> OTHER INFORMATION: Synthetic:  4 E2 nucleic acid sequence

<400> SEQUENCE: 25
agcggccgca gcagtggaca accaaaagca ccatcagtac cgaactccgc ctcgcactct      60
ggcagcgcgc ctaatacaag ttcagctccg ggtccggcg tttcttcaac ttcctctgat     120
tttcgcgaca gaagcgcttc tagcggccag cctaaagctc cgagtgtccc caattcagcg    180
tcccattcgg ggtctgcccc aaacacgtcg tccgcacccg gttcaggagt cagcagtacc    240
tcatctgact ccgggatcg gtcgcgaagc gttggacaac cgaaagcacc ctcggtgcca     300
aactccgcat cacatagtgg cagcgccccc aatacaagtt cagcgccagg gtccggggtg    360
agctctacaa gttcagattt tagagaccgc gatatctcta gcgggcagcc taaggctccc    420
tcagttccca actctgcttc ccactcgggg tctgcgccaa atacctctag cgcccctggc    480
tctggcgtgt cttccactag ctctgacttt cgggacaggg cgccagtag cggccaacct     540 aaagcacctt cagtgccaaa ttccgcatcg cattctgggt cggcccccaa tacttcctca    600
gcgccaggga gcagcagtgg cgcctagtag ggccggcaag gcc                      643

<210> SEQ ID NO 26
<211> LENGTH: 212
<212> TYPE: PRT
<213> ORGANISM: Artificial Sequence
<220> FEATURE:
<223> OTHER INFORMATION: Synthetic:  4 E2 amino acid sequence
<220> FEATURE:
<221> NAME/KEY: misc_feature
<222> LOCATION: (208)..(209)
<223> OTHER INFORMATION: Location of stop codon

<400> SEQUENCE: 26

Ser Gly Arg Ser Gly Gln Pro Lys Ala Pro Ser Val Pro Asn Ser
1               5                   10                  15

Ala Ser His Ser Gly Ser Ala Pro Asn Thr Ser Ser Ala Pro Gly Ser
            20                  25                  30

Gly Val Ser Ser Thr Ser Ser Asp Phe Arg Asp Arg Ser Ala Ser Ser
        35                  40                  45

Gly Gln Pro Lys Ala Pro Ser Val Pro Asn Ser Ala Ser His Ser Gly
    50                  55                  60

Ser Ala Pro Asn Thr Ser Ser Ala Pro Gly Ser Gly Val Ser Ser Thr
65                  70                  75                  80

Ser Ser Asp Phe Arg Asp Arg Ser Arg Ser Val Gly Gln Pro Lys Ala
                85                  90                  95

Pro Ser Val Pro Asn Ser Ala Ser His Ser Gly Ser Ala Pro Asn Thr
```

```
            100                 105                 110
Ser Ser Ala Pro Gly Ser Gly Val Ser Ser Thr Ser Ser Asp Phe Arg
            115                 120                 125

Asp Arg Asp Ile Ser Ser Gly Gln Pro Lys Ala Pro Ser Val Pro Asn
        130                 135                 140

Ser Ala Ser His Ser Gly Ser Ala Pro Asn Thr Ser Ser Ala Pro Gly
145                 150                 155                 160

Ser Gly Val Ser Ser Thr Ser Ser Asp Phe Arg Asp Arg Gly Ala Ser
                165                 170                 175

Ser Gly Gln Pro Lys Ala Pro Ser Val Pro Asn Ser Ala Ser His Ser
            180                 185                 190

Gly Ser Ala Pro Asn Thr Ser Ser Ala Pro Gly Ser Ser Ser Gly Ala
        195                 200                 205

Gly Arg Gln Gly
    210

<210> SEQ ID NO 27
<211> LENGTH: 637
<212> TYPE: DNA
<213> ORGANISM: Artificial Sequence
<220> FEATURE:
<223> OTHER INFORMATION: Synthetic:  4 KT3 nucleic acid sequence

<400> SEQUENCE: 27
agcggccgca gcagtggaca accaaaagca ccatcagtac cgaactccgc ctcgcactct      60
ggcagcgcgc ctaatacaag ttcagctccg gggtccaaac ctccaactcc cccacctgaa     120
cctgagacta gcgcttctag cggccagcct aaagctccga gtgtcccaa ttcagcgtcc      180 cattcggggt ctgccccaaa cacgtcgtcc gcaccggtt caaagccacc caccccacct      240
cccgagcccg aaacatcgcg aagcgttgga caaccgaaag caccctcggt gccaaactcc     300
gcatcacata gtggcagcgc ccccaataca agttcagcgc cagggtccaa accacctaca     360
cctccacccg aaccagagac cgatatctct agcgggcagc ctaaggctcc ctcagttccc     420
aactctgctt cccactcggg gtctgcgcca aatacctcta gcgccctg ctctaagcct      480 cccacaccac cccctgagcc tgaaactggc gccagtagcg ccaacctaa agcaccttca      540 gtgccaaatt ccgcatcgca ttctgggtcg gccccaata cttcctcagc gcagggagc      600 agcagtggcg cctagtaggg ccggcaaggc cggatcc                              637

<210> SEQ ID NO 28
<211> LENGTH: 208
<212> TYPE: PRT
<213> ORGANISM: Artificial Sequence
<220> FEATURE:
<223> OTHER INFORMATION: Synthetic:  4 KT3 amino acid sequence
<220> FEATURE:
<221> NAME/KEY: misc_feature
<222> LOCATION: (204)..(205)
<223> OTHER INFORMATION: Location of stop codon

<400> SEQUENCE: 28

Ser Gly Arg Ser Ser Gly Gln Pro Lys Ala Pro Ser Val Pro Asn Ser
1               5                   10                  15

Ala Ser His Ser Gly Ser Ala Pro Asn Thr Ser Ser Ala Pro Gly Ser
            20                  25                  30

Lys Pro Pro Thr Pro Pro Glu Pro Glu Thr Ser Ala Ser Ser Gly
        35                  40                  45

Gln Pro Lys Ala Pro Ser Val Pro Asn Ser Ala Ser His Ser Gly Ser
```

```
Ala Pro Asn Thr Ser Ser Ala Pro Gly Ser Lys Pro Thr Pro Pro
65                  70                  75                  80

Pro Glu Pro Glu Thr Ser Arg Ser Val Gly Gln Pro Lys Ala Pro Ser
                85                  90                  95

Val Pro Asn Ser Ala Ser His Ser Gly Ser Ala Pro Asn Thr Ser Ser
            100                 105                 110

Ala Pro Gly Ser Lys Pro Pro Thr Pro Pro Glu Pro Glu Thr Asp
        115                 120                 125

Ile Ser Ser Gly Gln Pro Lys Ala Pro Ser Val Pro Asn Ser Ala Ser
        130                 135                 140

His Ser Gly Ser Ala Pro Asn Thr Ser Ser Ala Pro Gly Ser Lys Pro
145                 150                 155                 160

Pro Thr Pro Pro Glu Pro Glu Thr Gly Ala Ser Ser Gly Gln Pro
                165                 170                 175

Lys Ala Pro Ser Val Pro Asn Ser Ala Ser His Ser Gly Ser Ala Pro
            180                 185                 190

Asn Thr Ser Ser Ala Pro Gly Ser Ser Gly Ala Gly Arg Gln Gly
        195                 200                 205

<210> SEQ ID NO 29
<211> LENGTH: 673
<212> TYPE: DNA
<213> ORGANISM: Artificial Sequence
<220> FEATURE:
<223> OTHER INFORMATION: Synthetic: 4 OLLAS nucleic acid sequence

<400> SEQUENCE: 29
agcggccgca gcagtggaca accaaaagca ccatcagtac cgaactccgc ctcgcactct      60
ggcagcgcgc ctaatacaag ttcagctccg gggtccagtg gctttgctaa tgaattgggc    120
cctagattga tgggaaagag cgcttctagc ggccagccta agctcccgag tgtccccaat    180
tcagcgtccc attcggggtc tgccccaaac acgtcgtccg cacccggttc atcagggttc    240
gcaaacgagc tcgggccaag acttatgggc aaatcgcgaa cgttggaca accgaaagca    300 ccctcggtgc caaactccgc atcacatagt ggcagcgccc ccaatacaag ttcagcgcca    360
gggtcctccg gctttgccaa tgagctggga ccccgcctta tgggcaaaga tatctctagc    420
gggcagccta aggctcccctc agttcccaac tctgcttccc actcggggtc tgcgccaaat    480
acctctagcg cccctggctc ttctgggttt gcaaatgagt tggggcctag gttgatgggc    540
aagggcgcca gtagcggcca acctaaagca ccttcagtgc caaattccgc atcgcattct    600
gggtcggccc ccaatacttc ctcagcgcca gggagcagca gtggcgccta gtagggccgg    660
caaggccgga tcc                                                        673

<210> SEQ ID NO 30
<211> LENGTH: 220
<212> TYPE: PRT
<213> ORGANISM: Artificial Sequence
<220> FEATURE:
<223> OTHER INFORMATION: Synthetic: 4 OLLAS amino acid sequence
<220> FEATURE:
<221> NAME/KEY: misc_feature
<222> LOCATION: (216)..(217)
<223> OTHER INFORMATION: Location of stop codon

<400> SEQUENCE: 30

Ser Gly Arg Ser Ser Gly Gln Pro Lys Ala Pro Ser Val Pro Asn Ser
1               5                   10                  15
```

Ala Ser His Ser Gly Ser Ala Pro Asn Thr Ser Ser Ala Pro Gly Ser
            20                  25                  30

Ser Gly Phe Ala Asn Glu Leu Gly Pro Arg Leu Met Gly Lys Ser Ala
        35                  40                  45

Ser Ser Gly Gln Pro Lys Ala Pro Ser Val Pro Asn Ser Ala Ser His
50                  55                  60

Ser Gly Ser Ala Pro Asn Thr Ser Ser Ala Pro Gly Ser Ser Gly Phe
65                  70                  75                  80

Ala Asn Glu Leu Gly Pro Arg Leu Met Gly Lys Ser Arg Ser Val Gly
                85                  90                  95

Gln Pro Lys Ala Pro Ser Val Pro Asn Ser Ala Ser His Ser Gly Ser
            100                 105                 110

Ala Pro Asn Thr Ser Ser Ala Pro Gly Ser Ser Gly Phe Ala Asn Glu
        115                 120                 125

Leu Gly Pro Arg Leu Met Gly Lys Asp Ile Ser Ser Gly Gln Pro Lys
130                 135                 140

Ala Pro Ser Val Pro Asn Ser Ala Ser His Ser Gly Ser Ala Pro Asn
145                 150                 155                 160

Thr Ser Ser Ala Pro Gly Ser Ser Gly Phe Ala Asn Glu Leu Gly Pro
                165                 170                 175

Arg Leu Met Gly Lys Gly Ala Ser Ser Gly Gln Pro Lys Ala Pro Ser
            180                 185                 190

Val Pro Asn Ser Ala Ser His Ser Gly Ser Ala Pro Asn Thr Ser Ser
        195                 200                 205

Ala Pro Gly Ser Ser Ser Gly Ala Gly Arg Gln Gly
210                 215                 220

<210> SEQ ID NO 31
<211> LENGTH: 577
<212> TYPE: DNA
<213> ORGANISM: Artificial Sequence
<220> FEATURE:
<223> OTHER INFORMATION: Synthetic:  4 AU1 nucleic acid sequence

<400> SEQUENCE: 31
agcggccgca gcagtggaca accaaaagca ccatcagtac cgaactccgc ctcgcactct      60
ggcagcgcgc ctaatacaag ttcagctccg gggtccgata cttatcgcta cattagcgct     120
tctagcggcc agcctaaagc tccgagtgtc cccaattcag cgtcccattc ggggtctgcc     180
ccaaacacgt cgtccgcacc cggttcagac acatacaggt atatttcgcg aagcgttgga     240
caaccgaaag caccctcggt gccaaactcc gcatcacata gtggcagcgc ccccaataca     300
agttcagcgc cagggtccga cacctaccgc tatatcgata tctctagcgg gcagcctaag     360
gctccctcag ttcccaactc tgcttcccac tcggggtctg cgccaaatac ctctagcgcc     420
cctggctctg atacatatcg ctacattggc gccagtagcg gccaacctaa agcaccttca     480
gtgccaaatt ccgcatcgca ttctgggtcg gcccccaata cttcctcagc gccagggagc     540
agcagtggcg cctagtaggg ccggcaaggc cggatcc                              577

<210> SEQ ID NO 32
<211> LENGTH: 188
<212> TYPE: PRT
<213> ORGANISM: Artificial Sequence
<220> FEATURE:
<223> OTHER INFORMATION: Synthetic:  4 AU1 amino acid sequence
<220> FEATURE:
<221> NAME/KEY: misc_feature

```
<222> LOCATION: (184)..(185)
<223> OTHER INFORMATION: Location of stop codon

<400> SEQUENCE: 32

Ser Gly Arg Ser Ser Gly Gln Pro Lys Ala Pro Ser Val Pro Asn Ser
1               5                   10                  15

Ala Ser His Ser Gly Ser Ala Pro Asn Thr Ser Ser Ala Pro Gly Ser
            20                  25                  30

Asp Thr Tyr Arg Tyr Ile Ser Ala Ser Ser Gly Gln Pro Lys Ala Pro
        35                  40                  45

Ser Val Pro Asn Ser Ala Ser His Ser Gly Ser Ala Pro Asn Thr Ser
    50                  55                  60

Ser Ala Pro Gly Ser Asp Thr Tyr Arg Tyr Ile Ser Arg Ser Val Gly
65                  70                  75                  80

Gln Pro Lys Ala Pro Ser Val Pro Asn Ser Ala Ser His Ser Gly Ser
                85                  90                  95

Ala Pro Asn Thr Ser Ser Ala Pro Gly Ser Asp Thr Tyr Arg Tyr Ile
            100                 105                 110

Asp Ile Ser Ser Gly Gln Pro Lys Ala Pro Ser Val Pro Asn Ser Ala
        115                 120                 125

Ser His Ser Gly Ser Ala Pro Asn Thr Ser Ser Ala Pro Gly Ser Asp
    130                 135                 140

Thr Tyr Arg Tyr Ile Gly Ala Ser Ser Gly Gln Pro Lys Ala Pro Ser
145                 150                 155                 160

Val Pro Asn Ser Ala Ser His Ser Gly Ser Ala Pro Asn Thr Ser Ser
            165                 170                 175

Ala Pro Gly Ser Ser Ser Gly Ala Gly Arg Gln Gly
            180                 185
```